(12) United States Patent
Park et al.

(10) Patent No.: US 12,297,513 B2
(45) Date of Patent: *May 13, 2025

(54) BIOSENSORS FOR DETECTING AND/OR NEUTRALIZING BIOAVAILABLE URANIUM AND RELATED U-SENSITIVE GENETIC MOLECULAR COMPONENTS, GENE CASSETTES, VECTORS, GENETIC CIRCUITS, COMPOSITIONS, METHODS AND SYSTEMS

(71) Applicant: LAWRENCE LIVERMORE NATIONAL SECURITY, LLC, Livermore, CA (US)

(72) Inventors: Dan Mcfarland Park, Dublin, CA (US); Yongqin Jiao, Pleasanton, CA (US)

(73) Assignee: LAWRENCE LIVERMORE NATIONAL SECURITY, LLC, Livermore, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/186,095

(22) Filed: Mar. 17, 2023

(65) Prior Publication Data

US 2023/0332251 A1 Oct. 19, 2023

Related U.S. Application Data

(63) Continuation of application No. 16/764,824, filed as application No. PCT/US2018/061667 on Nov. 16, 2018, now Pat. No. 11,608,536.

(60) Provisional application No. 62/587,753, filed on Nov. 17, 2017.

(51) Int. Cl.
| | |
|---|---|
| *C12Q 1/6897* | (2018.01) |
| *C12N 1/20* | (2006.01) |
| *C12Q 1/48* | (2006.01) |
| *G01N 33/84* | (2006.01) |
| *C12R 1/01* | (2006.01) |

(52) U.S. Cl.
CPC ......... *C12Q 1/6897* (2013.01); *C12N 1/205* (2021.05); *C12Q 1/485* (2013.01); *G01N 33/84* (2013.01); *C12R 2001/01* (2021.05)

(58) Field of Classification Search
CPC .................................................. C12Q 1/6897
See application file for complete search history.

(56) References Cited

U.S. PATENT DOCUMENTS

| | | |
|---|---|---|
| 11,608,536 B2 | 3/2023 | Park |
| 11,898,211 B2 | 2/2024 | Park |
| 2011/0117590 A1* | 5/2011 | Hillson ................. C07K 14/21 |
| | | 435/29 |

(Continued)

OTHER PUBLICATIONS

Record for GenBank Accession No. AE005992.1, Caulobacter crescentus CB15, section 318 of 359 of the complete genome, 2002.*

(Continued)

*Primary Examiner* — Rosanne Kosson
(74) *Attorney, Agent, or Firm* — Steinfl + Bruno LLP

(57) ABSTRACT

U biosensors, and related U-sensing genetic molecular components, genetic circuits, compositions, methods and systems are described, which in several embodiments can be used to detect and/or neutralize uraniunm and in particular bioavailable U.

24 Claims, 49 Drawing Sheets

Specification includes a Sequence Listing.

(56) References Cited

U.S. PATENT DOCUMENTS

2020/0370135 A1 11/2020 Park et al.
2024/0376556 A1 11/2024 Park

OTHER PUBLICATIONS

U.S. Appl. No. 16/764,824, filed May 15, 2020, US 20200370135A1 Nov. 26, 2020, U.S. Pat. No. 11,608,536 Mar. 21, 2023, Lawrence Livermore National Security, LLC, Dan Mcfarland Park; Yongqin Jiao.

Barrett, C. A.; Chouyyok, W.; Speakman, R. J.; Olsen, K. B.; Addleman, R. S., Rapid extraction and assay of uranium from environmental surface samples. Talanta, Oct. 2017, 173, 69-78.

Di Bernardo, P.; Zanonato, P. L.; Benetollo, F.; Melchior, A.; Tolazzi, M.; Rao, L., Energetics and Structure of Uranium(VI)-Acetate Complexes in Dimethyl Sulfoxide. Inorg. Chem. Aug. 2012, 51 (16), 9045-9055.

Speed, M. C.; Burkhart, B. W.; Picking, J. W.; Santangelo, T. J., An Archaeal Fluoride-Responsive Riboswitch Provides an Inducible Expression System for Hyperthermophiles. Appl Environ Microbiol, Apr. 2018, 84 (7) e02306-17. 8 pages.

Thavarajah, W.; Silverman, A. D.; Verosloff, M. S.; Kelley-Loughnane, N.; Jewett, M. C.; Lucks, J. B., Point-of-Use Detection of Environmental Fluoride via a Cell-Free Riboswitch-Based Biosensor. ACS Synthetic Biology, Jan. 17, 2020, 9 (1), 10-18. 18 pages.

2nd Restriction Requirement for U.S. Appl. No. 16/781,950, filed Feb. 4, 2020 on behalf of Lawrence Livermore National Security, LLC Mail Date: Jan. 11, 2023. 8 pages.

Non-Final Office Action for U.S. Appl. No. 16/781,950, filed Feb. 4, 2020 on behalf of Lawrence Livermore National Security, LLC. Mail Date: Jun. 1, 2023. 22 pages.

Notice of Allowance for U.S. Appl. No. 16/781,950, filed Feb. 4, 2020 on behalf of Lawrence Livermore National Security, LLC. Mail Date: Oct. 5, 2023. 8 pages.

Notice of Allowance issued for U.S. Appl. No. 16/764,824, filed May 15, 2020, on behalf of Lawrence Livermore National Security, LLC. Mail Date: Nov. 2, 2022. 26 Pages.

Record for GenBank Accession No. AE005992.1, Caulobacter crescentus CB15, section 318 to 359 of the complete genome, 2002. 7 pages.

Response to Rule 312 Communication issued for U.S. Appl. No. 16/764,824, filed May 15, 2020, on behalf of Lawrence Livermore National Security, LLC. Mail Date Jan. 4, 2023. 2 Pages.

Restriction Requirement issued for U.S. Appl. No. 16/764,824, filed May 15, 2020, on behalf of Lawrence Livermore National Security, LLC. Mail Date: Jul. 27, 2022. 8 Pages.

Restriction Requirement for U.S. Appl. No. 18/406,057, filed Jan. 5, 2024 on behalf of Lawrence Livermore National Security, LLC. Mailed on Sep. 20, 2024. 8 pages.

* cited by examiner

A

P$_{phyt}$ sequence

CCCAAAGAGGGTGTGGCCCAAAGAGGGTGTGGATTTCTCTTCGCGC
          tandem repeat (TR)

CACCCGTTTCGTCAGCCGGACGTCAGGTCCAGACGGCTAAGCTAGC
TGCGA    DR1           DR2
         Regulator Direct Repeat

B

P$_{1361}$ sequence

ATGTTCAGCGCCTGGTTACCGGCGATGGCGCGGTGTCAGCGTTCGG

GCGTTGCGATGCGTCAGGAGCGTGTCAGGATGCCTGTGGAATCCTA
AGCGC    DR1           DR2
         Regulator Direct Repeat

C

A. P_phyt DNA sequence
CGGACGGTGACCGGCAAACCACCGCTGTCATGAATGCGTTTTGAAGCTTCGCCATAACGCGCCTTGGGTA
TCCGGTTCGGAACGCGGCGCTTTCGTTGACCTCTGGCCACGGAGAATTCTCCATCCCAAAGAGGGTGTGG
CCCAAAGAGGGTGTGGATTTCTCTTCGCGCCACCCGTTT*CGTCAGCCGGACGTCAGGT*CCAGACGGCTAA
GCTAGCTGCgaGACatgAAAACGAG (SEQ ID NO:72)

B. P_phyt DR2 GTCA -> CAGT (mutation in bold)
CGGACGGTGACCGGCAAACCACCGCTGTCATGAATGCGTTTTGAAGCTTCGCCATAACGCGCCTTGGGTA
TCCGGTTCGGAACGCGGCGCTTTCGTTGACCTCTGGCCACGGAGAATTCTCCATCCCAAAGAGGGTGTGG
CCCAAAGAGGGTGTGGATTTCTCTTCGCGCCACCCGTTT*CGTCAGCCGGACCAGTGGT*CCAGACGGCTAA
GCTAGCTGCgaGACatgAAAACGAG (SEQ ID NO:73)

C. P_phyt DR1 GT -> CA (mutation in bold)
CGGACGGTGACCGGCAAACCACCGCTGTCATGAATGCGTTTTGAAGCTTCGCCATAACGCGCCTTGGGTA
TCCGGTTCGGAACGCGGCGCTTTCGTTGACCTCTGGCCACGGAGAATTCTCCATCCCAAAGAGGGTGTGG
CCCAAAGAGGGTGTGGATTTCTCTTCGCGCCACCCGTTT*CCACAGCCGGACGTCAGGT*CCAGACGGCTAA
GCTAGCTGCgaGACatgAAAACGAG (SEQ ID NO: 74)

D. P_phyt DR2 GT -> CA (mutation in bold)
CGGACGGTGACCGGCAAACCACCGCTGTCATGAATGCGTTTTGAAGCTTCGCCATAACGCGCCTTGGGTA
TCCGGTTCGGAACGCGGCGCTTTCGTTGACCTCTGGCCACGGAGAATTCTCCATCCCAAAGAGGGTGTGG
CCCAAAGAGGGTGTGGATTTCTCTTCGCGCCACCCGTTT*CGTCAGCCGGACCACAGGT*CCAGACGGCTAA
GCTAGCTGCgaGACatgAAAACGAG (SEQ ID NO: 75)

E. P_phyt short
GGATTTCTCTTCGCGCCACCCGTTT*CGTCAGCCGGACGTCAGGT*CCAGACGGCTAAGCTAGCTGCgaGAC
atgAAAACGAG (SEQ ID NO:76)

FIG. 8

F.   P<sub>1361</sub> DNA sequence

GAACGATAGCGCCGCCTGCGAGCGCGACCTCAGGCCTCGGACGAAGCGCGTCCGGGGCCTTTTCTTGTCG
ATGTTCAGCGCCTGGTTACCGGCGATGGCGCGGTGTCAGCGTTCGGGCGTTGCGATG*CGTCAGGAGCGTG*
*TCAGGA*TGCCTGTGGAATCCTAAGCGcCatgACCCAGTCCCGATCTTTCC (SEQ ID NO:77)

G.   P<sub>1361</sub> DR2 GTCA -> CAGT (mutation in bold)

GAACGATAGCGCCGCCTGCGAGCGCGACCTCAGGCCTCGGACGAAGCGCGTCCGGGGCCTTTTCTTGTCG
ATGTTCAGCGCCTGGTTACCGGCGATGGCGCGGTGTCAGCGTTCGGGCGTTGCGATG*CGTCAGGAGCGTC*
AGTG*GA*TGCCTGTGGAATCCTAAGCGcCatgACCCAGTCCCGATCTTTCC (SEQ ID NO:78)

H.   P<sub>1361</sub> DR2 GT -> CA (mutation in bold)

GAACGATAGCGCCGCCTGCGAGCGCGACCTCAGGCCTCGGACGAAGCGCGTCCGGGGCCTTTTCTTGTCG
ATGTTCAGCGCCTGGTTACCGGCGATGGCGCGGTGTCAGCGTTCGGGCGTTGCGATG*CGTCAGGAGCGTC*
AC*AGGA*TGCCTGTGGAATCCTAAGCGcCatgACCCAGTCCCGATCTTTCC (SEQ ID NO: 79)

I.   P<sub>1361</sub> short

GCGTTGCGATG*CGTCAGGAGCGTGTCAGGA*TGCCTGTGGAATCCTAAGCGcCatgACCCAGTCCCGATCT
TTCC (SEQ ID NO: 80)

FIG. 8 (cont.)

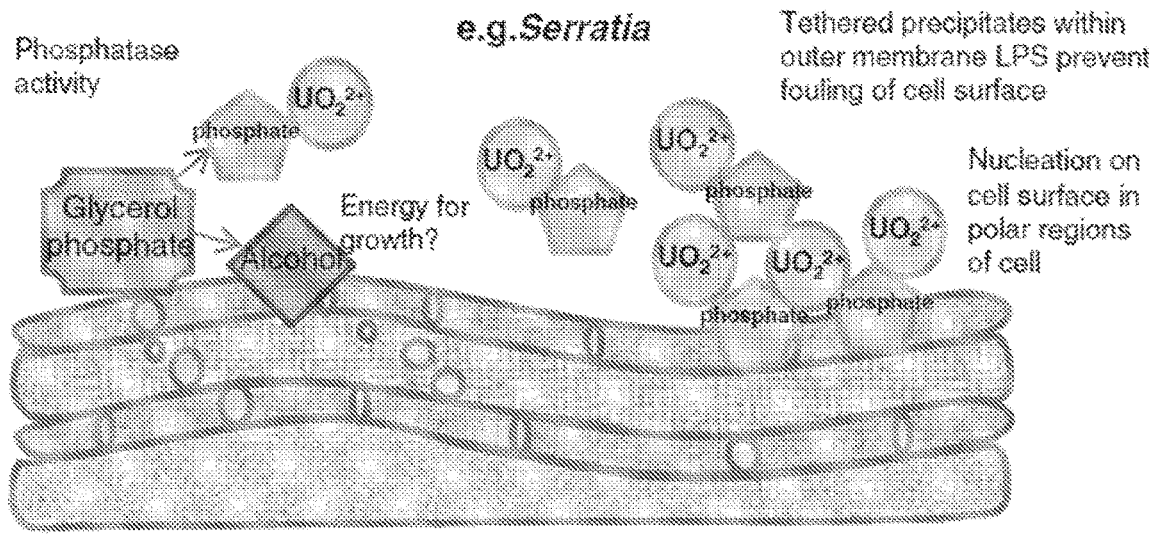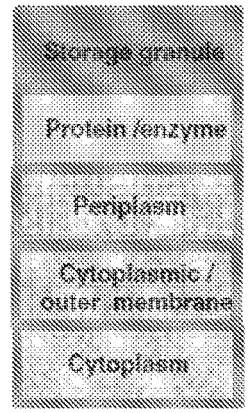
FIG. 16B

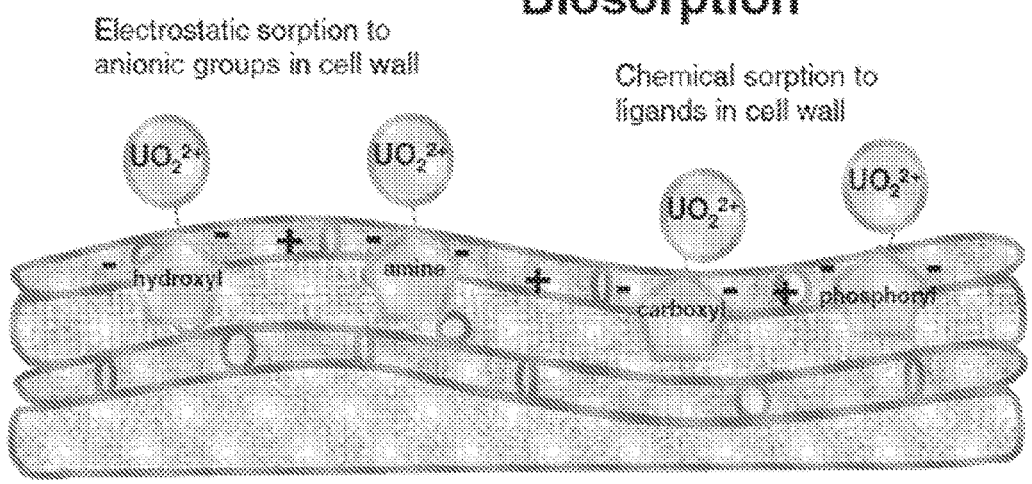
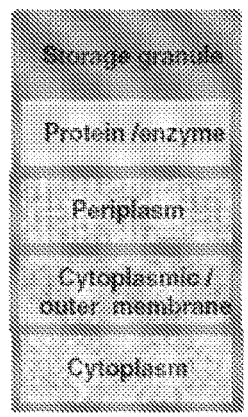
FIG. 16C

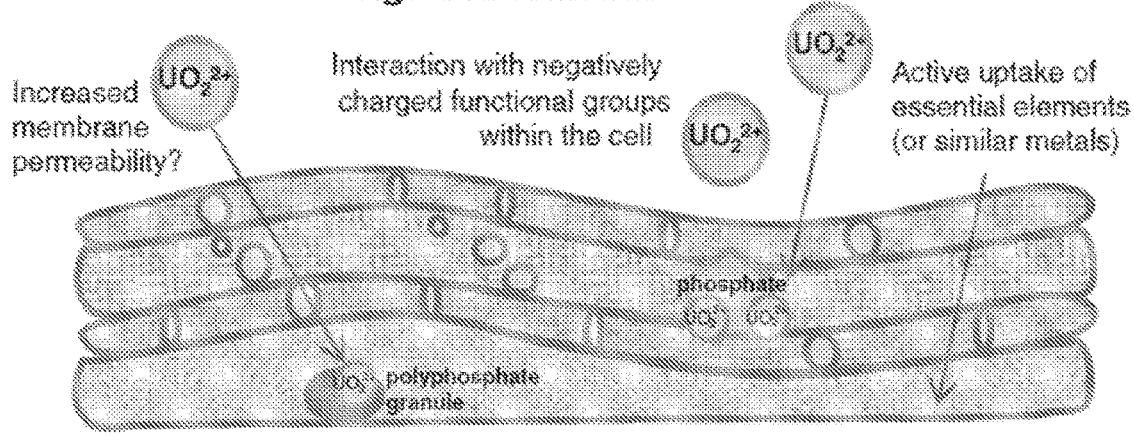
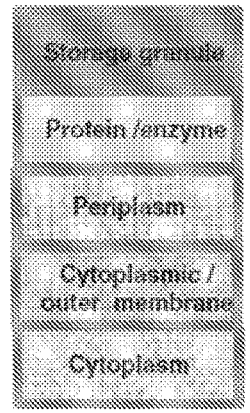
FIG. 16D

BIOSENSORS FOR DETECTING AND/OR NEUTRALIZING BIOAVAILABLE URANIUM AND RELATED U-SENSITIVE GENETIC MOLECULAR COMPONENTS, GENE CASSETTES, VECTORS, GENETIC CIRCUITS, COMPOSITIONS, METHODS AND SYSTEMS

CROSS REFERENCE TO RELATED APPLICATIONS

The present application is the continuation of U.S. application Ser. No. 16/764,824 filed on May 15, 2020 which in turn is the U.S. National Stage of International Application No. PCT/US2018/061667 filed internationally on Nov. 16, 2018, which, in turn claims priority to U.S. provisional application No. 62/587,753, entitled "Biosensors for Detecting And/Or Neutralizing Bioavailable Uranium And Related U-Sensitive Genetic Molecular Components, Gene Cassettes, Vectors, Genetic Circuits, Compositions, Methods And Systems" filed on Nov. 17, 2017, with docket number IL-13081, each of which is incorporated by reference in its entirety.

STATEMENT OF GOVERNMENT GRANT

The United States Government has rights in this invention pursuant to Contract No. DE-AC52-07NA27344 between the United States Department of Energy and Lawrence Livermore National Security, LLC, for the operation of Lawrence Livermore National Laboratory.

INCORPORATION BY REFERENCE STATEMENT FOR SEQUENCE LISTING

Further, the computer readable form of the sequence listing of the XML file IL-13081C1N1-2023-07-06-Sequence-Listing_ST26 created on Jul. 6, 2023 and having size 281,645 bytes measured on Windows Server 2019 Datacenter is incorporated herein by reference in its entirety.

FIELD

The present disclosure relates to uranium (U) biosensors and related U-sensitive genetic molecular components, gene cassettes, vectors, genetic circuits, compositions, methods and systems. In particular, the present disclosure relates to U biosensors and related methods and systems to detect and/or neutralize bioavailable uranium and more particularly bioavailable uranyl oxycation.

BACKGROUND

Various methods and systems such as spectroscopy as well as antibodies and DNA enzymes are available to monitor environmental U concentrations which is important to minimize human exposure and inform remediation strategies.

In particular, detection of U in an environment in situ, and more particularly detection of bioavailable U that can transverse the cell membrane and exert toxicity, is an important part of an evaluation of the potential risk of environmental U exposure.

However, despite availability of various approaches, development of sensing technologies that provide sensitive, selective and/or cost-effective detection of bioavailable U is still challenging.

SUMMARY

Provided herein are U biosensors, and related U-sensing genetic molecular components, gene cassettes, genetic circuits, compositions, methods and systems which in several embodiments can be used to detect and/or neutralize uranium and in particular bioavailable U.

According to a first aspect, a U-biosensor comprising a U-sensing genetic molecular component configured to report and/or neutralize uranium is described. The U-biosensor comprises a genetically modified bacterial cell capable of natively and/or heterologously expressing histidine kinase 1363 herein also UrpS, and U sensitive transcriptional regulator 1362 herein also UrpR.

In the U-biosensors, the genetically modified bacterial cell is an engineered bacterial cell comprising a U-sensing reportable genetic molecular component and/or a U-sensing/U-neutralizing genetic molecular component, each comprising a U-sensitive promoter in a configuration wherein the U-sensitive promoter directly initiates expression of the U-sensing reportable molecular component and/or of the U-neutralizing molecular component in presence of bioavailable U.

In the U-biosensor, the U-sensitive promoter comprises a 1362 (UrpR) binding site having a DNA sequence (SEQ ID NO: 1)
$N_1N_2N_3N_4N_5N_6N_7N_8N_9N_{10}N_{11}N_{12}N_{13}N_{14}N_{15}N_{16}N_{17}N_{18}$, wherein
$N_1$ is C or T, preferably C;
$N_2$ is G or A, preferably G;
$N_3$ is T or C, preferably T;
$N_4$ is C;
$N_5$ is A or G, preferably A;
$N_6$ is G or C, preferably G;
$N_7$ C or G;
$N_8$ is any nucleotide;
$N_9$ is any nucleotide;
$N_{10}$ is any nucleotide;
$N_{11}$ is any nucleotide;
$N_{12}$ is T or C;
$N_{13}$ is G;
$N_{14}$ is T or C, preferably T;
$N_{15}$ is C;
$N_{16}$ is A or C, preferably A;
$N_{17}$ is G; and
$N_{18}$ is C or G,
and wherein $N_1$ to $N_{17}$ selected independently.

In some embodiments, the genetically modified bacteria are bacteria incapable of natively expressing the histidine kinase 1363 (UrpS) and the U-sensitive transcriptional regulator 1362 (UrpR) (e.g. *E. Coli* bacteria). In those embodiments the bacterial cell is further engineered to include a U-sensing regulator genetic molecular component comprising an endogenous or exogenous gene encoding histidine kinase 1363 (UrpS), and an endogenous or exogenous gene encoding U-sensitive transcriptional regulator 1362 (UrpR) in a configuration wherein the a gene encoding histidine kinase 1363(UrpS), and a gene encoding response regulator 1362 are expressed upon activation of a controllable promoter.

In some embodiments, the genetically modified bacteria are bacteria capable of natively expressing histidine kinase 1363 (UrpS), and U-sensitive transcriptional regulator 1362 (UrpR) (e.g. proteobacteria such as certain Alpha proteobacteria, beta proteobacteria and/or gamma proteobacteria identifiable by a skilled person upon reading of the present disclosure). In some of those embodiments, the endogenous genes encoding the histidine kinase 1363, and the U-sensitive transcriptional regulator 1362 (UrpR), are knocked out and the genetically engineered bacterial cell is further engineered to include a U-sensing regulator genetic molecular component comprising an endogenous or exogenous gene encoding histidine kinase 1363(UrpS), and an endogenous or exogenous gene encoding U-sensitive transcriptional regulator 1362 (UrpR) in a configuration wherein the a gene encoding histidine kinase 1363 (UrpS), and a gene encoding response regulator 1362 (UrpR) are expressed upon activation of a controllable promoter.

According to a second aspect, a U biosensor comprising a U-sensitive genetic circuit is described. The U biosensor comprises a genetically modified bacterial cell capable of natively and/or heterologously expressing histidine kinase 1363 (UrpS) and response regulator 1362(UrpR). In the U-biosensor, the genetically modified bacterial cell is an engineered bacterial cell comprising a U-sensitive genetic circuit in which molecular components are connected one to another in accordance to a circuit design by activating, inhibiting, binding or converting reactions to form a fully connected network of interacting components. In the U-sensitive genetic circuit at least one molecular component is a U-sensing genetic molecular component in which a U-sensitive promoter is activated or repressed in presence of bioavailable U, the U sensitive promoter comprising a U-sensitive 1362 (UrpR) binding site having a DNA sequence (SEQ ID NO: 1)
$N_1N_2N_3N_4N_5N_6N_7N_8N_9N_{10}N_{11}N_{12}N_{13}N_{14}N_{15}N_{16}N_{17}N_{18}$, wherein
$N_1$ is C or T, preferably C;
$N_2$ is G or A, preferably G;
$N_3$ is T or C, preferably T;
$N_4$ is C;
$N_5$ is A or G, preferably A;
$N_6$ is G or C, preferably G; $N_7$C or G;
$N_8$ is any nucleotide;
$N_9$ is any nucleotide;
$N_{10}$ is any nucleotide;
$N_{11}$ is any nucleotide;
$N_{12}$ is T or C;
$N_{13}$ is G;
$N_{14}$ is T or C, preferably T;
$N_{15}$ is C;
$N_{16}$ is A or C, preferably A;
$N_{17}$ is G; and
$N_{18}$ is C or G,
and wherein $N_1$ to $N_{17}$ selected independently.

In the U-sensitive genetic circuit, at least one molecular component is a reportable molecular component (and in particular one or more reportable genetic molecular component and/or one or more reportable cellular molecular component), and/or a U-neutralizing molecular component, (in particular one or more U-neutralizing genetic molecular component and/or one or more U-neutralizing cellular molecular component), the reportable molecular component and/or the a U-neutralizing molecular component expressed when the genetic circuit operates according to the circuit design in presence of bioavailable U.

In some embodiments, the genetically modified bacteria are bacteria not capable of natively expressing the histidine kinase 1363 (UrpS) and the U-sensitive transcriptional regulator 1362 (UrpR) (e.g. *E. Coli* bacteria). In those embodiments, the bacterial cell is further engineered to include a U-sensing regulator genetic molecular component comprising an endogenous or exogenous gene encoding histidine kinase 1363(UrpS), and an endogenous or exogenous gene encoding U-sensitive transcriptional regulator 1362 (UrpR) in a configuration wherein the a gene encoding histidine kinase 1363 (UrpR), and a gene encoding response regulator 1362(UrpR) are expressed upon activation of a controllable promoter.

In some embodiments, the genetically modified bacteria are bacteria capable of natively expressing histidine kinase 1363(UrpS), and U-sensitive transcriptional regulator 1362 (UrpR) (e.g. proteobacteria, such as certain Alpha proteobacteria, beta proteobacteria and/or gamma proteobacteria identifiable by a skilled person upon reading of the present disclosure). In some of those embodiments, the endogenous genes encoding the histidine kinase 1363(UrpS), and the U-sensitive transcriptional regulator 1362(UrpR), can be preferably knocked out and the genetically engineered bacterial cell is further engineered to include a U-sensing regulator genetic molecular component comprising an endogenous or exogenous gene encoding histidine kinase 1363 (UrpS), and an endogenous or exogenous gene encoding U-sensitive transcriptional regulator 1362 in a configuration wherein the a gene encoding histidine kinase 1363 (UrpS), and a gene encoding response regulator 1362 (UrpR) are expressed upon activation of a controllable promoter.

According to a third aspect, a U-biosensor comprising a U-sensing genetic molecular component configured to report and/or neutralize U is described. The U-biosensor comprises a genetically modified bacterial cell capable of natively and/or heterologously expressing histidine kinase UzcS and U-sensitive transcriptional response regulator UzcR.

In the U-biosensors, the genetically modified bacterial cell is an engineered bacterial cell comprising a U-sensing reportable genetic molecular component and/or a U-sensing U-neutralizing genetic molecular component, each comprising a U-sensitive promoter in a configuration wherein the U-sensitive promoter directly initiates expression of the U-sensing reportable molecular component and/or of the U-sensing U-neutralizing molecular component in presence of bioavailable U.

In the U-biosensor, the U-sensitive promoter comprises an UzcR binding site having a DNA sequence:

(SEQ ID NO: 2)
CATTACN$_7$N$_8$N$_9$N$_{10}$N$_{11}$N$_{12}$TTAA wherein $N_7$-$N_{12}$ is independently any nucleotide, and in some embodiments any one of $N_7$—$N_{11}$ can independently be A.

In some embodiments, the genetically modified bacteria are bacteria not capable of natively expressing the histidine kinase UzcS, and the U-sensitive transcriptional response regulator UzcR (e.g. *E. Coli* bacteria), and the bacterial cell is further engineered to include a U-sensing regulator genetic molecular component comprising an endogenous or exogenous gene encoding the histidine kinase UzcS, and an endogenous or exogenous gene encoding the U-sensitive transcriptional response regulator UzcR, in a configuration wherein the gene encoding the histidine kinase UzcS, and the gene encoding the U-sensitive transcriptional response regulator UzcR, are expressed upon activation of a controllable promoter.

In some embodiments, the genetically modified bacteria are bacteria capable of natively expressing the histidine kinase UzcS, and the U-sensitive transcriptional response regulator UzcR (e.g. proteobacteria, such as certain Alpha proteobacteria, beta proteobacteria and/or gamma proteobacteria identifiable by a skilled person upon reading of the present disclosure). In some of those embodiments, in the bacterial cell, the endogenous genes encoding the histidine kinase UzcS, and the U-sensitive transcriptional response regulator UzcR, can be preferably knocked out and the genetically engineered bacterial cell can be further engineered to include a U-sensing regulator genetic molecular component comprising an endogenous or exogenous gene encoding histidine kinase UzcS, and an endogenous or exogenous gene encoding U-sensitive transcriptional response regulator UzcR in a configuration wherein the a gene encoding histidine kinase UzcS, and a gene encoding response regulator UzcR are expressed upon activation of a controllable promoter.

According to a fourth aspect, a U biosensor comprising a U-sensitive genetic circuit is described. The U biosensor comprises a genetically modified bacterial cell natively and/or heterologously expressing histidine kinase UzcS, and response regulator UzcR.

In the U-biosensors, the genetically modified bacterial cell is an engineered bacterial cell comprising a U-sensitive genetic circuit in which molecular components are connected one to another in accordance to a circuit design by activating, inhibiting, binding or converting reactions to form a fully connected network of interacting components. In the U-sensitive genetic circuit at least one molecular component is a U-sensing genetic molecular component in which a U-sensitive promoter is activated or repressed in presence of bioavailable U, the U sensitive promoter comprising a UzcR binding site having DNA sequence:

(SEQ ID NO: 2)
CATTACN$_7$N$_8$N$_9$N$_{10}$N$_{11}$N$_{12}$TTAA wherein N$_7$-N$_{12}$ is independently any nucleotide, and in some embodiments any one of N$_7$—N$_{11}$ can independently be A.

In the U-sensitive genetic circuit at least one molecular component is a reportable molecular component (and in particular one or more reportable genetic molecular component and/or one or more reportable cellular molecular component), and/or a U-neutralizing molecular component, (in particular one or more U-neutralizing genetic molecular component and/or one or more U-neutralizing cellular molecular component), the reportable molecular component and/or a U-neutralizing molecular component expressed when the genetic circuit operates according to the circuit design in presence of bioavailable U.

In some embodiments, the genetically modified bacteria are bacteria not capable of natively expressing the histidine kinase UzcS, and the U-sensitive transcriptional response regulator UzcR (e.g. *E. Coli* bacteria). In those embodiments, the bacterial cell is further engineered to include a U-sensing regulator genetic molecular component comprising an endogenous or exogenous gene encoding the histidine kinase UzcS, and an endogenous or exogenous gene encoding the U-sensitive transcriptional response regulator UzcR, in a configuration wherein the gene encoding the histidine kinase UzcS, and the gene encoding the U-sensitive transcriptional response regulator UzcR, are expressed upon activation of a controllable promoter.

In some embodiments, the genetically modified bacteria are capable of natively expressing the histidine kinase UzcS, and the U-sensitive transcriptional response regulator UzcR (e.g. proteobacteria, such as certain Alpha proteobacteria, beta proteobacteria and/or gamma proteobacteria identifiable by a skilled person upon reading of the present disclosure). In some of those embodiments, in the bacterial cell, the endogenous genes encoding the histidine kinase UzcS, and the U-sensitive transcriptional response regulator UzcR, are knocked out. and the genetically engineered bacterial cell is further engineered to include a U-sensing regulator genetic molecular component comprising an endogenous or exogenous gene encoding histidine kinase UzcS, and an endogenous or exogenous gene encoding U-sensitive transcriptional response regulator UzcR in a configuration wherein the gene encoding histidine kinase UzcS, and a gene encoding response regulator UzcR are expressed upon activation of a controllable promoter.

In some embodiments of the U-biosensors according to a third and a fourth aspect the genetically modified bacterial cell is a bacterial cell capable of natively expressing MarR family repressors such as marR$_1$ (CCNA_03498) and marR$_2$ (CCNA_02298) genes (e.g. proteobacteria, such as certain Alpha proteobacteria, beta proteobacteria and/or gamma proteobacteria identifiable by a skilled person upon reading of the present disclosure). In those embodiments, the bacterial cell is preferably further engineered to knock out at least one endogenous MarR family repressors such as marR$_1$ and marR$_2$ genes to provide an amplified U-biosensor configured to provide an amplified signal following activation of the U-sensitive genetic circuit.

In some preferred embodiments of the U-biosensors according to the third and the fourth aspect, the U-biosensor or the U-sensitive genetic circuit, further comprises an amplifier genetic molecular component comprising a U-sensitive promoter and UzcY and/or UzcZ in a configuration wherein the U-sensitive promoter directly initiates expression of the amplifier molecular component.

According to a fifth aspect, a method to provide a U biosensor is described, the method comprising
  genetically engineering a bacterial cell capable of natively and/or heterologously expressing histidine kinase 1363 (UrpS) and/or histidine kinase UzcS, and U sensitive response regulator 1362 (UrpR) and/or U sensitive response regulator UzcR, the genetically engineering performed by introducing into the cell one or more U-sensing genetic molecular components configured to report and/or neutralize U herein described, and/or one or more genetic molecular components of the U-sensitive genetic circuits described herein, and
  optionally operatively connecting one or more of the U biosensors to an electronic signal transducer adapted to convert a U biosensor reportable molecular component output into an electronic output.

In some embodiments wherein the bacterial cell is a cell incapable of natively expressing histidine kinase 1363 (UrpS) and response regulator 1362 (UrpR) and/or histidine kinase UzcS and response regulator UzcR, the method further comprises genetically engineering the cell to include a U-sensing regulator genetic molecular component comprising an endogenous or exogenous gene encoding histidine kinase 1363 (UrpS) and/or histidine kinase UzcS, and an endogenous or exogenous gene encoding U-sensitive transcriptional regulator 1362(UrpR) and/or response regulator UzcR in a configuration wherein the a gene encoding histidine kinase 1363 (UrpS) and/or histidine kinase UzcS, and a gene encoding response regulator 1362 (UrpR) response regulator UzcR are expressed upon activation of a controllable promoter.

In some embodiments wherein the bacterial cell is a cell capable of natively expressing histidine kinase 1363 (UrpS) and response regulator 1362 (UrpR) and/or histidine kinase UzcS and response regulator UzcR (e.g. proteobacteria, such as certain Alpha proteobacteria, beta proteobacteria and/or gamma proteobacteria identifiable by a skilled person upon reading of the present disclosure), the genetically engineering can preferably further comprises knocking out the natively expressed histidine kinase 1363 (UrpS) and response regulator 1362 (UrpR) and/or histidine kinase UzcS and response regulator UzcR of the bacterial cell, and introducing in the bacterial cell a U-sensing regulator component comprising an endogenous or exogenous gene encoding histidine kinase 1363 (UrpS) and/or histidine kinase UzcS, and an endogenous or exogenous gene encoding U-sensitive transcriptional regulator 1362 (UrpR) and/or response regulator UzcR in a configuration wherein the a gene encoding histidine kinase 1363 and/or histidine kinase UzcS, and a gene encoding response regulator 1362 (UrpR) response regulator UzcR are expressed upon activation of a controllable promoter.

According to a sixth aspect a U-sensing gene cassette described. The U-sensing gene cassette comprises one or more U-sensing genetic molecular components herein described and/or one or more U-sensing regulator genetic molecular components herein described. In some embodiments the U-sensing gene cassette is an expression cassette. In some embodiments, the gene cassette is comprised within a vector.

According to a seventh aspect a vector is described comprising a polynucleotide encoding for one or more U-sensing genetic molecular components herein described, one or more U-sensing regulator genetic molecular components herein described and/or one or more genetic molecular components of a U-sensitive genetic circuit described. The one or more vectors are configured to introduce one or more U-sensitive genetic molecular components and/or one or more genetic molecular components of a U-sensitive genetic circuit into a bacterial cell of a plurality of bacterial cells.

According to an eighth aspect, a U-sensing system is described. The U-sensing system comprises one or more vectors herein described and/or a plurality of bacterial cells natively and/or heterologously expressing histidine kinase 1363 (UrpS) and response regulator 1362 (UrpR) and/or histidine kinase UzcS and response regulator UzcR.

In some embodiments wherein the bacterial cell is a cell incapable of natively expressing histidine kinase 1363 (UrpS) and response regulator 1362 (UrpR) and/or histidine kinase UzcS and response regulator UzcR, the bacterial cell is further genetically engineered to include a U-sensing regulator genetic molecular component comprising an endogenous or exogenous gene encoding histidine kinase 1363(UrpS) and/or histidine kinase UzcS, and an endogenous or exogenous gene encoding U-sensitive transcriptional regulator 1362(UrpR) and/or response regulator UzcR in a configuration wherein the a gene encoding histidine kinase 1363(UrpS) and/or histidine kinase UzcS, and a gene encoding response regulator 1362 (UrpR) response regulator UzcR are expressed upon activation of a controllable promoter.

In some embodiments wherein the bacterial cell is a cell capable of natively expressing histidine kinase 1363 (UrpS) and response regulator 1362 (UrpR) and/or histidine kinase UzcS and response regulator UzcR (e.g. proteobacteria, such as Alphaproteobacteria, beta proteobacteria and/or gamma proteobacteria), the bacterial cells is preferably further genetically engineered to comprises knocking out the natively expressed histidine kinase 1363 (UrpS) and response regulator 1362 (UrpR) and/or histidine kinase UzcS and response regulator UzcR of the bacterial cell, and introducing in the bacterial cell a U-sensing regulator component comprising an endogenous or exogenous gene encoding histidine kinase 1363 (UrpS) and/or histidine kinase UzcS, and an endogenous or exogenous gene encoding U-sensitive transcriptional regulator 1362(UrpR) and/or response regulator UzcR in a configuration wherein the a gene encoding histidine kinase 1363 and/or histidine kinase UzcS, and a gene encoding response regulator 1362(UrpR) response regulator UzcR are expressed upon activation of a controllable promoter.

According to a ninth aspect, a U-sensing system is described. The system comprises one or more of the U biosensors herein described operatively connected to an electronic signal transducer adapted to convert a U biosensor reportable molecular component output into an electronic output.

According to a tenth aspect, a composition is described. The composition comprises one or more U biosensors, U-sensing gene cassettes and/or vectors herein described together with a suitable vehicle.

According to an eleventh aspect, a system comprising an electronic signal transducer adapted to convert a U biosensor reportable molecular component output into an electronic output is described. The system comprises an electronic signal transducer and one or more U biosensors herein described operatively connected to the electronic signal transducer.

According to a twelfth aspect, a method of detecting, reporting and/or neutralizing bioavailable U is described. The method comprises:
contacting one or more U biosensors herein described, or a system comprising an electronic transducer operatively connected to one or more U biosensors herein described, with a target environment comprising one or more target ranges of U concentration for a time and under conditions to detect, report and/or neutralize bioavailable U in the target environment.

According to a thirteenth aspect, one or more U-sensing genetic reportable components are also described the U sensing genetic reportable components comprising a U sensitive promoter comprising a U-sensitive 1362 (UrpR) binding site and/or a U sensitive promoter comprising a U sensitive UzcR binding site in a configuration wherein the U-sensitive promoter directly initiates expression of the U-sensing reportable molecular component and/or of the U-sensing U-neutralizing molecular component in presence of bioavailable U.

According to a fourteenth aspect, one or more U-sensitive genetic circuits are described wherein at least one molecular component is a U sensing genetic molecular component herein described and wherein at least one molecular component is a reportable molecular component, and/or a U-neutralizing molecular component, the reportable molecular component and/or the U-neutralizing molecular component expressed when the genetic circuit operates according to the circuit design in presence of bioavailable U.

In particular, in several embodiments U biosensors and related genetic molecular components, genetic circuits, compositions, methods and systems herein described are configured for selective and sensitive detection, reporting and/or neutralizing of bioavailable U, a toxic form of U.

The U biosensors, and related genetic molecular components, genetic circuits, compositions, methods and systems herein described provide in several embodiments a selective, sensitive, portable, easy to use, high-throughput measurement and or neutralizing of bioavailable U, with little or no sample preparation required.

The U biosensors, and related genetic molecular components, genetic circuits, compositions, methods and systems herein described allow in several embodiments construction of consolidated bioremediators comprising bacterial systems that possess all the necessary components for deployment in environmental cleanup efforts, for example by coupling U sensing with activation of one or more U-neutralizing components.

The U biosensors, and related genetic molecular components, genetic circuits, compositions, methods and systems herein described allow in several embodiments detection, reporting and/or neutralization of bioavailable U with low cost approaches as various proteobacterial cells, such as *Caulobacter*, can be inexpensively grown to high densities as will be understood by a skilled person.

The U biosensors, and related genetic molecular components, genetic circuits, compositions, methods and systems herein described can be used in connection with various applications wherein detection and/or neutralizing of uranium is desired. For example, the U biosensors, and related genetic molecular components, genetic circuits, compositions, methods and systems herein described can be used in biodefense and in particular to be used for non-proliferation purposes, in environmental monitoring and/or cleanup by regulatory agencies or communities, and in mining in particular for toxicology and safety concerns, as well as diagnostic applications. Additional exemplary applications include uses of the U biosensors, and related genetic molecular components, genetic circuits, compositions, methods and systems herein described in several fields including basic biology research, applied biology, bio-engineering, medical diagnostics, and in additional fields identifiable by a skilled person upon reading of the present disclosure.

The details of one or more embodiments of the disclosure are set forth in the accompanying drawings and the description below. Other features, objects, and advantages will be apparent from the description and drawings, and from the claims.

BRIEF DESCRIPTION OF THE DRAWINGS

The accompanying drawings, which are incorporated into and constitute a part of this specification, illustrate one or more embodiments of the present disclosure and, together with the detailed description and the examples, serve to explain the principles and implementations of the disclosure.

Panel A shows a schematic of a U-sensitive genetic circuit comprising uzcRS under the control of the native $P_{uzcR}$ promoters P1 and P2 and GFP expression under the control of UzcR-regulated promoter $P_{1968}$. In this genetic circuit, binding of U directly or through indirect stimulation of UzcS causes the UzcS-mediated phosphorylation and activation of UzcR, leading to the homodimerization of UzcR and DNA binding of the UzcR dimer at the m_5 binding sites in the $P_{1968}$ promoter. The genetic circuit shown in Panel A only requires one point of U sensing, by UzcRS. As expected, this genetic circuit produces a high fluorescence signal in response to U, Zn, and Cu, as shown in FIG. 5. Incremental improvements of this circuit are shown in Panel B and Panel C to enhance selectivity for U. Panel B shows a schematic of a U-sensitive genetic circuit where $P_I$ and $P_{II}$ are replaced with $P_{phyt}$ or $P_{1361}$ such that uzcRS expression is now dependent on activation by these U-specific promoters. This construct requires two points of U sensing for reporter activation, (1) activation of uzcRS transcription by $P_{phyt}$ or $P_{1361}$ and (2) stimulation of UzcRS transcriptional regulatory activity. This sensor shows greater signal in response to U compared to the genetic circuit shown in Panel A, as shown in FIG. 5 Panel A. Importantly, in the genetic circuit shown in FIG. 4 Panel B, Cu-sensing has been completely abolished while Zn induction with the range of inducing Zn concentrations narrowed compared to the UzcRS sensor alone; also, the ratio of the U signal output to that of Zn has been increased from 1.6 to 3.5 as shown in FIG. 5 Panel B. FIG. 4 Panel C shows a schematic of a U-sensitive genetic circuit where a negative feedback loop was incorporated into the circuit, whereby UzcR represses its own expression from $P_{phyt}$ or $P_{1361}$. Specifically, an m_5 UzcR binding site was placed downstream of the $P_{phyt}$ or $P_{1361}$ transcription start site. This genetic circuit shows minimized basal expression of uzcRS, while maintaining strong responsiveness to U, and further shifted ratio of U response to that of Zn to 5.5 as shown in FIG. 5 Panel C.

FIG. 5 Panel A shows graphs reporting quantification of GFP fluorescence produced by *C. crescentus* NA 1000 comprising the U-sensitive genetic circuit shown in FIG. 4 Panel A in response to exposure to 10 and 20 µM U (FIG. 5 Panel A left graph), 10, 20 and 40 µM Zn (FIG. 5 Panel A middle graph), or 80, 120 and 200 µM Cu (FIG. 5 Panel A right graph), from 0 to 4 hours after exposure. FIG. 5 Panel B shows graphs reporting quantification of GFP fluorescence produced by *C. crescentus* NA1000 comprising the U-sensitive genetic circuit shown in FIG. 4 Panel B in response to exposure to 10 and 20 µM U (FIG. 5 Panel B left graph), 10, 20 and 40 µM Zn (FIG. 5 Panel B middle graph), or 80, 120 and 200 µM Cu (FIG. 5 Panel B right graph), from 0 to 4 hours after exposure. FIG. 5 Panel C shows graphs reporting quantification of GFP fluorescence produced by *C. crescentus* NA1000 comprising the U-sensitive genetic circuit shown in FIG. 4 Panel C in response to exposure to 10 and 20 µM U (FIG. 5 Panel C left graph), 10, 20 and 40 µM Zn (FIG. 5 Panel C middle graph), or 80, 120 and 200 µM Cu (FIG. 5 Panel C right graph), from 0 to 4 hours after exposure. $P_{phyt}$ was used for the GFP fluorescence measurements shown in FIG. 5 Panels B-C. Experiments with U were performed in modified M5G medium (10 mM PIPES, pH 7, 1 mM NaCl, 1 mM KCl, 0.05% $NH_4Cl$, 0.01 mM Fe/EDTA, 0.2% glucose, 0.5 mM $MgSO_4$, 0.5 mM $CaCl_2$)) supplemented with 5 mM glycerol-2-phosphate as the phosphate source (M5G-G2P). Cells were grown to mid-exponential phase in M5G-G2P media, washed once with fresh media, then resuspended in fresh media containing the indicated U concentration. Experiments with Zn and Cu were performed in PYE.

FIG. 6A shows a schematic of an exemplary 'in parallel' AND gate, comprised of an HRP AND gate system, in which hrpS is placed under the control of $P_{phyt}$ or $P_{1361}$ and hrpR is placed under the control of $P_{urcB}$, a promoter activated by UzcRS. In this U-sensitive genetic circuit, U exposure stimulates production of both HrpS and HrpR, leading to activation of $P_{hrpL}$ and expression of GFP. FIG. 6B shows a schematic of an exemplary 'in parallel' AND gate, comprised of a tripartite GFP system, in which gfp10 subunit is placed under the control of $P_{phyt}$ or $P_{1361}$, gfp11 is placed under the control of $P_{urcB}$, and gfp1-9 is placed under the control of the *Caulobacter* S layer promoter, $P_{rsaA}$, which is a strong, constitutive promoter [4]. This system requires expression of subunits gfp10, gfp11 and gfp1-9 for tripartite GFP reporter assembly and fluorescence. Gfp-10 is shown fused to K1 and gfp11 is shown fused to E1, wherein K1 and E1 are exemplary interacting protein partners comprised of oppositely charged coiled-coils [5]. When K1 and E1 interact, GFP10 and GFP11 self-associate with GFP1-9 to constitute a functional GFP reporter. Other exemplary embodiments of the genetic circuit shown in FIG. 6B comprise placement of gfp1-9 under the control of $P_{phyt}/P_{1361}$, or under the control of a different non-U-sensitive promoter, such as $P_{xyt}$ that is responsive to xylose [6]. In addition.

In FIG. 7 Panel C, a phylogenetic footprinting approach was used to construct a 1362 DNA-binding motif. An alignment of 26 $P_{phyt}$ or $P_{1361}$ DNA sequences from exemplary members of the subclass Caulobacteridae, Bradyrhizobiaceae, Sphingomonadaceae, Hyphomicrobiaceae, and Rhodobacteracea are indicated, with larger letters representing a higher level of consensus between aligned sequences.

FIG. 8 shows DNA sequences of full-length $P_{phyt}$ (Panel A), $P_{phyt}$ with a mutation of four nucleotides in the second direct repeat sequence (DR2, shown in bold, Panel B), $P_{phyt}$ with a mutation of two nucleotides in the first direct repeat sequence (DR1, shown in bold, Panel C), $P_{phyt}$ with a mutation of two nucleotides in the second direct repeat sequence (DR2, shown in bold, Panel D), a shortened $P_{phyt}$ ($P_{phyt}$ short, Panel E), full-length $P_{1361}$ (Panel F), $P_{1361}$ with a mutation of four nucleotides in the second direct repeat sequence (DR2, shown in bold, Panel G), $P_{1361}$ with a mutation of two nucleotides in the second direct repeat sequence (DR2, shown in bold, Panel H), and a shortened $P_{1361}$ ($P_{1361}$ short, Panel I). The sequence of the large tandem repeat (TR) in $P_{phyt}$ is shown in uppercase, underlined. The direct repeat sequence that is likely bound by the U-sensitive transcriptional response regulator 1362 is shown in uppercase, italic (with direct repeat sequences underlined). Putative Transcription start sites (based on RNA-seq data) are shown in lowercase, underlined.

In FIG. 9 Panel A, fluorescence levels are shown for variants comprising full length $P_{phyt}$ promoter (Full length), a shortened $P_{phyt}$ (Short), $P_{phyt}$ with a mutation of four nucleotides in the second direct repeat sequence (DR2 GTCA->CAGT), $P_{phyt}$ with a mutation of two nucleotides in the first direct repeat sequence (DR1, GT->CA), and $P_{phyt}$ with a mutation of two nucleotides in the second direct repeat sequence (DR2, GT->CA). In FIG. 9 Panel B, fluorescence levels are shown for variants comprising full length $P_{1361}$ promoter (Full length), a shortened $P_{1361}$ (Short), $P_{1361}$ with a mutation of four nucleotides in the second direct repeat sequence (DR2 GTCA->CAGT), and $P_{1361}$ with a mutation of two nucleotides in the second direct repeat sequence (DR2, GT->CA). Cells were grown to mid-exponential phase in M5G-G2P media, washed once with fresh media, then resuspended in fresh media containing the indicated U concentration. Fluorescence was quantified following a two-hour exposure of cells to each U concentration and normalized to the $OD_{600}$.

FIG. 16B is from FIG. 2 of Newsome et al. (2014) [7] showing a schematic illustrating exemplary mechanisms of microbe-uranium interactions, such as biomineralisation [14-16].

FIG. 16C is from FIG. 2 of Newsome et al. (2014) [7] showing a schematic illustrating exemplary mechanisms of microbe-uranium interactions, such as biosorption [17, 18].

FIG. 16D is from FIG. 2 of Newsome et al. (2014) [7] showing a schematic illustrating exemplary mechanisms of microbe-uranium interactions, such as bioaccumulation [19] as presented in Newsome et al., (2014) [7].

In FIG. 17 Panels A and B, fluorescence levels are shown for wild type C. crescentus and strains deleted for CCNA_01362 (1362 response regulator) and CCNA_01363 (1363 histidine kinase). U induction of both $P_{phyt}$ and $P_{1361}$ is abolished by deletion of either CCNA_01362 (indicated by Δ CCNA_01362) or CCNA_01363 (indicated by Δ CCNA_01363), confirming that these genes encode the U sensitive transcriptional regulatory system required for U-responsive activation of the exemplary promoters $P_{phyt}$ and $P_{1361}$. Cells were grown to mid-exponential phase in M5G-G2P media, washed once with fresh media, then resuspended in fresh media containing the indicated U concentration. Fluorescence was quantified following a two-hour exposure of cells to each U concentration and normalized to the $OD_{600}$.

FIG. 17 Panel A shows a graph reporting exemplary quantification of GFP fluorescence produced by C. crescentus NA1000 comprising the U-sensitive genetic circuit shown in FIG. 6 Panel B upon exposure to U, Zn, Cu and Cd. In this circuit, the expression of gfp10-K1 is initiated by the shortened 1363/1362-regulated $P_{phyt}$ (Pphyt-short) and the expression of E1-gfp11 is initiated by the UzcRS-regulated promoter $P_{urcB}$. FIG. 17 Panel B shows a graph reporting exemplary quantification of GFP fluorescence produced by C. crescentus NA1000 comprising a control U-sensitive genetic circuit that incorporates input only from UzcRS. FIG. 17 demonstrates the enhanced selectivity of an exemplary 'in parallel' AND gate comprising two points of U-sensing by (1) 1363/1362 and (2) UzcRS two component systems. Cells were grown to mid-exponential phase in M5G-G2P media, washed once with fresh media, then resuspended in fresh media containing the indicated metal concentration. Fluorescence was quantified following a three-hour exposure of cells to each metal concentration and normalized to the $OD_{600}$.

DETAILED DESCRIPTION

Figure 1:
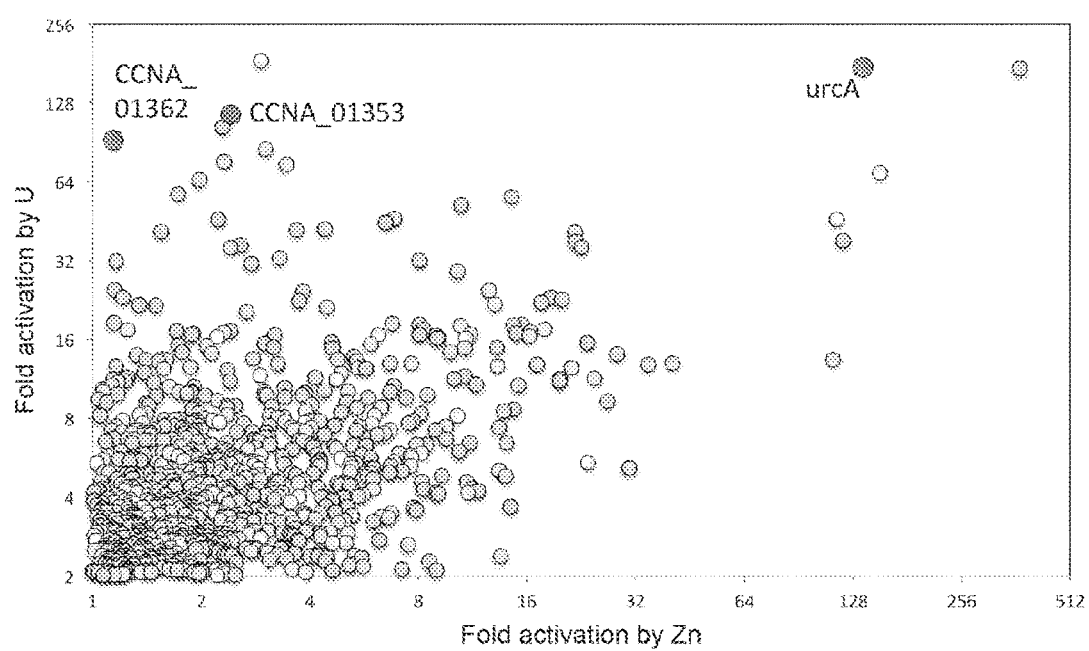
FIG. 1 shows a graph of pairwise comparison of fold-change in expression in *Caulobacter crescentus* of exemplary genes activated by Zn or U, analyzed using RNA-Seq. CCNA_01362 and CCNA_01353 (phytase) (dark grey data points shown as respectively labeled circles) are induced more than 100-fold by U but not induced by Zn. As such, the promoters regulating these genes, $P_{1361}$ and $P_{1353}$ ($P_{phyt}$) respectively, represent promising exemplary promoters for use in a whole-cell U biosensor. urcA (dark grey data point indicated as labeled circle), a gene regulated by UzcRS (FIG. 24A-C), is strongly induced by both U (FIG. 24A) and Zn (FIG. 23A).

Provided herein are U biosensors and related U-sensing genetic molecular components, genetic circuits, compositions, methods and systems which in several embodiments can be used to detect, report and/or neutralize U and in particular bioavailable U.

The term "bioavailable" as used herein refers to a molecule in particular a soluble molecule that is able to cross an organism's cellular membrane from the environment, or is otherwise able to exert a biological effect on an organism, if the organism has access to the molecule. In particular, with regard to a toxic molecule, a bioavailable toxic molecule is a toxic molecule that is able to exert toxicity on an organism contacted with the organism and/or with a toxic molecule sensing system of the organism. In some scenarios, the bioavailability can be inferred based on toxicity or activation of a tress response in an organism as will be understood by a skilled person. Thus, the term "bioavailable U" as used herein refers to a soluble molecular form of U that can cross an organism's cellular membrane from the surrounding environment or is otherwise able to exert a biological effect on an organism, e.g. following contact with the organism and/or with an organism U-sensing system. In particular, the term "bioavailable uranium" comprises uranyl ion, which has a linear structure with short U—O bonds, indicative of the presence of multiple bonds between uranium and oxygen and can bind four or more ligands in an equatorial plane. The uranyl ion forms many complexes, particularly with ligands that have oxygen donor atoms. Complexes of the uranyl ion are important in the extraction of uranium from its ores and in nuclear fuel reprocessing. As would be understood by persons skilled in the art, 'naked' or 'uncomplexed' uranyl oxycation is a bioavailable form of U. In contrast, for example, uranyl oxycation complexed with inorganic phosphate is not considered to be bioavailable.

The U biosensors and related U-sensing genetic molecular component, gene cassettes, genetic circuits, compositions, methods and systems described herein can be used in several embodiments to detect and report and/or neutralize bioavailable U, which in some embodiments comprises U in the form of uranyl ion or uranyl oxycation.

The term "uranyl oxycation" as used herein refers to the predominant form of U in oxygenated environments, comprising the +6 oxidation state ($UO_2^{+2}$), which has high chemical toxicity [24]. The US Environmental Protection Agency's maximum contaminant limit for U in drinking water is 30 µg/L (~0.13 µM), however, groundwater concentrations in the US frequently exceed this limit [25, 26].

In particular, the U biosensors herein described are whole-cell biosensors comprising a genetically engineered bacterial cell.

The term "bacterial cell", bacteria" used herein interchangeably with the terms "cell" or "host" indicates a large domain of prokaryotic microorganisms. The term "prokaryotic" is used herein interchangeably with the terms "cell" or "host" and refers to a microbial species which contains no nucleus or other organelles in the cell. Exemplary prokaryotic cells include bacteria. Typically, a few micrometers in length, bacteria have a number of shapes, ranging from spheres to rods and spirals, and are present in several habitats, such as soil, water, acidic hot springs, radioactive waste, the deep portions of Earth's crust, as well as in symbiotic and parasitic relationships with plants and animals. Bacteria in the sense of the disclosure refers to several prokaryotic microbial species which comprise Gram-positive bacteria, Proteobacteria, Cyanobacteria, Spirochetes and related species, *Planctomyces, Bacteroides, Flavobacteria, Chlamydia*, Green sulfur bacteria, Green non-sulfur bacteria including anaerobic phototrophs, Radioresistant micrococci and related species, *Thermotoga* and *Thermosipho* thermophiles as would be understood by a skilled person. More specifically, the wording "Gram positive bacteria" refers to cocci, nonsporulating rods and sporulating rods, such as, for example, *Actinomyces, Bacillus, Clostridium, Corynebacterium, Erysipelothrix, Lactobacillus, Listeria, Mycobacterium, Myxococcus, Nocardia, Staphylococcus, Streptococcus* and *Streptomyces*.

The term "proteobacteria" as used herein refers to a major phylum of Gram-negative bacteria. Many move about using flagella, but some are nonmotile or rely on bacterial gliding. As understood by skilled persons, taxonomic classification as proteobacteria is determined primarily in terms of ribosomal RNA (rRNA) sequences. The Proteobacteria are divided into six classes, referred to by the Greek letters Alpha through epsilon and the Acidithiobacillia and Oligoflexia, including Alphaproteobacteria, betaproteobacteria and gammaproteobacteria as will be understood by a skilled person.

The term "Alphaproteobacteria" as used herein refers to bacteria identifiable by those skilled in the art in the phylogenetic Class Alphaproteobacteri, in the Phylum Proteobacteria. As understood by those skilled in the art, Alphaproteobacteria is a diverse taxon and comprises several phototrophic genera, several genera metabolising C1-compounds (e.g., *Methylobacterium* spp.), symbionts of plants (e.g., *Rhizobium* spp.), endosymbionts of arthropods (*Wolbachia*) and intracellular pathogens (e.g. *Rickettsia*). As understood by those skilled in the art, taxonomic classification of Alphaproteobacteria can be identified by reference to publicly available online databases such as the List of Prokaryotic names with Standing in Nomenclature (LPSN) and National Center for Biotechnology Information (NCBI) and the phylogeny is based on 16S rRNA-based LTP release 106 by 'The All-Species Living Tree' Project. The Class Alphaproteobacteria is divided into three subclasses Magnetococcidae, Rickettsidae and Caulobacteridae [27]. In particular, the Caulobacteridae is a subclass composed of the orders Holosporales, Rhodospirillales, Sphingomonadales, Rhodobacterales, Caulobacterales, Rhizobhiales, Kiloniellales, Kordiimonadales, Parvularculales and Sneathiellales.

The term "betaproteobacteria" as used herein refers to a class of gram-negative bacteria, and one of the classes of the phylum Proteobacteria. [28] The Betaproteobacteria comprise more than 75 genera and 220 species of bacteria identifiable by persons skilled in the art. [29] Seven orders of betaproteobacteria have been described: Burkholderiales, Hydrogenophilales, Methylophilales, Neisseriales, Nitrosomonadales, Rhodocyclales, and Sulfuricellales. Examples of Betaproteobacteria genera comprise *Bordetella, Ralstonia, Neisseria* and *Nitrosomonas*, among others identifiable by skilled persons. While many Betaproteobacteria identifiable by skilled persons are found in environmental soil and water, others are obligate pathogens and can cause disease in a variety of hosts. Some members of betaproteobacteria can cause disease in various eukaryotic organisms. Several cause diseases in humans, such as members of the genus *Neisseria: N. gonorrhoeae* and *N. meningitides* which cause gonorrhea and meningitis respectively, as well as *Bordetella pertussis* which causes whooping cough. Other members infect plants, such as *Burkholderia cepacia* which causes bulb rot in onions as well as *Xylophilus ampelinus* which causes necrosis of grapevines. [29]

The term "gammaproteobacteria" as described herein refers to a class of gram-negative bacteria, and one of the classes of the phylum Proteobacteria. As would be identifiable by skilled persons, exemplary taxonomic orders, families and genera belonging to the class gammaproteobacteria comprise *Acidithiobacillus, Xanthomonadales, Chromatiales, Methylococcus, Beggiatoa, Legionellales, Ruthia, Vesicomyosocius, Thiomicrospira, Dichelobacter, Francisella, Moraxellaceae, Alcalinovorax, Saccharophagus, Reinekea, Oceanospirillaceae, Marinobacter, Pseudomonadaceae, Aeromonas, Vibrionales, Pasteurellales,* and *Enterobacteriales* among others. A number of bacteria have been described as members of gammaproteobacteria, but have not yet been assigned an order or family. These comprise bacteria of the genera *Alkalimarinus, Alkalimonas, Arenicella, Gallaecimonas, Ignatzschineria, Litorivivens, Marinicella, Methylohalomonas, Methylonatrum, Plasticicumulans, Pseudohongiella, Sedimenticola, Thiohalobacter, Thiohalomonas, Thiohalorhabdus, Thiolapillus,* and *Wohlfahrtiimonas* among others identifiable by skilled persons. Other examples of gammaproteobacteria genera comprise *Escherichia, Shigella, Salmonella, Yersinia, Buchnera, Haemophilus, Vibrio,* and *Pseudomonas*, among others identifiable by skilled persons. Some members of gammaproteobacterial are pathogenic in humans, for example some strains of the species *Salmonella* spp., *Yersinia pestis, Vibrio cholerae, Pseudomonas aeruginosa,* and *Escherichia coli*, among others identifiable by skilled persons. Some members of gammaproteobacteria are pathogenic in plants, such as *Xanthomonas axonopodis* pv. *citri, Pseudomonas syringae* pv. *actinidiae*, and *Xylella fastidiosa*, among others identifiable by skilled persons.

In some embodiments, the U biosensors herein described are whole-cell biosensors comprising a genetically engineered Alphaproteobacterial cell of the subclass Caulobacteridae. In particular in some embodiments, the U biosensors described herein can comprise a cell of any genus, species and/or strain of Caulobacteridae identifiable by those skilled in the art. Exemplary Caulobacteridae that can be used in U-biosensors herein described comprise species of the Families Bradyrhizobiaceae, Sphingomonadaceae, Caulobacteraceae, Hyphomicrobiaceae and Rhodobacteraceae which include species naturally comprising, as well as others identifiable by persons skilled in the art.

In particular, in some embodiments, U-biosensors herein described can comprise species from the order Caulobacterales, the family Caulobacteraceae, the genus *Caulobacter* and the species *Caulobacter crescentus* which is described herein as one of the representative species of the subclass Caulobacteridae.

In some embodiments of the U-biosensors herein described, the bacterial cell of the U-biosensor is capable of natively and/or heterologously expressing a U-sensitive histidine kinase 1363, and cognate response regulator 1362.

The term "histidine kinase P1363" or "UrpS" as used herein refers to a histidine kinase having the amino acid sequence

```
                                              (SEQ ID NO: 3)
MSGGSLRWRLIVGGMLAILAALAVAWLAMTWLFERHIVRRETADLTRAG

QVLVAGLRLEPNGAPVIDATLSDPRLSKAAGGFYWQVSTTSGSERSVSL

WDQALKPPQTAPAEGWSSRIAAGPFDDRVLLVERSVRPDRDGPAVLIQV

ASDEKVLRAARREFGRELAIFLGGLWAILSGAAALQVVLGLSPLTRVRA

DLARLRKSPSARMSLDHPREIAPLAEAINALAEAREADLARARRRAGDL

AHSLKTPLAALSAQSRRAREDGAVAAADGLDAAIASVAAALEAELARAR

AAAAREAVFAAETAPLAVAERLVAVLERTADGERLIFDIDVPADLKAPA

SEDVVTEMLGALIENAARHARRQVRISGAVVGQGAVLIVEDDGPGLDKG

RAEAALARGARLDEAGPGHGLGLAIVRDLAEASGAVLSMDRGDLGGLRA

MVSWTAPGAGP,
``` found in *C. crescentus* NA1000, or a sequence that when aligned with sequence SEQ ID NO: 3 has a BLAST score between 240 and 300, between 300 and 500, or preferably between 500 and 800, or more preferably over 800 but less than 100% homology or even more preferably having a BLAST Score of 851 and 100% homology with the sequence SEQ ID NO: 3.

The term "U sensitive response regulator 1362" or "response regulator 1362" or "UrpR" refers to a response regulator having amino acid sequence

```
                                              (SEQ ID NO: 4)
MMRALVVEDDPVVGPDLAKALSASGFVVDIARDGEDASFKGEVEDYALV

VLDLGLPRLDGLSVLRRWRANDRAFPVLILSARGDWTEKVEGIEAGADD

YLAKPFEMGELLARARGLVRRAAGRTSPVIGAGRLALDTRRMSATLDGA

PIRLSPLEFRLLDCLAHNPGRAVSAGELAEQLYGVADTADTNAIEALVA

RLRRKIGADVIETRRGFGYLLAGGTA
``` of *C. crescentus* NA1000 or a sequence that when aligned with sequence SEQ ID NO: 4 has a BLAST score between 200 and 250, or preferably between 250 and 300, or more preferably over 300 but less than 100% homology or even more preferably having a BLAST Score of 429 and 100% homology with the sequence SEQ ID NO: 4.

The term "BLAST" or "Basic Local Alignment Search Tool" is an algorithm for comparing primary biological sequence information, such as the amino-acid sequences of proteins or the nucleotides of DNA sequences. A BLAST search enables a researcher to compare a query sequence with a library or database of sequences, and identify library sequences that resemble the query sequence above a certain threshold. Accordingly, BLAST or Basis Local Alignment Search Tool uses statistical methods to compare a DNA or protein input sequence, also referred to as a query sequence to a database of nucleotide and protein (subject sequences) and returns sequences hits that have a level of similarity to the query sequence ranked based on the score.

The term "score" in the context of sequence alignments, indicates a numerical value that describes the overall quality of an alignment. Higher scores correspond to higher similarity and lower scores correspond to lower similarity. The score scale depends on the scoring system used for conducting the sequence alignment.

A BLAST score, also referred to as bit score or max score in the BLAST output is a normalized score with respect to the scoring system provided by the BLAST algorithm. The BLAST score defines the highest alignment score of a set of aligned segments from the same subject (database) sequences. The score is calculated from the sum of the match rewards and the mismatch, gap open an extend penalties independently for each segment. The BLAST score normally gives the same sorting order as the expect value (E value) in the BLAST alignment output.

A BLAST score can be obtained using BLAST software suite at the NCBI website and related references and in particular at the website https://blast.ncbi.nlm.nih.gov/Blast.cgi?PROGRAM=blastp&PAGE_TYPE=BlastSearch&LINKLOC=blasthome at the date of filing of the present disclosure, as will be understood to a person skilled in the art.

In embodiments herein described the "histidine kinase P1363" or "UrpS" and the "response regulator 1362" or "UrpR" typically form a two-component system herein also indicated as "1363/1362 TCS", UrpRS TCS" or "UrpRS".

The term "two component system" as used herein refers to a stimulus-response coupling mechanism that allows organisms to sense and respond to changes in many different environmental conditions [30]. Two-component systems typically consist of a membrane-bound histidine kinase that senses a specific environmental stimulus and a corresponding response regulator that mediates the cellular response, mostly through differential expression of target genes [31]. Although two-component signaling systems are found in all domains of life, they are most common in bacteria, particularly in Gram-negative and cyanobacteria [32]. Two-component systems accomplish signal transduction through the phosphorylation of a response regulator (RR) by a histidine kinase (HK). Histidine kinases are typically homodimeric transmembrane proteins containing a histidine phosphotransfer domain and an ATP binding domain. Response regulators can consist only of a receiver domain, but usually are multi-domain proteins with a receiver domain and at least one effector or output domain, often involved in DNA binding [32]. Upon detecting a particular change in the cellular environment, the HK performs an autophosphorylation reaction, transferring a phosphoryl group from adenosine triphosphate (ATP) to a specific histidine residue. The cognate response regulator (RR) then catalyzes the transfer of the phosphoryl group to an aspartate residue on the response regulator's receiver domain [33,34]. This typically triggers a conformational change that activates the RR's effector domain, which in turn produces the cellular response to the signal, usually by activating or repressing expression of target genes [32].

Figure 3A:
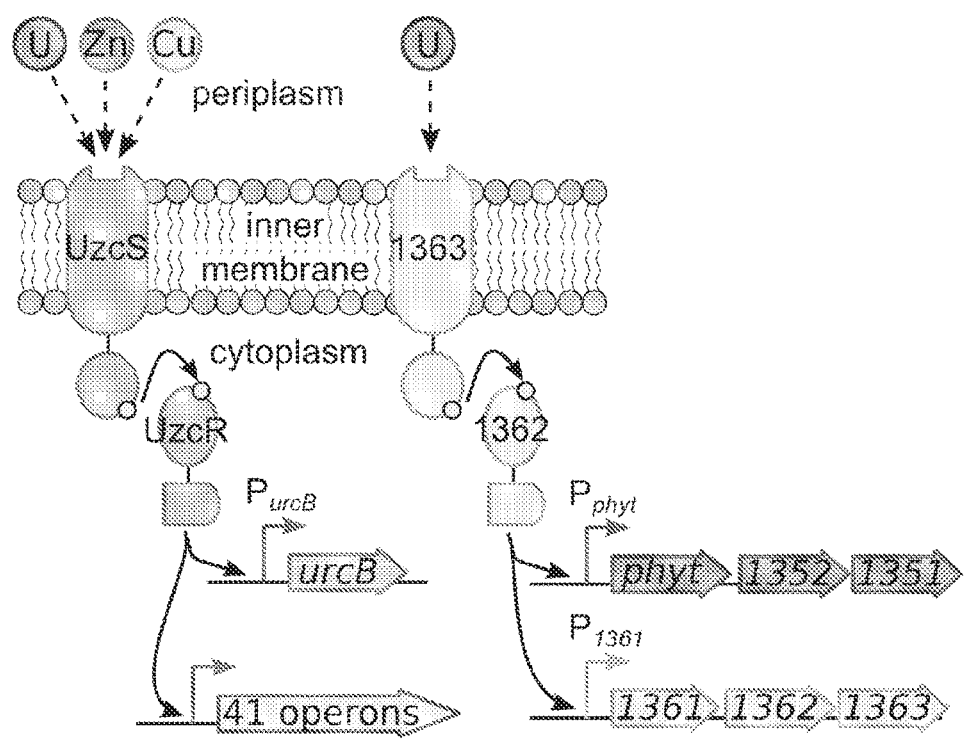
FIG. 3A shows schematics of two exemplary independent two component systems (TCS) that are sensitive to U in *Caulobacter crescentus*. Shown on the left side of FIG. 3A is a schematic of the putative mechanism of action of the UzcRS TCS, which was characterized as a transcriptional activator of at least 40 operons in response to U/Zn/Cu [3]. Shown on the right side of FIG. 3A is a schematic of the putative mechanism of action of the 1363/1362 TCS, wherein a histidine kinase 1363 (encoded by CCNA_01363) and a response regulator 1362 (encoded by CCNA_01362) activate promoters comprising the 1362 regulator direct repeat DNA binding site, e.g. $P_{phyt}$ and $P_{1361}$, in response to U. 1363 is membrane-bound and senses U either through a direct (U binding to 1363) or indirect mechanism. Upon U sensing, it is expected that 1363 autophosphorylates and then transphosphorylates 1362, activating 1362 for DNA binding of the 1362 direct repeat, e.g. in $P_{phyt}$ or $P_{1361}$. Possible additional stimuli for 1363/1362 remain unknown (indicated by the circled question mark).

An exemplary illustration of two-component system formed by the U-sensitive histidine kinase 1363 (UrpS) and the cognate response regulator 1362 (UrpR) is shown in the schematics of FIG. 3A.

Genes encoding histidine kinase 1363 (UrpS) and response regulator 1362 (UrpR) herein described are herein also indicated as 1363 gene or 1363 and 1362 gene or 1362, respectively as will be understood by a skilled person.

A representative example of histidine kinase $P_{1363}$ (UrpS) and response regulator 1362 (UrpR) in a two component system herein described are provided by the histidine kinase encoded by 1363 gene CCNA_01363 in *Caulobacter crescentus* (SEQ ID NO:3), and the response regulator 1362 encoded by 1362 gene CCNA_01362 (SEQ ID NO:4), forming a two component systems respectively as will be understood by a skilled person.

In some embodiments the histidine kinase $P_{1363}$ (UrpS) and response regulator p1362 (UrpR) can be heterologously expressed in the bacterial cell through genetic engineering of the cell performed to include in the cell a U-sensing regulator genetic molecular component comprising an endogenous or exogenous gene encoding histidine kinase 1363 (UrpS) and an endogenous or exogenous gene encoding U-sensitive transcriptional regulator 1362 (UrpR) in a configuration wherein the gene encoding histidine kinase 1363 and the gene encoding response regulator 1362 (UrpR) response regulator UzcR are expressed upon activation of a controllable promoter.

In some embodiments the histidine kinase P1363 (UrpS) and response regulator p1362 (UrpR) can be natively expressed in the bacterial cell. In particular in some embodiments, the host cell of the U-biosensors herein described is capable of natively expressing the proteins of the U-sensing two-component system 1363 (UrpS) and 1362 (UrpR) described herein. Those embodiments typically comprise certain proteobacterial cell such as Alphaproteobacteria, betaproteobacteria or gammaproteobacteria comprising an endogenous 1363/1362 TCS (UrpRS) which can be identified and selected by methods to detect 1363 (UrpS) and/or 1362 (UrpR) genes in a candidate bacterial cell identifiable by a skilled person.

For example, presence of a 1363/1362 TCS or UrpRS in a proteobacterial cell can be identified by wet bench experiments, such as PCR, Southern blotting and additional techniques identifiable by a skilled person performed with histidine kinase P1363 (UrpS) and response regulator p1362 (UrpR) and/or fragments thereof used as primers or probes for the related detection, followed by isolation and sequencing of the identified 1363 gene and/or 1362 gene as will be understood by a skilled person.

In addition or in the alternative, presence of a 1363/1362 TCS (UrpRS) in a proteobacterial cell can be identified by performing a sequence alignment using BLASTP or PSI-BLAST or other alignment algorithms known to persons skilled in the art with the 1363 (UrpS) amino acid sequence of *C. crescentus* NA1000 (SEQ ID NO:3) and/or the 1362 (UrpR) protein sequence of *Caulobacter crescentus* NA1000 (SEQ ID NO:4) as a query sequence against protein sequences of a given proteobacterial cell, as would be understood by a skilled person.

In some embodiments, the U sensing bacterial cell can comprise proteobacteria capable of natively expressing a 1363 (UrpS) protein having 100% homology to 1363 (UrpS) protein of *C. crescentus* NA1000 (SEQ ID NO: 3), and/or having a BLAST Score of 851 when aligned with SEQ ID NO: 3, (herein also 1363/1362 Tier 1 proteobacteria or UrpRS Tier 1 proteobacteria) such as proteobacteria *C. crescentus* NA1000 and *C. crescentus* CB15.

In some embodiments, the U sensing bacterial cell can comprise proteobacteria capable of natively expressing 1363 (UrpS) proteins having a BLAST Score over 800 when aligned to 1363 (UrpS) protein of *C. crescentus* NA1000 (SEQ ID NO: 3) and with less than 100% homology to *C. crescentus* NA1000 1363) SEQ ID NO: 3, (herein also 1363/1362 Tier 2 proteobacteria or UrpRS Tier 2 proteobacteria) such as exemplary proteobacterium *C. crescentus* CB2 among others identifiable by persons skilled in the art.

In some embodiments, the U sensing bacterial cell can comprise proteobacteria capable of natively expressing 1363 (UrpS) proteins having a BLAST Score of 500-800 when aligned to 1363 (UrpS) protein of *C. crescentus* NA1000 (SEQ ID NO: 3) (herein also 1363/1362 Tier 3 or UrpRS Tier 3) such as proteobacteria *Caulobacter henricii, Caulobacter* sp. CCH5-E12,

*Caulobacter* sp. OV484, *Caulobacter* sp. Root487D2Y, *Caulobacter* sp. Root1455, *Caulobacter* sp. 12-67-6, *Caulobacter* sp. Root487D2Y, *Caulobacter* sp. Root1455, *Caulobacter* sp. UNC358MFTsu5.1, *Caulobacter* sp. AP07 and *Caulobacter*, among others identifiable by persons skilled in the art.

In some embodiments, the U sensing bacterial cell can comprise proteobacteria capable of natively comprising a 1362 (UrpR) binding site (SEQ ID NO: 1) in a phytase or 1361 promoter, also referred to herein as "Pphyt" and "P1361", respectively (herein also indicated as 1363/1362 Tier 4 proteobacteria or UrpRS Tier 4 proteobacteria). Exemplary proteobacteria within these embodiments comprise *Caulobacter* sp. Root342, *Phenylobacterium* sp. Root700, *Caulobacter crescentus* NA1000, *Caulobacter* sp. Root1455, *Caulobacter* sp. Root487D2Y, *Paracoccus* sp. 228, *Caulobacteraceae* bacterium OTSz_A_272, *Novosphingobium* sp. AP12 PMI02, *Hyphomicrobium* sp. MC1, *Hyphomicrobium denitrificans, Brevundimonas* sp. Root1279 *Sphingopyxis* sp. Root1497, *Afipia* sp. P52-10, *Caulobacter* sp. Root342 *Hyphomicrobium denitrificans, Sphingobium* sp. YBL2, *Sphingobium baderi* LL03, *Sphingobium indicum* B90A, and *Roseovarius indicus* strain DSM 26383, among others identifiable by persons skilled in the art.

In some embodiments, the U sensing bacterial cell can comprise proteobacteria capable of natively expressing 1363 (UrpS) proteins having a BLAST Score of 300-500 when aligned to 1363 protein of *C. crescentus* NA1000 (SEQ ID NO: 3) (herein also indicated as 1363/1362 Tier 5 proteobacteria or UrpRS Tier 5 proteobacteria) such as exemplary proteobacteria *Phenylobacterium* sp. Root700, *Phenylobacterium* sp. Root700, *Caulobacter* sp. 39-67-4, *Sphingopyxis* sp. SCN 67-31, *Phenylobacterium* sp. SCN 70-31, *Sphingopyxis flava*, Caulobacteraceae bacterium OTSz_A_272, *Sphingobium baderi*, *Caulobacterales* bacterium 68-7, Alpha proteobacterium U9-li, *Caulobacter* sp. 35-67-4, *Sphingopyxis granuli, Sphingopyxis macrogoltabida, Brevundimonas* sp. Root1279, *Sphingopyxis macrogoltabida, Brevundimonas* sp. Root1279, *Sphingopyxis macrogoltabida, Hyphomonas polymorpha, Porphyrobacter mercurialis*, Caulobacteraceae bacterium TIH1-2, Hyphomonadaceae bacterium UKL13-1, *Sphingopyxis macrogoltabida, Porphyrobacter mercurialis*, and *Novosphingobium* sp. PASSN1, among others identifiable by persons skilled in the art.

In some embodiments, the U sensing bacterial cell can comprise proteobacteria capable of natively expressing 1363 (UrpS) proteins having a BLAST Score of 240-300 when aligned to 1363 protein of *C. crescentus* NA1000 (SEQ ID NO3), (herein indicated also as 1363/1362 Tier 6 proteobacteria or UrpRS Tier 6 proteobacteria) identifiable by persons skilled in the art.

In some embodiments, the U sensing bacterial cell can comprise proteobacteria capable of natively expressing 1363 proteins having a BLAST Score of 200-240 when aligned to 1363 protein of *C. crescentus* NA1000 (SEQ ID NO:3) (herein also indicated as 1363/1362 Tier 7 proteobacteria or UrpRS Tier 7 proteobacteria), identifiable by persons skilled in the art.

In some embodiments, the U sensing bacterial cell can comprise proteobacteria capable of natively expressing 1363 (UrpS) proteins having a BLAST Score of less than 200 when aligned to 1363 (UrpS) protein of *C. crescentus* NA1000 (SEQ ID NO: 3) (herein also indicated as 1363/1362 Tier 8 proteobacteria or UrpRS Tier 8 proteobacteria), identifiable by persons skilled in the art (herein also indicated as Tier 8 proteobacteria).

In embodiments of the U biosensor herein described wherein the host cell is a proteobacterial cell of any one of 1363/1362 Tiers 1 to 6 (UrpRS Tiers 1 to 6), the host proteobacterium can comprise a bacterial cell with a natively and/or heterologously expressed 1363/1362 TCS (UrpRS) endogenous to the host proteobacterium. In embodiments wherein the host cell is a bacterial cell other than proteobacteria or a proteobacteria of 1363/1362 Tiers 7 and 8, the host is engineered to include a heterologous 1363/1362 TCS system in a configuration capable of heterologous expression in the host bacteria as will be understood by a skilled person. In some embodiments wherein the host cell is a proteobacteria of 1363/1362 Tier 6, the host can be firstly tested for the presence of a natively expressed 1363/1362 TCS endogenous to the host proteobacteria according to procedure identifiable by a skilled person. The test can be performed by transforming the cell with a plasmid or other vector containing Pphyt or P1361-regulated gfp fusion and assaying the system for U-dependent induction of GFP as will be understood by a skilled person. If the host cell does not possess a natively expressed 1363/1362 TCS, the host can be engineered to include a heterologous 1363/1362 TCS system in a configuration capable of heterologous expression in the host bacteria.

In embodiments wherein a heterologous 1363/1362 TCS (UrpRS) is introduced into the host cell, the heterologous 1363/1362 TCS can be a 1363/1362 TCS system from a 1363/1362 Tier 1, a 1363/1362 Tier 2, a 1363/1362 Tier 3, a 1363/1362 Tier 4 or a 1363/1362 Tier 5 proteobacteria, and it is preferably a 1363/1362 TCS from a 1363/1362 Tier 2 proteobacteria and more preferably from a 1363/1362 Tier 1 proteobacteria. In those embodiments wherein a heterologous 1363/1362 TCS is introduced into a host cell, the native 1363/1362 TCS of the host cell is preferably knocked out, in particular in embodiments wherein the host organism is a proteobacteria of any one of 1363/1362 Tiers 1 to 6. The native 1363/1362 TCS of the host cell can be knocked out by deleting or inactivating the 1362 gene cluster only or by deleting or otherwise inactivating both the 1362 and 1363 gene clusters.

In some embodiments, U-biosensors herein described the proteobacterial cell is capable of natively and/or heterologously expressing a U-sensitive histidine kinase UzcS, and a transcriptional response regulator UzcR.

The term "histidine kinase UzcS", "UzcS" in the sense of the disclosure refers to a histidine kinase having the amino acid sequence:

(SEQ ID NO: 5)
MRLPRLLRTTPFRLTLLFLALFAAAASAFLGYIYVATAGEVNRRAQAEI

SREFESLEAAYRQGGVDALNQTIVERATSERPFLYFLADKDGKRISGSI

EESPVSGFTGDGPEWASFKVTETDLDGAEVKAAARGVQQRLDNGEILFV

GADVDASEAYVRKIVRALWGAGALVILLGMAGGVLISRNVSRSMQGLVD

VVNAVRGGDLHARARVRGTRDEYDELAEGLNDMLDRIERLMGGLRHAGD

AIAHDLRSPLTRLRARMEVALIDAENGKGDPVAALETALQDADGVLKTF

NAVLAIARLQAAGSAPDQRQFDASELAGDMAELYELSCEDKGLDFKAEI

-continued
```
VPALTIKGNREFLAQALANILDNAIKYTPEGGAIMLRARRTSSGELEFS

VTDTGPGVPEADRARVVQRFVRLENSRSEPGAGLGLSLVSAVATSHGGR

LELAEGPGEYNGMGPGLRVALVLPRVE
``` or a sequence that when aligned with sequence SEQ ID NO: 5 has a BLAST score has a BLAST score greater than 300 and less than 500, or preferably greater than 500 and less than 767, or more preferably a BLAST score greater than 800 and a homology with SEQ ID NO: 5 less than 100%, or even more preferably BLAST score of 925 and an homology of 100% with SEQ ID NO: 5.

The term "transcriptional response regulator UzcR" or "UzcR" as used herein indicates a transcriptional regulator having the amino acid sequence:

```
                                          (SEQ ID NO: 6)
MRILIIEDDLEAAGAMAHGLKEAGYDVAHAPDGEAGLAEAQKGGWDVLV

VDRMMPKMDGVTVVETLRREGDQTPVLFLSALGEVNDRVVGLKAGADDY

LVKPYAFPELMARVEALSRRRETGAVATTLKVGELEMNLINRTVHRQGK

EIDLQPREFQLLEFMMRHAGQSVTRTMLLEKVWEYHFDPQTNVIDVHIS

RLRSKIDKGFDRAMLQTVRGAGYRLDP
``` or a sequence that when aligned with sequence SEQ ID NO: 6 has a BLAST score greater than 250 and less than 300, or preferably greater than 300 and less than 400, or more preferably a BLAST score greater than 400 and a homology with SEQ ID NO: 6 less than 100%, or even more preferably a BLAST score of 452 and an homology of 100% with SEQ ID NO: 6.

Figure 3B:
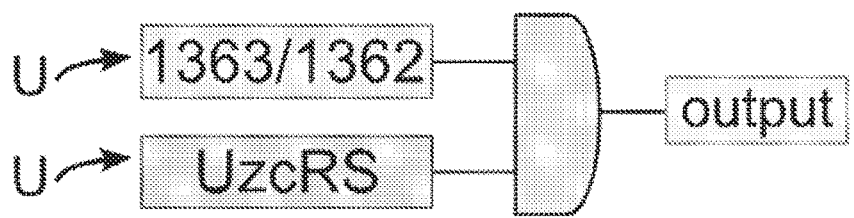
FIG. 3B shows a schematic of an exemplary U-sensitive AND gate that incorporates two independent points of uranyl sensing inputs (the two-component systems 1363/1362 AND UzcRS), which are both required to affect an output (such as a reportable molecular component and/or a U-neutralizing molecular component). The 1363/1362 two-component system is specifically activated by uranyl. The UzcRS two component system is activated for transcriptional regulation by uranyl, as well as zinc, copper and cadmium [3].

In U-biosensors herein described, the U-sensitive histidine kinase UzcS, and transcriptional response regulator UzcR form a two-component system in the sense of the disclosure, also referred to herein as "UzcRS two-component system" or "UzcRS TCS" which is similar to the 1363/1362 TCS system herein described and exemplified by the schematics of FIG. 3.

In particular, the term "UzcRS two component system" or UzcRS TCS" as used herein refers to a regulatory system responsible for U, Zn, and Cu-dependent regulation of numerous genes in *Caulobacter crescentus* [3]. The UzcRS two component system comprises an OmpR/PhoB family response regulator (RR) and a histidine kinase (HK) containing a 123 amino acid periplasmic domain, placing it in the periplasmic-sensing class of histidine kinases [31].

Genes encoding histidine kinase UzcS and response regulator UczR herein described are herein also indicated as UzcS gene or UzcS and UczR gene or UczR, respectively as will be understood by a skilled person.

A representative example of histidine kinase UzcS and transcriptional response regulator UzcR in a UzcRS two components system herein described are provided by histidine kinase encoded by UzcS gene CCNA_02842in *C. crescentus* NA1000 (SEQ ID NO: 5) and by a transcriptional response regulator, for example encoded by UzcR gene CCNZ_02485in *C. crescentus* NA1000 (SEQ ID NO: 6) as will be understood by a skilled person.

In some embodiments the histidine kinase UzcS and transcriptional response regulator UzcR can be heterologously expressed in the bacterial cell through genetic engineering of the cell performed to include in the cell a U-sensing regulator genetic molecular component comprising an endogenous or exogenous gene encoding histidine kinase UzcS and an endogenous or exogenous gene encoding U-sensitive transcriptional response regulator UzcR in a configuration wherein the gene encoding histidine kinase UzcS and the gene encoding response regulator UzcR are expressed upon activation of a controllable promoter.

In some embodiments the histidine kinase UzcS and transcriptional response regulator UzcR are natively expressed in the bacterial cell. In particular in some embodiments, the host cell of the U-biosensors herein described is capable of natively expressing the proteins of the U-sensing UzcS/UzcR TCS described herein. Those embodiments typically comprise certain proteobacterial cell such as Alphaproteobacteria, betaproteobacteria or gammaproteobacteria comprising an endogenous UzcS/UzcR TCS which can be identified and selected by methods to detect UzcS and/or UzcR genes in a candidate bacterial cell identifiable by a skilled person.

For example, presence of a UzcS/UzcR TCS in a proteobacterial cell can be identified by wet bench experiments, such as PCR, Southern blotting and additional techniques identifiable by a skilled person performed with histidine kinase UzcS and response regulator UzcR and/or fragments thereof used as primers or probes for the related detection, followed by isolation and sequencing of the identified UzcS gene and/or UzcR gene as will be understood by a skilled person. The presence of an UzcS/UzcR TCS can also be identified by introducing in the cell a UzcR-regulated GFP fusion promoter and detecting GFP fluorescence thus testing for U-dependent fluorescence as will be understood by a skilled person.

In addition or in the alternative, a UzcS/UzcR TCS in a proteobacterial cell can be identified by performing a sequence alignment using BLASTP or PSI-BLAST or other alignment algorithms known to persons skilled in the art with the UzcS amino acid sequence of *C. crescentus* NA1000 (SEQ ID NO: 5) and/or the UzcR protein sequence of *Caulobacter crescentus* NA1000 (SEQ ID NO: 6) as a query sequence against protein sequences of a given proteobacterial cell, as would be understood by a skilled person.

In some embodiments, the U sensing bacterial cell can comprise proteobacteria capable of natively expressing UzcS proteins having 100% homology to UzcS protein of *C. crescentus* NA1000 (SEQ ID NO: 5) and a BLAST score of 925 when aligned to sequence SEQ ID NO: 5 (herein also indicated as UzcS/UzcR Tier 1 proteobacteria).

In some embodiments, the U sensing bacterial cell can comprise proteobacteria capable of natively expressing UzcS proteins having a homology of less than 100% to UzcS protein of *C. crescentus* NA1000 (SEQ ID NO: 5) and a BLAST score greater than 800 when aligned to sequence SEQ ID NO: 5 (herein also indicated as UzcRS Tier 2 proteobacteria).

In some embodiments, the U sensing bacterial cell can comprise proteobacteria capable of natively expressing UzcS proteins a BLAST score greater than 767 and lower than 800 when aligned to sequence SEQ ID NO: 5 (herein also indicated as UzcRS Tier 3 proteobacteria).

In some embodiments, the U sensing bacterial cell can comprise proteobacteria capable of natively expressing UzcS proteins having a BLAST score greater than 500 and less than 767 when aligned to sequence SEQ ID NO: 5 (herein also indicated as UzcRS Tier 4 proteobacteria).

In some embodiments, the U sensing bacterial cell can comprise proteobacteria capable of natively expressing UzcS proteins having a BLAST score greater than 300 and less than 500 when aligned to sequence SEQ ID NO: 5 (herein also indicated as UzcRS Tier 5 proteobacteria).

In some embodiments, the U sensing bacterial cell can comprise proteobacteria capable of natively expressing UzcS proteins having a BLAST score greater than 250 and less than 300 when aligned to sequence SEQ ID NO: 5 (herein also indicated as UzcRS Tier 6 proteobacteria).

In some embodiments, the U sensing bacterial cell can comprise proteobacteria capable of natively expressing UzcS proteins having a BLAST score greater than 200 and less than 250 when aligned to sequence SEQ ID NO: 5 (herein also indicated as UzcRS Tier 7 proteobacteria).

In some embodiments, the U sensing bacterial cell can comprise proteobacteria capable of natively expressing UzcS proteins having a BLAST score less than 200 when aligned to sequence SEQ ID NO: 5 (herein also indicated as UzcRS Tier 8 proteobacteria).

In embodiments of the U biosensor herein described wherein the host cell is a proteobacterial cell of any one of UzcRS Tiers 1 to 6, the host proteobacterium can comprise a bacterial cell with a natively and/or heterologously expressed UzcRS TCS endogenous to the host proteobacterium. In embodiments wherein the host cell is a bacterial cell other than proteobacteria or a proteobacteria of UzcRS Tiers 7 and 8, the host is engineered to include a heterologous UzcRS TCS system in a configuration capable of heterologous expression in the host bacteria as will be understood by a skilled person.

In embodiments wherein a heterologous UzcRS TCS is introduced into the host cell, the heterologous UzcRS TCS can be a UzcRS TCS system from a 1363/1362 Tier 1, a UzcRS Tier 2, a UzcRS Tier 3, a UzcRS Tier 4 or a UzcRS Tier 5 proteobacteria, and it is preferably a UzcRS TCS from a UzcRS Tier 2 proteobacteria and more preferably UzcRS TCS from a UzcRS Tier 1 proteobacteria. In those embodiments wherein a heterologous UzcRS TCS is introduced into a host cell, the native UzcRS TCS of the host cell is preferably knocked out, in particular in embodiments wherein the host organism is a proteobacteria of any one of UzcRS Tiers 1 to 6. The native UzcRS TCS of the host cell can be knocked out by deleting or otherwise inactivating the UzcR gene cluster only or by deleting or otherwise inactivating both the UzcR and UzcS gene clusters according to techniques identifiable by a skilled person (e.g. by microdeletion, clean deletion via double recombination, recombineering (e.g., Wanner method [35]) insertional inactivation, CRISPRi, CRISPR-mediate recombination, transposon insertion, mutational inactivation, methylation and/or epigenetic inactivation as well as other techniques identifiable by a skilled person).

In some embodiments of the U-biosensors herein described, a bacterial cell capable of natively and/or heterologously expressing histidine kinase 1363, and transcriptional response regulator 1362, and/or capable of natively and/or heterologously expressing a U-sensitive histidine kinase UzcS, and a transcriptional response regulator UzcR, is genetically engineered to include a U-sensitive genetic molecular component configured to report and/or neutralize U.

The term "molecular component" as used herein indicates a chemical compound comprised in a cellular environment. Exemplary molecular components thus comprise polynucleotides, such as ribonucleic acids or deoxyribonucleic acids, polypeptides, polysaccharides, lipids, amino acids, peptides, sugars and/or other small or large molecules and/or polymers that can be found in a cellular environment.

The term "genetic molecular component" as used herein indicates a molecular unit formed by a gene, an RNA transcribed from the gene or a portion thereof and optionally a polypeptide or a protein translated from the transcribed RNA.

In embodiments herein described, a genetic molecular component comprises a promoter operatively connected to the gene of the genetic molecular component, so that the promoter is configured to initiate transcription of said gene. As would be understood by those skilled in the art, promoters are typically located adjacent to the transcription start sites of genes, on the same strand and upstream on a DNA sequence (towards the 5' region of the sense strand), and for transcription to occur, the enzyme that synthesizes RNA, known as RNA polymerase, attaches to the promoter. Promoters contain DNA sequences identifiable by those skilled in the art and described herein, such as those that provide binding sites for RNA polymerase and also for proteins that function as transcription regulatory factors that can either activate or repress gene transcription.

The term "transcription regulatory factor" or "transcription factor" as used herein refers to any type of factors that can function by acting on a regulatory DNA element such as a promoter or enhancer sequence. The transcription regulatory factors can be broadly classified into a transcription repression factor (also referred to as "repressor") and a transcription activation factor (also referred to as "activator"). The transcription repression factor acts on a regulatory DNA element to repress the transcription of a gene, thereby reducing the expression level of the gene. The transcription activation factor acts on a regulatory DNA element to promote the transcription of a gene, thereby increasing the expression level of the gene. Both the transcription repression factors and the transcription activation factors can be used as one or more components in the gene circuits herein described. In particular, a transcription regulatory factor has typically at least one DNA-binding domain that can bind to a specific sequence of enhancer or promoter sequences. Some transcription factors bind to a DNA promoter sequence near the transcription start site and help form the transcription initiation complex. Other transcription factors bind to other regulatory sequences, such as enhancer sequences, and can either stimulate or repress transcription of the related gene. Examples of specific transcription repression factors include TetR, LacI, LambdaCI, PhlF, SrpR, QacI, BetR, LmrA, AmeR, LitR, met, and others identifiable by a skilled person, as well as homologues of known repression factors, that function in both prokaryotic and eukaryotic systems. Examples of transcription activation factors include AraC, LasR, LuxR, IpgC, MxiE, Gal4, GCN4, GR, SP1, CREB, and additional activation factors identifiably by a skilled person as well as homologues of known activation factors, that function in both prokarayotic and eukaryotic systems also identifiable by a skilled person. Exemplary inducible regulators that can be used in *Caulobacter* comprise VanR (regulated by vanillate) and XylR (regulated by xylose), as well as others identifiable by those skilled in the art.

A gene comprised in a genetic molecular component is a polynucleotide that can be transcribed to provide an RNA and typically comprises coding regions as well as one or more regulatory sequence regions which is a segment of a nucleic acid molecule which is capable of increasing or decreasing transcription or translation of the gene within an organism either in vitro or in vivo. In particular coding regions of a gene herein described can comprise one or more protein coding regions which when transcribed and translated produce a polypeptide, or if RNA is the final product only a functional RNA sequence that is not meant to be translated. Regulatory regions of a gene herein described comprise promoters, transcription factor binding sites, operators, activator binding sites, repressor binding sites, enhancers, protein-protein binding domains, RNA binding domains, DNA binding domains, silencers, insulators and additional regulatory regions that can alter gene expression in response to stimuli as will be recognized by a person skilled in the art.

An RNA of a genetic molecular component comprises any RNA that can be transcribed from a gene, such as a messenger ribonucleic acid (mRNA), short interfering ribonucleic acid, and ribonucleic acid capable of acting as regulating factors in the cell. mRNA comprised in a genetic molecular component comprise regions coding for the protein as well as regulatory regions e.g. ribosome binding site domains ("RBS"), which is a segment of the upstream (5') part of an mRNA molecule to which the ribosomal machinery of a cell binds to position the message correctly for the initiation of translation. RBSs control the accuracy and efficiency with which the translation of mRNA begins. mRNA can have additional control elements encoded, such as riboregulator sequences or other sequences that form hairpins, thereby blocking the access of the ribosome to the Shine-Delgarno sequence and requiring an external source, such as an activating RNA, to obtain access to the Shine-Delgarno sequence. Other RNAs that serve regulatory roles that can comprise the genetic molecular component include riboswitches, aptamers (e.g. malachite green, Spinach), aptazymes, guide CRISPR RNAs, and other RNAs known to those skilled in the art.

A protein comprised in a molecular component can be proteins with activating, inhibiting, binding, converting, or reporting functions. Proteins that have activating or inhibiting functions typically act on operator sites encoded on DNA, but can also act on other molecular components. Proteins that have binding functions typically act on other proteins, but can also act on other molecular components. Proteins that have converting functions typically act on small molecules, and convert small molecules from one small molecule to another by conducting a chemical or enzymatic reaction. Proteins with converting functions can also act on other molecular components. Proteins with reporting functions have the ability to be easily detectable by commonly used detection methods (absorbance, fluorescence, for example), or otherwise cause a reaction on another molecular component that causes easy detection by a secondary assay (e.g. adjusts the level of a metabolite that can then be assayed for). The activating, inhibiting binding, converting, or reporting functions of a protein typically form the interactions between genetic components of a genetic circuit. Exemplary proteins that can be comprised in a genetic molecular component comprise monomeric proteins and multimeric proteins, proteins with tertiary or quaternary structure, proteins with linkers, proteins with non-natural amino acids, proteins with different binding domains, and other proteins known to those skilled in the art. Specific exemplary proteins include TetR, LacI, LambdaCI, PhlF, SrpR, QacI, BetR, LmrA, AmeR, LitR, met, AraC, LasR, LuxR, IpgC, MxiE, Gal4, GCN4, GR, SP1, CREB, and others known to a skilled person in the art.

A "U-sensing genetic molecular component" or "U-sensitive genetic molecular component" as used herein indicates a genetic molecular component wherein the gene of the genetic molecular component is under control of a U-sensing or U-sensitive promoter.

In particular, in some embodiments herein described, wherein the host cell is capable of natively and/or heterologously expressing the histidine kinase P1363 and response regulator p1362, at least one U-sensitive promoter comprises a U-sensitive 1362 binding site having a DNA sequence (SEQ ID NO: 1)
$N_1N_2N_3N_4N_5N_6N_7N_8N_9N_{10}N_{11}N_{12}N_{13}N_{14}N_{15}N_{16}N_{17}N_{18}$, wherein
$N_1$ is C or T, preferably C;
$N_2$ is G or A, preferably G;
$N_3$ is T or C, preferably T;
$N_4$ is C; $N_5$ is A or G, preferably A;
$N_6$ is G or C, preferably G;
$N_7$ C or G;
$N_8$ is any nucleotide;
$N_9$ is any nucleotide;
$N_{10}$ is any nucleotide;
$N_{11}$ is any nucleotide;
$N_{12}$ is T or C;
$N_{13}$ is G;
$N_{14}$ is T or C, preferably T;
$N_{15}$ is C;
$N_{16}$ is A or C, preferably A;
$N_{17}$ is G; and
$N_{15}$ is C or G
and wherein $N_1$ to $N_{17}$ are selected independently.

In some embodiments of the U-sensing promoter comprising SEQ ID NO: 1, nucleotide $N_1$ of the regulator direct repeat is in a position from about 16 nucleotides downstream of the transcription start site of the genetic molecular component as described herein to about 40 nucleotides upstream of the transcription start site of the genetic molecular component or genetic molecular component.

In some embodiments, the U-sensitive promoter further comprises nucleotides $N_{19}N_{20}N_{21}$ (SEQ ID NO: 83), downstream of SEQ ID NO: 1 wherein each of $N_{19}$ to $N_{21}$ can independently be any nucleotide, and therefore $N_{19}$ is any nucleotide $N_{20}$ is any nucleotide; and $N_{21}$ is G.

In some embodiments of the U biosensors described herein, the 1362 binding site has a DNA sequence
CGTCAGCNNNNTGTCAGC (SEQ ID NO:7),
CGTCAGGNNNNTGTCAGG (SEQ ID NO: 8),
CGTCAGCNNNNTGTCAGG (SEQ ID NO:9),
CGTCAGCNNNNCGTCAGG (SEQ ID NO: 10),
TGTCAGCNNNNTGTCAGC (SEQ ID NO: 11),
CGCCTGCNNNNCGTCAGC (SEQ ID NO: 12),
CGTCAGGNNNNCGTCAGC (SEQ ID NO: 13),
CGTCAGCNNNNTGTCAGC (SEQ ID NO: 14),
TGTCAGGNNNNTGTCAGC (SEQ ID NO: 15),
CGTCAGCNNNNCGTCAGT (SEQ ID NO: 16),
CCGCGGGNNNNTGTCAGG (SEQ ID NO: 17),
CGTCGGGNNNNAGACCGG (SEQ ID NO: 18),
CGTCCGGNNNNCGTCAGA (SEQ ID NO: 19),
CAACGCCNNNNCGTCAGC (SEQ ID NO: 20),
CATCAGGNNNNCGTCAGC (SEQ ID NO: 21),
CGCAGGGNNNNTGCAAGC (SEQ ID NO: 22),
CATCAGCNNNNCGTCAGC (SEQ ID NO: 23), CGTCATCNNNNTGTCACG (SEQ ID NO: 24),
CGTCAGCNNNNCATCAGC (SEQ ID NO: 25),
CTTCGCGNNNNCGTCCGG (SEQ ID NO: 26),
CGTCAGGNNNGGTCAGG (SEQ ID NO: 27), or
TGTCAGCNNNNATCCTGC (SEQ ID NO: 28), wherein N can be any nucleotide.

In some embodiments, wherein the U-biosensor comprises a genetically engineered proteobacterial cell capable of natively and/or heterologously expressing histidine kinase UzcS, and U-sensitive transcriptional response regulator UzcR, at least one U-sensitive promoter comprises a UzcR binding site with an m_5 site configured for binding UzcR, having a DNA sequence:

(SEQ ID NO: 2)
CATTACN$_7$N$_8$N$_9$N$_{10}$N$_{11}$N$_{12}$TTAA wherein N$_7$-N$_{12}$ is independently any nucleotide, and in some embodiments N$_7$-N$_{11}$ can independently be A. In an embodiment, each of N$_7$-N$_{12}$ can be A.

In some embodiments, in the proteobacterial cell, the endogenous genes encoding the histidine kinase UzcS, and the U-sensitive transcriptional response regulator UzcR, are knocked out and the genetically engineered proteobacterial cell is further engineered to include a U-sensing regulator genetic molecular component comprising an endogenous or exogenous gene encoding histidine kinase UzcS, and an endogenous or exogenous gene encoding U-sensitive transcriptional response regulator UzcR in a configuration wherein the a gene encoding histidine kinase UzcS, and a gene encoding response regulator UzcR are expressed upon activation of a controllable promoter.

In some embodiments, the U-sensitive promoter comprises a UzcR binding site can be either a constitutively active promoter or an inducible promoter. In preferred embodiments, the promoter is constitutively active.

The term "m_5 site" or ""UczR binding site" as used herein refers to a semi-palindromic consensus DNA binding site of sequence CATTACN$_7$N$_8$N$_9$N$_{10}$N$_{11}$N$_{12}$TTAA (SEQ ID NO:2) [3], wherein N$_7$—N$_{12}$ is independently any nucleotide, and in some embodiments any one of N$_7$—N$_{11}$ can independently be A. One UzcR dimer likely to binds one m_5 site [3]. For example, a variant of an m_5 site wherein CATTAC (SEQ ID NO:29) is mutated to CAATAG (SEQ ID NO:30) is not bound by UzcR and a variant of an m_5 site wherein TTAA (SEQ ID NO:31) is mutated to TAAT (SEQ ID NO:32) is no longer activated by UzcR [3].

In embodiments herein described, UzcRS-regulated promoters comprise those having naturally-occurring m_5 sites or m_5 sites that are introduced into a promoter through genetic engineering. Accordingly, UzcRS-regulated promoters comprise DNA sequence elements required for RNA Polymerase binding, as well as one or more m_5 sites, such that the promoter is configured to be regulated by the UzcRS two-component system. Similar to promoters comprising 1362 binding sites, in UzcRS-regulated promoters, the σ-RNAP biding sites typically have low sequence homology to the canonical σ$^{73}$-RNAP −10 and −35 hexamer sequences. Accordingly, typically transcriptional activation of native UzcRS-regulated promoters occurs through binding of UzcR to the promoter, consistent with little observed transcriptional activation in absence of UzcR.

In some embodiments, an UzcRS-regulated promoter can comprise 1-3 copies of the m_5 site. In particular, in some embodiments, when one or more m_5 sites are located at a position from about −50 to about −100 upstream of the TSS, preferably at a position −52/53 or −62/63 upstream of the TSS, considering the first nucleotide of Seq ID NO:2 as the first nucleotide of the m_5 site upstream from the TSS (see the position of the first nucleotide (C on the 5' end) of the binding site in FIG. 25 A) wherein the m_5 site is configured for activation of the UzcRS-regulated promoter (see e.g. configurations of FIG. 25B); [3]). In some embodiments, one or more m_5 sites are located at a position 52 to 53 bp upstream of the TSS or at a position 62 or −63 bp upstream of the TSS considering the first nucleotide of Seq ID NO: 2 as the first nucleotide of the m_5 site upstream from the TSS (see the position of the first nucleotide (C on the 5' end) of the binding site in FIG. 25 A) wherein the m_5 site is configured for activation of the UzcRS-regulated promoter (see e.g. FIG. 25 B).

Figure 25:
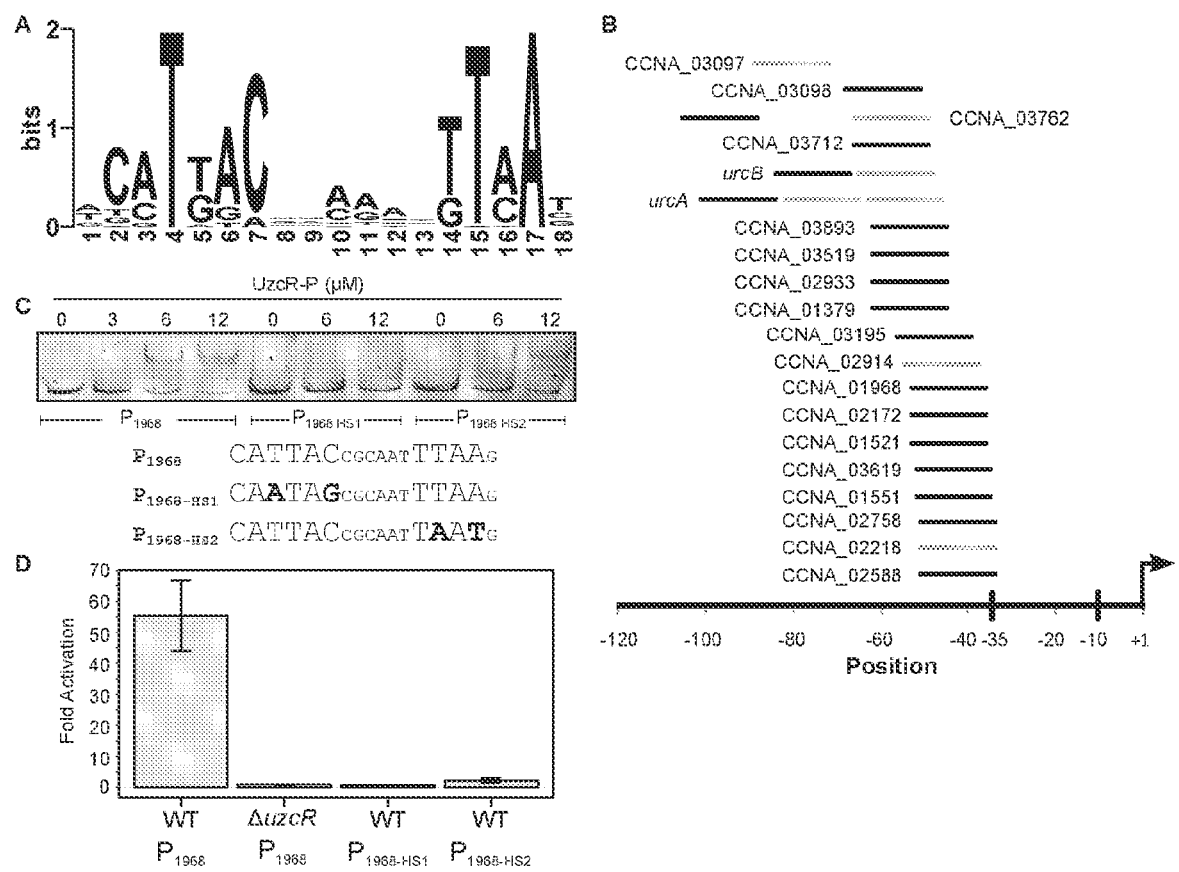
FIG. 25 shows an exemplary identification of the UzcR sequence recognition motif in some embodiments herein described. Panel (A): The 18-bp UzcR (m_5) sequence logo was constructed from the alignment of 49 UzcR boxes identified within the sequence regions bound by UzcR in vivo using MEME [21]. The sequence conservation (bits) is depicted by the height of the letters with the relative frequency of each base depicted by its relative height. Panel (B): Location of the predicted UzcR binding sites with respect to the previously determined Transcription Start Site (TSS) [22] for the directly activated operons. For urcA and urcB, the approximate TSSs as determined by tiled microarray analysis [23] were used. Note that multiple copies of the m_5 motif were found within some binding regions. For urcA and urcB, the approximate TSSs as determined by tiled microarray analysis [23] were used. The length of the line is representative of the length of the binding site with the line color denoting a directional orientation on the coding strand (black) or noncoding strand (gray). Panel (C): EMSA assays of UzcR-P binding to wild type and mutant $P_{1968}$ fragments. Each UzcR half site was individually eliminated by mutation away from consensus (bolded nucleotides). The Assays were performed with 5' 6-FAM-labeled DNA and UzcR-P, generated by phosphorylation of UzcR with carbamoyl phosphate. The concentrations indicate the total UzcR-P used in the assay and arrow depicts the shifted complex. A representative example of three biological replicates is depicted Panel (D): Effects of mutations in each UzcR half site on CCNA_01968 promoter activity in wild type and ΔuzcR backgrounds. Promoter-gfpmut3 fusions with the wild type and mutant $P_{1968}$ fragments described in Panel (B) were constructed and fluorescence was quantified following a two-hour treatment with or without M Zn using a Biotek plate reader (ex: 480/em: 516). The fluorescence signal was normalized to the $oD_{600}$ and fold activation was calculated by dividing the normalized fluorescence in the presence of Zn by the fluorescence in the uninduced condition. Error bars represent that standard deviation calculated using a formula for propagation of standard error [20] This figure is taken from the Appendix B the disclosure of which is incorporated herein by reference in its entirety.

In some embodiments, one or more m_5 sites are located at a position within 100 nucleotides upstream of the TSS considering the first nucleotide of Seq ID NO: 2 as the first nucleotide of the m_5 site upstream from the TSS (see the position of the first nucleotide (C on the 5' end) of the binding site in FIG. 25 A). In some embodiments, when one or more m_5 sites are located at a position from about −49 upstream of the TSS to +25 downstream of the TSS, in particular,−33 upstream of the TSS to +15 nt downstream of the TSS, the m_5 site is configured for repression of the UzcRS-regulated promoter.

In some embodiments herein described, the U-sensitive promoter is configured such that upon binding of the response regulator UzcR to the m_5 site, the U-sensitive promoter is activated and transcription of a gene operatively connected to the U-sensitive promoter within the related genetic molecular component is initiated.

In other embodiments, the U-sensitive promoter is configured such that upon binding of the U-sensitive transcriptional regulator to the U-sensitive transcriptional UzcR binding site, the U-sensitive promoter is repressed and transcription of a gene operatively connected to the U-sensitive promoter within the related U-sensing genetic molecular component is not initiated. In particular, in some embodiments one or more m_5 sites are located at a position −49 to +25 bp from the TSS considering the first nucleotide of Seq ID NO: 2 as the first nucleotide of the m_5 site upstream from the TSSThe approximate range is −49 to +25 bp from the TSS (see the position of the first nucleotide (C on the 5' end) of the binding site (FIG. 25A).

For example, in an exemplary embodiment wherein a promoter is repressed by UzcR, a m_5 site is engineered downstream of a transcription start site of a U-sensitive promoter such as a P$_{1361}$ promoter or P$_{phyt}$ promoter (see Example 2). In these exemplary embodiments, insertion of a m_5 site downstream of the TSS of e.g. P$_{phyt}$ minimizes activation of P$_{phyt}$ in both the presence and absence of U. As would be understood by skilled persons, the latter is preferable as it minimizes UzcRS expression levels when no U is present, minimizing cross-reactivity with Zn and Cu.

Examples of promoters regulated by UzcRS comprise P$_{urcA}$, P$_{urcB}$, P$_{1968}$, and others identifiable by those skilled in the art, such as those described in Park et al., 2017 [3] herein incorporated by reference in its entirety (see also Example 11).

In several embodiments, one or more U-sensing promoters herein described are comprised within a U sensing genetic molecular component which is a genetically engineered polynucleotide construct configured to regulate expression of one or more RNA and/or protein-encoding genes through the one or more U-sensing promoter.

In some embodiments, the U-sensitive promoter includes a 1362 binding site functioning as a binding site for natively expressed U-sensitive transcriptional regulator 1362 and/or a UzcR binding site for natively expressed UzcR. In some embodiments of the U-biosensors herein described, the histidine kinase 1363, and U-sensitive transcriptional regulator 1362 are therefore encoded respectively by 1363 and 1362 genes natively encoded in the genome of the proteobacterial cell and the encoded 1363 and 1362 proteins can be natively expressed in the proteobacterial cell. Similarly, in some embodiments of the U-biosensors herein described, the histidine kinase UzcR, and U-sensitive transcriptional regulator UzcS are therefore encoded respectively by uczR and uczS genes natively encoded in the genome of the proteobacterial cell and the encoded UczR and UczS proteins are natively expressed in the proteobacterial cell.

In other embodiments of U-biosensors herein described, 1363 and 1362 genes and/or the uczR and uczS genes are introduced into the proteobacterial cell of (e.g. a species of the subclass Caulobacteridae) within one or more U-sensing regulator genetic molecular components configured to express the proteins 1363 and 1362 and/or UczR and UczS proteins upon activation of a controllable promoter.

In those embodiments, the genetic molecular components comprise the 1363 1362, uczR and/or uczS genes together with one or more regulatory regions configured to directly initiate expression of operatively connected 1363 and 1362 genes and/or operatively connected uczR and uczS genes. In some embodiments, a genetic molecular component introduced into the proteobacterial cell can comprise 1363 and 1362 genes and/or uczR and uczS genes in a same genetic molecular component, while in other embodiments the 1363 gene, the 1362 gene, the uczR gene and/or the uczS gene are comprised in different genetic molecular components. In some embodiments, the one or more regulatory regions operatively connected to the 1363 and/or 1362 genes and/or to the uczR and uczS genes, can comprise any promoter identifiable by skilled persons that is capable of initiating gene expression in a Caulobacteridae cell. Exemplary promoters that can be used to express 1363 and/or 1362 in Caulobacteridae comprise inducible promoter systems such as VanR (regulated by vanillate) and XylR (regulated by xylose), as well as others identifiable by those skilled in the art. In some embodiments, any constitutive promoter identifiable by those skilled in the art that has been characterized as functional to express an operatively linked gene of interest in a proteobacterial species of interest can be used to express 1363 and 1362 and/or uczR and uczS genes in the proteobacterial species of interest.

In some embodiments of U biosensors described herein wherein one or more genetic molecular components comprising a 1363 gene, 1362 gene, a uczS and/or uzcR genes are introduced into a proteobacterial cell, the proteobacterial cell is further genetically engineered so that expression of its native a 1363 gene, 1362 gene, a uczS and/or uzcR gene is inactivated by gene knockout.

In some embodiments, in the proteobacterial cell, the endogenous genes encoding histidine kinas 1363, transcriptional regulator 1362, histidine kinase UzcS, and/or the U-sensitive transcriptional regulator UzcR are knocked out and the genetically engineered proteobacterial cell is further engineered to include a U-sensing regulator component comprising a gene encoding histidine kinase UzcS, and a gene encoding response regulator UzcR in a configuration wherein the a gene encoding histidine kinase UzcS, and a gene encoding response regulator UzcR are expressed upon activation of a controllable promoter.

In some embodiments, the promoter controlling the expression of the heterologous 1363 gene, the 1362 gene, the UczR gene and/or the UczS gene can be either a constitutively active promoter or an inducible promoter. In preferred embodiments, the promoter is constitutively active.

In some embodiments of U biosensors described herein wherein one or more genetic molecular components comprising the 1363 and/or 1362 genes and/or the uczR and/or uczS genes are introduced into a proteobacterial cell, the proteobacterial cell is further genetically engineered so that expression of the host endogenous 1363 gene, 1362 gene, uczR gene and/or uczS gene is inactivated by gene knockout. Methods for performing genetic knockout are identifiable by persons skilled in the art, such as gene targeting using techniques such as homologous recombination, or transposon-mediated mutagenesis, or gene editing techniques such as those using CRISPR/Cas9 among others known to those skilled in the art.

In several embodiments, the U sensing genetic molecular component herein described is a genetically engineered polynucleotide construct configured to regulate expression of one or more RNA and/or protein-encoding genes through one or more U-sensing promoter.

In some embodiments herein described, the U-sensitive promoter is configured such that upon binding of the U-sensitive transcriptional regulator 1362 or UzcR to the U-sensitive corresponding binding site, the U-sensitive promoter is activated and transcription of a gene operatively connected to the U-sensitive promoter within the related genetic molecular component is initiated.

In particular, in some embodiments, when the U-sensing promoter comprises a 1362 binding site is located in a position wherein nucleotide Nis of the regulator direct repeat (SEQ ID NO: 1) is from about 17 nucleotides upstream of the transcription start site of the genetic molecular component to about 40 nucleotides upstream of the transcription start site of the genetic molecular component, the regulator direct repeat is configured to function as a transcriptional activator binding site.

In other embodiments, the U-sensitive promoter is configured such that upon binding of the U-sensitive transcriptional regulator to the U-sensitive transcriptional 1362 binding site, the U-sensitive promoter is repressed and transcription of a gene operatively connected to the U-sensitive promoter within the related U-sensing genetic molecular component is not initiated.

In particular, in some embodiments, when the U-sensing promoter comprises a 1362 binding site, the 1362 binding site can be located in a position wherein nucleotide $N_1$ of the regulator direct repeat (SEQ ID NO:1) is from about 16 nucleotides downstream of the transcription start site of the genetic molecular component to about 16 nucleotides upstream of the transcription start site of the genetic molecular component or genetic molecular component, the 1362 binding site configured to function as a transcriptional repressor binding site. As would be understood by those skilled in the art, typically, within a given promoter polynucleotide sequence, substitution of a regulator repeat binding site polynucleotide sequence described herein for a promoter polynucleotide sequence comprising a −35 and/or a −10 hexamer sequence of the promoter, or one or more nucleotides at the transcriptional start site or downstream of the transcriptional start site, is expected to provide a promoter comprising a 1362 binding site configured to repress transcription of the promoter.

In preferred embodiments of the U-sensitive genetic molecular component described herein comprising the 1362 binding site, the regulator direct repeat is located in a position wherein nucleotide Nis of the regulator direct repeat (SEQ ID NO:1) is from about 17 nucleotides upstream of the transcription start site of the U-sensing genetic molecular component to about 40 nucleotides upstream of the transcription start site of the genetic molecular component or genetic molecular component, such that the regulator direct repeat is configured to function as a transcriptional activator binding site As understood by those skilled in the art, positions in the promoter are designated relative to the transcriptional start site, where transcription of DNA begins for the gene of interest. Positions upstream (towards the 5' end of the promoter) are negative numbers counting back from −1, for example −10 is a position 10 base pairs upstream of the transcription start site.

The term "transcription start site" or "TSS" as used herein refers to the location where transcription starts at the 5' end of an encoded gene sequence. The location of the transcription start site is typically referred to as +1 relative to the 3' end of a promoter operatively connected to the gene. As would be understood by persons skilled in the art, a putative transcription start site can be detected using techniques such as differential RNA-seq (dRNA-seq) [36], which can differentially detect primary transcripts having triphosphorylated 5' ends, and processed RNAs which do not. Additional techniques to detect transcription start sites known in the art comprise bioinformatic analysis to identify enrichment of promoter elements upstream of a putative transcriptional start site, and experimental validation of selected putative transcription start sites, for example using primer extension methods [37], or by using Northern blots to detect the associated RNAs, among other techniques identifiable by those skilled in the art [38].

In some exemplary embodiments of the U biosensors described herein, the U-sensitive promoter comprising the 1362 binding site is a $P_{1361}$ promoter. The term "$P_{1361}$ promoter" as used herein refers to the promoter that natively regulates expression of an operon comprising CCNA_01361, CCNA_1362 and CCNA_1363 genes in *Caulobacter crescentus*. The DNA sequence of $P_{1361}$ is shown in Table 4.

In some exemplary embodiments of the U biosensors described herein, the U-sensitive promoter comprising the 1362 binding site is a $P_{phyt}$ promoter. The term "$P_{phyt}$ promoter" as used herein refers to the promoter that natively regulates expression of an operon comprising CCNA_01353, CCNA_01352_, and CCNA_01351 genes in *Caulobacter crescentus*. The DNA sequence of $P_{phyt}$ is shown in Table 4. As understood by those skilled in the art, *Caulobacter crescentus* (Poindexter 1964) refers to a Gram-negative, oligotrophic bacterium widely distributed in fresh water lakes and streams. *Caulobacter* is an obligate aerobe with a ubiquitous presence in aqueous environments where it is well-adapted to life under low-nutrient conditions [39]. *Caulobacter* species tolerate high concentrations of U [40, 41], are found in U-contaminated sites [42], and can mineralize U through the formation of uranyl phosphate precipitates [43]. Multi-omics studies to elucidate the U stress response pathways in *C. crescentus* have revealed many highly-induced genes that are not induced by Cd, Cr, Pb or Se [40].

In some embodiments, the U-sensitive promoter is a UzcRS-regulated promoters comprising DNA sequence elements required for RNA Polymerase binding, as well as one or more sequence elements for binding UzcR known as an m_5 site [3], as understood by those skilled in the art and herein also identified as UczR binding site. Examples of promoters regulated by UzcRS comprise $P_{urcA}$, $P_{urcB}$, $P_{1968}$, and others identifiable by those skilled in the art, such as those described in Park et al., 2017 [3].

In embodiments herein described, UzcRS-regulated promoters comprise those having naturally-occurring m_5 sites or m_5 sites that are introduced into a promoter through genetic engineering. Accordingly, UzcRS-regulated promoters comprise DNA sequence elements required for RNA Polymerase binding, as well as one or more m_5 sites, such that the promoter is configured to be regulated by the UzcRS two-component system. Similar to promoters comprising 1362 binding sites, in UzcRS-regulated promoters, the σ-RNAP biding sites typically have low sequence homology to the canonical $\sigma^3$-RNAP-10 and −35 hexamer sequences. Accordingly, typically transcriptional activation of native UzcRS-regulated promoters occurs through binding of UzcR to the promoter, consistent with little observed transcriptional activation in absence of UzcR.

In some embodiments, an UzcRS-regulated promoter can comprise 1-3 copies of the m_5 site. In particular, in some embodiments, when one or more m_5 sites are located at a position from about −34 to about −100 upstream of the TSS, preferably at a position −43 to −53 upstream of the TSS, the m_5 site is configured for activation of the UzcRS-regulated promoter [3]. In other embodiments, when one or more m_5 sites are located at a position from about −33 upstream of the TSS to +15 nt downstream of the TSS, the m_5 site is configured for repression of the UzcRS-regulated promoter.

Accordingly, in some embodiments described herein, a promoter can be either activated or repressed by UzcR. For example, in an exemplary embodiment wherein a promoter is repressed by UzcR, a m_5 site is engineered downstream of a transcription start site of a U-sensitive promoter such as a $P_{1361}$ promoter or $P_{phyt}$ promoter (see Example 2). In these exemplary embodiments, insertion of a m_5 site downstream of the TSS of e.g. $P_{phyt}$ minimizes activation of $P_{phyt}$ in both the presence and absence of U. As would be understood by skilled persons, the latter is preferable as it minimizes UzcRS expression levels when no U is present, minimizing cross-reactivity with Zn and Cu.

In some embodiments, the U-sensitive promoter can be a promoter genetically engineered to comprise the U-sensitive 1362 binding site. In some exemplary embodiments, it is expected that a promoter can be engineered comprising a U-sensitive 1362 binding site having Nis of SEQ ID NO:1 at a position of about −40 to−42 upstream of the transcription start site, as in exemplary promoters $P_{1361}$ and $P_{phyt}$ (see e.g. FIG. 7).

The U-sensitive promoters described herein can further comprise a holo-RNA Polymerase (RNAP) binding site. As understood by those skilled in the art, promoters in bacteria, such as members of Caulobacteridae require DNA sequence elements for σ-RNAP binding for initiation of transcription. In particular, in Caulobacteridae promoters comprising the 1362 binding site such as exemplary promoters $P_{1361}$ and $P_{phyt}$, the σ-RNAP biding site typically have low sequence homology to the canonical $\sigma^{73}$-RNAP-10 and −35 hexamer sequences. As such, activation of a promoter comprising a 1362 binding site at a position configured for transcriptional activation (e.g. wherein nucleotide Nis of the regulator direct repeat is located about −17 to about −40 upstream of the TSS), such as exemplary promoters $P_{1361}$ and $P_{phyt}$, σ-RNAP binding likely requires binding of the U-responsive transcriptional factor to the 1362 binding site, consistent with the observed low level of transcriptional activation in absence of U (see Examples section).

The term "holoenzyme" as used herein refers to enzymes that contain multiple protein subunits, such as RNA polymerases, wherein the holoenzyme is a complete complex containing all the subunits needed for activity. The term "holoenzyme" can also refer to an enzyme together with one or more cofactors required for activity. For example, in bacteria, a promoter is recognized by RNA polymerase (RNAP) and an associated sigma factor, and the complex is referred to as an "RNAP holoenzyme" or "holo-RNAP". An example of a RNAP holoenzyme in Caulobacteridae is RNAP holoenzyme containing σ-[73].

Figure 2:
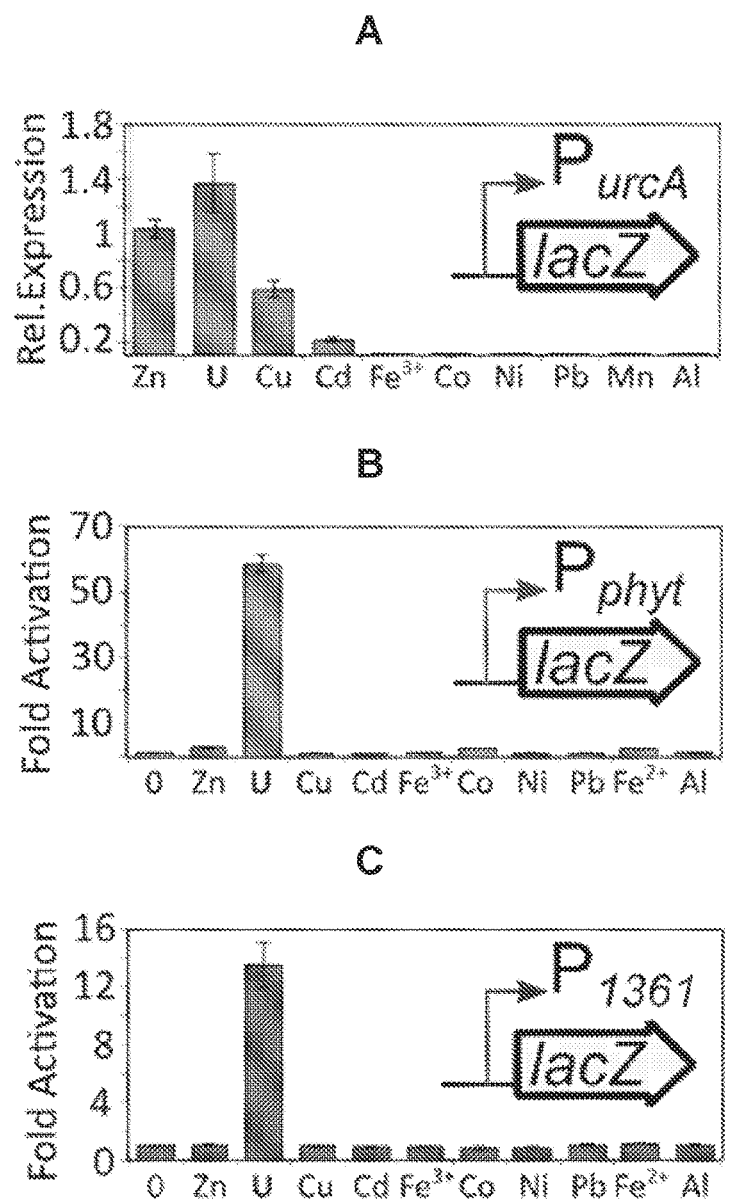
FIG. 2 shows graphs reporting determination of metal specificity of native U-responsive promoters in *Caulobacter crescentus*. The metal specificity of chromosomal $P_{urcA}$-lacZ (Panel A), $P_{phyt\text{-}lacZ}$ (Panel B), and $P_{1361}$-lacZ (Panel C) was determined by treating mid-exponential phase cells with a range of concentrations of various metal salts for two hours before determining β-galactosidase activity using the method of Miller [1]. Cell growth was performed in peptone yeast extract (PYE) media supplemented with 50 mM MES pH 6.1. For Panel A, the relative expression was determined by normalizing the β-galactosidase activity observed by treatment with each metal to that of Zn. For Panels A and B, fold activation was calculated by dividing the activity with no added metal from the activity following metal exposure. Error bars represent the standard deviation calculated using a formula for propagation of standard error [2]. See FIG. 23 for more comprehensive metal specificity plot for $P_{urcA\text{-}lacZ}$.

The U biosensors comprising the U-sensitive molecular component and/or U-sensitive genetic circuits comprising 1363/1362 TCS and/or UczRS TCS described herein in several embodiments can show improved selectivity for U compared to those previously described, such as in Hillson et al., 2007 [44], as illustrated in the Examples. As shown in FIGS. 1 and 2, the previously unknown exemplary U-responsive *Caulobacter crescentus* promoters $P_{1361}$ and $P_{phyt}$ show highly selective gene expression upregulation in response to U, in contrast to *Caulobacter crescentus* promoter $P_{urcA}$ [44], which also shows upregulation of gene expression in response to other metals such as Zn, Cu and Cd. Accordingly, a U-sensitive promoter, such as a $P_{1361}$ or a $P_{phyt}$ promoter, or a U-sensitive promoter genetically engineered to comprise the U-sensitive 1362 binding site can be used as a stand-alone selective U-sensing promoter.

In a U-sensitive genetic molecular component herein described, the U-Sensing promoter of the present disclosure directly or indirectly controls the expression of a reportable molecular component and/or a U-neutralizing molecular component.

The term "reportable molecular component" as used herein indicates a molecular component capable of detection in one or more systems and/or environments. The terms "detect" or "detection" as used herein indicates the determination of the existence, presence or fact of a target in a limited portion of space, including but not limited to a sample, a reaction mixture, a molecular complex and a substrate. The "detect" or "detection" as used herein can comprise determination of chemical and/or biological properties of the target, including but not limited to ability to interact, and in particular bind, other compounds, ability to activate another compound and additional properties identifiable by a skilled person upon reading of the present disclosure. The detection can be quantitative or qualitative. A detection is "quantitative" when it refers, relates to, or involves the measurement of quantity or amount of the target or signal (also referred as quantitation), which includes but is not limited to any analysis designed to determine the amounts or proportions of the target or signal. A detection is "qualitative" when it refers, relates to, or involves identification of a quality or kind of the target or signal in terms of relative abundance to another target or signal, which is not quantified.

In some embodiments, the reportable molecular component can be a molecular component linked to or comprising a label wherein the term label refers to a compound capable of emitting a labeling signal, including but not limited to radioactive isotopes, fluorophores, chemiluminescent dyes, chromophores, enzymes, enzymes substrates, enzyme cofactors, enzyme inhibitors, dyes, metal ions, nanoparticles, metal sols, ligands (such as biotin, avidin, streptavidin or haptens) and the like. The term "fluorophore" refers to a substance or a portion thereof which is capable of exhibiting fluorescence.

In embodiments of the U-sensitive genetic molecular component described herein, the genetic molecular component comprises a "reporter gene", which can be any genetically-encoded reportable molecular component.

As would be understood by persons skilled in the art, the terms "genetically-encoded reportable molecular component", "genetically encoded reporter" or "reporter gene" comprises polynucleotide-encoded RNA and/or proteins having reportable characteristics identifiable by those skilled in the art and as described herein. Using genetic engineering techniques known to those skilled in the art, a reporter gene can be placed under the regulatory control of a promoter, and expression of the genetically-encoded reportable molecular component thereby serves as an indication of activation of the promoter in a host organism comprising the reporter gene. A reporter gene can be fused to another gene under the regulatory control of the promoter, such as a gene encoding a protein natively regulated by the promoter, so that the promoter regulates the expression of a fusion gene encoding a fusion protein comprised of the natively regulated protein covalently linked to the reportable molecular component. As would be understood by those skilled in the art, it is typical to use a reporter gene that is not natively expressed in the host organism, since the expression of the genetically-encoded reportable molecular component is used as a marker of activation of the promoter in the host organism. Exemplary genetically encoded reportable molecular components comprise fluorescent proteins such as green fluorescent protein (GFP) from *Aequorea victoria* or *Renilla reniformis*, red fluorescent protein from *Discosoma* species (dsRED), and variants thereof, beta galactosidase encoded by lacZ gene, luciferase and others identifiable to those skilled in the art. In exemplary embodiments described herein, exemplary reporters comprise a fluorescent protein which is a mutant variant of GFP referred to as 'gfpmut3' [45].

In some embodiments, the U-biosensors comprising U-sensitive genetic molecular components and/or U-sensitive genetic circuits described herein are configured to produce a U-neutralizing molecular component in presence of U.

The term "U-neutralizing molecular component" as used herein refers to any component capable of decreasing the bioavailable U concentration.

In some embodiments, the U-neutralizing molecular component is a U-neutralizing genetic molecular component comprising a "U-neutralizing gene". The term "U-neutralizing genetic molecular component" as used herein refers to a genetic molecular component in which the gene of the genetic molecular component is a U-neutralizing gene and wherein polynucleotide-encoded RNA and/or proteins have U-neutralizing characteristics identifiable by those skilled in the art upon reading of the present disclosure, such as proteins having enzymatic functions capable of allowing bioreduction, biomineralization, biosorption, or bioaccumulation of bioavailable U, as described herein.

The term "bioreduction" as used herein refers to altering the redox state of uranium from aqueous U (VI) to insoluble U (IV). As would be understood by persons skilled in the art, in the absence of oxygen, some bacteria are able to respire different electron acceptors to gain energy for metabolism. As anoxia progresses, the most energetically favorable electron acceptors are used in sequence, starting with the reduction of nitrate, then proceeding through Mn(IV), Fe(III) and sulfate, and finally the reduction of carbon dioxide to produce methane. At circumneutral pH, U(VI) has a similar redox couple to Fe(III), and natively Fe(III)-reducing bacteria are able to respire U(VI) as an alternative electron acceptor, reducing it to insoluble U(IV) [12]. Other groups natively capable of U(VI) reduction comprise bacteria such as sulfate-reducing bacteria [46], fermentative bacteria [47], acid-tolerant bacteria [48] and myxobacteria [49]. In some embodiments where a bioreduction component is comprised in the U-biosensor herein described, the host cell is preferably selected among cells natively expressing the components required to perform uranium bioreduction, which can be engineered to include one or more U-sensing genetic molecular component and/or other components of the U-sensing genetic circuit herein described. In other embodiments, a host cell can be *E. Coli* or other facultative anaerobe genetically engineered to include one or more U-sensing genetic molecular component and/or other components of the U-sensing genetic circuit herein described as well as genetic molecular components required to perform U-bioreduction as will be understood by a skilled person Accordingly, in some embodiments uranium bioreduction can be used as a bioremediation technique, stimulated by adding an electron donor to promote enzymatic reduction of aqueous U(VI) to insoluble U(IV) [50-55]. Enzymatic reduction of U(VI) can be catalyzed using U-neutralizing genes such as those expressing cytochrome c [46, 56, 57]. In addition, chelators can be used to solubilize U(VI) and/or electron shuttles to mediate extracellular electron transfer, such as U-neutralizing genes expressing flavin mononucleotide or riboflavin [11, 58-61]. Therefore, in some embodiments of the U biosensors described herein, exemplary U-neutralizing genes comprise cytochrome c genes, flavin mononucleotide genes, or riboflavin genes which can be natively expressed in suitable host possibly further engineered to include one or more U-sensing genetic molecular components and/or U-sensing genetic circuit herein described.

The terms "biomineralization" and "bioprecipitation" as used herein refers to a process by which metals precipitate with microbially generated ligands such as sulfide or phosphate, or as carbonates or hydroxides in response to localized alkaline conditions at the cell surface. Thereafter, the uranium precipitate can be removed. In some embodiments. In some embodiments, the U can be comprised into a stable mineral that sediment out and not be re-leached over time. In addition or in the alternative U-removal can be performed by some form of on-site filtration identifiable by a skilled person. In particular, sequestration of uranium as insoluble uranyl U(VI) phosphate biominerals can be used for in situ biomineralization for sites where bioreduction may not be feasible due to high nitrate concentrations or where there is risk of reoxidation reoccurring, e.g., in sites comprising carbonate [62, 63].

Accordingly, in some embodiments, the U-biosensors described herein can be engineered to catalyze precipitation of uranium such as uranyl phosphates. For example, bacteria can be engineered to precipitate uranyl phosphates [64] by expressing U-neutralizing genes such as acid-phosphatase genes [65] or alkaline-phosphatase genes [66] or phytase genes. In some embodiments, an exogenous source of phosphate can be added such as glycerol phosphate [16] or tributylphosphate [67]. Therefore, in some embodiments of the U biosensors described herein, exemplary U-neutralizing genes comprise acid-phosphatase genes, or alkaline-phosphatase genes. In an exemplary embodiment, the U-neutralizing gene is phoY, encoding an alkaline phosphatase that has been shown to allow the coupling of release of inorganic phosphorus (Pi) from organophosphates with U-Pi precipitation in *Caulobacter crescentus* [43], or phytase, that can be used to liberate phosphate from phytate, an environmental source of phosphate (see Example 10). In some embodiments, Pphyt or P1361 can be used to drive expression of a alkaline phosphatase. In some embodiments, the U-biosensors described herein can be engineered to comprise additional genetic molecular components configured to express one or more genes encoding proteins having enzymatic functions to catalyze release of inorganic phosphate from organophosphates (via hydrolytic cleavage catalyzed by phosphatases), inorganic phosphite (via enzymatic oxidation) and phosphonates (via cleavage catalyzed by C-P lyases), or from nucleic acids [68], phytate [69] or phospholipids [70].

The term "bioaccumulation" as used herein refers to accumulation of metals such as uranium in bacteria. For example, intracellular uranium accumulation occurs as uranyl phosphates in bacteria such as *Pseudomonas* species (Kazy et al., 2009; [71], VanEngelen et al., 2010; [72], Choudhary and Sar, 2011, [73]). In particular, overexpression of the polyphosphate kinase gene (ppk) encoding the PPK enzyme can be used to produce high levels of polyphosphate, a phosphate polymer with chain lengths of two to a few hundred, to allow precipitation of uranyl phosphate at the cell membrane (Renninger et al. 2004 Applied and Environmental Microbiology 70:7404 [74]). Accordingly, in some embodiments of the U biosensors described herein, exemplary U-neutralizing genes comprise ppk genes.

The terms "biosorption" or "bioadsorption" as used herein refers to the passive uptake of uranium to the surface of microbial cells, wherein bacterial cell envelopes possess an electronegative charge, so are able to attract metal cations which sorb to the surface. In some embodiments of the U biosensors described herein, exemplary U-neutralizing genes comprise genes encoding proteins configured to bind U to the cell surface of the U biosensor. In an exemplary embodiment, the U-neutralizing gene is an ompA-SUP fusion gene encoding a rationally engineered super uranyl binding protein (SUP) having femtomolar affinity [75] (see Example 10). The encoded ompA fusion is configured to anchor SUP to the outer membrane, allowing adsorption of U to the cell surface. In other exemplary embodiments, the U-neutralizing gene is a fusion gene comprising the ompA protein fused to a Calmodulin EF-Hand Peptide (CaM) [76] that has been engineered for high U selectivity. In other exemplary embodiments, the U-neutralizing gene is a fusion gene comprising the Calmodulin EF-Hand Peptides (CaM) or SUP fused with the rsaA (S-layer) gene (see Example 10), for example using the method outline in Nomellini [77]. Accordingly, in some embodiments, proteobacteria can be engineered to provide U biosensors comprising U-neutralizing components configured to produce a U biosorption output, following a methodology such as has been used in *Caulobacter* for rare earth element adsorption [78].

Accordingly, U-biosensors comprising U-neutralizing molecular components described herein can be used in several embodiments for U bioremediation.

The term "bioremediation" as used herein refers to a waste management technique that involves the use of organisms to neutralize pollutants from a contaminated site. Bioremediation can be performed in situ or ex situ. In situ bioremediation involves treating the contaminated material at the site, while ex situ involves the removal of the contaminated material to be treated elsewhere.

Figure 15:
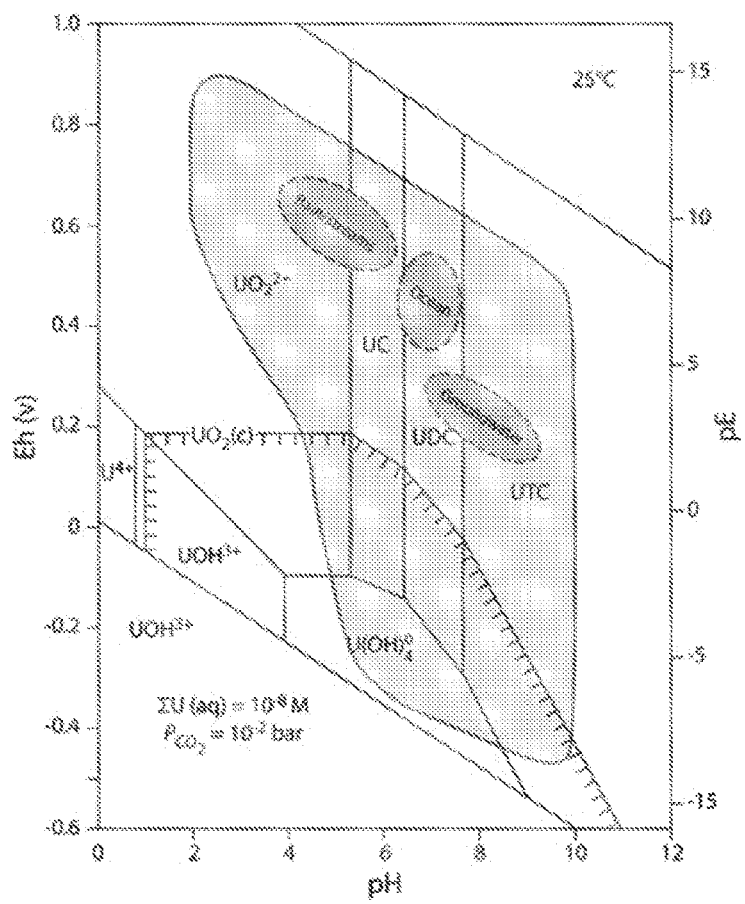
FIG. 15 is FIG. 1 from Newsome et al. (2014) [7] showing an exemplary Eh-pH diagram (which maps out possible stable (equilibrium) phases of an aqueous electrochemical system) for aqueous species in the $U-O_2-CO_2-H_2O$ system in pure water at 25° C. and 1 bar total pressure for $\Sigma U=10^{-8}$ M and a typical groundwater $CO_2$ pressure of $PCO_2=10^{-2.0}$ bar [8]. UC, UDC and UTC represent the aqueous complexes $UO_2CO_3O$, $UO_2(CO_3)_2^{2-}$ and $UO_2(CO_3)_3^{4-}$. The position of the $UO_{2(c)}$ solid solution boundary for $\Sigma U=10^{-8}$ M is stippled. The shaded area represents the range of conditions of common natural waters [9] as presented in Newsome et al., (2014) [7].
Figure 16A:
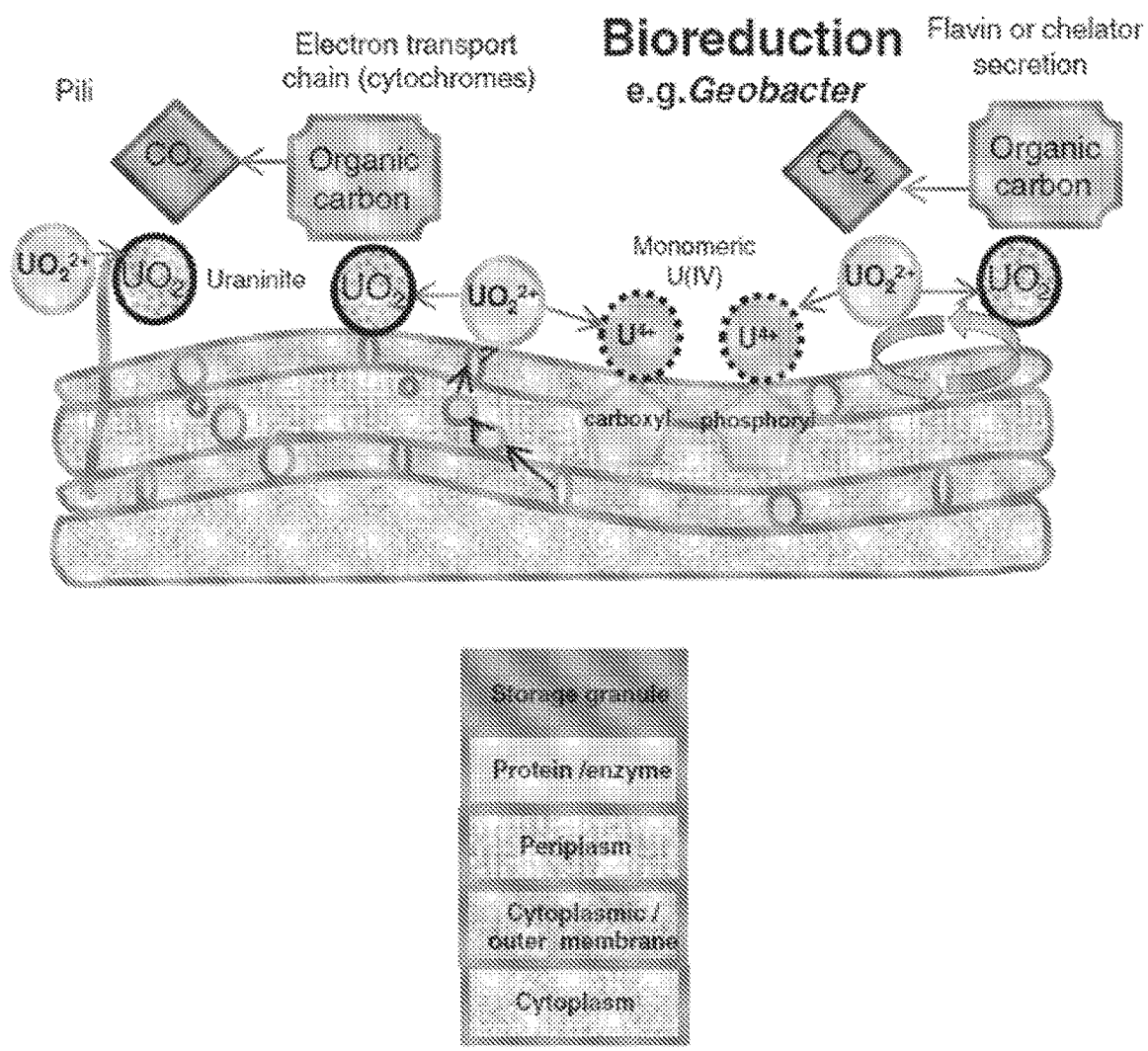
FIG. 16A is from FIG. 2 of Newsome et al. (2014) [7] showing a schematic illustrating exemplary mechanisms of microbe-uranium interactions, such as bioreduction [10-13].

As would be understood by persons skilled in the art, mobility of uranium in the environment depends on its speciation and redox state (e.g., see FIG. 15). It is present as mobile U(VI) in oxidizing conditions, predominantly as the uranyl ion ($UO_2^{2+}$) or hydroxyl complexes below ~pH 6.5, or as uranyl carbonate complexes at higher pH [79]. In the absence of carbonate, the uranyl ion and its complexes sorb strongly onto the surface of iron oxides and organics [62, 80, 81] and onto the edge sites of clay minerals [82, 83]. Sorption decreases in the presence of complexing ligands such as humic and fulvic acids, and in the presence of competing cations such as $Ca^{2+}$ and $Mg^{2+}$ [84]. Under reducing conditions, relatively insoluble and immobile U(IV) predominates, typically as the mineral uraninite, or as other U(IV) minerals [10, 85].

Biogeochemical interactions play a key role in controlling the speciation and mobility of uranium, through direct metabolic processes such as microbial respiration, or indirectly by changing ambient redox/pH conditions, producing ligands or new biominerals, or altering mineral surfaces. In addition to controlling uranium mobility via "natural attenuation", these biogeochemical processes can be stimulated to accelerate clean-up of contaminated environments through bioremediation.

Preventing uncontrolled dispersion and transport of uranium in groundwater is a primary remediation goal at contaminated sites. Accordingly, stimulating bacterial interactions to fix aqueous uranium into insoluble minerals in situ can provide a relatively inexpensive and non-intrusive solution to remediating uranium contamination. Exemplary mechanisms of different microbe-uranium interactions are illustrated in FIGS. 16A-D, comprising bioreduction, biomineralization, biosorption, and bioaccumulation [7], among other identifiable by those skilled in the art.

In embodiments of the U-biosensors described herein configured to have a U-neutralizing molecular component output to perform a U bioremediation function in response to bioavailable U, the preferred U-neutralizing molecular component output is a U-neutralizing molecular component having a U biomineralization function.

In some embodiments of a U-sensing genetic molecular component, the reporter gene or U-neutralization gene is contiguous with the U-sensitive promoter, wherein the 5' end of the reporter gene is immediately adjacent to the 3' end of the U-sensitive promoter. In other embodiments, the reporter gene is not contiguous with the promoter, such that one or more nucleotides are located between the 3' end of the U-sensitive promoter and the 5' end of the reporter gene. For example, in some embodiments, a ribosome binding site can be inserted between the 3' end of the U-sensitive promoter (downstream of the TSS) and the 5' end of the reporter gene.

In some embodiments, the U biosensors described herein comprise any non-pathogenic member of Caulobacteridae. In some embodiments described herein, the U biosensor comprises Caulobacteridae such as *C. crescentus* strains NA1000, CB15, and OR37, an environmental isolate from a U-contaminated site that exhibits high heavy metal tolerance [86]. In Examples provided herein, an exemplary host organism is *C. crescentus* strain NA1000.

In some embodiments of the U biosensor described herein, the cell can be any Caulobacteridae having a genome that natively comprises promoters having 1362 binding sites, such as exemplary promoters $P_{1361}$ or $P_{phyt}$, or a homolog thereof.

In some embodiments, a U-sensing genetic molecular component herein described, is comprised in a U-sensitive genetic circuit together with a reporter molecular component and/or a U-neutralizing molecular component. In particular, in a U-sensitive genetic circuit molecular the U-sensing genetic molecular component, the reporter molecular component, and/or the U-neutralizing molecular components as well as possibly other components are connected one to another in accordance to a circuit design by activating, inhibiting, binding or converting reactions to form a fully connected network of interacting components. In a U-sensitive genetic circuit herein described, at least one molecular component is a U-sensing genetic molecular component in which a U-sensitive promoter having a regulator direct repeat sequence of SEQ ID NO: 1 or any of SEQ ID NO:7-28) is activated or repressed in presence of bioavailable U. In a U-sensitive genetic circuit herein described at least one molecular component is a reportable molecular component and/or a U-neutralizing molecular component when the genetic circuit operates according to the circuit design in presence of bioavailable U.

The term "genetic circuit" as used herein indicates a collection of molecular components connected one to another by biochemical reactions according to a circuit design. In particular, in a genetic circuit the molecular components are connected one to another by the biochemical reactions so that the collection of molecular components is capable to provide a specific output in response to one or more inputs.

In genetic circuits in the sense of the present disclosure, the molecular components forming parts of the genetic circuit can be genetic molecular components or cellular molecular components.

The term "cellular molecular component" indicates a molecular component not encoded by a gene, or indicates a molecular component transcribed and/or translated by a gene but comprised in the circuit without the corresponding gene. Exemplary cellular components comprise polynucleotides, polypeptides, polysaccharides, small molecules and additional chemical compounds that are present in a cellular environment and are identifiable by a skilled person. Polysaccharides, small molecules, and additional chemical compounds can include, for example, NAD, FAD, ATP, GTP, CTP, TTP, AMP, GMP, ADP, GDP, Vitamin B1, B12, citric acid, glucose, pyruvate, 3-phosphoglyceric acid, phosphoenolpyruvate, amino acids, PEG-8000, FiColl 400, spermidine, DTT, b-mercaptoethanol maltose, maltodextrin, fructose, HEPES, Tris-Cl, acetic acid, aTc, IPTG, 30C12HSL, 30C6HSL, vanillin, malachite green, Spinach, succinate, tryptophan, and others known to those skilled in the art. Polynucleotides can include RNA regulatory factors (small activating RNA, small interfering RNA), or "junk" decoy DNA that either saturates DNA-binding enzymes (such as exonuclease) or contains operator sites to sequester activator or repressor enzymes present in the system (for example, as in [87]). Polypeptides can include those present in the genetic circuit but not produced by genetic components in the circuit, or those added to affect the molecular components of the circuit.

In some embodiments of genetic circuits herein described, one or more molecular components is a recombinant molecular component that can be provided by genetic recombination (such as molecular cloning) and/or chemical synthesis to bring together molecules or related portions from multiple sources, thus creating molecular components that would not otherwise be found in a single source.

In embodiments herein described, a genetic circuit comprises at least one genetic molecular component or at least two genetic molecular components, and possibly one or more cellular molecular components, connected one to another in accordance to a circuit design by activating, inhibiting, binding or converting reactions to form a fully connected network of interacting components.

The term "activating" as used herein in connection with a molecular component of a genetic circuit refers to a reaction involving the molecular component which results in an increased presence of the molecular component in the cellular environment. For example, activation of a genetic molecular component indicates one or more reactions involving the gene, RNA and/or protein of the genetic molecular component resulting in an increased presence of the gene, RNA and/or protein of the genetic molecular component (e.g. by increased expression of the gene of the molecular component, and/or an increased translation of the RNA). An example of "activating" described herein comprises the initiation of expression of a gene regulated by a UzcRS-regulated promoter by a UzcR protein (e.g., see Example 2).

Activation of a molecular component of a genetic circuit by another molecular component of the circuit can be performed by direct or indirect reaction of the molecular components. Examples of a direct activation of a genetic molecular component comprised in a circuit the production of an alternate sigma factor (molecular component of the circuit) that drives the expression of a gene controlled by the alternate sigma factor promoter (other molecular component of the circuit), or the production of a small ribonucleic acid (molecular component of the circuit) that increases expression of a riboregulator-controlled RNA (molecular component of the circuit). Specific examples of this include the activity of sigma28 or sigma54 as demonstrated in [88]. Examples of indirect activation of a genetic molecular component comprise the production of a first protein that inhibits an intermediate transcriptional repressor protein, wherein the intermediate transcriptional repressor protein represses the production of a target gene, such that the first protein indirectly activates expression of the target gene.

The term "inhibiting" as used herein in connection with a molecular component of a genetic circuit refers to a reaction involving the molecular component of the genetic circuit and resulting in a decreased presence of the molecular component in the cellular environment. For example, inhibition of a genetic molecular component indicates one or more reactions involving the gene, RNA and/or protein of the genetic molecular component resulting in a decreased presence of the gene, RNA and/or protein (e.g. by decreased expression of the gene of the molecular component, and/or a decreased translation of the RNA). Inhibition of a cellular molecular component indicates one or more reactions resulting in a decreased production or increased conversion, sequestration or degradation of the cellular molecular components (e.g. a polysaccharide or a metabolite) in the cellular environment.

Inhibition can be performed in the genetic circuit by direct reaction of a molecular component of the genetic circuit with another molecular component of the circuit or indirectly by reaction of products of a reaction of the molecular components of the genetic circuit with another molecular component of the circuit.

The term "binding" as used herein in connection with molecular components of a genetic circuit refers to the connecting or uniting two or more molecular components of the circuit by a bond, link, force or tie in order to keep two or more molecular components together, which encompasses either direct or indirect binding where, for example, a first molecular component is directly bound to a second molecular component, or one or more intermediate molecules are disposed between the first molecular component and the second molecular component another molecular component of the circuit. Exemplary bonds comprise covalent bond, ionic bond, van der Waals interactions and other bonds identifiable by a skilled person.

In some embodiments, the binding can be direct, such as the production of a polypeptide scaffold that directly binds to a scaffold-binding element of a protein. In other embodiments, the binding may be indirect, such as the co-localization of multiple protein elements on one scaffold. In some instances, binding of a molecular component with another molecular component can result in sequestering the molecular component, thus providing a type of inhibition of said molecular component. In some instances, binding of a molecular component with another molecular component can change the activity or function of the molecular component, as in the case of allosteric interactions between proteins, thus providing a type of activation or inhibition of the bound component. An example of "binding" as described herein comprises the binding of UzcR to an m_5 site in a UzcRS-regulated promoter (e.g., see Example 2).

The term "converting" as used herein in connection with a molecular component of the circuit refers to the direct or indirect conversion of the molecular component into another molecular component. An example of this is the conversion of chemical X by protein A to chemical Y that is then further converted by protein B to chemical Z. An example of "converting" as described herein comprises the cleavage of o-nitrophenyl-β-D-galactoside (ONPG) by beta-galactosidase encoded by the lacZ gene (e.g. see Example 1).

In embodiments of the U-sensitive genetic circuit described herein, the molecular components are connected one with another according to a circuit design in which a molecular component is an input and another molecular component is an output. In particular, a genetic circuit typically has one or more input or start molecular component which activates, inhibits, binds and/or convert another molecular component, one or more output or end molecular component which are activated, inhibited, bound and/or converted by another molecular component, and intermediary molecular components each inhibiting, binding and/or converting another molecular component and being activated, inhibited, bound and/or converted by another molecular component. In embodiments of the U-sensitive genetic circuits herein described, the input is bioavailable U and the output is a reportable molecular component and/or a U-neutralizing molecular component.

In embodiments of the U biosensor described herein, the U-sensitive genetic circuit comprises at least one U-sensing genetic molecular component in which a U-sensitive promoter is activated or repressed in presence of bioavailable U, the U sensitive promoter comprising a U-sensitive transcriptional 1362 binding site. In these embodiments, in the U-sensitive genetic circuit at least one molecular component is a reportable molecular component and/or a U-neutralizing molecular component when the genetic circuit operates according to the circuit design in presence of bioavailable U.

An exemplary genetic circuit described herein comprises, a U sensing genetic molecular component in which a U-sensitive promoter such as $P_{phyt}$ or a $P_{1361}$ is configured to initiate expression of a lacZ gene encoding the beta-galactosidase enzyme (U-sensing genetic molecular component), wherein the beta-galactosidase enzyme converts the substrate ONPG (cellular molecular component) to yield galactose and o-nitrophenol which has a yellow color (reportable molecular component).

In some embodiments of the U biosensor, the U-sensitive genetic circuit comprises at least one U-sensing genetic molecular component in which a U-sensitive promoter is activated or repressed in presence of bioavailable U, the U sensitive promoter comprising a U-sensitive transcriptional 1362 binding site. In these embodiments, in the U-sensitive genetic circuit at least one molecular component is a reportable molecular component and/or a U-neutralizing molecular component when the genetic circuit operates according to the circuit design in presence of bioavailable U. In some embodiments, the U-sensitive genetic circuit further comprises at least one genetic molecular component in which a UzcRS two-component system regulated promoter is activated or repressed in presence of bioavailable U.

In an exemplary embodiment of the U-sensitive genetic circuits described herein, at least one U-sensitive genetic molecular component comprises a U-sensitive promoter such as $P_{phyt}$ or a $P_{1361}$ configured to initiate expression of a uzcS gene (CCNA_02842) and a uzcR gene (CCNZ_02485), encoding proteins UzcS and UzcR, respectively (first U-sensing genetic molecular component) and further comprises a second U-sensing genetic molecular component in which a UzcRS two-component system regulated promoter is configured to initiate expression of a reporter gene (e.g. GFP, an exemplary reportable molecular component), in which binding of UzcR protein to the UzcRS-regulated promoter activates the UzcRS-regulated promoter (see Example 2). As understood by those skilled in the art, uzcS and uzcR are genes that are natively comprised in a uzcRS operon in Caulobacter and other Alphaproteobacteria, as described in Park et al., 2017 [3].

The term "uzcRS operon" as used herein refers to the genetically encoded UzcRS two-component system, comprising the uzcS gene (CCNA_02842) and the uzcR gene (CCNZ_02485), and operatively linked promoters and regulatory elements [3]. In an exemplary C. crescentus NA1000 genome, uzcR and uzcS are physically separated by genes $parD_3$ and $parE_3$ encoding the ParDE3 toxin antitoxin (TA) system, together forming a putative four-gene operon [3, 89]. Although uzcR and uzcS are conserved throughout Alphaproteobacteria, the insertion of parDE3 between uzcR and uzcS is unique to a subset of the Caulobacter genus; uzcR and uzcS are adjacently located in the majority of closely related Alphaproteobacteria [3] including C. crescentus OR37, an environmental isolate from a U-contaminated site [86].

Accordingly, in some embodiments of the U biosensors described herein, the U biosensor can be any genetically engineered proteobacteria and in particular a genetically engineered Caulobacteridae which comprises a UzcRS two component system.

In some preferred embodiments, a U-sensitive genetic circuit further comprises one or more genetic molecular components comprising one or more negative regulators of UzcRS that function to maintain UzcRS in an OFF state in absence of metal (see Example 9). In particular, in some exemplary embodiments, the U biosensor described herein comprises a chromosomal copy of UzcRS negative regulators 1 and 2 (Example 9) under transcriptional regulation of their native promoters. In other embodiments, one or more genetic molecular components comprising exemplary UzcRS negative regulators 1 and 2 are placed under control of inducible transcriptional regulatory elements in order to desensitize UzcS to a particular signal. For example, overexpression of CCNA_03680-CCNA_03681 reduces the sensitivity of UzcRS for Zn and Cu. In some embodiments, the MarR-type regulators CCNA_03498 and/or CCNA_02289 can be deleted in the host Caulobacteridae genome to increase sensitivity of uzcRS for U.

In an exemplary embodiment of the U-sensitive genetic circuits described herein, the U-sensitive genetic circuit comprises a U-sensitive promoter such as $P_{phyt}$ or a $P_{1361}$ configured to initiate expression of a hrpS gene encoding an HrpS protein (first U-sensing genetic molecular component) and further comprises a second U-sensing genetic molecular component in which a UzcRS two-component system regulated promoter is configured to initiate expression of an hrpR gene encoding an HrpR protein. The U-sensitive genetic circuit further comprises a third genetic molecular component comprising a hrpL promoter ($P_{hrpL}$) configured to initiate expression of a reporter gene (e.g. GFP, an exemplary reportable molecular component), in which binding of both HrpS and HrpR are required for σ54 dependent activation of the $P_{hrpL}$ and expression of HrpS or HrpR alone is not sufficient for transcriptional activation. (see Example 3).

As understood by those skilled in the art, hrpR and hrpS refer to genes that are natively comprised in a σ54 dependent hrpR/hrpS hetero-regulation module from the hrp (hypersensitive response and pathogenicity) system for Type III secretion in Psuedomonas syringae [90-92], wherein both HrpS and HrpR are required for 654 dependent activation of the hrpL promoter ($P_{hrpL}$) and expression of HrpS or HrpR alone is not sufficient for transcriptional activation.

In some embodiments of the U-sensitive genetic circuits described herein, at least two genetic molecular components comprise complimentary protein fragments of a transcription factor, which are configured to associate together to form a functional transcription factor, such as those based on a bacterial two-hybrid system.

As would be understood by those skilled in the art, the term "bacterial two-hybrid" as used herein refers to a technique used to detect protein-protein interactions and protein-DNA interactions by testing for physical interactions (such as binding) between two proteins or a single protein and a DNA molecule, respectively. As understood by those skilled in the art, the bacterial two-hybrid system relies on the activation of downstream reporter gene(s) upon binding of a transcription factor onto an upstream activating sequence (UAS), wherein the transcription factor is split into two separate fragments, called the binding domain (BD) and activating domain (AD). The BD is a domain configured to bind to the UAS and the AD is a domain configured to activate transcription of the operatively linked gene. Thus, the bacterial two-hybrid system is a protein-fragment complementation assay that requires both the BD and the AD for reporter expression. An exemplary bacterial two-hybrid system utilizes an E. coli omega protein, which copurifies with RNA polymerase, and can function as a transcriptional activator when linked covalently to a DNA-binding protein. The E. coli omega protein can function as an activation target when this covalent linkage is replaced by a pair of interacting polypeptides fused to the DNA-binding protein and to omega, respectively [93].

Accordingly, in an exemplary embodiment of the U-sensitive genetic circuits described herein, the U-sensitive genetic circuit comprises a U-sensitive promoter such as $P_{phyt}$ or a $P_{1361}$ configured to initiate expression of a BD gene encoding an BD protein (first U-sensing genetic molecular component) and further comprises a second U-sensing genetic molecular component in which a UzcRS two-component system regulated promoter is configured to initiate expression of an AD gene encoding an AD protein. The U-sensitive genetic circuit further comprises a third genetic molecular component comprising a promoter comprising binding sites for the BD and the AD, configured to activate expression of the reporter gene, e.g. GFP or the U-neutralizing gene (third genetic molecular component), in which binding of both BD and AD are required activation of the third genetic molecular component and expression of the reportable molecular component and/or the U-neutralizing molecular component (see Example 5). For example, it is expected that a 1363/1362 regulated promoter (e.g., $P_{phyt}$) can be used to initiate expression of alpha-gal11 (an exemplary AD), and a UzcRS regulated promoter (e.g., $P_{urcB}$) can be used to initiate expression of λ-gal4 (an exemplary BD) and $P_{lacOR2-62}$ that contains the UAS to initiate expression of a reporter gene, such as GFPmut3 (see Example 5).

In some embodiments of the U biosensor, the U-sensitive genetic circuit comprises at least one U-sensing genetic molecular component in which a U-sensitive promoter is activated or repressed in presence of bioavailable U, the U sensitive promoter comprising a U-sensitive transcriptional 1362 binding site and/or a UzcR binding site. In these embodiments, in the U-sensitive genetic circuit at least one molecular component is a reportable molecular component and/or a U-neutralizing molecular component when the genetic circuit operates according to the circuit design in presence of bioavailable U, wherein the reportable genetic component and/or a U-neutralizing molecular component is formed by an assembly of two or more subunits of the reportable molecular component and/or a U-neutralizing molecular component. In some embodiments where a 1362 binding site is present, the U-sensitive genetic circuit further preferably comprises at least one genetic molecular component in which an UzcRS two-component system regulated promoter is activated or repressed in the presence of bioavailable U.

In an exemplary embodiment of the U-sensitive genetic circuits described herein (see Example 4), the U-sensitive genetic circuit comprises a U-sensitive promoter such as $P_{phyt}$ or a $P_{1361}$ configured to initiate expression of a gfp10-K1 fusion gene encoding a GFP10-K1 fusion protein (first U-sensing genetic molecular component) and further comprises a second U-sensing genetic molecular component in which a UzcRS two-component system regulated promoter is configured to initiate expression of an E1-gfp11 gene encoding E1-GFP11 fusion protein. The U-sensitive genetic circuit further comprises a third genetic molecular component comprising a gfp1-9 gene regulated by a non-U-responsive, xylose inducible promoter ($P_{xyl}$), a constitutively active promoter (e.g., $P_{rsaA}$) or by $P_{phyt}/P_{1361}$.

Accordingly, the term "tripartite GFP" as used herein refers to a GFP reporter that requires expression and assembly of GFP10, GFP11 and GFP1-9 together for GFP reporter function [5]. As understood by those skilled in the art, tripartite GFP assembly and reporter function is based on tripartite association between two twenty amino-acids long GFP tags, GFP10 and GFP11, which are fused to interacting protein partners, in addition to a complementary GFP1-9 detector. When the interacting protein partners interact, GFP10 and GFP11 self-associate with GFP1-9 to form a functional GFP [5]. In embodiments described herein, any protein interaction pair can be used for the tripartite system. Exemplary interacting protein partners comprise oppositely charged K1/E1 coiled coils, FKBP12-FRB rapamycin inducible protein interaction [5], or the leucine zipper of GCN4 [94] among others known to those skilled in the art.

In some embodiments of the U biosensor, the U-sensitive genetic circuit comprises at least one U-sensing genetic molecular component in which a U-sensitive promoter is activated or repressed in the presence of bioavailable U, the U sensitive promoter comprising a U-sensitive transcriptional 1362 binding site and/or a UzcR binding site. In these embodiments, in the U-sensitive genetic circuit at least one molecular component is a reportable molecular component and/or a U-neutralizing molecular component when the genetic circuit operates according to the circuit design in the presence of bioavailable U, wherein the reportable molecular component and/or the U-neutralizing molecular component is post-transcriptionally and/or post-translationally converted by the U-sensitive genetic circuit in presence of bioavailable U. In some embodiments wherein at least one of the U sensing promoter is 1362 binding sites, the U-sensitive genetic circuit further preferably comprises at least one genetic molecular component in which a UzcRS two-component system regulated promoter is activated or repressed in presence of bioavailable U.

Accordingly, in an exemplary embodiment of the U sensing genetic molecular components described herein, the U-sensitive genetic molecular component comprises a U-sensitive promoter such as $P_{phyt}$ or a $P_{1361}$ configured to initiate expression of a protease configured to cleave at a cleavage sequence comprised in a linker peptide in a Förster resonance energy transfer (FRET) sensor protein (first U-sensing genetic molecular component), and further comprises a second U-sensing genetic molecular component in which a UzcRS two-component system regulated promoter is configured to initiate expression of the FRET sensor protein. Thus, in presence of bioavailable U, the U-sensitive genetic circuit is configured to express and cleave the FRET sensor protein.

As understood by those skilled in the art, the terms "Förster resonance energy transfer", "FRET", "fluorescence resonance energy transfer", "resonance energy transfer", "RET" or "electronic energy transfer", and "EET" as used herein refers to a mechanism describing energy transfer between two light-sensitive molecules (chromophores) [95]. A donor chromophore, initially in its electronic excited state, can transfer energy to an acceptor chromophore through nonradiative dipole-dipole coupling [96]. The efficiency of this energy transfer is inversely proportional to the sixth power of the distance between donor and acceptor, making FRET extremely sensitive to small changes in distance. Measurements of FRET efficiency can be used to determine if two fluorophores are within a certain distance of each other [97]. Such measurements can be used as a research tool in fields such as biology and chemistry. For example, one common pair fluorophores for biological use is a cyan fluorescent protein (CFP)—yellow fluorescent protein (YFP) pair [98]. Both are color variants of green fluorescent protein (GFP). Thus, for example, a genetically-encoded fusion of CFP and YFP covalently linked by a protease cleavage sequence can be used as a cleavage assay, wherein if the linker is intact, excitation at the absorbance wavelength of CFP (414 nm) causes emission by YFP (525 nm) due to FRET. If the linker is cleaved by a protease, FRET is abolished and emission is at the CFP wavelength (475 nm) [99].

In some embodiments, a U biosensor herein described comprises two or more U-sensitive genetic molecular components and/or U-sensitive genetic circuits, wherein each of the U-sensitive genetic molecular components expresses a different reporter gene and/or a U-neutralizing gene, and/or each of the U-sensitive genetic circuits comprise a different reportable molecular component and/or U-neutralizing molecular component, in presence of bioavailable U. For example, exemplary different reportable molecular components can comprise a first genetically-encoded reporter (e.g., GFP) and a second, different genetically-encoded reporter (e.g., dsRED).

In some embodiments, the U biosensors described herein can comprise a UzcRS U-sensitive genetic molecular component comprising a reporter gene or a U-neutralizing gene operatively connected to a UzcRS-regulated promoter, such as $P_{urcA}$, $P_{urcB}$, and others identifiable by those skilled in the art, such as those described in Park et al., (2017) [3]. In those embodiments, the UzcRS U-sensitive genetic molecular component can be comprised in the biosensor alone or in combination with a 1363/1362 U sensitive genetic molecular component comprising a reporter gene or a U neutralizing gene operatively connected to a 1362 regulated promoter.

In the U biosensors described herein, one or more genetic molecular components of the U-sensitive genetic circuits described herein can comprise genomic DNA of the proteobacterial cell and in particular of the Caulobacteridae cell. The one or more genetic molecular components can comprise native genomic DNA in the Caulobacteridae cell or can be introduced into the genome of the Caulobacteridae cell through genetic engineering, or comprised in the Caulobacteridae cell in one or more extra-genomic polynucleotides or vectors, using standard genetic engineering methods known to those skilled in the art and described herein.

In embodiments described herein, the U biosensors—can detect uranium in a range dependent on the composition of the growth media since media components influence bioavailability.

In the U biosensors herein described comprising one or more U-sensitive genetic molecular components, in the absence of bioavailable U, 1362 is not bound to the 1362 binding site of a 1362 U-sensitive genetic molecular component and/or UzcR is not bound to an m_5 site of the UczR U-sensitive genetic molecular component, and reporter gene and/or U-neutralizing gene is not expressed. In a second target range, in presence of bioavailable U, 1362 is bound to the 1362 binding site of the U-sensitive genetic molecular component and/or UzcR is not bound to an m_5 site of the U-sensitive genetic molecular component, and the reporter gene and/or U-neutralizing gene is expressed.

In some embodiments, a U-sensing genetic molecular component and/or U sensing genetic circuits herein described comprising UzcR binding site and a UzcRS TCS can detect Uranium in ~1 micromolar concentrations as will be understood by a skilled person upon reading of the present disclosure. In some embodiments a U-sensing genetic molecular component and/or U sensing genetic circuits herein described comprising 1362 binding site and a 1363/1362 TCS can detect Uranium at ~500 nM in aqueous conditions lacking Pi or glycerol-phosphate as will be understood by a skilled person upon reading of the present disclosure.

In the U biosensors herein described comprising a U-sensitive genetic circuit comprising one or more U-sensing genetic molecular components in which a U-sensitive promoter is activated or repressed in presence of bioavailable U, the U sensitive promoter comprising a U-sensitive transcriptional 1362 binding site and/or a UczR binding site, in a first target range of bioavailable U the endogenous proteobacteria U-sensitive transcriptional regulator is not bound to the 1362 binding site and/or the UczR binding site of the U-sensitive promoter and the U-sensitive genetic circuit does not comprise a reportable molecular component and/or a U-neutralizing molecular component, when the genetic circuit operates according to the circuit design. In a second target range of bioavailable U, the endogenous proteobacteria U-sensitive transcriptional regulator is bound to the 1362 binding site and/or to the UczR binding site of the U-sensitive promoter and the U-sensitive genetic circuit comprises a reportable molecular component and/or a U-neutralizing molecular component when the genetic circuit operates according to the circuit design.

In some embodiments, a U-sensitive genetic circuit which comprises a 1362 binding site further comprises at least one genetic molecular component comprising a UzcRS-regulated promoter comprising a UczR binding site. In these embodiments, in the second target range of bioavailable U concentration, activation or repression of the UzcRS-regulated promoter is also required as an input for the U-sensitive genetic circuit to comprise a reportable molecular component and/or a U-neutralizing molecular component when the genetic circuit operates according to the circuit design, wherein activation or repression of the U-sensitive promoter comprising the regulator direct repeat together with activation or repression of the UzcRS-regulated promoter is herein referred to as an "AND gate", wherein the term "AND" is an operation of Boolean logic.

As would be understood by persons skilled in the art, Boolean logic is a branch of algebra in which the values of the variables are the truth values 'true' and 'false', usually denoted by the digital logic terms '1' and '0' respectively. Instead of elementary algebra where the values of the variables are numbers, and the main operations are addition and multiplication, the main operations of Boolean logic are the conjunction 'AND', the disjunction 'OR', and the negation 'NOT'. As understood by those skilled in the art, it is thus a formalism for describing logical relations in the same way that ordinary algebra describes numeric relations. The term "AND gate" refers to a digital logic gate that implements logical conjunction—it behaves according to the truth table shown in Table 1. A 'true' output (1) results only if both the inputs to the AND gate are 'true' (1). If neither or only one input to the AND gate is 'true' (1), a 'false' (0) output results. Therefore, the output is always 0 except when all the inputs are 1.

TABLE 1

'AND gate' truth table:

| Input | | Output |
|---|---|---|
| A | B | A AND B |
| 0 | 0 | 0 |
| 0 | 1 | 0 |
| 1 | 0 | 0 |
| 1 | 1 | 1 |

In particular, the term "AND gate" as used herein refers to the logical relation between two genetic molecular components in a U-sensitive genetic circuit, wherein inputs 'A' and 'B' in Table 1 are two independently activated or repressed genetic molecular components, wherein a first independently activated or repressed genetic molecular component comprises a first promoter having a U-sensitive transcriptional 1362 binding site, and a second independently activated or repressed genetic molecular component comprises a UzcRS-two-component system regulated promoter, and the output 'A AND B' in Table 1 is the reportable molecular component and/or a U-neutralizing molecular component of the U-sensitive genetic circuit.

As would be understood by those skilled in the art, any 'AND gate' genetic system can be employed in the U-sensitive genetic circuits described herein, such as those described in [100, 101].

In some embodiments, the U-sensitive genetic circuits described herein comprise U-sensing genetic molecular components whose expression is regulated independently by (1) a U-sensitive promoter comprising a 1362 binding site, such as $P_{phyt}$ or $P_{1361}$ and (2) UzcRS two-component system, and comprise an AND gate wherein 'inputs' of activation or repression of both (1) a U-sensitive promoter comprising a 1362 binding site, such as $P_{phyt}$ or $P_{1361}$ and (2) UzcRS two-component system-regulated promoter is required for the reportable molecular component 'output' and/or the U-neutralizing molecular component 'output' according to the U-sensitive genetic circuit design (FIG. 3).

In some embodiments of the U-sensitive genetic circuit, the at least two independently activated or repressed U-sensing genetic molecular components are arranged 'in series' in the U-sensitive genetic circuit. In an 'in-series' AND gate of a U-sensitive genetic circuit, output of the reportable molecular component and/or the U-neutralizing molecular component according to the genetic circuit design requires two or more of the independently activated or repressed U-sensing genetic molecular components to be activated or repressed in temporal succession, wherein the activation or repression of the first independently activated or repressed U-sensing genetic molecular component precedes the activation or repression of the second independently activated or repressed U-sensing genetic molecular component.

The term "in series" as used herein refers to a genetic circuit in which genetic molecular components are connected through biochemical reactions along a single linear circuit path. With regard to Table 1, in an 'in series' AND gate, the temporal sequence of the activation or repression of the independently activated U-sensing genetic molecular components denoted by inputs 'A' and 'B' is such that the second input 'B' is dependent on a prior activation or repression of the first input 'A' in linear succession according to the genetic circuit design.

In exemplary embodiments described herein, an in-series AND gate comprised in a U-sensitive genetic circuit comprises a first U-sensing genetic molecular component comprising a U-sensitive promoter having a 1362 binding site, such as a $P_{1361}$ promoter or a $P_{phyt}$ promoter, and further comprises a UzcRS two component system-dependent promoter, wherein expression of a uzcR and uzcS genes are under the transcriptional control of a U-sensitive promoter comprising a 1362 binding site, such as a $P_{1361}$ promoter or a $P_{phyt}$ promoter (see Example 2).

In some embodiments of the U-sensitive genetic circuit, at least two independently activated or repressed U-sensing genetic molecular components are arranged 'in parallel' in the U-sensitive genetic circuit, herein referred to as an 'in parallel' AND gate. With regard to Table 1, in contrast to the 'in series' AND gate, in an 'in parallel' AND gate, the temporal sequence of inputs 'A' and 'B' is such that a second input 'B' is not dependent on a prior first input 'A' in linear succession, but rather inputs 'A' and 'B' can occur simultaneously. In other words, the term "in parallel" as used herein refers to a genetic circuit in which genetic molecular components are connected through biochemical reactions along more than one circuit path.

In an 'in parallel' AND gate system, output of the reportable molecular component and/or the U-neutralizing molecular component according to the genetic circuit design requires two or more of the independently activated or repressed U-sensing genetic molecular components to be activated or repressed in parallel.

In several embodiments herein described, the in-parallel AND gate comprised in a U-sensitive genetic circuit comprises at least two independently activated or repressed U-sensing genetic molecular components, each comprising a different promoter, (1) a U-sensitive promoter comprising a 1362 direct repeat binding site, such as a $P_{1361}$ or $P_{phyt}$, and (2) a UzcRS-regulated promoter, wherein promoters (1) and (2) act as independently activated or repressed parallel inputs into the U-sensitive genetic circuit, functioning as two independent points of U-sensing in response to their respective U-sensitive transcriptional regulators. In these embodiments, the reportable molecular component output and/or a U-neutralizing molecular component output of the U-sensitive genetic circuit is present only when both of the two independently activated or repressed U-sensing genetic molecular components are activated or repressed according to the U-sensing genetic circuit design.

Thus, in several embodiments, a U-sensitive genetic circuit comprising an 'in parallel' AND gate can provide improved selectivity for U, as output of the reportable molecular component and/or the U-neutralizing molecular component is dependent on two independent points of U-sensing in response to two different U-sensitive transcriptional regulators. Persons skilled in the art will recognize that this also reduces the probability of a false positive output, in the first target range of bioavailable U concentration, such as in response to non-U stimuli (such as Zn or Cu).

Figure 6A:
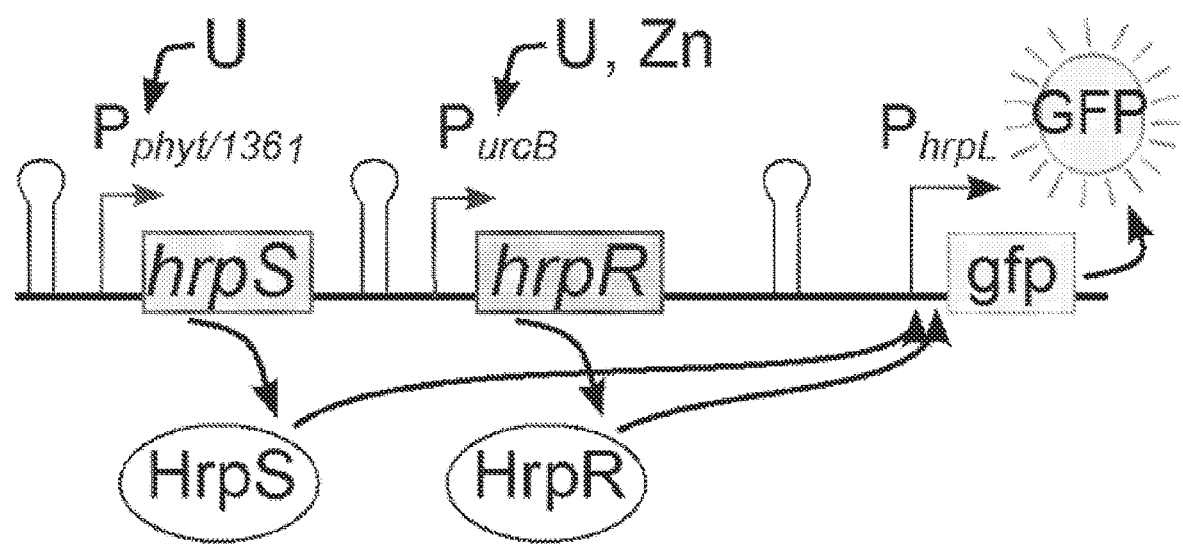
FIG. 6A and FIG. 6B show schematics of two exemplary U-sensitive genetic circuits with 'in parallel' AND gates comprising two points of U-sensing by (1) 1363/1362 two-component system (exemplified by U-sensitive transcriptional regulator direct repeat-containing promoters $P_{phyt}$ or $P_{1361}$) and (2) UzcRS two component system (exemplified by UzcRS-responsive promoter $P_{urcB}$).
Figure 6B:
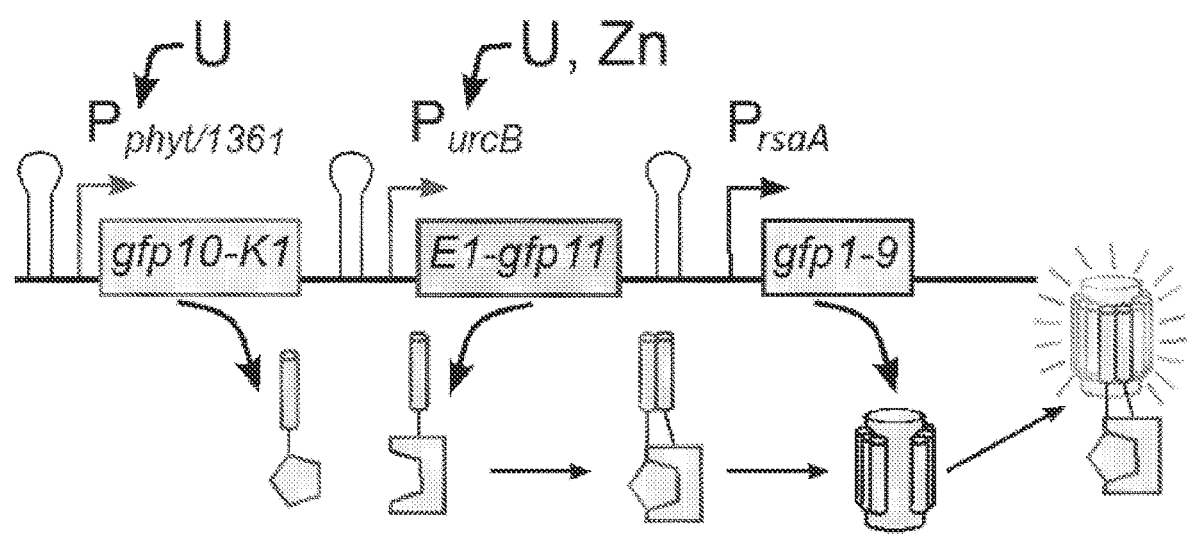
Figure 6C:
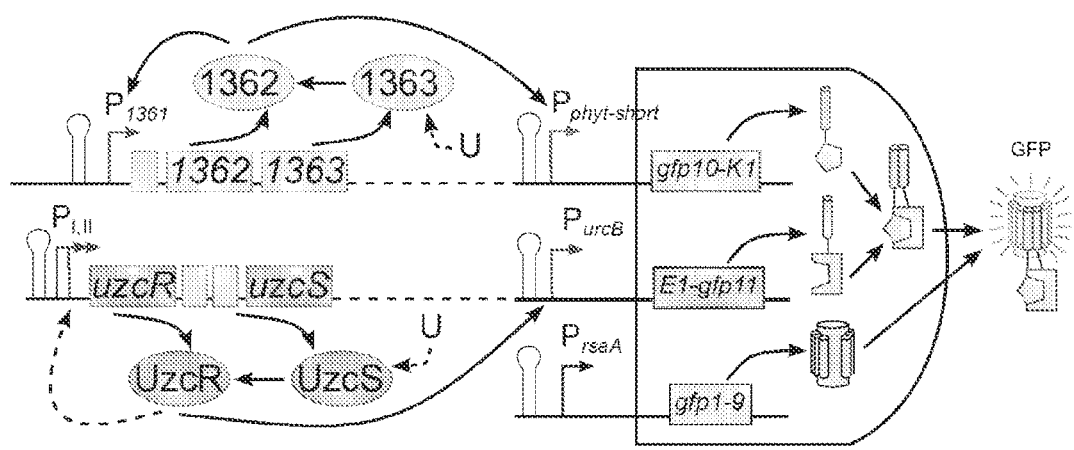
FIG. 6C shows a more detailed version of FIG. 6B, depicting how the two independent U sensing systems are integrated into the AND gate.

In some embodiments described herein, an 'in parallel' AND gate comprises an HRP AND gate. The term "HRP AND gate" as used herein refers to an AND gate system from *Pseudomonas syringae* that was developed in *E. coli* [102]. The HRP AND gate system comprises an orthogonal $\sigma^{54}$ dependent hrpR/hrpS hetero-regulation module from the hrp (hypersensitive response and pathogenicity) system for Type III secretion in *Psuedomonas syringae* [90-92], as described above. In the HRP AND gate system, both HrpS and HrpR are required for $\sigma^{54}$ dependent activation of the hrpL promoter ($P_{hrpL}$) and expression of HrpS or HrpR alone is not sufficient for transcriptional activation. In exemplary embodiments described herein, two different promoters, (1) a U-sensitive promoter comprising a 1362 binding site, such as a $P_{1361}$ or $P_{phyt}$, and (2) a UzcRS-regulated promoter, act as independently activated inputs to initiate the transcription of hrpR and hrpS, respectively, functioning as two independent points of U-sensing in response to their respective U-sensitive transcriptional regulators (FIG. 6 Panel A). In exemplary embodiments described herein, transcription of the output hrpL promoter is activated only when both proteins HrpR and HrpS bind the upstream activator sequence to remodel a closed σ54-RNAP-hrpL transcription complex to an open one through ATP hydrolysis [102]. In an exemplary HRP AND gate described herein, the output shown is GFP reporter expression (FIG. 6 Panel A).

The performance of the HRP AND gate can be described using a Hill function for the promoter steady-state input-output response (transfer function) in the form:

$$f([I]) = k\alpha + [I]^{n1}/(K_1^{n1} + [I]^{n1})) \quad \text{Eq. (1)}$$

where [I] is the concentration of the inducer, such as bioavailable U; $K_1$ and nj are the Hill constant and coefficient, respectively, relating to the promoter-regulator/inducer interaction; k is the maximum expression level due to induction; and a is a constant relating to the basal level of the promoter due to leakage [102] and further in the form:

$$f([R],[S]) = [G]/[G]_{max} = ([R]/K_R)^{nR}([S]/K_S)^{nS}/((1+([R]/K_R)^{nR})(1+([S]/K_S)^{nS})) \quad \text{Eq. (2)}$$

which describes the normalized output of the AND gate as a function of the levels of the two activator proteins ([R] for HrpR, [S] for HrpS) at steady state. $[G]_{max}$ is the maximum activity observed for the output. $K_R$, $K_s$ and $n_R$, $n_s$ are the Hill constants and coefficients for HrpR and HrpS, respectively [102].

In an exemplary HRP AND gate (see Example 3), the expression of hrpS is placed under the control of a U-sensitive promoter comprising a 1362 binding site, such as a $P_{Phyt}$ or $P_{1361}$, while hrpR is placed under the control of $P_{urcB}$, a UzcRS-dependent promoter that has lower basal activity compared to $P_{urcA}$ [3]. In Example 3, the $P_{hrpL}$ promoter regulating gfp expression requires $P_{Phyt}/P_{1361}$ and $P_{urcB}$ to be active to generate a fluorescent signal.

In some embodiments, an 'in parallel' AND gate comprises a tripartite GFP AND gate. As described herein, in the tripartite GFP AND gate system, reporter function is based on tripartite association between two twenty amino-acids long GFP tags, GFP10 and GFP11, which are fused to interacting protein partners, in addition to a complementary GFP1-9 detector. When the interacting protein partners interact, GFP10 and GFP11 self-associate with GFP1-9 to form a functional GFP [5].

In an exemplary tripartite GFP AND gate (see Example 4), expression of a gfp10-K1 fusion gene is placed under control of a U-sensitive promoter comprising a 1362 direct repeat binding site, such as a $P_{phyt}$ or $P_{1361}$, expression of a E1-gfp11 fusion gene is placed under control of a UzcRS-responsive promoter, such as $P_{urB}$, and expression of gfp1-9 is placed under control of a non-U-responsive, strong, constitutively active promoter, $P_{rsaA}$. Thus, in Example 4, assembly and function of tripartite GFP requires both U binding and activation independently of a U-sensitive promoter comprising a 1362 binding site, such as a $P_{phyt}/P_{1361}$ and a UzcRS-responsive promoter.

In some embodiments, an 'in parallel' AND gate system comprises a bacterial two-hybrid AND gate.

In an exemplary bacterial two-hybrid AND gate (see Example 5). In some embodiments, an 'in parallel' AND gate system comprises a FRET sensor AND gate.

In some embodiments, the U-sensitive genetic circuits described herein comprise a combination of two or more 'in series' and/or 'in parallel' AND gates as described herein, wherein the two or more AND gates are connected by activating, inhibiting, binding or converting reactions.

Figure 14:
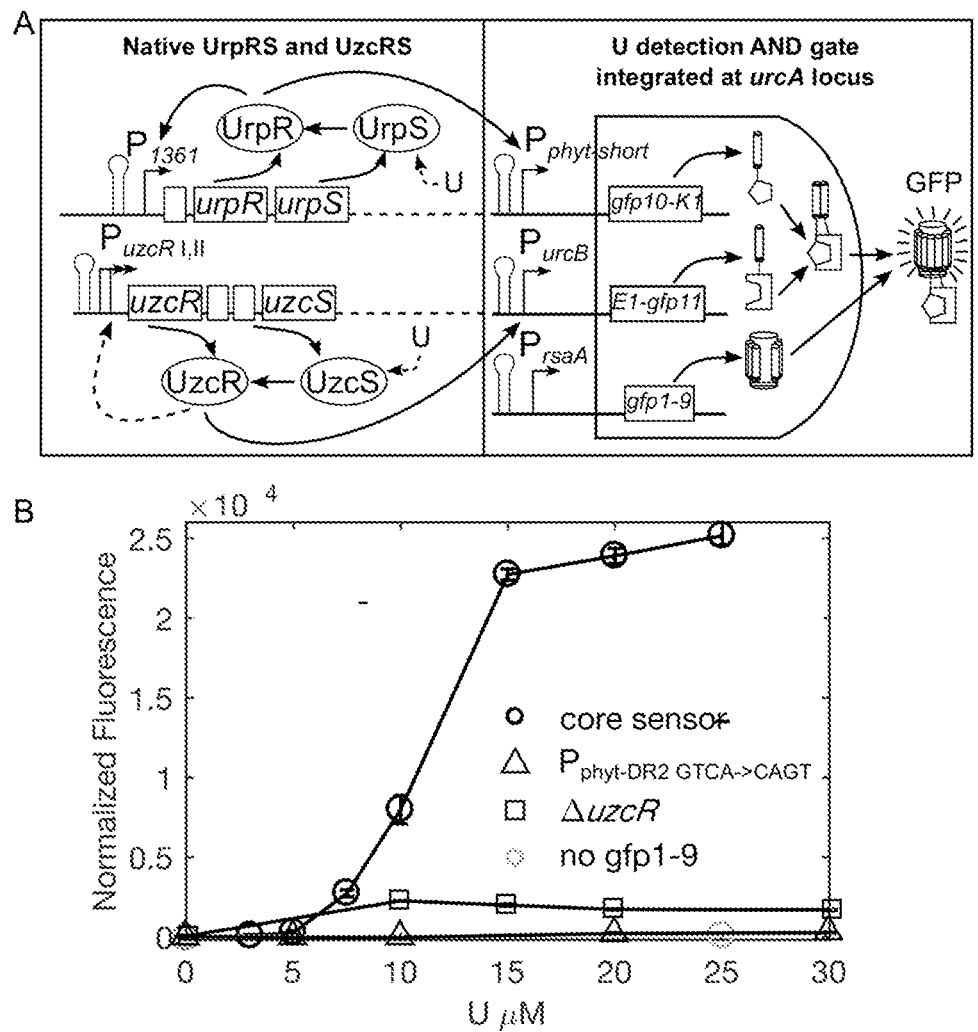
FIG. 14 shows an exemplary embodiment of a U-responsive AND gate design. Panel A shows a schematic of an example of an 'in series' AND gate combined with an 'in parallel' AND gate in a U sensitive genetic circuit. In the exemplary combined circuit, the $P_{urcB}$ promoter in the exemplary 'in parallel' tripartite GFP AND gate is activated by UzcR, and expression of UzcR and UzcS is under transcriptional regulation of $P_{phyt}$ in an 'in series' AND gate. Grey arrows depict regulator modifications made to the base 'in parallel' AND gate to generate the combined 'in series', 'in parallel' AND gate circuit. In the tripartite GFP system, gfp10 subunit is placed under the control of $P_{phyt}$-short, gfp11 is placed under the control of $P_{urcB}$, and gfp1-9 is placed under the control of the Caulobacter S layer promoter, $P_{rsaA}$, which is a strong, constitutive promoter.[4] This genetic circuit was integrated into the chromosomal urcA locus and integrates regulatory input from the native, autoregulatory UzcRS and UrpRS TCS, depicted in the gray box. Panel B shows the fluorescence output profile of the core sensor and control variants lacking critical regulatory components over a range of U concentrations. Error bars represent the average of biological triplicates.

For example, FIG. 14 shows an exemplary combination of an 'in series' AND gate and an 'in parallel' AND gate (see Example 8). In this exemplary embodiment, the exemplary 'in series' AND gate shown in FIG. 4 Panel C and the exemplary 'in parallel' tripartite GFP AND gate shown in FIG. 6 Panel B are connected, such that the $P_{phyt}$-regulated UzcR no longer activates expression of GFP regulated by $P_{1968}$ as in FIG. 4 Panel C, but rather activates expression of E1-gfp11 regulated by $P_{urcB}$ within the tripartite GFP 'in parallel' AND gate. As a result, in the exemplary combined configuration shown in FIG. 14 is that activation of $P_{urCB}$ in the 'in parallel' tripartite GFP AND gate is restricted to U-selective activation of UzcR and UzcS expression by $P_{phyt}$ in the 'in series' AND gate, whereas in the 'in parallel' tripartite GFP AND gate shown in FIG. 6 Panel B $P_{urcB}$ can be activated by U, Zn or Cu. Thus, an advantage of the combination of these exemplary AND gates is increased selectivity for U.

In particular in some embodiments, circuit contains the native uzcRS genes placed under the control of the $P_{phyt}$ promoter—the chromosomal P1 and P2 promoters are swapped with Pphyt as described herein. This could be done by deleting uzcRS and using a plasmid-based system to reintroduce these genes into the circuit. In those embodiments, the circuit leverages the improved selectivity of U over Zn observed in the sensor depicted in FIG. 4 Panel C-A U/Zn ratio of 5.5.

As would be understood by persons skilled in the art, in order for the U-biosensors described herein to operate in response to bioavailable U, the U-sensitive genetic circuits described herein comprise one or more genetic molecular components that are orthogonal to the proteobacteria cell of the U biosensor.

In some embodiments, the circuit components of U-sensing circuit herein described are stably integrated in the host. In some embodiments, the 'in series' AND gate described herein was constructed using the native uzcR and uzcS genes. In some of these embodiments the chromosomal P1 and P2 promoters have been replaced with Pphyt.

Figure 13:
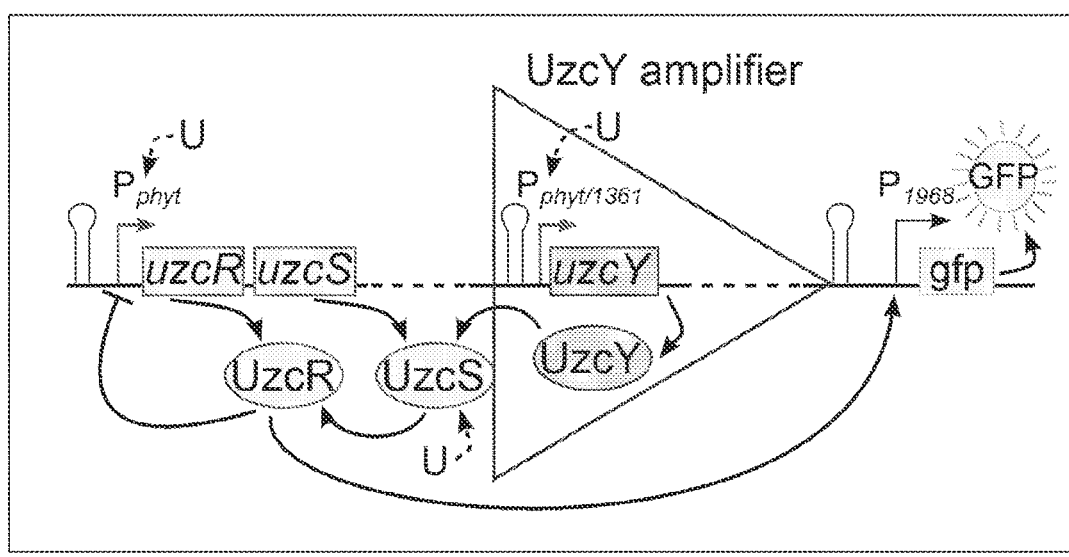
FIG. 13 shows a schematic of an exemplary signal amplifier module incorporated within a U sensing circuit. The signal amplifier uzcY is placed under the control of the U-specific promoters $P_{phyt}/P_{1361}$ such that signal amplification is restricted to conditions of U exposure.

In some embodiments of the U-sensitive genetic molecular components and/or U-sensitive genetic circuit herein described comprising UzcR binding and a UzcRS TCS, the U-sensing genetic molecular component and/or U-sensing genetic circuit can further comprise an amplifier genetic molecular component comprising a U-sensitive promoter and/or a controllable promoter operatively connected to the UzcY and/or UzcZ in a configuration wherein the U-sensitive promoter and/or a controllable promoter directly initiates expression of the amplifier molecular component (see FIG. 13).

The term "UzcY" as used herein indicates a protein having the amino acid sequence:

```
                                        (SEQ ID NO: 33)
MTRDQDTLRMLAEVEAANADLARRAKAPLWYHPALGLLVGALIAVQGQP

TSILLVFYAAYIAGLALLVRAYKRHTGLWVSGYRAGRTRWVALGLATLT

MIGGVIAVWLLRERGLTAAPLIFGAIVAVIVTVGGFVWEAAFRADLRDG

RPL
``` or a sequence that when aligned with sequence SEQ ID NO: 33 has a BLAST score has a BLAST score greater than 50 and less than 100, or preferably greater than 100 and less than 200, or more preferably a BLAST score greater than 200 and a homology with SEQ ID NO: 33 less than 100%, or even more preferably BLAST score of 289 and an homology of 100% with SEQ ID NO: 33.

The term "UzcZ" as used herein indicates a protein having the amino acid sequence:

```
                                        (SEQ ID NO: 34)
MRRGSQPMHAPISATERSTIAQIGGRNAPIGALRAFVTLLVIAHHTVLA

YTPNPPPIGDFSQAPYLWQAFPVRDPQKFELFGLLTLINDLFFMSLMFF

ISGLFVADGLRAKGNGGLLSGRAARLGVPFVLAAGLLAPLAYFPAWLQA

GGDVSIAGFASAWLDLPSWPSGPAWFLWVLLAFGAIVTLLNLIAPGVID

ALGRLVRGADRKPGLFFLGLVIASAVAYIPMSATFTFMHWTQLGPFTVQ

TSRVVHYFVYFLAGVAVGAAGVGQGLTDSEGKLAKRWWAWQAAPILPVV

GVIAVIIMAFSPKPPPRVALDIGGGVMFALACATLSFAALATFLRFVKK

TGPVAASLQANAYGMYLTHYVFTTWLAWLLLPQAWGGLAKGAAVFVGAT

LLSWILTMALRRLPLLGRIL
``` or a sequence that when aligned with sequence SEQ ID NO: 34 has a BLAST score has a BLAST score greater than 200 and less than 475, or preferably greater than 470 and less than 700, or more preferably a BLAST score greater than 700 and a homology with SEQ ID NO: 34 less than 100%, or even more preferably BLAST score of 801 and an homology of 100% with SEQ ID NO: 34.

In particular, in U-biosensors herein described comprising UzcR binding and a UzcRS TCS, the amplifier molecular component acts as a 'genetic signal amplifier' configured to increase an output, e.g. expression or levels of a reportable molecular component and/or a U-neutralizing molecular component at a given bioavailable U concentration, thus enabling more sensitive detection and reporting and/or neutralizing of bioavailable U at lower concentrations.

Genes encoding activators UzcY and UczZ herein described are herein also indicated as uzcY gene or uzcY and uczZ gene or uczZ, respectively as will be understood by a skilled person.

In particular, in some embodiments the U-sensitive genetic circuit comprises one or more amplifier genetic molecular components comprising uzcY gene CCNA_03497 encoding *Caulobacter Crescentus* N100 UzcY (SEQ ID NO: 33) and/or uzcZ gene CCNA_02291 encoding for *Caulobacter Crescentus* N100 UzcZ (SEQ ID NO: 34) under a promoter that can be either a constitutively active promoter or an inducible promoter. In preferred embodiments, the promoter is constitutively active.

In some embodiments the uzcY and/or uzcZ gene are under the transcriptional regulation of a promoter comprising a regulator direct repeat, such as exemplary promoters $P_{phyt}$ or $P_{1361}$. In an exemplary embodiment described herein, the U-sensitive genetic circuit comprises CCNA_03497 placed under the control of $P_{phyt}$ so that U exposure enhances the sensitivity of UzcRS for U (see Example 7).

In some embodiments of the U-sensitive genetic molecular components and/or U-sensitive genetic circuit herein described comprising UzcR binding and a UzcRS TCS, the bacteria are capable of natively expressing endogenous MarR family repressors such as marR1 and/or marR2 genes.

The term "MarR1" as used herein indicates a protein of amino acid sequence:

(SEQ ID NO: 35)
MSAALDPVIHAPNRLQMCCMLAAVDTIDFATVREALDVSESVLSKHVKT

LEEAGYVKVKKAASDGRQRTWLSLSKPGREALKGHLAALKAMMAGVPEA or a sequence that when aligned with sequence SEQ ID NO: 35 has a BLAST score greater than 65 and less than 100, or preferably greater than 100 and less than 150, or more preferably a BLAST score greater than 150 and a homology with SEQ ID NO: 35 less than 100%, or even more preferably BLAST score of 199 and a homology of 100% with SEQ ID NO: 35.

The term "MarR2" as used herein indicates a protein having amino acid sequence:

(SEQ ID NO: 36)
MAPRFDISGLDDVIHGRVRLGIVAYLASAEVADFTELKDVLEVTQGNLSI

HLRKLEEAGYVSIDKSFVGRKPLTRVRLTDTGRAAFSSYLRAMGQLVEQA

GGG or a sequence that when aligned with sequence SEQ ID NO: 36 has a BLAST score has a BLAST score greater than 75 and less than 100, or preferably greater than 100 and less than 150, or more preferably a BLAST score greater than 150 and a homology with SEQ ID NO: 36 less than 100%, or even more preferably BLAST score of 206 and a homology of 100% with SEQ ID NO: 36.

Figure 12:
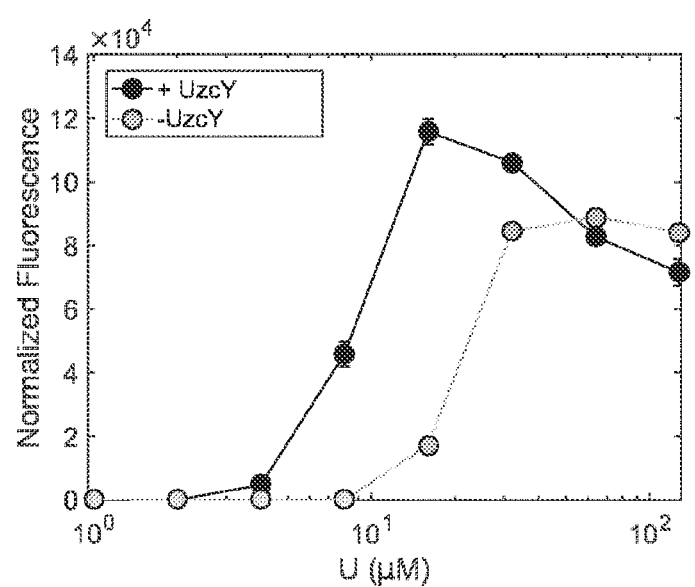
FIG. 12 shows a graph reporting data showing activity of an exemplary native signal amplifier module for UzcRS. The graph shows increase in fluorescence at various U concentrations in a CCNA_03499 mutant (+UzcY) or in wild type cells (-UzcY), relative to conditions in absence of metal. Fluorescence was normalized to cell density ($OD_{600}$).
Figure 26:
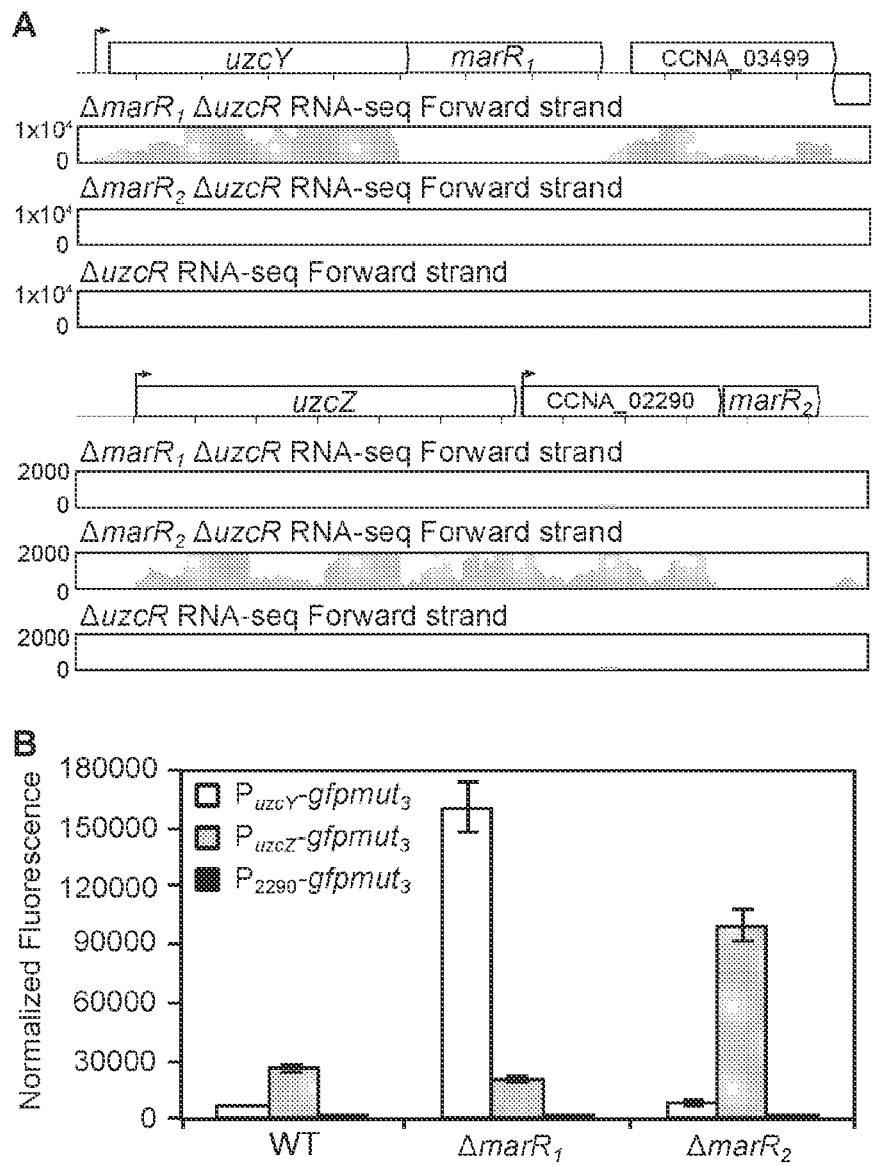
FIG. 26 shows exemplary MarR regulators repressing expression of the membrane proteins UzcY and UzcZ according to some embodiments herein described. Panel (A): Operon diagram and RNA-seq expression profile of the autoregulatory $marR_1$ (top) and $marR_2$ (bottom) operons. The RNA-seq data for a $\Delta marR_1$ ΔuzcR (top), $\Delta marR_2$ ΔuzcR (middle) and ΔuzcR (bottom) is depicted for each operon. The black arrows depict the location of the $P_{UZCY}$ and $P_{UZCZ}$ transcription start sites. Panel (B): Effect of $marR_1$ and $marR_2$ deletions on the expression of the uzcY, uzcZ and CCNA02290 promoters. The Fluorescence of promoter-gfp fusions was quantified at mid-exponential phase and normalized to the $OD_{600}$. Error bars represent the standard deviation of biological triplicates.

In preferred embodiments, of U In particular, in U-biosensors herein described comprising UzcR binding and a UzcRS TCS, wherein the host is capable of natively expressing endogenous MarR family repressors such as marR1 and/or marR2 genes, at least one gene of the endogenous MarR family, preferably all genes of the endogenous MarR family, is knocked out to provide an amplified U-biosensor configured to provide an amplified signal following activation of the U-sensitive genetic circuit (see Example 7 and FIG. 12). In particular, by deleting MarR family repressor, uzcY expression is induced (see FIG. 26), thus leading to the stimulation of UzcS activity and causing a hypersensitive output in response to low metal concentration.

Genes encoding for repressors MarR1 and MarR2 herein described are herein also indicated as marR1 gene or MarR1 and marR2 gene or MarR2, respectively as will be understood by a skilled person.

In some embodiments, wherein the host is *Caulobacter crescentus* NA1000 the protein MarR1 and MarR2 are the protein encoded by marR1 gene CCNA_03498 found in *Caulobacter crescentus* NA1000 (SEQ ID NO: 35) and protein encoded by marR2 gene CCNA_02289 found in *Caulobacter crescentus* NA1000 (SEQ ID NO: 36) respectively.

In some embodiments of the U-sensitive genetic molecular components and/or U-sensitive genetic circuit herein described comprising UzcR binding and a UzcRS TCS, the bacteria are capable of natively expressing an UzcRS Regulating Transporter Atpase aminoPeptidase (herein also urtAP).

In particular, UrtAP is an ATP-binding cassette transporter (ABC transporters) comprising UrtA an ATPase and UrtP a peptidase which contains 13 transmembrane domains and a C-terminal peptidase domain.

The term "UrtA" as used herein indicates a protein encoded by a gene having a protein conding region adjacent in the genome and cotranscribed with urtP, the protein having amino acid sequence:

(SEQ ID NO: 143)
MLIIENLTHVYGNGTRALDEVSLTIPRGMYGLLGPNGAGKSTLMRTIATL

QAPTSGHIRFGDIDVLKHPEELRKTLGYLPQDFGVYPRVSAYDMLDHMAV

LKGISGGKERKATVEHLLNQVNLWDVRKKAIAGFSGGMRQRFGIAQALIG

DPRLIIVDEPTAGLDPEERNRFLNLLAEIGENVVVILSTHIVEDVSDLCP

AMAIICNGAIVREGAPADLVAQLKGRIWKKIIDKAELEAAKARYKVISTR

LLAGRTVIHIESETDPGDGFTAVEGGLEDVYFSTLSSTRSRQAA or a sequence that when aligned with sequence SEQ ID NO: 143 has a BLAST score greater than 250 and less than 500, or preferably greater than 500 and less than 599, and a homology with SEQ ID NO: 143 less than 100%, or even more preferably BLAST score of 599 and a homology of 100% with SEQ ID NO: 143. The term "urtP" as used herein indicates a protein of amino acid sequence:

(SEQ ID NO: 144)
MFGKIAGFELRYQLKSPVFWVVAVIFFLMTFGAATIDQIRIGGGGNIHKN

APYAIAQTHLILAIFYMFVTTAFVANVVVRDDETGFGPILRSTRIRKFDY

LYGRFTGAFLAAAISFLVVPLAIFVGSFMPWVDPERLGPNDLNAYLFSYF

ALALPAILLTSAIFFALATVTRSMMWTYVGVIAFLVLYDIAGIALDRPEY

EKGAALWEPLGTAAFGLATKYWTASERNSLTPPLAGALLFNRVFVLVLAA

GFLALAYSLFRFQSAELSGQRKSAKKTKAAPTEAAPAASGPLPTPVFDRR

TAWAQLVVRTRLDMGQVFKSPAFFVLLFLGLANAMGALWFATEAGRYGGV

VYPVTRILLFPLLGSFGLIPIIIAIYYSGELVWREREKKTHEIIDATPVP

-continued

```
DWAFVAPKTLAISLVLISTLLISVVAAMLSQVFHGYFNFELEKYLLWYVL

PQALDFILLAVLAVFLQTISPHKFIGWALMVIYIVSTITFTNLGFEHKLY

NYGATTETPFSDMNGLGKFWMGAWWLRAYWTAFALVLLVLAYGLWRRGTE

SRLLPRLRRLPLRLNGGAGALMGVSLVAFAGLGGFIYVNTNVWNEYRTNI

DGEKWQAEYEKTLLPFENTPQPKIIAQTLDIDIQPHAPSLETKGSYVLEN

KTGAALKEIHVRFDRDLEVKGLSIEGARPKKTFEKFNYRIFAFDTPMAPG

EQRKMSFITLRAQRGFPNSGAETRVVDNGTFVNNLEIAPILGMSRDGLLT

DRAKRRKYGLPPEQRMAKLGDVSSMQFNGLRKDADFIQSDITVTTVADQT

PIAPGYKVSDSVRNGRRTARFVTEAPIMPFVSIQSARYKVAEETYKGVQL

AVYYDPQHAWNIDRMKTSMKRSLDYMGTNFSPYQFRQLRYQEFPDYAQFA

QSFANTIPWSEGMFFISDYRDPTKIDMVTYVGAHEIGHQWWAHQVIGANQ

QGGAMLSETFAQYSALMVMKHTYGEDQIRKFLKFELDSYLRARGGDVIDE

QPLYKVENQPYIYYRKGSLVMYRLQDQIGEEAVNRALRKLIADHAFKGAP

YPTTLDFMAALRAEAPADKQALITDLFEKITLYDLKTKSAAVKKRADGKF

DVTVVVEAQKKYADGKGKETVAALNETMEIGLFTAKPGDKGFVAKNVVLY

QRRPIRSGENTFTFIVDKAPTFAGIDPYNTVIDRNGDDNTVKVGG
``` or a sequence that when aligned with sequence SEQ ID NO: 144 has a BLAST score greater than 600 and less than 800, or preferably greater than 800 and less than 1200 or greater than 1000 and less than 1200, or more preferably a BLAST score greater than 1200 and less than 2000, or more preferably a BLAST score equal to or higher than 2000 or even more preferably BLAST score of 2436 and a homology of 100% with UrtP sequence from *Caulobacter crescentus* NA1000 or *Caulobacter crescentus* CB15 and in particular with SEQ ID NO: 144.

In preferred embodiments, of U In particular, in U-biosensors herein described comprising UzcR binding and a UzcRS TCS, wherein the host is capable of natively expressing endogenous urtAP, at least one gene of the endogenous urtAP, preferably all genes of the endogenous urtAP, is knocked out to provide an amplified U-biosensor configured to provide an amplified signal following activation of the U-sensitive genetic circuit. In particular, by deleting the endogenous urtAP, it is expected that the UzcRS TCS will be stimulated and exhibit greater uranium sensitivity.

Genes encoding for UrtA and UrtP herein described are herein also indicated as urtA gene or UrtA and urtP gene or UrtP, respectively as will be understood by a skilled person.

Detection of a host capable of expressing endogenous urtAP can be performed by detecting UrtP or urtP as urtA is more conserved as will be understood by a skilled person.

In some embodiments, wherein the host is *Caulobacter crescentus* NA1000 the protein UrtA and UrtP are the protein encoded by UrtA gene CCNA_03681 found in *Caulobacter crescentus* NA1000 (SEQ ID NO: 143) and protein encoded by UrtP gene CCNA_03680 found in *Caulobacter crescentus* NA1000 (SEQ ID NO: 144) respectively.

In some embodiments herein described, a method to provide a U biosensor is provided, the method comprising genetically engineering a bacterial cell capable of natively and/or heterologously expressing histidine kinase 1363 and/or histidine kinase UzcS, and U sensitive response regulator 1362 and/or U sensitive response regulator UzcR, the genetically engineering performed by introducing into the cell one or more U-sensing genetic molecular components configured to report and/or neutralize U herein described, and/or one or more genetic molecular components of the U-sensitive genetic circuits described herein, and optionally operatively connecting one or more of the U biosensors to an electronic signal transducer adapted to convert a U biosensor reportable molecular component output into an electronic output.

Polynucleotide and protein molecules as described herein can be genetically engineered using recombinant techniques known to those of ordinary skill in the art. In particular, in some embodiments, a promoter comprising the U-sensitive 1362 binding site and/or an UzcR binding site can be genetically engineered by introducing into a polynucleotide comprising a promoter DNA sequence a polynucleotide comprising the U-sensitive 1362 binding site and/or a UzcR binding site, as described herein. In other embodiments, a U-sensitive promoter comprising the 1362 binding site and/or a UzcR binding site can be genetically engineered by de novo designing a synthetic promoter DNA sequence comprising the 1362 binding site and/or the UzcR binding site.

Production and manipulation of the polynucleotides described herein are within the skill in the art and can be carried out according to recombinant techniques described, for example, in Sambrook et al. 1989. *Molecular Cloning: A Laboratory Manual,* 2d ed., Cold Spring Harbor Laboratory Press, Cold Spring Harbor, N.Y. [103] and Innis et al. (eds). 1995. PCR Strategies, Academic Press, Inc., San Diego, [104] which are incorporated herein by reference.

It is understood that terms herein referring to nucleic acid molecules such as "polynucleotide" and "nucleotide sequence" comprise any polynucleotides such as DNA and RNA molecules and include both single-stranded and double-stranded molecules whether it is natural or synthetic in origin.

The term "polynucleotide" as used herein indicates an organic polymer composed of two or more monomers including nucleotides, or analogs thereof. The isoelectric point of a polynucleotide in the sense of the disclosure is less than 7 as will be understood by a skilled person. The term "nucleotide" refers to any of several compounds that consist of a ribose or deoxyribose sugar joined to a purine or pyrimidine base and to a phosphate group and that is the basic structural unit of nucleic acids. The term "nucleotide analog" refers respectively to a nucleotide in which one or more individual atoms have been replaced with a different atom or with a different functional group. Accordingly, the term "polynucleotide" includes nucleic acids of any length, and in particular DNA, RNA, analogs and fragments thereof. A polynucleotide of three or more nucleotides is also called "nucleotidic oligomer" or "oligonucleotide". In particular, polynucleotides in the sense of the disclosure comprise biological molecules comprising a plurality of nucleotides. Exemplary nucleic acids include deoxyribonucleic acids, ribonucleic acids, and synthetic analogues thereof, including peptide nucleic acids. Polynucleotides can typically be provided in single-stranded form or double-stranded form and in liner or circular form as will be understood by a person of ordinary skill in the art.

In some embodiments herein described, the polynucleotide is a DNA molecule that can be in a linear or circular form, and encodes one or more proteins under the control of a promoter recognizable by an enzyme such as an RNA polymerase, that is capable of transcribing the encoded DNA.

The term "protein" as used herein indicates a polypeptide with a particular secondary and tertiary structure that can interact with another molecule and in particular, with other biomolecules including other proteins, DNA, RNA, lipids, metabolites, hormones, chemokines, and/or small molecules. The term "polypeptide" as used herein indicates an organic linear, circular, or branched polymer composed of two or more amino acid monomers and/or analogs thereof. The term "polypeptide" includes amino acid polymers of any length including full-length proteins and peptides, as well as analogs and fragments thereof. A polypeptide of three or more amino acids is also called a protein oligomer, peptide, or oligopeptide. In particular, the terms "peptide" and "oligopeptide" usually indicate a polypeptide with less than 100 amino acid monomers. In particular, in a protein, the polypeptide provides the primary structure of the protein, wherein the term "primary structure" of a protein refers to the sequence of amino acids in the polypeptide chain covalently linked to form the polypeptide polymer. A protein "sequence" indicates the order of the amino acids that form the primary structure. Covalent bonds between amino acids within the primary structure can include peptide bonds or disulfide bonds, and additional bonds identifiable by a skilled person. Polypeptides in the sense of the present disclosure are usually composed of a linear chain of alpha-amino acid residues covalently linked by peptide bond or a synthetic covalent linkage. The two ends of the linear polypeptide chain encompassing the terminal residues and the adjacent segment are referred to as the carboxyl terminus (C-terminus) and the amino terminus (N-terminus) based on the nature of the free group on each extremity. Unless otherwise indicated, counting of residues in a polypeptide is performed from the N-terminal end ($NH_2$-group), which is the end where the amino group is not involved in a peptide bond to the C-terminal end (—COOH group) which is the end where a COOH group is not involved in a peptide bond. Proteins and polypeptides can be identified by x-ray crystallography, direct sequencing, immunoprecipitation, and a variety of other methods as understood by a person skilled in the art. Proteins can be provided in vitro or in vivo by several methods identifiable by a skilled person. In some instances where the proteins are synthetic proteins in at least a portion of the polymer two or more amino acid monomers and/or analogs thereof are joined through chemically-mediated condensation of an organic acid (—COOH) and an amine (—$NH_2$) to form an amide bond or a "peptide" bond.

As used herein the term "amino acid", "amino acid monomer", or "amino acid residue" refers to organic compounds composed of amine and carboxylic acid functional groups, along with a side-chain specific to each amino acid. In particular, alpha- or α-amino acid refers to organic compounds composed of amine (—NH2) and carboxylic acid (—COOH), and a side-chain specific to each amino acid connected to an Alpha carbon. Different amino acids have different side chains and have distinctive characteristics, such as charge, polarity, aromaticity, reduction potential, hydrophobicity, and pKa. Amino acids can be covalently linked to form a polymer through peptide bonds by reactions between the amine group of a first amino acid and the carboxylic acid group of a second amino acid. Amino acid in the sense of the disclosure refers to any of the twenty naturally occurring amino acids, non-natural amino acids, and includes both D an L optical isomers.

In some embodiments, the sequence of a polynucleotide encoding a genetic molecular component described herein can be homologous to the polynucleotide sequence of the genetic molecular component described herein. For purposes of the present disclosure, two polynucleotide (RNA or DNA) sequences are substantially homologous when at least 80% (preferably at least 85% and most preferably at least 90%) of the nucleotides match over the defined length of the sequence using algorithms such as CLUSTAL or PHILIP. Sequences that are substantially homologous can be identified in a polynucleotide hybridization experiment under stringent conditions as is known in the art. See, for example, Sambrook et al. [103]. Sambrook et al. describe highly stringent conditions as a hybridization temperature 5-10° C. below the $T_m$ of a perfectly matched target and probe; thus, sequences that are "substantially homologous" would hybridize under such conditions. Stringency conditions can be adjusted to screen for moderately similar fragments, such as homologous sequences from distantly related organisms, to highly similar fragments, such as genes that duplicate functional enzymes from closely related organisms. Generally, stringent conditions are selected to be about 5° C. lower than the thermal melting point (Tm) for the specific sequence at a defined ionic strength and pH. However, stringent conditions encompass temperatures in the range of about 1° C. to about 20° C., depending upon the desired degree of stringency as otherwise qualified herein.

As used herein, "substantially similar" refers to polynucleotides wherein changes in one or more nucleotide bases can result in substitution of one or more amino acids, but do not affect the functional properties of the polypeptide or protein encoded by the nucleotide sequence. "Substantially similar" also refers to modifications of the nucleic acid fragments of the instant disclosure such as deletion or insertion of nucleotides that do not substantially affect the functional properties of the resulting polynucleotide or transcript. It is therefore understood that the disclosure encompasses more than the specific exemplary nucleotide or amino acid sequences and includes functional equivalents thereof. Alterations in a nucleic acid fragment that result in the production of a chemically equivalent amino acid at a given site, but do not affect the functional properties of the encoded polypeptide, are well known in the art.

Methods of alignment of sequences for comparison are well known in the art. Thus, the determination of percent identity between any two sequences can be accomplished using a mathematical algorithm. Non-limiting examples of such mathematical algorithms are the algorithm of Myers and Miller [105], the local homology algorithm of Smith et al. [106]; the homology alignment algorithm of Needleman and Wunsch [107]; the search-for-similarity-method of Pearson and Lipman [108]; the algorithm of Karlin and Altschul [109], modified as in Karlin and Altschul [110].

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters.

As used herein, "sequence homology", "homology", "sequence identity" or "identity" in the context of two nucleic acid or polypeptide sequences makes reference to the nucleotides or residues in the two sequences that are the same when aligned for maximum correspondence over a specified comparison window. When percentage of sequence identity is used in reference to proteins, it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule.

As used herein, "percentage homology" "percentage of sequence identity" means the value determined by comparing two optimally aligned sequences over a comparison window, wherein the portion of the polynucleotide sequence in the comparison window may comprise additions or deletions (gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

As used herein, "reference sequence" is a defined sequence used as a basis for sequence comparison. A reference sequence may be a subset or the entirety of a specified sequence; for example, as a part of a full-length cDNA or partial genomic DNA sequence, or the complete cDNA or gene sequence. A reference sequence can comprise, for example, a sequence identifiable a database such as GenBank and others known to those skilled in the art.

The term "substantial homology" or "substantial identity" of polynucleotide sequences means that a polynucleotide comprises a sequence that has at least 80% sequence identity, preferably at least 85%, more preferably at least 90%, most preferably at least 95% sequence identity compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial homology or identity of amino acid sequences for these purposes normally means sequence identity of at least 80%, preferably at least 85%, more preferably at least 90%, and most preferably at least 95%.

The polypeptides and proteins of the disclosure can be altered in various ways including amino acid substitutions, deletions, truncations, and insertions. Novel proteins having properties of interest can be created by combining elements and fragments of proteins of the present disclosure, as well as with other proteins. Methods for such manipulations are generally known in the art. Thus, the polynucleotides described herein comprise both the naturally occurring sequences as well as genetically engineered forms. Likewise, the proteins of the disclosure encompass naturally occurring proteins as well as variations and modified forms thereof.

It is furthermore to be understood that the polynucleotides of the present disclosure comprise both synthetic molecules and molecules obtained through recombinant DNA techniques known in the art.

The bacterial cells described herein can be genetically engineered using methods known to those skilled in the art. The polynucleotides, genetic molecular components and molecular components comprised in vectors described herein can be introduced into the cells using transformation techniques such as electroporation, heat shock, and others known to those skilled in the art and described herein. In some embodiments, the U-sensitive genetic molecular components and/or genetic molecular components of the U-sensitive genetic circuits are introduced into the organism to persist as a plasmid or integrate into the genome. In some embodiments, the cells can be engineered to chromosomally integrate a polynucleotide comprising one or more U-sensitive genetic molecular components and/or genetic molecular components comprised in the U-sensitive genetic circuits described herein, using methods such as sacB counterselection procedure [111]. For example, in some embodiments described herein, the U-sensitive genetic molecular components or genetic circuit components are inserted into the *Caulobacter* chromosome (see Examples). In some exemplary embodiments, a custom designed low copy vector, such as with a pBBR1 oriV origin and a cat (chloramphenicol acetyltransferase) gene can be used for reporter expression or to introduce the signal amplifier gene (CCNA_03497) (see Examples).

In embodiments herein described, a system is provided. The system comprises a plurality of proteobacterial cells and one or more vectors comprising one or more U-sensitive genetic molecular components and/or one or more genetic molecular components of a U-sensitive genetic circuit. The one or more vectors are configured to introduce one or more U-sensitive genetic molecular components and/or one or more genetic molecular components of a U-sensitive genetic circuit into an Alphaproteobacterial cell.

As understood by those skilled in the art, vectors comprising a U-sensitive genetic molecular components or genetic molecular components such as promoters or RNA- or protein-coding genes described herein or fragments thereof can be engineered using techniques such as In-Fusion cloning and other methods identifiable by those skilled in the art, to generate vectors suitable for genetically engineering the proteobacterial cells described herein. Polynucleotides encoding genetic molecular components such as promoters and genes encoding RNA and proteins described herein can be isolated from genomic DNA or cDNA comprising the polynucleotides of interest, such as polynucleotides isolated from organisms such as *Caulobacter* or other Caulobacteridae, using standard Polymerase Chain Reaction (PCR)-based methods known in the art. Plasmids comprising reporter genes and/or U-neutralizing genes described herein are commercially available from vendors such as Thermo-Fisher and Clontech, and other sources such as Addgene, among others known to those skilled in the art. Polynucleotides can also be designed and synthesized de novo, such as using gBlock synthesis (IDT Technologies) as described herein.

In embodiments herein described, a composition is provided. The composition comprises one or more U biosensors or vectors herein described together with a suitable vehicle.

The term "vehicle" as used herein indicates any of various media acting usually as solvents, carriers, binders or diluents for the one or more U-sensitive genetic molecular components, vectors, or cells herein described that are comprised in the composition as an active ingredient. In particular, the composition including the one or more U-sensitive genetic molecular components, vectors, or cells herein described can be used in one of the methods or systems herein described.

In embodiments herein described, a system comprising an electronic signal transducer adapted to convert a U biosensor reportable molecular component output into an electronic output is provided. The system comprises an electronic signal transducer and one or more U biosensors herein described operatively connected to the electronic signal transducer. In some embodiments, the system comprises an electronic signal transducer and one or more U biosensors herein described comprised in a composition together with a suitable vehicle.

The term "electronic signal transducer" as used herein refers to an electronic device typically comprising a bio-recognition component, a biotransducer component, and an electronic system which can comprise a signal amplifier, processor, data display, and data communicator. Transducers and electronics can be combined, such as in CMOS-based microsensor systems [112, 113].

Figure 41:
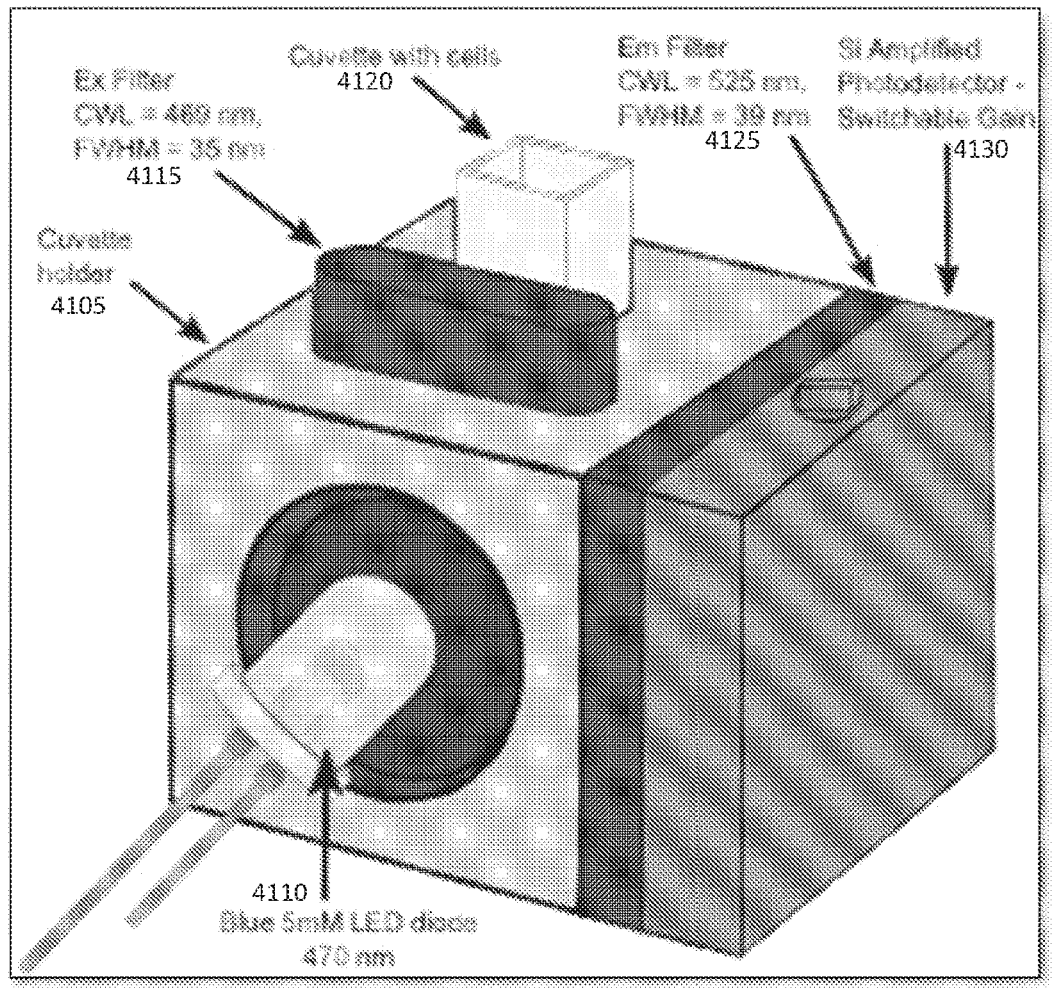
FIG. 41 shows a schematic illustration of an exemplary transducer device configured to convert an optical signal from a biosensor herein described into an electrical current using inexpensive, commercially available components (e.g., a blue LED for excitation, optical filters configured for excitation/emission of GFP, and a photodiode for detection).
Figure 42:
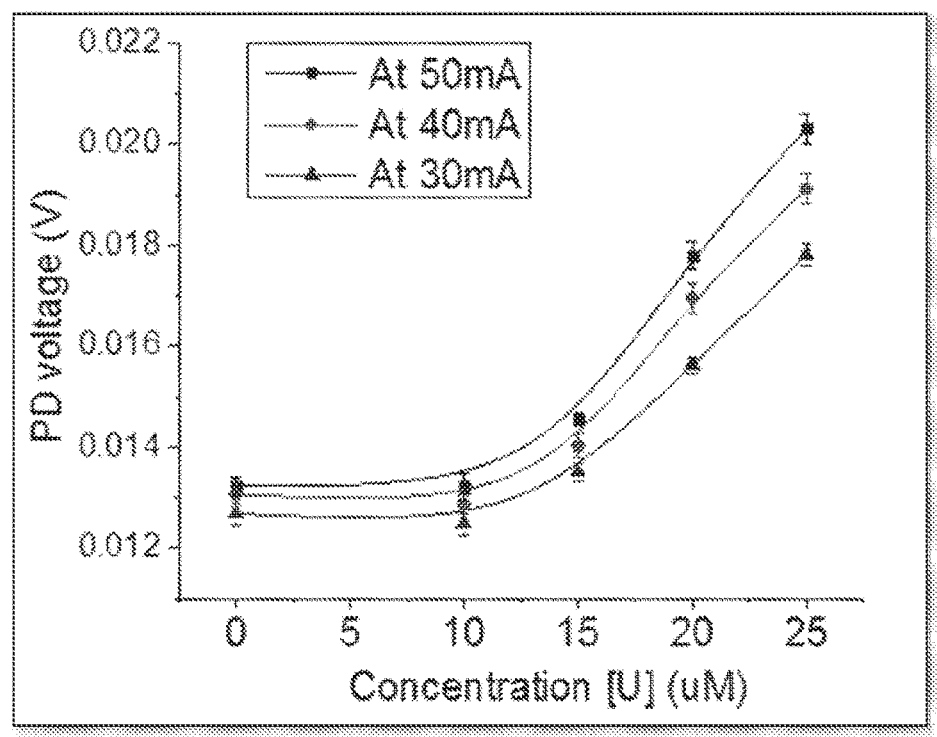
FIG. 42 shows the output voltage as a function of U concentration at three different currents using the exemplary transducer device depicted in FIG. 41. Measurements were taken two hours after uranium exposure.

As shown in FIG. 41, the transducer can be exemplarily fashioned with a blue LED (light emitting diode) (ex. 5 mM, emitting excitation light centered at 470 nm wavelength) 4110 that shines excitation light into a cuvette holder 4105. A curvette holder is a containing device for the filters and curvette, opaque so that the only light in is from the LED and the only light striking the photodetector is the filtered emission light). The blue light passes through an excitation filter (ex filter) 4115 with a center wavelength (CWL) at 469 nm (blue) and a full width at half maximum of 35 nm (narrow bandwidth). This causes a narrow spectrum of excitation light to hit upon the sample in the cuvette 4120. The cuvette is a transparent container for the sample (cells). The emitted light (emission light) from the sample, caused by excitation from the excitation light, passes through an emission filter (em filter) 4125 that has a CWL of 525 nm and a FWHM of 39 nm (a narrow bandwidth of green light). This emission light is read by a silicon amplified photodetector 4130 (with switchable gain for sensitivity control), turning the emission light into an electrical signal for analysis. In some embodiments, the recognition component, often called a bioreceptor, can use biomolecules from organisms or receptors modeled after biological systems to interact with the reportable molecular component output comprising a target analyte of interest. This interaction is measured by the biotransducer which outputs a measurable signal proportional to the presence of the target analyte in the sample. A biotransducer is the recognition-transduction component of the device. In some embodiments, it can comprise a bio-recognition layer and a physicochemical transducer, which acting together converts a biochemical signal to an electronic or optical signal. The bio-recognition layer typically can contain an enzyme or another binding protein such as antibody. For example, polynucleotides, sub-cellular fragments such as organelles (e.g. mitochondria) and receptor carrying fragments (e.g. cell wall), single whole cells, or a plurality of cells optionally on synthetic scaffolds, can also comprise the bio-recognition layer. The physicochemical transducer is typically in contact with the recognition layer. In some embodiments, as a result of the presence and biochemical action of the target analyte of interest, a physico-chemical change is produced within the biorecognition layer that is measured by the physicochemical transducer producing a signal that is proportionate to the concentration of the analyte. The physicochemical transducer can be electrochemical, optical, electronic, gravimetric, pyroelectric or piezoelectric, as understood by those skilled in the art.

In some embodiments, a quantitative, field-portable U biosensor system comprises one or more U biosensors described herein coupled with an electronic signal transducer to convert the cellular output reportable molecular component signal (e.g., fluorescence) into an electronic output signal. In some embodiments, one or more U biosensors described herein are coupled in conjunction with established, inexpensive, commercially available transducer devices known to those skilled in the art, using one of several immobilization methods such as those utilizing carbon nanotubes or nanoparticles to adhere U biosensor host organism cells to the transducer. In particular embodiments, wherein the U biosensor host organism is *C. crescentus*, the holdfast organelle that facilitates irreversible adhesion to surfaces can be used to couple the cells to the electronic signal transducer, eliminating the need for exogenous immobilization substrates.

In embodiments herein described, a method of detecting and reporting and/or neutralizing bioavailable U is provided. The method comprises:

contacting one or more U biosensors, or a system comprising an electronic transducer operatively connected to one or more U biosensors, with a target environment comprising one or more target ranges of bioavailable U concentration for a time and under conditions to detect and report and/or neutralize bioavailable U in the target environment.

In some embodiments, a method to detect bioavailable U with a U-sensing genetic molecular component and/or U sensing genetic circuit genetic including a fluorescent label such as GFP is with a fluorometer to quantify GFP or other fluorophore's fluorescence. This can be accomplished with high sensitivity in the laboratory using a microplate reader or in the field using a mini-fluorometer. In some of those embodiments, the method can comprise adding an environmental sample to a 96-well plate or cuvette containing a U-biosensor herein described.

The term "target environment" as used herein indicates the aggregate of components and related conditions wherein a U biosensor can be operated.

In some embodiments, the target environment comprises a sample obtained from a field site. In some embodiments, the sample is provided by means of an operator, such as a human or a machine, to the host organism optionally operatively connected to the electronic transducer. In other embodiments, the sample is provided, in absence of an operator, to the host organism optionally operatively connected to the electronic transducer. In some embodiments, the host organism, optionally operatively connected to the electronic transducer, can be in situ in a field site comprising the target environment.

In an exemplary embodiment, wherein the host is *Caulobacter crescentus* NA1000 the biosensor is expect to work within a pH range of 6-8, temperature range of ~RT-~37 C. Additional growth nutrients other than inorganic phospate can be added. In some embodiments, the host can be *Caulobacter crescentus* OR37 strain isolated from the Oak Ridge Field site as an environmentally robust host: including a greater pH, heavy metal, and U tolerance with respect to *Caulobacter crescentus* NA1000.

In some embodiments, the reporting of bioavailable U can be observed directly, such as by visualizing the output of a reportable molecular component, such as fluorescence of a reportable molecular component, e.g., GFP, wherein the expression and/or function of the reportable molecular component is activated by the U biosensor. In some embodiments, the reporting of bioavailable U can be observed indirectly and/or remotely, such as through transduction of reportable molecular component output into an electronic output, which can be quantified by a computer, and which can optionally be communicated to a location at a distance from the target environment by a data communicator, either through wired or wireless communication.

Therefore, in several embodiments U biosensors herein described provide selective and sensitive detection and reporting of bioavailable U, a toxic form of U.

In several embodiments, the U biosensors, and related U-sensitive genetic molecular components, genetic circuits, compositions, methods and systems described herein provide a cost-effective, selective, sensitive, portable, easy to use, high-throughput measurement of bioavailable U, with little or no sample preparation required.

Additionally, in some embodiments U biosensors described herein can be used in the construction of consolidated bioremediators comprising bacterial systems that possess all the necessary components for deployment in environmental cleanup efforts. Applications of the U biosensors described herein comprise uses in biodefense (e.g., to be used for non-proliferation purposes), environmental monitoring, and mining (for toxicology and safety concerns), among other uses identifiable by those skilled in the art.

EXAMPLES

The U biosensors, and related U-sensitive genetic molecular components, genetic circuits, compositions, methods and systems herein disclosed are further illustrated in the following examples, which are provided by way of illustration and are not intended to be limiting.

In particular, the following examples illustrate exemplary methods and protocols for providing and using U biosensors, and related U-sensitive genetic molecular components, genetic circuits, compositions, methods and systems. A person skilled in the art will appreciate the applicability and the necessary modifications to adapt the features described in detail in the present section, to additional U biosensors, and related U-sensitive genetic molecular components, genetic circuits, compositions, methods and systems according to embodiments of the present disclosure.

The following methods were used:

Bacterial strains, media, and materials. All strains were derived from wild type *C. crescentus* strain NA1000 (ATCC 19089) and listed in Table 2.

TABLE 2

Strain and Plasmid Table

| Strain or plasmid | Description | Source or reference |
|---|---|---|
| Strains: | | |
| NA1000 | Wild-type *C. crescentus*, a derivative of CB15 capable of being synchronized | [114] |
| JOE2321 | *C. crescentus* CB15N ΔCC_1634 | [115] |
| DMP912 | NA1000 ΔCCNA_01362 (urpR) | Present Disclosure |
| DMP913 | NA1000 ΔCCNA_01363 (urpS) | Present Disclosure |
| DMP470 | JOE2321 $P_{phyt}$-lacZ | Present Disclosure |
| DMP899 | DMP470 CCNA_01362::tn5 (1478156) | Present Disclosure |
| DMP898 | DMP470 CCNA_01362::tn5 (1478165) | Present Disclosure |
| DMP900 | DMP470 CCNA_01362::tn5 (1479640) | Present Disclosure |
| DMP901 | DMP470 CCNA_01362::tn5 (1479738) | Present Disclosure |
| DMP791 | $P_{phyt}$-gfp10_m2_K1, $P_{urcB}$-E1_gfp11_m4, $P_{rsaA}$-gfp1-9 NA1000 ΔuzcR | Present Disclosure |
| DMP213 | NA1000 ΔuzcS | [116] |
| DMP683 | NA1000 $P_{phyt}$-gfp10_m2_K1, $P_{urcB}$_E1_gfp11_m4, $P_{xyl}$-gfp1-9 | [3] |
| DMP804 | NA1000 $P_{phyt}$-gfp10_m2_K1, $P_{urcB}$_E1_gfp11_m4, $P_{rsaA}$-gfp1-9 | Present Disclosure |
| DMP895 | NA1000 $P_{phyt\text{-}short}$-gfp10_m2_K1, $P_{urcB}$-E1_gfp11_m4, $P_{rsaA}$-gfp1-9 | Present Disclosure |
| DMP877 | NA1000 $P_{phyt}$-gfp10_m2_K1, $P_{urcB}$-E1_gfp11_m4, $P_{phyt\text{ }short}$-gfp1-9 | Present Disclosure |
| DMP911 | NA1000 $P_{urcB}$-gfp10_m2_K1, $P_{urcB}$-E1_gfp11_m4, $P_{rsaA}$-gfp1-9 | Present Disclosure |
| DMP994 | NA1000 $P_{phyt}$-gfp10_m2_K1, $P_{1361}$-E1_gfp11_m4, $P_{rsaA}$-gfp1-9 | Present Disclosure |
| DMP863 | NA1000 ΔCCNA_03498-3499 | Present Disclosure |
| DMP993 | DMP863 $P_{phyt\text{-}short}$-gfp10_m2_K1, $P_{urcB}$-E1_gfp11_m4, $P_{rsaA}$-gfp1-9 | Present Disclosure |
| DMP1009 | DMP863 $P_{phyt\text{-}short}$-CCNA_03497, $P_{phyt\text{-}short}$-gfp10_m2_K1, $P_{urcB}$-E1_gfp11_m4, $P_{rsaA}$-gfp1-9 | Present Disclosure |
| DMP1011 | NA1000 ΔuzcR $P_{phyt\text{-}short}$-gfp10_m2_K1, $P_{urcB}$_E1_gfp11_m4, $P_{rsaA}$-gfp1-9 | Present Disclosure |
| DMP910 | NA1000 $P_{phyt}$-DR1 GTCA->CAGT-gfp10_m2_K1, $P_{urcB}$-E1_gfp11_m4, $P_{rsaA}$-gfp1-9 | Present Disclosure |
| Plasmids: | | |
| VMCS2::Tn5Pvan | Contains the transposon Tn5Pvan | [117] |
| pNPTS138 | Non-replicating vector for integration and allelic replacement; oriT, kan (Km$^R$), sacB | M. R. K. Alley, unpublished |
| pDMP450 | Cat gene from pR9TT and pBBR ori and rep from pPROBE'-gfp[LVA], $P_{mrC}$-gfp mut$_3$ | Unpublished |
| pDMP460 | $P_{phyt}$-gfp mut$_3$ | Present Disclosure |
| pDMP463 | $P_{1361}$-gfp mut$_3$ | Present Disclosure |
| pDMP745 | $P_{phyt}$-DR2 GTCA->CAGT- gfpmut$_3$ | Present Disclosure |
| pDMP746 | $P_{phyt\text{-}short}$-gfpmut$_3$ | Present Disclosure |
| pDMP747 | $P_{1361}$- DR2 GTCA->CAGT-gfpmut$_3$ | Present Disclosure |
| pDMP786 | $P_{phyt}$ -DR1 GT->CA-gfpmut$_3$ | Present Disclosure |
| pDMP787 | $P_{phyt}$ -DR2 GT->CA-gfpmut$_3$ | Present Disclosure |
| pDMP788 | $P_{1361}$-DR2 GT->CA-gfpmut$_3$ | Present Disclosure |
| pDMP789 | $P_{1361\text{-}short}$-gfpmut$_3$ | Present Disclosure |
| pDMP1118 | pET52b-urpR | Present Disclosure |
| DMP791 | Pphyt-gfp10_m2_K1, PurcB_E1_gfp11_m4, PrsaA-glp1-9 | Present Disclosure |
| pDMP82 | pNPTS138 $P_{urcA}$-lacZ | [3] |
| pDMP82 | pNPTS138 $P_{urcA}$-lacZ | [3] |
| pDMP792 | pNPTS138-$P_{phyt}$-gfp10_m2_K1, $P_{urcB}$-E1_gfp11_m4, $P_{rsaA}$-gfp1-9 | Present Disclosure |
| pDMP883 | pNPTS138-$P_{phyt\text{-}short}$-gfp10_m2_K1, $P_{urcB}$-E1_gfp11_m4, $P_{rsaA}$-gfp1-9 | Present Disclosure |
| pDMP664 | pNPTS138-$P_{phyt}$-gfp10_m2_K1, $P_{urcB}$_E1_gfp11_m4, $P_{xyl}$-gfp1-9 | Present Disclosure |
| pDMP712 | $P_{phyt}$-gfp10_m2_K1, $P_{urcB}$_E1_gfp11_m4, $P_{xyl}$-gfp1-9 | Present Disclosure |
| pDMP932 | pNPTS138-$P_{urcB}$-gfp10_m2_K1, $P_{urcB}$-E1_gfp11_m4, $P_{rsaA}$-gfp1-9 | Present Disclosure |

TABLE 2-continued

Strain and Plasmid Table

| Strain or plasmid | Description | Source or reference |
|---|---|---|
| pDMP952 | pNPTS138-$P_{phyt}$-gfp10_m2_K1, $P_{1362}$-E1_gfp11_m4, $P_{rsaA}$-gfp1-9 | Present Disclosure |
| pDMP808 | pNPTS138-$P_{phyt}$-gfp10_m2_K1, $P_{phyt}$-E1_gfp11_m4, $P_{phyt-short}$-gfp1-9 | Present Disclosure |
| pDMP1113 | pNPTS138-$P_{phyt}$-CCNA_03497 | Unpublished |
| pDMP1114 | pNPTS138-$P_{phyt-short}$-CCNA_03497 | Present Disclosure |

Cell growth and fluorescence characterization experiments were performed in modified M5G medium (10 mM PIPES, pH 7, 1 mM NaCl, 1 mM KCl, 0.05% $NH_4Cl$, 0.01 mM Fe/EDTA, 0.2% glucose, 0.5 mM $MgSO_4$, 0.5 mM $CaCl_2$)) supplemented with 5 mM glycerol-2-phosphate as the phosphate source (M5G-G2P) to facilitate uranium solubility at the start of growth assays. U stocks were prepared in nitric acid as previously described [118]. A 10,000 ppm $ThCl_4$ stock was prepared in 5% nitric acid. 50-100 mM stock solutions of $Pb(NO_3)_2$, $NiSO_4$, $ZnCl2$, $CuSO_4$, $CaCl_2$), $MnCl_2$, $MgSO_4$, $K_2CrO_4$, $Na_2SeO_3$, $FeCl_3$, $CoCl_2$, $FeSO_4$, $NaAsO_2$ were prepared in Milli-Q $H_2O$ and a 1 g $l^{-1}$ $AlCl_3$ ICP-MS standard in HCl was used for Al addition. All strains were grown at 30° C. with shaking at 220 RPM in Erlenmeyer flasks or at 1000 RPM in 96-well plates in a PHMP-4 Thermoshaker (Grant Instruments). Strain manipulation was performed in PYE medium, containing 0.2% (wt/vol) Bacto peptone (Difco), 0.1% yeast extract (Difco), 1 mM $MgSO_4$, and 0.5 mM $CaCl_2$) and appropriate antibiotics. *Escherichia coli* HST08 (Clontech) was used for cloning following standard procedures.

Clean deletions and site-directed mutagenesis. In frame deletions of CCNA_01362 and CCNA_01363 were obtained by a two-step sacB counterselection procedure [119] as described previously[l3] using the primers depicted in Table 3.

TABLE 3

Primers and qblocks

| Primer name | Primer sequence | SEQ ID NO |
|---|---|---|
| Phyt-138_F | TAACCCTTTGCAAACCGGACGGTGACCGGCAAAC | 145 |
| Phyt-138_R | GATGAACTTGCGCATGGCGGAGCCCCTCGTTTTc | 146 |
| 138_PurcA_F | ATGCGCAAGTTCATCATGAGCC | 147 |
| 138_PurcA_R | GTTTGCAAAGGGTTAATCGACGCC | 148 |
| pNTPS138_urcR_F | gGAACGATAGCGCCGGACGGTGACCGGCAAAC | 149 |
| pNTPS138_urcR_R | CGCACAAAATCCTCATCCTGAGC | 150 |
| BamHI_Pphyt_F | GACGGATCCCGGACGGTGACCGGCAAAC | 151 |
| EcoRI_Pphyt_R | GACGAATTCCCTCGTTTTcatGTCTCGCAGCTAGC | 152 |
| BamHI_P1362 | GACGGATCCGAACGATAGCGCCGCCTGC | 153 |
| EcoRI_P1362 | GACGAATTCGGAAAGATCGGGACTGGGTGATGGCGCTTAGGATTCCACAG | 154 |
| Pphyt_EMSA_R | CGTTTTcatGTCTCGCAGCTAGC | 155 |
| 1362_gene_F | CTCTTTCAGGGACCCTTGATGCGCGCGCTCGTC | 156 |
| 1362_gene_R_GC | CACCAGAGCGAGCTCTCACGCCGTCCCGCCGGC | 157 |
| pET52_F | GAGCTCGCTCTGGTGCCAC | 158 |
| PET52_R | GGGTCCCTGAAAGAGGACTTCAAG | 159 |
| urcR_UR_F | caattgaagccggctCAGAAGGTCGACGCCCTGG | 160 |
| urcR_UR_R | CGCACAAAATCCTCATCCTGAGC | 161 |
| Pphyt_urcR-loc_F | gGAACGATAGCGCCGGACGGTGACCGGCAAAC | 162 |
| Pphyt_urcR-loc_R | AATCAGAATGCGcatGGCGGAGCCCCTCG | 163 |
| Pphyt-uzcR_vect_F | atgCGCATTCTGATTATCGAGGACG | 164 |
| Pphyt-uzcR_vect_R | CGGCGCTATCGTTCcctagg | 165 |
| Pphyt_rsaFb_F | GTGAAAAAAGCTTAACTCGAGGGGCTCCGCCatgC | 166 |

TABLE 3-continued

Primers and qblocks

| Primer name | Primer sequence | SEQ ID NO |
|---|---|---|
| Pphyt_rsaFb_R | TTAAGCTTTTTTCACGCAGTCTCGCAGCTAGCTTAGCCG | 167 |
| P1362_rsaFb_F | GTGAAAAAAGCTTAACTCCGAGCTCCCTAACTAACTAAtcATCT | 168 |
| P1362_rsaFb_R | TTAAGCTTTTTTCACGCAGTGATGGCGCTTAGGATTCCACAG | 169 |
| gfp19_amp_for_pxyl_F | tggggagacgaccaTATGCGTAAGGGCGAAGAGCTG | 170 |
| gfp19_amp_for_pxyl_R | cacggctggctgcagGCCGAATTTCAGGGGTACAGCA | 171 |
| Pphyt_TR_elim_F | GATCCCGGGGATTTCTCTTCGCGCCACC | 172 |
| Pphyt_promoter_shorten_R | GAAATCCCCGGGATCCCTGTGCTCTAGA | 173 |
| XbaI_PurcB | GACTCTAGACGAAGACTGGGCGGGCAG | 174 |
| BglII_PurcB_R | GACAGATCTCGGTTTGGGTGGTCGCTTGG | 175 |
| PrsaA_frag_F | TtgtcgacgtatgacgtttgctctatAGC | 176 |
| PrsaA_frag_R | CGTTCACATCGCCATCCAGCTC | 177 |
| gfp_for_PrsaA_F | ATGGCGATGTGAACGGCCATAAG | 178 |
| gfp_for_PrsaA_R | gtcatacgtcgacaaGCCGAATTTCAGGGGTACAGCA | 179 |
| Pphyt_SD_amp_R | ATGTTTTTCCTCCTTATAAAGTAGATCTTTAGTTAGTTAGGG | 180 |
| gfp1-9_for_pphyt-short_F | AAGGAGGAAAAACATATGCGTAAGGGCGAAGAGCTG | 181 |
| gfp1-9_for_phyt_R | GAAATCCCCGGGATCGCCGAATTTCAGGGGTACAGCA | 72 |
| urcA_loc_DR_F | GGTCGCTACCATTACCAGTTGGTC | 182 |
| urcA_loc_UR_R | TGCTTGGGTCGTTTGAGTATATGGT | 183 |
| HRP_chrom_int_F | CAAACGACCCAAGCAGGTGTCGCCCTTCGCTGAAC | 184 |
| HRP_chrom_int_R | GTAATGGTAGCGACCCCAAGCTCAGCTAATTAAGCCTCGAG | 185 |
| PurcA_UR_F | ggctggcgccaagctTGGCCGGCCGCACGCAAGGGCAGA | 186 |
| PurcA_UR_R | TTATTTTTGACACCAGACCAACTGG | 187 |
| PurcA_DR_F | TGGTGTCAAAAATAATCGCACAGGCGACCGC | 188 |
| PurcA_DR_R | gcgaattcgtggatcCAGGCGTCGAGGTGAAGTA | 189 |
| kan_elim_F | ATTCTTCCTTTTTCAATATTATTGAAGCATTTATCAG | 190 |
| kan_elim_R | AAGCTTAATAAGATGATCTTCTTGAGATCG | 191 |
| KpnI_P1362 | GACggtaccGAACGATAGCGCCGCCTGC | 192 |
| AvrII_P1362 | GACcctaggGGAAAGATCGGGACTGGGTGATGGCGCTTAGGATTCCACAG | 193 |
| 3497_for_Pphyt_plas_F | GGAAGATCTACTTTATAAGGAGGAAAAACATATGACCCGAGACCAAGACAC | 194 |
| 3497_for_Pphyt_plas_R | GACCTCGAGTCATAGGGGGCGTCC | 195 |

TABLE 3-continued

Primers and gblocks

| Primer name | Primer sequence | SEQ ID NO |
|---|---|---|
| 3497_for_Pphyt_short_chrome_R | TCATAGGGGGCGTCCGTCG | 196 |
| Pphyt_short_for_chrom_3497 | GGGATTTCTCTTCGCGCCACC | 197 |
| Chrome_3497_vect_amp_F | GGACGCCCCCTatgAGCG | 198 |
| chrome_vector_amp_R | GCGAAGAGAAATCCCATCATCGCCAGCCCTAGCG | 199 |
| Tripartite GFP gblock* | CAGAGATCTACTTTATAAGGAGGAAAAACATATGG ATCTGCCCGACGATCATTACCTGTCCACCCAGACC ATCCTGTCGAAGGATCTGAATGGCACCGACGTGGG CTCCGGTGGCGGGAGTGGTGGTGGCGGGAGCAAGG TCTCCGCCCTCAAGGAGAACGTTAGCGCCCTGAAA GAGAAAGTCTCGGCCCTGACCGAAAAGGTCTCCGC CCTTAAGGAAAAGGTGAGCGCTCTCAAAGAGTAAc caggcatcaaataaaacgaaaggctcagtcgaaag actgggcctttcgttttatctgttgtttgtcggtg aacgctctctactagagtcacactggctcaccttc gggtgggcctttctgcgtttataggtaccCGAAGA CTGGGCGGGCAGCAGCCCACTCCCAAGCGCCCACC AATTATGACTTCTTTTTCATAGACTTAATTCGACG TCATGAAGCAGTCGTAACGGGTGTTCGCCATCCGA CCGCTCTACATCCTCGATCAACGGATCGCCAAGCG ACCACCCAAACCGcctaggtaactaaagattaact ttataaggaggaaaaacatATGAAGGTCTCCGCCC TTGAAAATGAGGTCTCGGCTCTCGAAAAGGAGGTG TCGGTCCTGGAGAAAGAAGTCAGCGCGCTTGAGAA GGAGGTCCGTGCCCTGGAGAAGAGTGGCGGTGGGG GGTCTGGGGGCGGTTCTGGGGGCGGCTCCACCTCG GAGAAGCGTGACCACATGGTGCTGCTCGAATATGT CACCGCCGCCGGGATCACCGATGCCTCCTAAgact cctgttgatagatccagtaatgacctcagaactcc atctggatttgttcagaacgctcggttgccgccgg gcgttttttattggtgagaatGAAAAATGCTGTAC CCCTGAAATTCGGCTAttgtcgacgtatgacgttt gctctatagccatcgctgctcccatgcgcgccact cggtcgcaggggtgtgggatttttttgggagAC AATCCTCATGCGTAAGGGCGAAGAGCTGTTCACGG GCGTCGTCCCCATCCTCATCGAGCTGGATGGCGAT GTGAACGGCCATAAGTTCTTCGTCCGTGGGGAAGG CGAGGGGGATGCCACCATCGGCAAGCTGAGCCTCA AGTTCATCTGCACCACCGGCAAGCTCCCGGTCCCC TGGCCGACGCTCGTCACGACCCTCACCTACGGGGT GCAGTGCTTTTCCCGTTACCCCGACCACATGAAGC GGCACGACTTCTTTAAGTCGGCCATGCCCGAAGGC TACGTGCAGGAGCGCACCATCTATTTTAAGGACGA TGGCACGTATAAGACCCGCGCGGAGGTCAAGTTCG AAGGGGATACCCTGGTCAACCGTATCGAGCTGAAG GGCATCGACTTTAAGGAAGATGGCAACATCCTCGG GCACAAGCTCGAATATAATTTTAACTCCCATAAGG TCTACATCACCGCCGACAAGCAAAACAACGGCATC AAGGCGAACTTTACGATCCGTCACAATGTGGAGGA CGGCAGCGTCCAGCTCGCGGATCATTATCAACAGA ATACCCCCATCGGCGATGGTCCCGTCCTCCTCCCG TAGCTCGAGATT | 200 |

*Synthesized (Integrated DNA Technologies, gBlock) with the following components listed in 5' to 3' orientation: promoterless gfp10-m2_k1(bolded), rrnBT1 and T7Te transcription terminators (BBa_B0015; (lowercase)), P̄$_{urcB}$ (uppercase)-untraslated region and RBS (lowercase) E1-gfp11-M4(bolded), lamda T$_0$ terminator (lowercase), the rsaA promoter (P$_{rsaA}$[4]; lowercase) controlling expression of gfp 1-9 (bolded). This DNA region is visually depicted in FIG. 31.

Site-directed mutagenesis was performed by amplifying the entire plasmid with the primer sets listed in Table 3. Chromosomal integration and counter selection were performed as described above, and successful substitutions were confirmed by sequencing.

Transposon screen for regulators of P$_{phyt}$. A chromosomally integrated P$_{phyt}$-lacZ fusion was constructed using the two-step sacB counterselection procedure[111] to swap the P$_{urcA}$ promoter in pDMP82[3] with P$_{phyt}$. To accomplish this, a P$_{phyt}$ fragment was amplified from the C. crescentus genome with the primer pair Phyt-138_F/Phyt-138_R (Table 3) and cloned into pDMP82 that was linearized using the primers 138_P$_{urcA}$_F and 138_P$_{urcA}$_F using In-Fusion cloning. The P$_{phyt}$-lacZ fusion was integrated at the chromosomal urcA locus in lacA mutant strain JOE2321, yielding strain DMP470. For the transposon screen, DMP470 was electroporated with VMCS2::Tn5Pvan[117] and plated onto PYE agar plates containing 25 μg ml$^{-1}$ kanamycin. ~12,000 colonies were scraped into a PYE master solution that was frozen and stored at –80° C. The Transposon library was diluted and spread on M5G-G2P agar containing 40 µg ml$^{-1}$ Xgal and 25 µM uranyl nitrate, yielding a total of ~36,000 colonies. Colonies exhibiting a white colony phenotype were selected and nested semi-arbitrary PCR was used to map the location of each transposon as described previously. [117]

Construction of promoter-gfp transcriptional fusions. Plasmid-borne $P_{phyt}$-gfp and $P_{1361}$-gfp fusions were generated by amplifying $P_{phyt}$ and $P_{1361}$ fragments from the Caulobacter genome with the primer pairs BamHI_Pphyt_F/EcoRI_Pphyt_R and BamHI_P1362/EcoRI_P1362, respectively, digested with BamHI and EcoRI and cloned into the similarly digested pDMP450, generating pDMP460 and pDMP463. The promoter-gfp fusions were shortened and/or mutated by amplifying pDMP460 and pDMP463 with the primer pairs described in Table 3 and re-ligating using infusion cloning.

Tripartite GFP AND gate sensor construction. A gblock (Tripartite GFP gblock; Table 6) was synthesized (Integrated DNA Technologies, gBlock) with the following components listed in 5' to 3' orientation: promoterless gfp10-m2_k1, rrnBT1 and T7Te transcription terminators (BBa_B0015), $P_{urcB}$-E1-gfp11-M4, lamda To terminator, and gfp1-9 under the control of the rsaA promoter ($P_{rsaA}$[4]). gfp10-m2_k1 was placed under the control of $P_{phyt}$ by digesting the Tripartite GFP gblock with BglII and XhoI and ligating into the similarly digested pDMP460 to form pDMP791. DNA sequence encompassing the entire tripartite DNA and an insulating upstream rrnbT1 transcription terminator was amplified with primers HRP_chrome_int F and HRP_chrome_int R and cloned into pDMP82 that was amplified with the primers urcA_loc_DR_F and urcA-loc_UR_R using infusion cloning to form pDMP792. A variant containing GFP10-m2_k1 under the control of a shortened version of $P_{phyt}$ (i.e., the core sensor) was constructed by amplifying pDMP792 with Pphyt_TR_elim_F and Pphyt_promoter_shorten_R and re-ligating using infusion cloning, forming pDMP883. A variant of this AND gate containing gfp1-9 under the control of the xylose inducible promoter ($P_{xyl}$ [6]) was constructed by amplifying the 360 bp $P_{xyl}$ fragment using Pxyl_F and Pxyl_R and cloning into pDMP792 that were amplified with gfp1-9_amp_for_pxyl_F gfp1-9_amp_for_pxyl_R using infusion cloning to form pDMP664. All tripartite GFP AND gate variants were then integrated into the chromosomal urcA locus using a two-step sacB counterselection procedure,[120] forming DMP804, DMP895, and DMP683

A control tripartite variant containing both GFP10-m2_k1 and E1-GFP11-M4 under the control of $P_{urcB}$ was constructed by directionally cloning a $P_{urcB}$ fragment, generated with primers XbaI_PurcB and BglII_PurcB_R and digested with XbaI and BglII, into the similarly digested pDMP712. Similarly, a tripartite variant containing both GFP10-m2_k1 and E1-GFP11-M4 under the control of UrtAP was constructed by directionally cloning a $P_{1362}$ fragment, generated with primers KpnI_P1362 and AvrII_P1362 and digested with KpnI and AvrII, into the similarly digested pDMP712. Both control AND gates were cloned into the pNPTS138 double recombination plasmid by amplifying with primers HRP_chrome_int F and R and cloning into pDMP82 that was amplified with the primers urcA_loc_DR_F and urcA-loc_UR_R using Infusion cloning. Finally, the $P_{xyl}$ promoter in both constructs was swapped for $P_{rsaA}$ by cloning $P_{rsaA}$, amplified with PrsaA_frag_F and PrsaA_frag_R, into the template vectors that were linearized with the primers gfp_for_PrsaA_F and gfp_for_PrsaA_R, forming pDMP932 and pDMP952. These tripartite GFP AND gate variants were then integrated into the chromosomal urcA locus using a two-step sacB counterselection procedure,[120] to form DMP911 and DMP994.

A U sensing AND gate strain (DMP993) with constitutive UzcY expression was generated by integrating the core sensor (pDMP 883) into the urcA locus of a strain deleted for CCNA_03498 and CCNA_03499 (DMP863). UzcY expression was restricted to conditions of U exposure by placing uzcY expression under the control of $P_{phyt\text{-}short}$ as follows. uzcY was amplified from the C. crescentus chromosome with primers 3497_for_Pphyt_plas_F and 3497_for_Pphyt_plas_R, digested with BglII and XhoI, and cloned into the similarly digested pDMP746. The DNA containing the $P_{phyt\text{-}short}$-CCNA_03497 fusion was then amplified with 3497_for_Pphyt_short_chrome_R and Pphyt_short_for_chrom_3497 and cloned into pDMP1113 that was linearized using the primers chrome_3497_vect_amp_F and chrome_vector_amp_R to The resulting suicide vector (form pDMP1114) was used to integrate $P_{phyt\text{-}short}$-uzCY into DMP993 to form DMP1009.

Metal induction experiments. Unless otherwise specified, all metal induction experiments were performed with M5G-G2P. Cells were grown to early-exponential phase, washed once with M5G-G2P, and then resuspended in the same volume of fresh M5G-G2P. Washed cells were added in 195 µl aliquots to black 96-well clear bottom plates containing 5 µl of the appropriate metal solution. Cell fluorescence and $OD_{600}$ were determined using a Biotek plate reader (Ex: 480/Em: 516) 2-3 hours post-metal exposure. The mean fluorescence and $OD_{600}$ value for each data point was subtracted by the respective values for a M5G-G2P blank and then the fluorescence was normalized to the $OD_{600}$. The relationship between the U concentration and the GFP output rate was modeled using a Hill function:

$$y = y_{min} + \frac{Y_{max} - Y_{min}}{1 + \left(\frac{x}{K}\right)^\eta}$$

where $y_{min}$ represents basal normalized fluorescence, $y_{max}$ is the maximum normalized fluorescence, x represents the U concentration, $\eta$ is the Hill coefficient, and K is the concentration of U required for half maximal fluorescence expression. The best fit values were found by using the lsqcurvefit function in Matlab.

Cloning, overexpression, and purification of Strep-UrpR. urpR was amplified with primers 1362_gene_F and 1362_gene_R_GC and cloned into pET 52-b that was amplified with pET52b_F and pET52b_R using infusion cloning to generate plasmid pDMP1118. E. coli BL21(DE3) plys, containing pDMP1118, was grown at 37° C. until an OD600 of 0.5 was reached. Isopropyl-1-thio-b-D-galactopyranoside (IPTG) was added to 0.5 mM, and the cells were shifted to 30° C. for four hours of induction. Cells were harvested and stored at −20° C. The cells pellet was thawed and resuspended in 1.4 ml B-PER™ Complete Bacterial Protein Extraction Reagent (ThermoFisher), followed by addition of EDTA to 1 mM, and rocking for 15 min at room temperature. Insoluble cell debris was pelleted via centrifugation (20, 000×g, 10 min at 4° C.). Strep-UrpR was isolated from cell lysates using a Strep-tactin column as described in the manufacturer's protocol (IBA Lifesciences). The protein concentration of UrpR (reported here as monomers) was determined using a Bradford protein assay (Biorad) with lysozyme as a standard.

Electrophoretic mobility shift assays. A $P_{phyt}$ promoter fragment containing the region from 13 to 245 with respect to the translation initiation site was amplified from pDMP460 and pDMP475 with primers BamHI_Pphyt_F and Pphyt_EMSA_R, the latter of which was labeled with fluorescein on the 5' end. Prior to the EMSA, the Strep Tag was removed from UzrpR using HRV 3C protease (Thermo Fisher) according to the manufacturer's protocol. UrpR was phosphorylated by incubation in phosphorylation buffer (50 mM Tris, pH 7.9, 150 mM NaCl, 10 mM $MgCl_2$) with 50 mM disodium carbamyl phosphate (Sigma-Aldrich) for 1 h at 30° C. (Lynch and Lin, 1996) and immediately used in the binding assays. EMSAs were performed by incubating phosphorylated UrpR with $P_{phyt}$ DNA (50 nM) for 10 min at 37° C. in buffer containing 50 mM Tris-HCl (pH 7.9), 200 mM NaCl, 10 mM $MgCl_2$, 0.1 mg $ml^{-1}$ BSA, 5% glycerol, 1 mM DTT, and 50 μg $ml^{-1}$ poly- dI-dC. A 5% TBE mini-protean polyacrylamide gel was pre- run with 0.5×TBE at 120 V for 30 min in a Mini-PROTEAN tetra cell (Bio-Rad) prior to loading samples. Samples were run at 100V for 45 min, and the reaction products were visualized using a Biorad Gel Doc XR1 System.

Site 300 sample collection. Standard operating procedures for sampling and sample handling at LLNL Site 300 have been described in detail [121] and are consistent with the guidance and requirements of the U.S. EPA. The groundwater samples used in this study were collected from each well with either an electrical submersible pump or a bailer. Well samples were placed on ice, filtered using a 0.2 m filter, and stored at 4° C.

Inductively coupled—plasma mass spectrometry/optical emission spectrometry. Site 300 samples were diluted in 2% (v/v) nitric acid (trace metal grade) and spiked with an internal holmium standard. U was quantified using a Thermo XSeriesII ICP-MS run in standard mode. The sample introduction system was an ESI PFA-ST nebulizer pumped at 120 l/min. Zn, Pb, Cu, Cd, and Cr were quantified using a Thermo iCAP 7400 radial ICP-OES in standard operating mode. Standard curves were generated using a 100 mM uranyl nitrate stock solution and 10 ppm Zn, Pb, Cu, Cd, and Cr ICP-MS standards (Inorganic Ventures).

$P_{phyt}$-lacZ and $P_{1361}$-lacZ reporter constructs. Chromosomally integrated $P_{phyt}$-lacZ and $P_{1361}$-lacZ translational fusions were constructed using a two-step sacB counterselection procedure [111] to swap the $P_{urcA}$ promoter in pDMP82[3] with either $P_{phyt}$ or $P_{1361}$. pDMP82 contains the necessary sequence to generate a translational $P_{urcA}$-lacZ fusion at the $P_{urcA}$ locus in which the sequence 24 nt downstream of the urcA start codon is fused to *E. coli* lacZ. To accomplish this, the $P_{phyt}$ and $P_{1361}$ fragments were amplified from the *Caulobacter* genome with the primer pairs Phyt-138_F/Phyt-138_R and 1362_138_F/1362_138_R (Table 4), respectively and cloned into pDMP82 that was linearized using the primers 138_PurcA_F and 138_PurcA_F (Table 4) using In-Fusion cloning.

TABLE 4

| Primer name | Primer sequence | SEQ ID NO: |
|---|---|---|
| Phyt-138_F | TAACCCTTTGCAAACCGGACGGTGACCGGCAAAC | 37 |
| Phyt-138_R | GATGAACTTGCGCATGGCGGAGCCCCTCGTTTTc | 38 |
| 1362_138_F | TAACCCTTTGCAAACGAACGATAGCGCCGCCTGC | 39 |
| 1362_138_R | TCCCTCTGGCTGGGCGGAAAGATCGGGACTGGGT GATGGCGCTTAGGATTCCACAG | 40 |
| 138_PurcA_F | ATGCGCAAGTTCATCATGAGCC | 41 |
| 138_PurcA_R | GTTTGCAAAGGGTTAATCGACGCC | 42 |
| pNTPS138_urcR_F | gGAACGATAGCGCCGGACGGTGACCGGCAAAC | 43 |
| pNTPS138_urcR_R | CGCACAAAATCCTCATCCTGAGC | 44 |
| urcR_UR_F | caattgaagccggctCAGAAGGTCGACGCCCTGG | 45 |
| urcR_UR_R | CGCACAAAATCCTCATCCTGAGC | 46 |
| Pphyt_urcR-loc_F | gGAACGATAGCGCCGGACGGTGACCGGCAAAC | 47 |
| Pphyt_urcR-loc_R | AATCAGAATGCGcatGGCGGAGCCCCTCG | 48 |
| Pphyt-uzcR_vect_F | atgCGCATTCTGATTATCGAGGACG | 49 |
| Pphyt-uzcR_vect_R | CGGCGCTATCGTTCcctagg | 50 |
| Pphyt_rsaFb_F | GTGAAAAAAGCTTAACTCGAGGGGCTCCGCCatg c | 51 |
| Pphyt_rsaFb_R | TTAAGCTTTTTTCACGCAGTCTCGCAGCTAGCTT AGCCG | 52 |

TABLE 4-continued

DNA primers:

| Primer name | Primer sequence | SEQ ID NO: |
|---|---|---|
| P1362_rsaFb_F | GTGAAAAAAGCTTAACTCCGAGCTCCCTAACTAACTAAtcATCT | 53 |
| P1362_rsaFb_R | TTAAGCTTTTTTCACGCAGTGATGGCGCTTAGGATTCCACAG | 54 |
| gfp19_amp_for_pxyl_F | tggggagacgaccaTATGCGTAAGGGCGAAGAGCTG | 55 |
| gfp19_amp_for_pxyl_R | cacggctggctgcagGCCGAATTTCAGGGGTACAGCA | 56 |
| Pphyt_TR_elim_F | GATCCCGGGGATTTCTCTTCGCGCCACC | 57 |
| Pphyt_promoter_shorten_R | GAAATCCCCGGGATCCCTGTGCTCTAGA | 58 |
| XbaI_PurcB | GACTCTAGACGAAGACTGGGCGGGCAG | 59 |
| BglII_PurcB_R | GACAGATCTCGGTTTGGGTGGTCGCTTGG | 60 |
| PrsaA_frag_F | TtgtcgacgtatgacgtttgctctatagC | 61 |
| PrsaA_frag_R | CGTTCACATCGCCATCCAGCTC | 62 |
| gfp_for_PrsaA_F | ATGGCGATGTGAACGGCCATAAG | 63 |
| gfp_for_PrsaA_R | gtcatacgtcgacaaGCCGAATTTCAGGGGTACAGCA | 64 |
| Pphyt_SD_amp_R | ATGTTTTTCCTCCTTATAAAGTAGATCTTTAGTTAGTTAGGG | 65 |
| gfp1-9_for_pphyt-short_F | AAGGAGGAAAAACATATGCGTAAGGGCGAAGAGCTG | 66 |
| gfp1-9_for_phyt_R | GAAATCCCCGGGATCGCCGAATTTCAGGGGTACAGCA | 67 |
| urcA_loc_DR_F | GGTCGCTACCATTACCAGTTGGTC | 68 |
| urcA_loc_UR_R | TGCTTGGGTCGTTTGAGTATATGGT | 69 |
| HRP_chrom_int_F | CAAACGACCCAAGCAGGTGTCGCCCTTCGCTGAAC | 70 |
| HRP_chrom_int_R | GTAATGGTAGCGACCCCAAGCTCAGCTAATTAAGCCTCGAG | 71 |
| PurcA_UR_F | ggctggcgccaagctTGGCCGGCCGCACGCAAGGCAGA | 73 |
| PurcA_UR_R | TTATTTTTGACACCAGACCAACTGG | 74 |
| PurcA_DR_F | TGGTGTCAAAAATAATCGCACAGGCGACCGC | 75 |
| PurcA_DR_R | gcgaattcgtggatcCAGGCGTCGAGGTGAAGTA | 76 |
| kan_elim_F | ATTCTTCCTTTTTCAATATTATTGAAGCATTTATCAG | 131 |
| kan_elim_R | AAGCTTAATAAGATGATCTTCTTGAGATCG | 132 |
| Cat_R | CATCTTATTAAGCTTTTACGCCCCGCCCTGCCAC | 133 |
| Cat_F | TGAAAAAGGAAGAATATGGAGAAAAAAATCACTGGATATACCACCGTTG | 134 |
| pBBR1-rep_F | GACGCTAGCctgcgcaacccaagtgctacc | 135 |
| pBBR1-rep_R | CAGAAGCTTggatatgtggacgatggccgc | 136 |
| P1968_BamHI_F | GACGGATCCGAGTCAGTTGAGCCAGGCGTG | 137 |
| P1968_EcoRI_R | GACGAATTCCGTTCAGTCCATACGCGACTGTG | 138 |

TABLE 4-continued

DNA primers:

| Primer name | Primer sequence | SEQ ID NO: |
|---|---|---|
| P1968_HS1_mut_F | ATAGCGCAATTTAAGTGGTCTCTGGCC | 139 |
| P1968_HS1_mut_R | CTTAAATTGCGCTATTGACGGGGATTTAACGGCAGC | 140 |
| P1968_HS2_mut_F | AATGTGGTCTCTGGCCCTCCG | 141 |
| P1968_HS1_mut_R | GCCAGAGACCACATTAATTGCGGTAATGACGGGGAT | 142 |

Both fragments were cloned into the HindIII and BamHI-digested pNPTS138 (Table 5) using In-Fusion cloning and integrated into the chromosome of a *Caulobacter crescentus* lacA mutant strain JOE2321 (Table 5) or NA1000 strain (Table 5) using the double-crossover allele replacement as described above, yielding strains DMP89 and DMP90, respectively (Table 5), integrated at the $P_{urcA}$ locus.

TABLE 5

*Caulobacter crescentus* strains and plasmids:

| Strain or plasmid | Description | Source or reference |
|---|---|---|
| Strains: | | |
| JOE2321 | *C. crescentus* CB15N ΔCC_1634 | [122] |
| DMP89 | JOE2321 $P_{urcA}$-lacZ | Unpublished |
| DMP90 | NA1000 $P_{urcA}$-lacZ | Unpublished |
| DMP470 | JOE2321 $P_{phyt}$-lacZ | Unpublished |
| DMP471 | JOE2321 $P_{1361}$-lacZ | Unpublished |
| | NA1000 ΔuzcR | [116] |
| DMP701 | NA1000 ΔparDE$_3$ $P_{1968}$-gfp mut$_3$ | [123] |
| DMP702 | NA1000 ΔparDE$_3$ Pphyt-uzcRS $P_{1968}$-gfp mut$_3$ | Unpublished |
| DMP703 | NA1000 ΔparDE$_3$ Pphyt$_{m\_5}$-uzcRS $P_{1968}$-gfp mut$_3$ | Unpublished |
| DMP674 | pNPTS138 ΔparDE$_3$ P2844 elim | Unpublished |
| DMP690 | ΔparDE3 P1362-uzcRS | Unpublished |
| DMP679 | ΔparDE3 P1362-rsafB-BS-uzcRS | Unpublished |
| DMP643 | Pphyt-rsafB-BS-uzcRS | Unpublished |
| DMP601 | ΔparDE3 Pphyt-uzcRS | Unpublished |
| DMP681 | NA1000 Pphyt-hrpS, PurcB-hrpR, PhrpL-gfpmut3 | Unpublished |
| DMP683 | NA1000 $P_{phyt}$-gfp10_m2_K1, $P_{urcB}$_E1_gfp11_m4, $P_{rsaA}$-gfp1-9 | Unpublished |
| DMP804 | NA1000 $P_{phyt}$-gfp10_m2_K1, $P_{urcB}$_E1_gfp11_m4, $P_{xyl}$-gfp1-9 | Unpublished |
| DMP877 | NA1000 $P_{phyt}$-gfp10_m2_K1, $P_{urcB}$_E1_gfp11_m4, $P_{phyt\ short}$-gfp1-9 | Unpublished |
| DMP878 | NA1000 $P_{1361}$-gfp10_m2_K1, $P_{urcB}$_E1_gfp11_m4, $P_{phyt\ short}$-gfp1-9 | Unpublished |
| DMP895 | NA1000 $P_{phyt-short}$-gfp10_m2_K1, $P_{urcB}$_E1_gfp11_m4, $P_{rsaA}$-gfp1-9 | Unpublished |
| DMP213 | NA1000 ΔuzcS | [3] |
| DMP561 | NA1000 pDMP558 | [3] |
| DMP562 | NA1000 ΔuzcR pDMP558 | [3] |
| DMP563 | NA1000 pDMP559 | [3] |
| DMP564 | NA1000 pDMP560 | [3] |
| DMP911 | NA1000 $P_{urcB}$-gfp10_m2_K1, $P_{urcB}$_E1_gfp11_m4, $P_{rsaA}$-gfp1-9 | Unpublished |
| DMP912 | NA1000 ΔCCNA_01362 | Unpublished |
| DMP913 | NA1000 ΔCCNA_01363 | Unpublished |
| Plasmids: | | |
| pNPTS138 | Non-replicating vector for integration and allelic replacement; oriT, kan (Km$^R$), sacB | M. R. K. Alley, unpublished |
| pDMP450 | Cat gene from pR9TT and pBBR ori and rep from pPROBE'-gfp[LVA], $P_{mrC}$-gfp mut$_3$ | Unpublished |
| pDMP460 | $P_{phyt}$-gfp mut$_3$ | Unpublished |
| pDMP463 | $P_{1361}$-gfp mut$_3$ | Unpublished |
| pDMP462 | Synthetic promoter probe vector containing gfpmut3 | Unpublished |
| pDMP460 | Cat gene from pR9TT and pBBR ori and rep from pPROBE'-gfp[LVA] | [3] |
| pDMP558 | $P_{1968}$-gfpmut3 | [3] |
| pDMP559 | $P_{1968}$(5'-CAATAG-3')-gfpmut3 | [3] |
| PDMP560 | $P_{1968}$(5'-TAAT-3')-gfpmut3 | [3] |
| pDMP499 | pNPTS138 derived vector for D51A substitution in UzcR | [3] |
| pDMP614 | pNPTS138 derived vector for $P_{phyt}$-lacZ integration into urcA locus | Unpublished |
| pDMP609 | pNPTS138 derived vector for $P_{1361}$-lacZ integration into urcA locus | Unpublished |
| pDMP610 | $P_{hrpL}$- gfp mut$_3$ | Unpublished |
| pDMP621 | pNPTS138-Pphyt$_{m\_5}$-uzcRS | Unpublished |
| pDMP673 | pNPTS138-P1361$_{m\_5}$-uzcRS | Unpublished |
| pDMP460 | $P_{phyt}$-gfpmut$_3$ | Unpublished |
| pDMP463 | $P_{1362}$- gfpmut$_3$ | Unpublished |

TABLE 5-continued

*Caulobacter crescentus* strains and plasmids:

| Strain or plasmid | Description | Source or reference |
|---|---|---|
| pDMP791 | Pphyt-gfp10_m2_K1, PurcB_E1_gfp11_m4, PrsaA-gfp1-9 | Unpublished |
| pDMP881 | P1362-gfp10_m2_K1, PurcB_E1_gfp11_m4, PrsaA-gfp1-9 | Unpublished |
| pDMP82 | pNPTS138 $P_{urcA}$-lacZ | [3] |
| pDMP792 | pNPTS138-Pphyt-gfp10_m2_K1, PurcB_E1_gfp11_m4, PrsaA-gfp1-9 | Unpublished |
| pDMP883 | pNPTS138-Pphyt-short-gfp10_m2_K1, PurcB_E1_gfp11_m4, PrsaA-gfp1-9 | Unpublished |
| pDMP932 | pNPTS138-PurcB-gfp10_m2_K1, PurcB_E1_gfp11_m4, PrsaA-gfp1-9 | Unpublished |
| pDMP692 | pNPTS138-P1362-gfp10_m2_K1, PurcB_E1_gfp11_m4, PrsaA-gfp1-9 | Unpublished |
| pDMP664 | pNPTS138-$P_{phyt}$-tripartite-GFP | Unpublished |
| pDMP665 | pNPTS138-$P_{1362}$-tripartite-GFP | Unpublished |
| pDMP712 | $P_{phyt}$-gfp10_m2_K1, $P_{urcB}$_E1_gfp11_m4, Pxyl-gfp1-9 | Unpublished |
| pDMP713 | P1361-gfp10_m2_K1, $P_{urcB}$_E1_gfp11_m4, Pxyl-gfp1-9 | Unpublished |
| pDMP808 | pNPTS138-$P_{phyt}$-gfp10_m2_K1, Pphyt_E1_gfp11_m4, Pphyt-short-gfp1-9 | Unpublished |
| pDMP809 | pNPTS138-P1362-gfp10_m2_K1, Pphyt_E1_gfp11_m4, Pphyt-short-gfp1-9 | Unpublished |
| pDMP745 | $P_{phyt}$-DR1 GTCA->CAGT- gfpmut$_3$ | Unpublished |
| pDMP746 | $P_{phyt}$-large-TR-elim-gfpmut$_3$ | Unpublished |
| pDMP747 | P1361- DR1 GTCA->CAGT-gfpmut$_3$ | Unpublished |
| pDMP786 | $P_{phyt}$-DR1 GT->CA-gfpmut$_3$ | Unpublished |
| pDMP787 | $P_{phyt}$-DR2 GT->CA-gfpmut$_3$ | Unpublished |
| pDMP788 | $P_{1361}$-DR2 GT->CA-gfpmut$_3$ | Unpublished |
| pDMP789 | $P_{1361}$ shorten- gfpmut$_3$ | Unpublished |
| pDMP748 | pNPTS138-PurcB-gfp10_m2_K1, PurcB_E1_gfp11_m4, Pxyl-gfp1-9 | Unpublished |
| pDMP741 | PurcB-gfp10_m2_K1, PurcB_E1_gfp11_m4, Pxyl-gfp1-9 | Unpublished |
| pDMP558 | $P_{1968}$-gfpmut$_3$ | [3] |

$P_{phyt}$-gfp and $P_{1361}$-gfp constructs. Plasmid-borne $P_{phyt}$-gfp and $P_{1361}$-gfp fusions were generated by amplifying $P_{phyt}$ and $P_{1361}$ fragments from the *Caulobacter* genome with the primer pairs Phyt-138_F/Phyt-138_R and 1362_138_F/1362_138_R (Table 4), respectively, digested with BamHI and EcoRI and cloned into the similarly digested pDMP450 (Table 5), generating pDMP460 and pDMP463 (Table 5).

Construction of a CCNA_01968 promoter-gfp transcriptional fusion. A synthetic vector with a $P_{15}$A origin, kanamycin resistance cassette and gfpmut3 gene insulated with an upstream rrnB terminator 1 (DNA2.0) was used as a template to construct promoter-gfp fusions. First, the cat gene (chloramphenicol acetyltransferase) from pNJH123 was amplified with the primers cat_F and cat_R and cloned into pDMP462 that was linearized with the primers kan_elim_F and kan_elim_R using infusion cloning. The p15A origin was then swapped with a pBRR-rep1 origin that was amplified from pPROBE-GFP' using the primers pBBR1-rep_F and pBBR1-rep_R and the restriction enzymes NheI and HindIII, generating pDMP460. The DNA sequence region from 170 to −9 with respect to the translation initiation site of CCNA_01968 was amplified with P1968_BamHI_F and P1968_EcoRI_R, digested with EcoRI and BamHI, and cloned into the similarly digested pDMP460 to construct a CCNA_01968-promoter gfp fusion (pDMP558). Site directed mutagenesis was performed with the primers P1968_HS1_mut_F and P1968_HS1_mut_R to mutate UzcR half site one from 5'-CATTAC-3' to 5'-CAATAG-3' and primers P1968_HS2_mut_F and P1968_HS2_mut_R and to mutate the half site two from 5'-TTAA-3' to 5'-TAAT-3', generating pDMP559 and pDMP560, respectively.

Engineering of constructs to place the uzcRS operon under the transcriptional control of $P_{phyt}$/$P_{1361}$. The two mapped promoters of uzcR were replaced with $P_{1361}$ and $P_{phyt}$ as follows. First, a synthetic DNA containing the rrnb T1 and T7Te transcription terminators (BBA_0B0015) followed by a $P_{1361}$ fusion with the first 168 nucleotides of uzcR was prepared (Integrated DNA Technologies, Inc.) Then, pDMP499 (Table 5), a pNPTS138-based vector containing the DNA sequence for substituting the aspartate residue at position 51 for alanine was amplified with primers pNTPS138_urcR_F and pNTPS138_urcR_R (Table 4) and the 531 bp region upstream of the uzcR promoters was amplified with urcR_UR_F and urcR_UR_R (Table 4). All three DNAs were ligated together to make pDMP610 (Table 5). $P_{phyt}$ was swapped for $P_{1361}$ using infusion cloning with the fragments generating by amplifying pDMP610 (Table 5) with Pphyt-uzcR_vect_F/Pphyt-uzcR_vect_R and pDMP614 with Pphyt_urcR-loc_F/Pphyt_urcR-loc_R (Tables 4 and 5).

The resulting suicide vectors pDMP609 and pDMP614 (Table 5) were electroporated into FC922 (Table 5) and the P1361-uzcRS (DMP690) and Pphyt-uzcRS strains (DMP601) (Table 5) were obtained by a two-step sacB counterselection procedure [111]. The UzcR binding site from the rsaFb promoter TGCGTGAAAAAAGCTTAACT (SEQ ID NO:26) was inserted downstream of the transcriptional start site of $P_{phyt}$ and $P_{1361}$ as follows. Plasmids pDMP609 and pDMP614 and were amplified with the primer pairs P1362_rsaFb_F/P1362_rsaFb_F and Pphyt-r-saFb_F/Pphyt_rsaFb_F, respectively (Table 5) and re-ligated using InFusion cloning. The resulting suicide vectors pDMP673 and pDMP621 (Table 5) were electroporated into *Caulobacter* strain FC922 and the P1361m_5-uzcRS (DMP679) and Pphytm_5-uzcRS (DMP643) strains (Table 5) were obtained by the two-step sacB counterselection procedure. All strains were transformed with pDMP558, encoding a CCNA_01968 promoter gfpmut3 fusion (Table 5).

Engineering of constructs to place expression of hrpS under control of $P_{Phyt}$ or $P_{1361}$, and hrpR under control of $P_{urcB}$. $P_{hrpL}$ DNA (SEQ ID 80) was synthesized (IDT), then digested with BamHI and BglII and ligated into the similarly digested pDMP450, generating pDMP610. Next, the synthetic Pphyt-hrpS_PurcB-hrpR DNA fragment was digested with XbaI and BamHI and cloned into the similarly digested pDMP610 to generate pDMP612. pDMP612 was cloned into NA1000 to produce DMP681.

TABLE 6

DNA sequences of genetic molecular components:

| Genetic molecular component | DNA sequence | SEQ ID NO: |
|---|---|---|
| $P_{1361}$ promoter | GAACGATAGCGCCGCCTGCGAGCGCGACCTCAGGC CTCGGACGAAGCGCGTCCGGGGCCTTTTCTTGTCG ATGTTCAGCGCCTGGTTACCGGCGATGGCGCGGTG TCAGCGTTCGGGCGTTGCGATGCGTCAGGAGCGTG TCAGGATGCCTGTGGAATCCTAAGCGCCATCACCC AGTCCCGATCTTTCC | 77 |
| $P_{phyt}$ promoter | CCGGACGGTGACCGGCAAACCACCGCTGTCATGAA TGCGTTTTGAAGCTTCGCCATAACGCGCCTTGGGT ATCCGGTTCGGAACGCGGCGCTTTCGTTGACCTCT GGCCACGGAGAATTCTCCATCCAAAGAGGGTGTG GCCCAAAGAGGGTGTGGATTTCTCTTCGCGCCACC CGTTTCGTCAGCCGGACGTCAGGTCCAGACGGCTA AGCTAGCTGCGAGACatgAAAACGAGGGGCTCCGC C | 78 |
| rrnBT1-T7T3-P1361-uzcr (1-168 nt) | TGAGGATTTTGTGCGccaggcatcaaataaaacga aaggctcagtcgaaagactgggcctttcgttttat ctgttgtttgtcggtgaacgctctctactagagtc acactggctcaccttcgggtgggcctttctgcgtt tatacctaggGAACGATAGCGCCGCCTGCGAGCGC GACCTCAGGCCTCGGACGAAGCGCGTCCGGGGCCT TTTCTTGTCGATGTTCAGCGCCTGGTTACCGGCGA TGGCGCGGTGTCAGCGTTCGGGCGTTGCGATGCGT CAGGAGCGTGTCAGGATGCCTGTGGAATCCTAAGC GCCATCACCCAGTCCCGATCTTTCCGAGCTCCCTA ACTAACTAAtcATCTACTTTATAAGGAGGAAAAAC ATatgCGCATTCTGATTATCGAGGACGACCTGGAA GCCGCCGGCGCCATGGCGCACGGGCTCAAGGAAGC CGGCTACGACGTCGCCCACGCGCCGGACGGCGAGG CGGGCCTGGCCGAGGCCCAGAAGGGCGGCTGGGAC GTGCTGGTCGTCGCCCGGATGATGCCCAAG | 79 |
| PhrpL | GACGGATCCGCCGGATTATGTCCGCTGAGTGGGTC ACGGTCCCGGATCAGTTCCCTTGCGAAGCTGACCG ATGTTTTTGTGCCAAAAGCTGTTGTGGCAAAAAAC GGTTTGCGCAAAGTTTTGTATTACAAAGAATTTCA CATTTTAAAATATCTTTATAAATCAATCAGTTATT TCTATTTTTAAGCTGGCATGGTTATCGCTATAGGG CTTGTACAGATCTGTC | 80 |
| Tri-partite GFP gblock | CAGAGATCTACTTTATAAGGAGGAAAAACATATGG ATCTGCCCGACGATCATTACCTGTCCACCCAGACC ATCCTGTCGAAGGATCTGAATGGCACCGACGTGGG CTCCGGTGGCGGGAGTGGTGGTGGCGGGAGCAAGG TCTCCGCCCTCAAGGAGAACGTTAGCGCCCTGAAA GAGAAAGTCTCGGCCCTGACCGAAAAGGTCTCCGC CCTTAAGGAAAAGGTGAGCGCTCTCAAAGAGTAAc caggcatcaaataaaacgaaaggctcagtcgaaag actgggcctttcgttttatctgttgtttgtcggtg aacgctctctactagagtcacactggctcaccttc gggtgggcctttctgcgtttataggtaccCGAAGA CTGGGCGGGCAGCAGCCCACTCCCAAGCGCCCACC AATTATGACTTCTTTTTCATAGACTTAATTCGACG TCATGAAGCAGTCGTAACGGGTGTTCGCCATCCGA CCGCTCTACATCCTCGATCAACGGATCGCCAAGCG ACCACCCAAACCGcctaggtaactaaagattaact ttataaggaggaaaaacatATGAAGGTCTCCGCCC TTGAAAATGAGGTCTCGGCTCTCGAAAAGGAGGTG TCGGTCCTGGAGAAAGAAGTCAGCGCGCTTGAGAA GGAGGTCCGTGCCCTGGAGAAGAGTGGCGGTGGGG GGTCTGGGGGCGGTTCTGGGGGCGGCTCCACCTCG GAGAAGCGTGACCACATGGTGCTGCTGAATATGT CACCGCCGCCGGGATCACCGATGCCTCCTAAGact cctgttgatagatccagtaatgacctcagaactcc atctggatttgttcagaacgctcggttgcgccgg gcgttttttattggtgagaatGAAAAATGCTGTAC CCCTGAAATTCGGCTAttgtcgacgtatgacgttt gctctatagccatcgctgctcccatgcgcgccact cggtcgcaggggtgtgggattttttttgggagAC AATCCTCATGCGTAAGGGCGAAGAGCTGTTCACGG GCGTCGTCCCCATCCTCATCGAGCTGGATGGCGAT GTGAACGGCCATAAGTTCTTCGTCCGTGGGGAAGG CGAGGGGATGCCACCATCGGCAAGCTGAGCCTCA | 81 |

TABLE 6-continued

DNA sequences of genetic molecular components:

| Genetic molecular component | DNA sequence | SEQ ID NO: |
|---|---|---|
| | AGTTCATCTGCACCACCGGCAAGCTCCCGGTCCCC TGGCCGACGCTCGTCACGACCCTCACCTACGGGGT GCAGTGCTTTTCCCGTTACCCCGACCACATGAAGC GGCACGACTTCTTTAAGTCGGCCATGCCCGAAGGC TACGTGCAGGAGCGCACCATCTATTTTAAGGACGA TGGCACGTATAAGACCCGCGCGGAGGTCAAGTTCG AAGGGGATACCCTGGTCAACCGTATCGAGCTGAAG GGCATCGACTTTAAGGAAGATGGCAACATCCTCGG GCACAAGCTCGAATATAATTTTAACTCCCATAAGG TCTACATCACCGCCGACAAGCAAAACAACGGCATC AAGGCGAACTTTACGATCCGTCACAATGTGGAGGA CGGCAGCGTCCAGCTCGCGGATCATTATCAACAGA ATACCCCCATCGGCGATGGTCCCGTCCTCCTCCCG TAGCTCGAGATT | |
| Pphyt-hrpS_PurcB-hrpR | TGAGGATTTTGTGCGccaggcatcaaataaaacga aaggctcagtcgaaagactgggcctttcgttttat ctgttgtttgtcggtgaacgctctctactagagtc acactggctcaccttcgggtgggcctttctgcgtt tatacctaggGAACGATAGCGCCGCCTGCGAGCGC GACCTCAGGCCTCGGACGAAGCGCGTCCGGGGCCT TTTCTTGTCGATGTTCAGCGCCTGGTTACCGGCGA TGGCGCGGTGTCAGCGTTCGGGCGTTGCGATGCGT CAGGAGCGTGTCAGGATGCCTGTGGAATCCTAAGC GCCATCACCCAGTCCCGATCTTTCCGAGCTCCCTA ACTAACTAAtcATCTACTTTATAAGGAGGAAAAAC ATatgCGCATTCTGATTATCGAGGACGACCTGGAA GCCGCCGGCGCCATGGCGCACGGGCTCAAGGAAGC CGGCTACGACGTCGCCCACGCGCCGGACGGCGAGG CGGGCCTGGCCGAGGCCCAGAAGGGCGGCTGGGAC GTGCTGGTCGTCGACCGGATGATGCCCAAG | 82 |

Example 1: Identification of U-Selective Promoters $P_{1361}$ and $P_{phyt}$ in *Caulobacter crescentus*

The highest U-induced gene urcA (uranium response in *Caulobacter*) has been exploited as a U sensor that can detect micromolar U concentrations in contaminated ground water [44]. However, previously the molecular mechanisms governing $P_{urcA}$ regulation were not examined, nor its cross-reactivity with environmentally relevant metal cations. To address this, the specificity was characterized and the transcriptional regulatory mechanism governing expression of the $P_{urcA}$ was identified [3]. Although most metals failed to induce $P_{urcA}$, significant induction was observed with the metal ions Zn and Cu and to a lesser degree, Cd (FIG. 2 Panel A).

The UzcRS two-component system was identified as the regulatory system responsible for U, Zn, and Cu-dependent activation of $P_{urcA}$ and 41 other promoters in the *Caulobacter* genome [3]. Together, these data suggest that the $P_{urcA}$ does not have satisfactory selectivity to function as a standalone sensor of environmental U. Nevertheless, since UzcRS exhibits a U-concentration dependence in a wide range of media conditions, a sensor that incorporates UzcRS as one component within a more advanced U-sensitive genetic circuit comprising an additional point of U sensing that is independent of the UzcRS system could produce an effective U sensor.

To identify additional U responsive genes that are not cross-reactive with other metal cations, gene expression was monitored in the presence of U and Zn using RNA-seq (FIG. 1). Two additional promoters ($P_{1361}$ (promoter of operon containing CCNA_01362) and $P_{phyt}$ (promoter of CCNA_01353)) that are strongly responsive to U but not to Zn. To further characterize the specificity of these promoters, the DNA sequences corresponding to each promoter were cloned upstream of lacZ and gfpmut3 reporter genes and reporter expression was monitored following exposure to 10 different metals. Surprisingly, the data revealed that both promoters lack cross-reactivity with metal ions commonly encountered in the environment (FIG. 2 Panels B-C). Furthermore, U-dependent induction of these promoters was not dependent on UzcRS; $P_{1361}$-gfp expression was induced 10.5 (±0.8) for wild type and 9.6 (±0.5) for a strain deleted for uzc during exposure to 20 µM U, suggesting that that regulation of these promoters is governed by a regulatory mechanism distinct from $P_{urcA}$. In other words, U-sensing by $P_{phyt}/P_{1361}$ and $P_{urcA}$ is mediated through independent mechanisms. As such, these sensors are suitable for U sensor construction.

Figure 4:
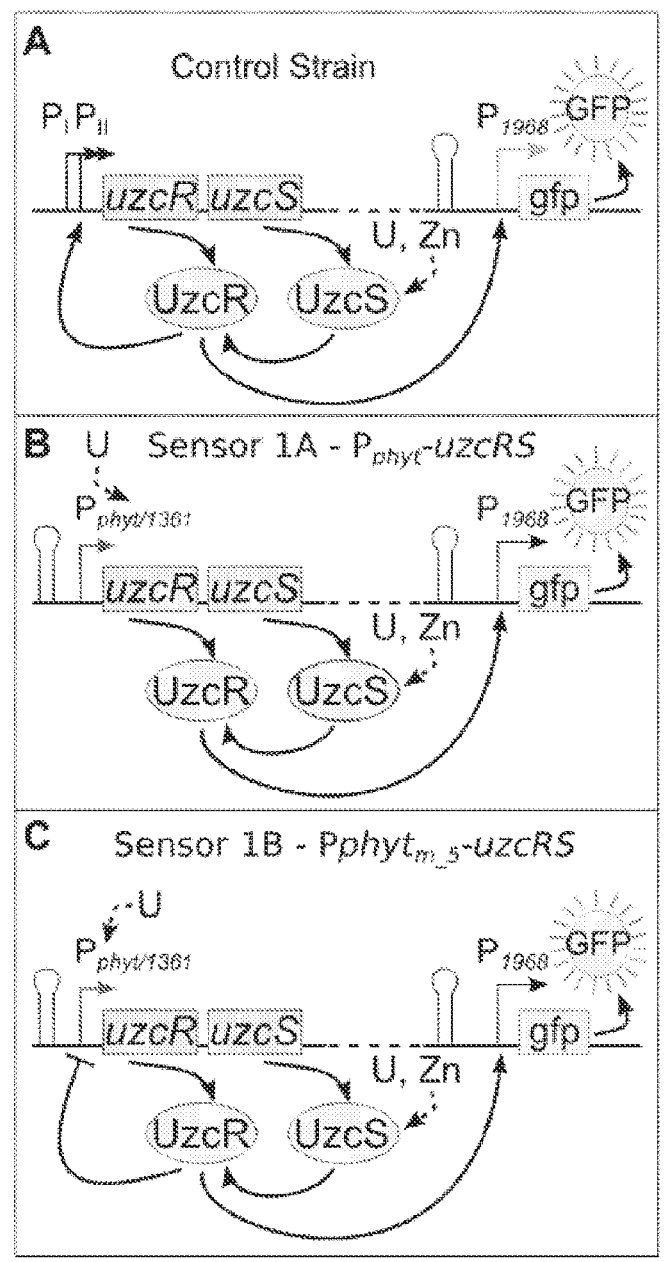
FIG. 4 Panels A-C shows schematics illustrating the stepwise genetic engineering of an exemplary U-sensitive genetic circuit with incremental improvements from Panel A to Panel C to enhance specificity for U, resulting in a genetic circuit comprising an 'in series' AND gate comprising two points of U-sensing by (1) $P_{phyt}$ or $P_{1361}$ and (2) UzcRS two component system.

Example 2: Engineering of a U-Sensitive Genetic Circuit Comprising an 'in Series' AND Gate Wherein the uzcRS Operon is Placed Under the Transcriptional Control of $P_{phyt}/P_{1361}$ In the *C. crescentus* NA1000 genome, uzcR and uzcS are physically separated by genes encoding the ParDE3 toxin anti-toxin (TA) system, together forming a putative four-gene operon [89]. Although uzcR and uzcS are conserved throughput much of Alphaproteobacteria, the insertion of parDE3 between uzcR and uzcS is unique to a subset of the *Caulobacter* genus; uzcR and uzcS are adjacently located in the majority of closely related Alphaproteobacteria [3] including *C. crescentus* strain OR37, an environmental isolate from a U-contaminated site [86]. The $parDE_3$ system does not contribute to the metal-dependent regulation by UzcRS [3]. Given this result and the potential toxicity associated with $parDE_3$ overexpression, the $parDE_3$ TA system was deleted, so that uzcR and uzcS are adjacently located. The expression of uzcR is controlled by two promoters ($P_1$ and $P_2$) in *C. crescentus* [3], which enables sufficient basal expression of uzcRS to activate transcription in response to metal (U, Zn, Cu). There is also a putative UzcR binding site located upstream of $P_1$ that likely yields a positive feedback loop. Indeed, UzcR protein levels increase in a uzcS-dependent manner in response to metal sensing. Deletion of the $parDE_3$ TA system and the parD promoter places uzcS expression under the exclusive control of $P_1$ and $P_2$ (FIG. 4 Panel A). A "control strain" of *Caulobacter* was generated comprising a U-sensitive genetic circuit in which uzcR is under the control of $P_1$ and $P_2$ and uzcS under the control of $P_1$ and $P_2$, (FIG. 4 Panel A). As expected, this strain produces a high fluorescence signal in response to U, Zn, Cu (FIG. 5 Panel A left, middle, right graphs, respectively). Incremental improvements were made to this circuit to enhance specificity, as described below.

Figure 5:
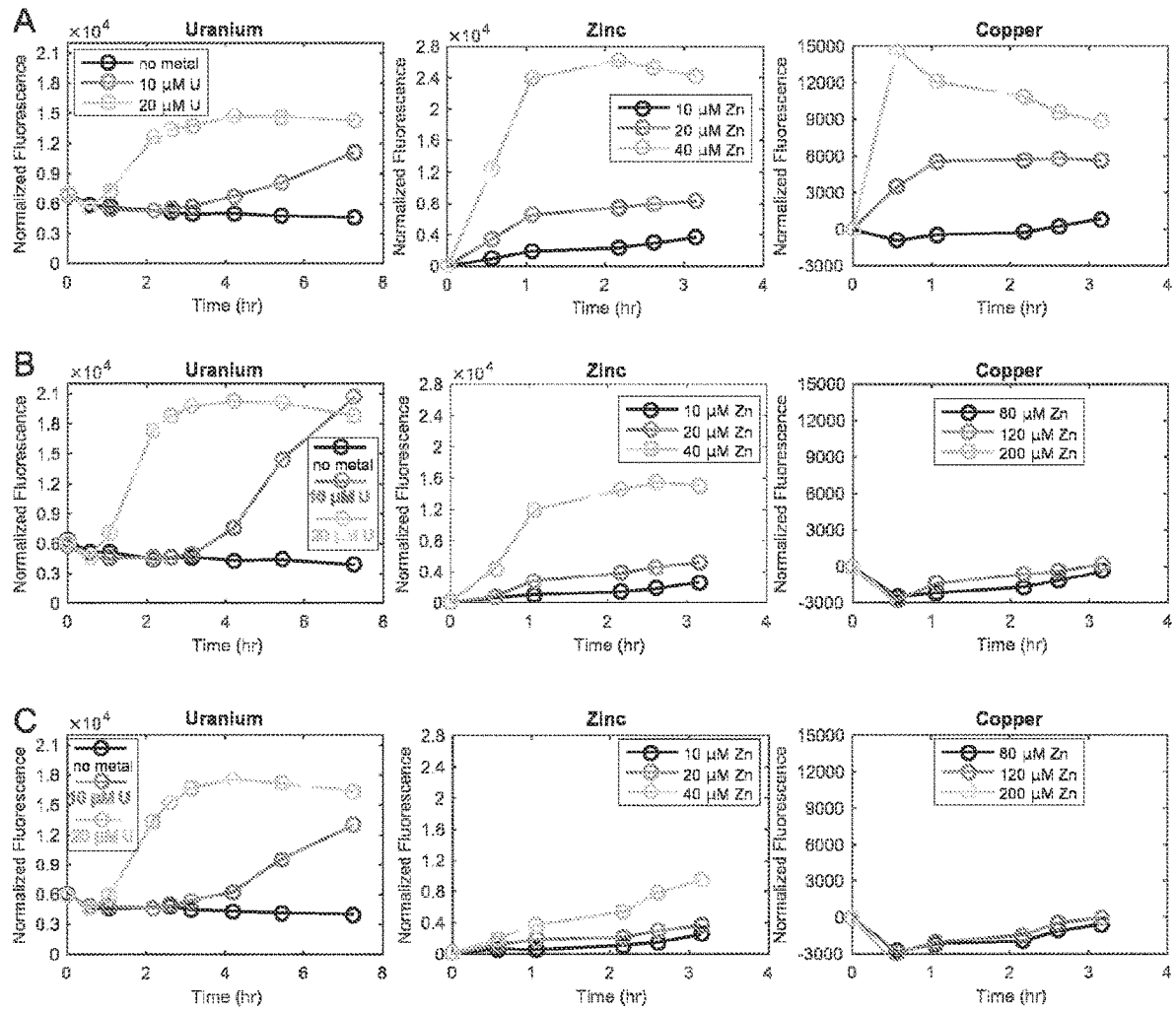
FIG. 5 shows graphs of exemplary GFP reporter fluorescence produced by the U-sensitive genetic circuits shown in FIG. 4, comprised in the host organism *C. crescentus* NA1000, upon exposure to U, Zn or Cu.

To enhance the selectivity of UzcRS for U, P1 and P2 were replaced with $P_{phyt}$ or $P_{1361}$ such that uzcRS expression is dependent on activation by these U-specific promoters (FIG. 4 Panel B). This genetic circuit requires two points of U sensing for reporter activation, (1) activation of uzcRS transcription by $P_{phyt}$ or $P_{1361}$ and (2) stimulation of UzcRS transcriptional activity. *Caulobacter* comprising this sensor showed greater reporter expression signal in response to U (FIG. 5 Panel B, left graph) compared to the control (FIG. 5 Panel A, left graph). Importantly, Cu-sensing has been completely abolished (FIG. 5 Panel B, right graph) while Zn induction with the range of inducing Zn concentrations narrowed (FIG. 5 Panel B, middle graph) compared to the $P_{urcA}$ sensor alone (FIG. 5 Panel A, middle graph). The ratio of the U signal output to that of Zn has been increased from 1.6 to 3.5 (FIG. 5 Panel B, left and right graphs).

To further improve specificity of U sensing, a negative feedback loop was incorporated into the circuit, whereby UzcR represses its own expression from $P_{phyt}$ or $P_{1361}$, in order to minimize the basal expression of the uzcRS operon. Specifically, a UzcR binding site was placed downstream of the $P_{phyt}$ or $P_{1361}$ transcription start site (FIG. 4 Panel C). Although the UzcR binding site from the rsaFb promoter was used, any m_5 site is suitable. *Caulobacter* comprising this sensor showed strong responsiveness to U (FIG. 5 Panel C, left graph) and further shifted ratio of U response to that of Zn to 5.5 (FIG. 5 Panel C, left and right graphs).

Example 3: Engineering of a U-Sensitive Genetic Circuit Comprising an 'in Parallel' HRP AND Grate This Example describes the engineering of a U-sensitive genetic circuit comprising an 'in parallel' AND gate that utilizes the HRP AND gate system from *Pseudomonas syringae* that was recently developed in *E. coli* [102]. In this system, both HrpS and HrpR are required for $\sigma^{54}$ dependent activation of the hrpL promoter ($P_{hrpL}$). Expression of HrpS or HrpR alone is not sufficient for transcriptional activation.

The genetic circuit described in this Example contains genetic components whose expression is controlled independently by (1) $P_{phyt}$ or $P_{1361}$ and (2) UzcRS systems, and reporter expression requires both HrpS and HrpR to be expressed.

To generate this U-sensing AND gate, the expression of hrpS was placed under the control of $P_{Phyt}$ or $P_{1361}$, while hrpR was placed under the control of Purc, a UzcRS-dependent promoter that was recently identified that has lower basal activity compared to $P_{urcA}$ [3] (FIG. 6 Panel A). A $P_{hrpL}$-gfp fusion was generated as a reporter and requires $P_{Phyt}/P_{1361}$ and $P_{urB}$ to be active to generate a fluorescent signal.

Example 4: Engineering of a U-Sensitive Genetic Circuit Comprising an 'in Parallel' Tripartite GFP AND Gate This Example describes the engineering of a U-sensitive genetic circuit comprising an 'in parallel' AND gate that utilizes the tripartite GFP system [5], which requires expression of gfp10, gfp11 and gfp1-9 for reporter expression (FIG. 6 Panel B).

To construct an in parallel AND gate comprising the tripartite GFP system a gblock (Tripartite GFP gblock) was synthesized (Integrated DNA Technologies, gBlock) with the following components listed in 5' to 3' orientation: GFP10-m2_k1, rrnBT1 and T7Te transcription terminators, E1-GFP11-M4 under the control of the UzcRS promoter ($P_{urcB}$), lamdaT$_0$ terminator, gfp1-9 under the control of the rsaA promoter ($P_{rsaA}$ [4]). GFP10-m2_k1 was placed under the control of $P_{phyt}$ or $P_{1361}$ by digesting Tripartite GFP gblock with BglII and XhoI and ligating into the similarly digested pDMP460 and pDMP463, respectively, to form pDMP791 and pDMP881. DNA sequence encompassing the entire $P_{phyt}/P_{1361}$ tripartite DNA and an insulating upstream rrnbT1 transcription terminator was amplified with primers HRP_chrome_int F and R and cloned into pDMP82 that was amplified with the primers urcA_loc_DR_F and urcA-loc_UR_R using infusion cloning to form pDMP792 and pDMP692. A variant of this AND gate containing gfp1-9 under the control of the xylose inducible promoter (Pxyl [6])

was constructed by amplifying the 360 bp $P_{xyl}$ fragment using Pxyl_F and Pxyl_R and cloning into pDMP792 ($P_{phyt}$ version) and pDMP692 ($P_{1361}$ version) that were amplified with gfp1-9_amp_for_pxyl_F gfp1-9_amp_for_pxyl_R using infusion cloning to form pDMP664 and pDMP 665, respectively. A variant of this AND gate containing gfp1-9 under the control of the shortened $P_{phyt}$ promoter was constructed by amplifying pDMP736 with Pphyt_TR_e-lim_F and Pphyt_SD_amp_R and cloning this 137 bp fragment into pDMP712 ($P_{phyt}$ version) or pDMP713 ($P_{1361}$ version) that was amplified with gfp1-9_for_pphyt-short_F and gfp1-9_for_phyt_R using infusion cloning to form pDMP808 and pDMP809. A variant containing GFP10-m2_k1 under the control of a shortened version of $P_{phyt}$ and gfp1-9 under the control of $P_{rsaA}$ was constructed by amplifying pDMP792 with Pphyt_TR_elim_F and Pphyt_promoter_shorten_R and re-ligating using infusion cloning, forming pDMP883. Lastly, a control tripartite variant containing both GFP10-m2_k1 and E1-GFP11-M4 under the control of $P_{urcB}$ was constructed in three parts. First, a $P_{urcB}$ fragment generated with primers XbaI_PurcB and BglII_PurcB_R was digested with XbaI and BglII and directionally cloned into the similarly digested pDMP712, forming pDMP741. Next, DNA sequence encompassing the entire $P_{urcB}$ tripartite DNA and an insulating upstream rrnbT1 transcription terminator was amplified with primers HRP_chrome_int F and R and cloned into pDMP82 that was amplified with the primers urcA_loc_DR_F and urcA-loc_UR_R using infusion cloning to form pDMP748. Finally, the $P_{xyl}$ promoter was swapped for $P_{rsaA}$ by cloning PrsaA, amplified with PrsaA_frag_F and PrsaA_frag_R, into pDMP748 that was amplified with gfp_for_PrsaA_F and gfp_for_PrsaA_R, forming pDMP932. These tripartite GFP AND gate variants were then integrated into the chromosomal urcA locus using a two-step sacB counterselection procedure [120].

Figure 11:
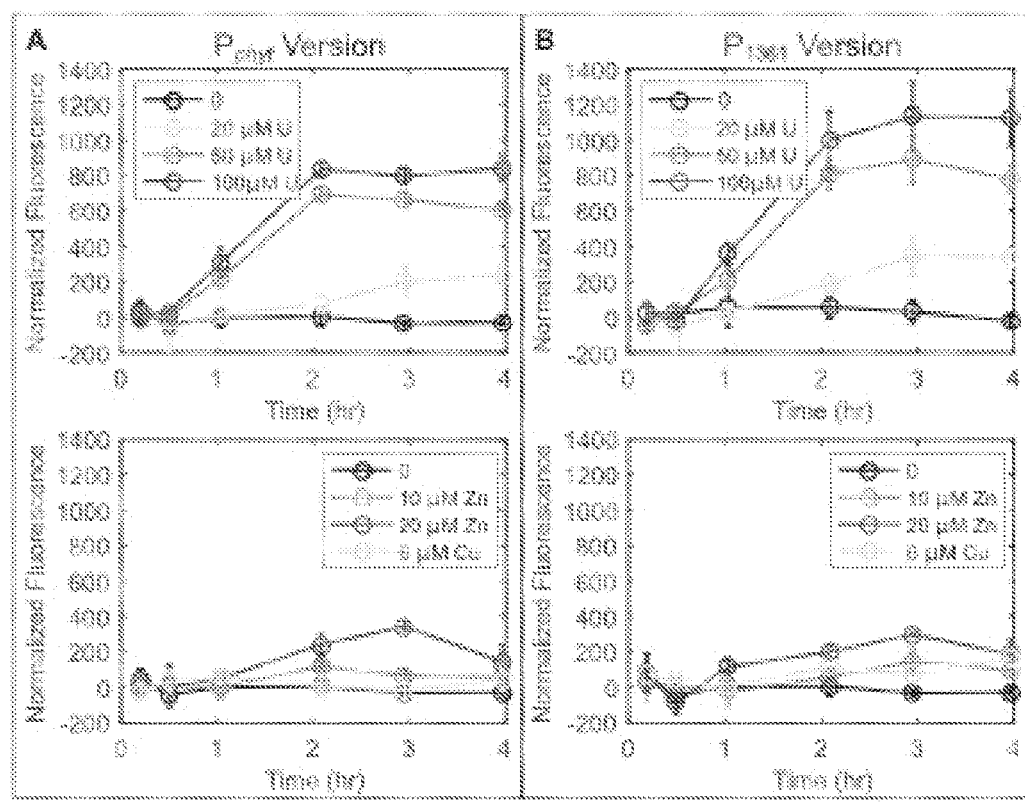
FIG. 11 shows graphs reporting exemplary data corresponding to the exemplary U-sensitive genetic circuit in FIG. 6 Panel B. Graphs reporting quantification of GFP fluorescence produced by C. crescentus NA1000 comprising the U-sensitive genetic circuit shown in FIG. 6 Panel B with gfp10 under the control of $P_{phyt}$ (Panel A) or $P_{1361}$ (Panel B) in response to exposure to 20, 50, and 100 µM U (FIG. 11 Panels A and B, upper graphs), or 10, 20 µM Zn and 6 µM Cu (FIG. 11 Panels A and B, lower graphs). In this version of the circuit, gfp1-9 is controlled by $P_{xyl}$ and gfp1-9 expression is induced with 10 mM xylose. Fluorescence output for both $P_{phyt}$ and $P_{1361}$ sensor variants is plotted as a function of time following metal exposure and was normalized to the fluorescence of a strain lacking the UzcR regulator. Cells were grown to mid-exponential phase in M5G-G2P media, washed once with fresh media, then resuspended in fresh media containing the indicated metal concentration.

FIG. 11 shows graphs reporting exemplary data corresponding to the exemplary U-sensitive tripartite GFP genetic circuit.

Tripartite GFP system with PrsaA-gfp1-9: Can detect U in the 2-20 uM range. When a growth media containing Glycerol-2-phosphate as the P source is used, the signal amplitude is higher but the responsive range is shifted to 8 uM-30 uM. Higher concentrations have a diminished signal output. The shifted range likely reflects U coordination by glycerol-2-phosphate that reduces the bioavailability.

Figure 22:
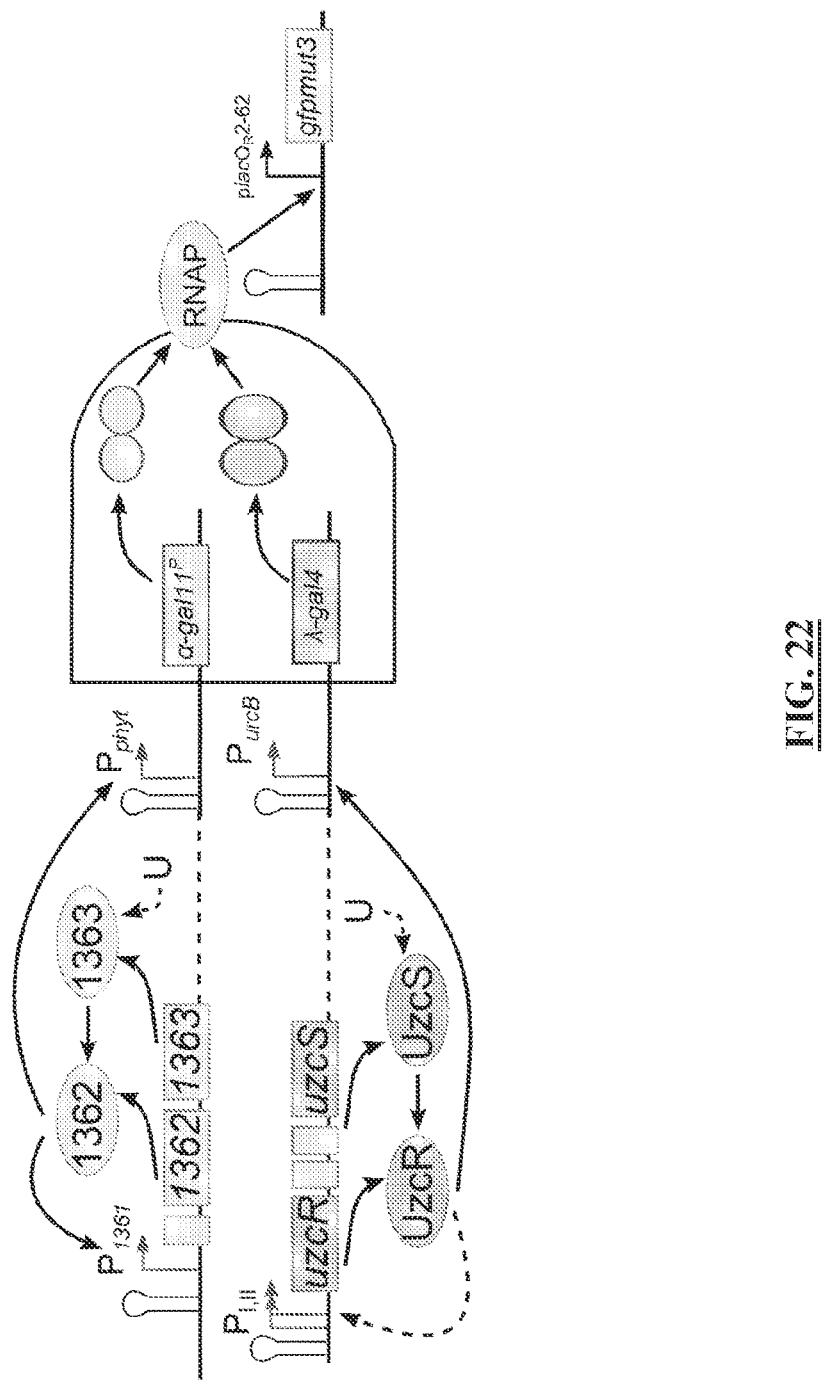
FIG. 22 shows a schematic showing an exemplary AND gate comprised in a U-sensitive genetic circuit wherein an Alpha-gal11P fusion and a lambda repressor-gal4 fusion are expected to be driven by a combination of $P_{phyt}/P_{1361}$ and any UzcRS regulated promoter.
Figure 23:
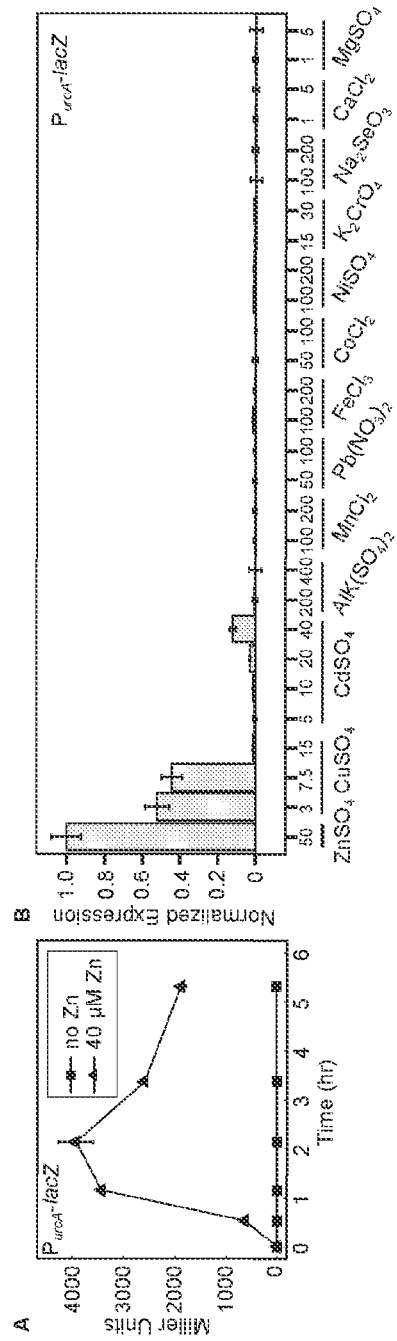
FIG. 23 shows in some embodiments the determination of metal specificity of $P_{ureA}$. Panel (A): Time course of chromosomal $P_{urcA}$-laCZ induction after treatment of early exponential phase cells with or without Zn. Cells were grown in PYE and the β-galactosidase activity at each time point is depicted. Error bars represent the standard deviation of biological triplicates. Panel (B): Metal specificity of $P_{urcA}$ was determined by treating mid-exponential phase cells with various metal cations in modified M5G media supplemented with 1.3 mM inorganic phosphate for two hours before determining β-galactosidase activity. Expression values were normalized to the level of expression with 50 µM Zn and error bars represent that standard deviation calculated using a formula for propagation of standard error [20]. The depicted metal concentrations are in units of µM except for $CaCl_2$) and $MgSO_4$ that were added at mM concentrations.
Figure 24:
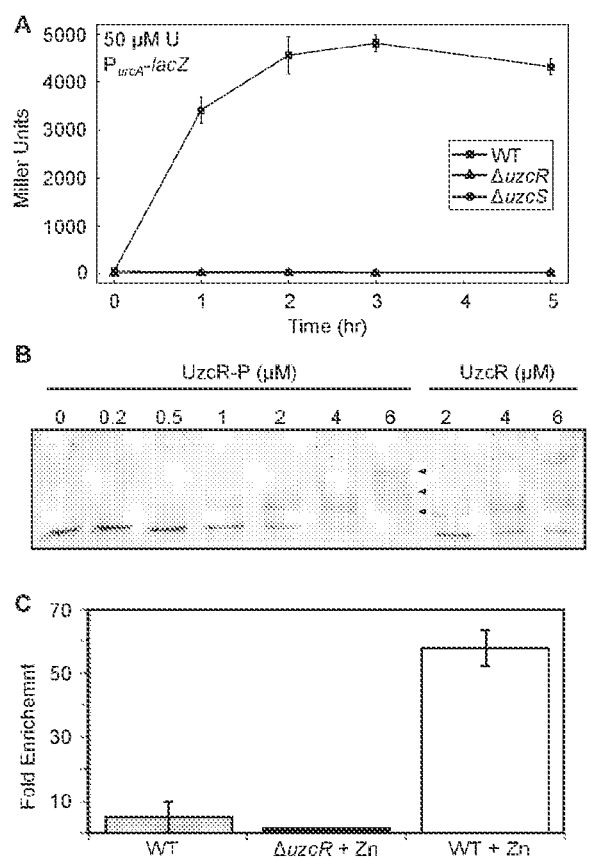
FIG. 24 shows an exemplary direct activation of $P_{urcA}$ by UzcRS according to some embodiments herein described. Panel (A): Time course of $P_{urcA}$-laCZ expression following treatment with uranyl nitrate in M5G media supplemented with 5 mM glycerol-2-phosphate as the phosphate source media for wild type (WT), ΔuzcR and ΔuzcS. Panel (B): EMSA assay of UzcR binding to a 5' 6-FAM (Fluorescein)-labeled urcA promoter fragment. UzcR-P was phosphorylated with carbamoyl phosphate and the concentrations indicate the total UzcR used in the assay. Arrows depict shifted complexes. Panel (C): In vivo binding of UzcR to $P_{urcA}$ using ChIP-qRT PCR. Data are plotted as the fold enrichment at $P_{urcA}$ relative to the control region (sodA) for wild type (WT) with or without 40 µM Zn and ΔuzcR with 40 µM Zn.

Example 5: Engineering of a U-Sensitive Genetic Circuit Comprising an 'in Parallel' Bacterial Two-Hybrid System AND Gate This Example describes the engineering of a U-sensitive genetic circuit comprising an 'in parallel' AND gate that utilizes the bacterial two-hybrid system [93]. In such an embodiment, the alpha-gal11P fusions and lamda repressor-gal4 fusion are expected to be driven by a combination of $P_{phyt}$/$P_{1361}$ and any UzcRS regulated promoter (see FIG. 22).

Figure 7:
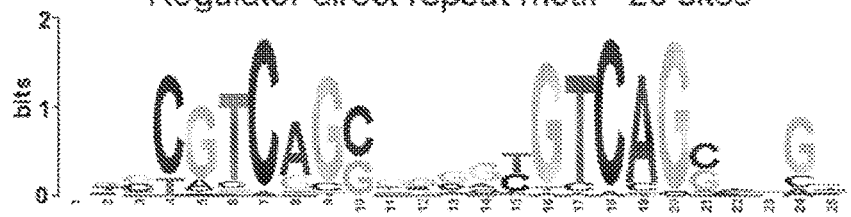
FIG. 7 shows schematics of regulatory sequences within $P_{phyt}$ (FIG. 7 Panel A), showing the sequence CCCAAAGAGGGTGTGGCCCAAAGAGGGTGTGGAT-TTCTCTTCGCGCCACCCGTTTCG TCAGCCGGAC-GTCAGGTCCAGACGGCTAAGCTAGCTGCGA (SEQ ID NO:131) and $P_{1361}$ (FIG. 7 Panel B), showing the sequence ATGTTCAGCGCCTGGTTACCGGC-GATGGCGCGGTGTCAGCGTTCGGGCGTTGCGATG CGTCAGGAGCGTGTCAGGATGCCTGTGGAATC-CTAAGCGC (SEQ ID NO:132) with arrows above nucleotides indicating putative transcription start sites.

Example 6. Identification of a Putative U-Sensitive Transcriptional Regulatory DNA Binding Site in $P_{phyt}$ and $P_{1361}$ Promoter Sequences Using a bioinformatic approach, a putative regulator binding site was identified in proximity to the transcription start site in $P_{phyt}$ and $P_{1361}$ that is comprised of two direct repeat elements (e.g., CGTCAGC (SEQ ID NO:77)); FIG. 7 Panels A and B). This binding site is conserved amongst Caulobacteridae Bradyrhizobiaceae, Sphingomonadaceae, Hyphomicrobiaceae, and Rhodobacteracea, facilitating a phylogenetic footprinting approach to construct a putative regulator DNA-binding motif (FIG. 7 Panel C), using 26 DNA sequences of $P_{phyt}$ and $P_{1361}$ from *Caulobacter* sp. Root342, *Phenylobacterium* sp. Root700, *Caulobacter crescentus* NA1000, *Caulobacter* sp. Root1455, *Caulobacter* sp. Root487D2Y, *Paracoccus* sp. 228, Caulobacteraceae bacterium OTSz_A_272, *Novosphingobium* sp. AP12 PMI02, *Hyphomicrobium* sp. MC1, *Hyphomicrobium denitrificans*, *Brevundimonas* sp. Root1279, *Sphingopyxis* sp. Root1497, *Afipia* sp. $P_{52}$-10, *Caulobacter* sp. Root342, *Hyphomicrobium denitrificans*, *Sphingobium* sp. YBL2, *Sphingobium baderi* LL03, *Sphingobium indicum* B90A, and *Roseovarius indicus* strain DSM 26383.

Figure 9:
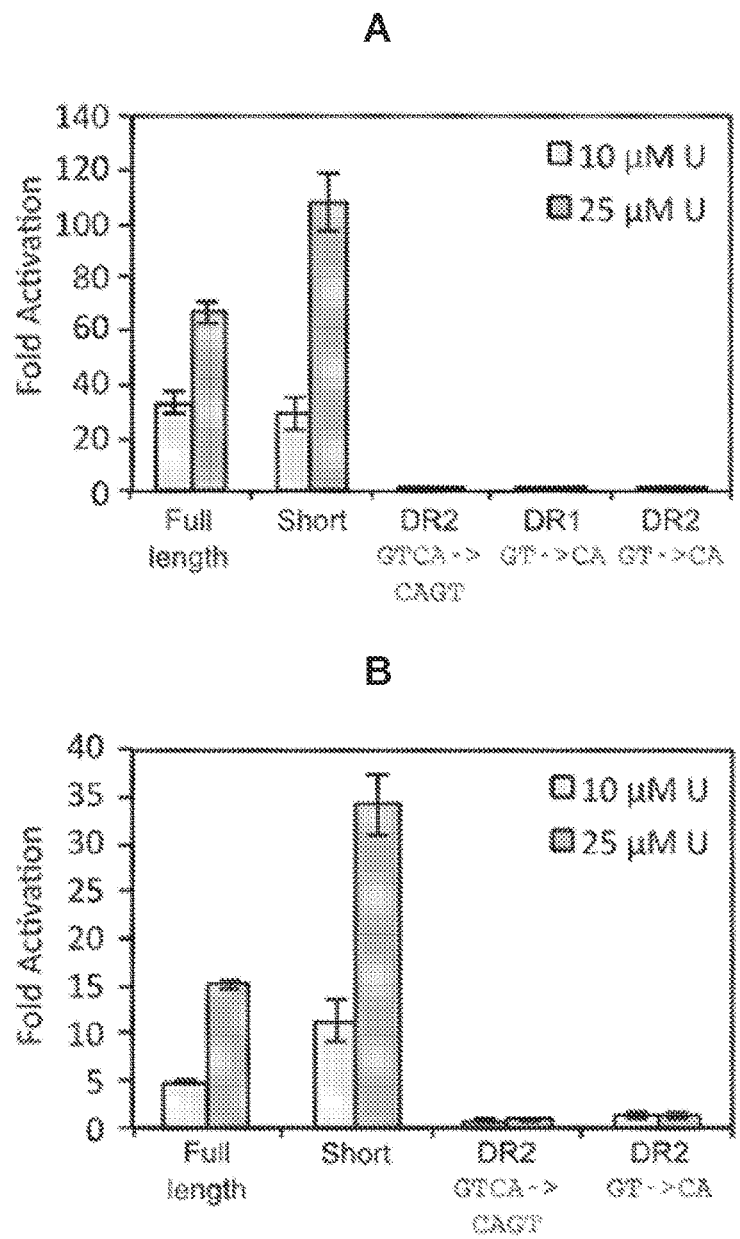
FIG. 9 shows graphs reporting quantification of exemplary fluorescence levels of $P_{phyt}$-gfp (FIG. 9 Panel A) and $P_{1361}$-gfp (FIG. 9 Panel B) variants in response to U at 10 µM or 25 M in the host organism *C. crescentus* NA1000.

The functional role of the putative regulator site within each promoter was tested by mutating conserved nucleotides within each direct repeat away from consensus, as shown in FIG. 8 Panels B, C, D, G and H. Mutations within either direct repeat abrogated U-dependent activation of both the $P_{phyt}$ and $P_{1361}$ promoters in the host organism *C. crescentus* NA1000 suggesting that the U-responsive regulator is natively a transcriptional activator (FIG. 9 Panels A and B).

$P_{phyt}$ (but not $P_{1361}$) also contains a large tandem repeat (TR;32 bp) located further upstream from the putative regulator site (FIG. 8 Panel A). To test the function of this TR in U-dependent induction of $P_{phyt}$ the size of the $P_{phyt}$ DNA was reduced from 238 bp to 81 bp, eliminating the TR and all upstream DNA (FIG. 8 Panel C). The data shown in FIG. 9 Panel A indicate that the TR is not required for U induction. Similarly, a shortened version of $P_{1361}$ that included only nine bp upstream of the regulator binding site (FIG. 8 Panel I) retained U-dependent regulation (FIG. 9 Panel B). Collectively, these data indicate that the DNA sequence extending beyond the regulator binding site within $P_{1361}$ and $P_{phyt}$ are not required for U-dependent activation.

To create a synthetic uranium repressed promoter, the consensus direct repeat UrpR binding site can be integrated within a promoter region, such that UrpR DNA binding will interfere with RNA ploymerase binding and/or transcription. The UrpR binding site should be integrated at a location that overlaps, but does not alter the sequence of the −35 and/or −10 promoter elements or the TSS; disturbing −35 and/or −10 promoter elements will yield a promoter with low basal activity. Ideally, multiple locations will be tested to optimize results. While this promoter can be used to control transcription of any biological reporter, destabilized gfp (e.g., GFP-LVA[124]) is expected to yield the best results given the enhanced degradation rate. Highly stable reporters (e.g., GFP) will require several rounds of cell division to observe a uranium (e.g. UrpR) dependent decrease in reporter activity.

Example 7. Signal Amplifier Module

A positive regulator protein UzcY, encoded by CCNA_03497, was identified, which functions as a "natural" signal amplifier for the UzcRS system. Under normal growth conditions, uzcY is repressed by the MarR family transcription factor (CCNA_03498), and thus has no effect on UzcRS activity. However, when UzcY expression is induced through relief of CCNA_03498 repression or by ectopic expression, it stimulates UzcS activity through a direct interaction, causing a hypersensitive output in response to the metal inducers U, Zn, and Cu. This has the effect of dramatically increasing the output signal amplitude in response to low U (or Zn/Cu) concentrations, thus increasing sensitivity, and lowering the U detection limit of UzcRS by over 4-fold (FIG. 12).

To enhance the sensitivity of U sensors, this "natural" signal amplifier module can be integrated into U sensor circuitry. To accomplish this, in an exemplary circuit the U-specific promoter $P_{phyt}$ or $P_{1361}$ is used to drive expression of uzcY (e.g., see FIG. 13) such that UzcY levels are modulated in a U-concentration dependent manner. The low U detection limit of $P_{phyt}$ and $P_{1361}$ (~500 nM) is expected to allow signal amplification at environmentally relevant U concentrations, which is expected to improve U sensitivity and lower the detection limit in view of exemplary data demonstrating that both of these properties can be achieved with the native UzcRS system (e.g., see FIG. 12). Additionally, by restricting UzcY-mediated signal amplification to conditions of U exposure (e.g. by placing UzcY under regulatory control of a U-selective promoter such as $P_{1361}$ or $P_{phyt}$, the selectivity for U is expected to be further enhanced.

Example 8. Combination of 'in Parallel' and 'in Series' AND Gate Circuits

An example of combining 'in series' and 'in parallel' AND gate circuits within the same cell to enhance selectivity is shown in FIG. 14. An advantage of this exemplary circuit is that the UzcRS input is U selective whereas in the original 'in parallel' circuit as shown in FIG. 6 Panel B, the UzcRS-regulated promoter $P_{urcB}$ is cross-reactive with Zn and Cu.

Example 9. Negative Regulators of UzcRS

Figure 27:
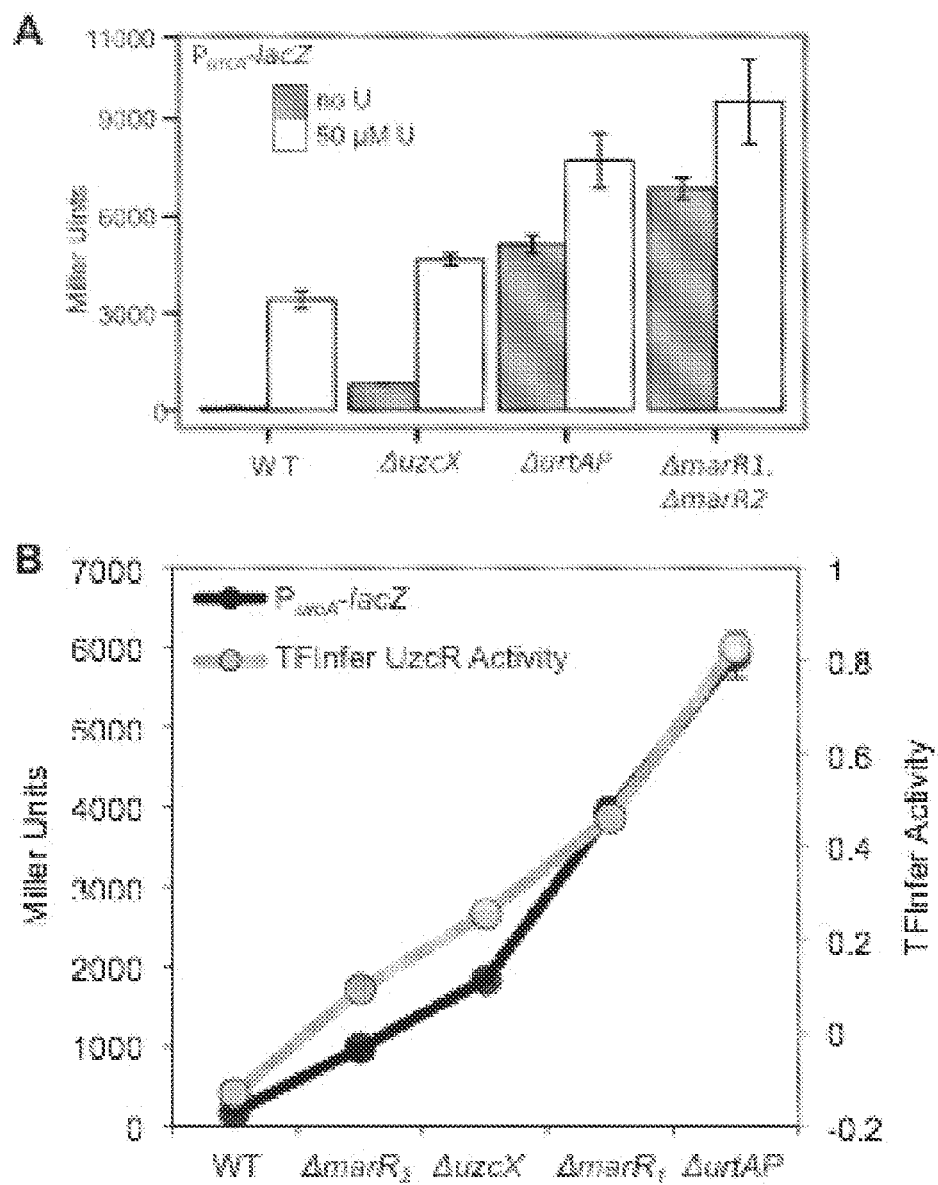
FIG. 27 shows exemplary effect of UzcRS regulator mutants in minimal media and U induction and TFInfer activity of UzcR in negative regulator mutants according to some embodiments herein described. Panel (A): Genes containing transposon insertions that led to high basal $P_{urcA}$-laCZ activity were deleted and the resulting strains were transformed with plasmid-borne $P_{urcA}$-lacZ (pNJH123). Cells were grown to mid-exponential phase in M5G supplemented with glycerol-2-phosphate, washed once with fresh media, then resuspended in fresh media containing 50 µM U. β-galactosidase assays were performed following 1 h exposure to U. Error bars represent the standard deviation of triplicate measurements. Panel (B): The activity of UzcRS was inferred from the log 2 fold change values for 37 UzcR regulon members determined in each mutant relative to WT. $P_{urcA}$-lacZ expression data from FIG. 1A is plotted for comparison.

The following four different negative regulators of UzcRS that are encoded in the *Caulobacter* chromosome were identified (see FIG. 27). None of these regulators are required for U sensing by UzcRS, however, their levels modulate the sensitivity to U.

Negative regulator 1: CCNA_03681 and CCNA_03680 encode an ABC transporter ATPase and an ABC-2 family transporter fused to a C-terminal aminopeptidase N domain, respectively (urtAP). Together these proteins form an ABC transporter with a C-terminal aminopeptidase domain.

Negative regulator 2: CCNA_02866 (also referred to herein as uzcX), encodes a membrane protein of unknown function that is located within a prophage region of the genome and part of the UzcR direct regulon (~8-fold activated by UzcR (Park et al., 2017) [3].

Negative regulator 3: A MarR family regulator CCNA_03498 that represses expression of an operon containing CCNA_03497, CCNA_03498 and CCNA_03499 (see FIG. 26). Expression of CCNA_03497 (occurs when repression mediated by CCNA_03498 is lifted) hypersensitizes UzcS to metal inducers.

Negative regulator 4: A second, paralogous MarR family regulator CCNA_02289 that represses expression of an operon containing CCNA_02291, CCNA_02290 and CCNA_02289 (see FIG. 26). Expression of CCNA_02291 (occurs when repression mediated by CCNA_02289 is lifted) hypersensitizes UzcS to metal inducers.

Example 10. U Biosensor Having U-Neutralization Output

This Example describes a U biosensor having exemplary U-neutralization outputs in response to bioavailable U.

Figure 21:
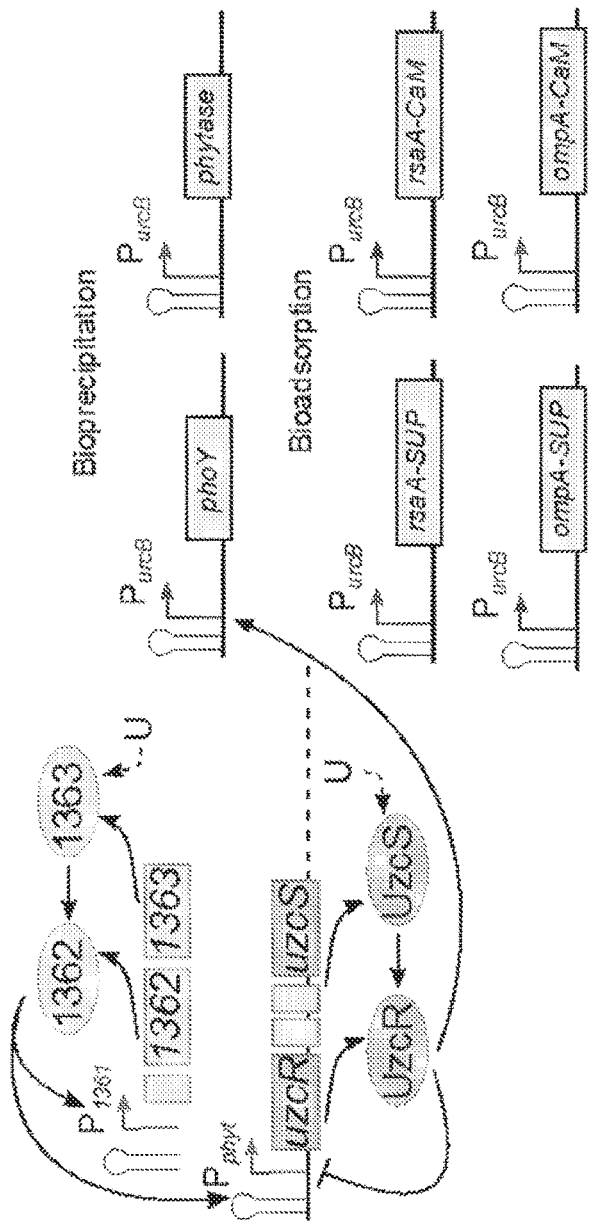
FIG. 21 shows a schematic showing exemplary U-sensitive genetic circuits having exemplary U-neutralizing outputs to allow U bioprecipitation or bioadsorption.

FIG. 21 shows a schematic showing exemplary U-sensitive genetic circuits having exemplary U-neutralizing outputs to allow U bioprecipitation or bioadsorption. In the exemplary U-sensitive genetic circuits, an exemplary AND gate comprises a $P_{phyt}$ promoter configured to initiate expression of UzcR and UzcS in presence of bioavailable U, and a $P_{urcB}$ promoter (activated by UzcR) configured to initiate expression of exemplary U-neutralizing genes phoY or phytase (to provide a U bioprecipitation output), or fusion genes of rsaA-SUP, rsaA-CaM, ompA-SUP, or ompA-CaM (to provide a bioadsorption output).

Example 11. UzcR Regulated Promoter

Table 7 shows a list of UzcR regulated promoters. Bolded regions are putative UzcR m_5 sites and single boded nucleotide is TSS.

TABLE 7

Exemplary UzcR regulated promoters

| Promoter | Promoter sequence | SEQ ID NO |
|---|---|---|
| CCNA_03906 (PurcA) | CCCTTTGCAAACCATATACTCAAACGACCCAAGCAATATGGTCA CAAAAACTTCAAACATTACAGACTGTTTAGAATATTAAAGCCCC GTAATTCTCTTAATTACGCGTCATGACTGAGGTGTAACGAGACT TCGCGAGAACCCGAATGTATCCAATATTCATCGGCGCAGCGAAC AGCGCCCAGCCAGAGGGATACTTCA | 84 |
| CCNA_01185 (PurcB) | GAAGACCCAAGTTTTGCGGTTAATCATTTACGAAGACTGGGCGG GCAGCAGCCCACTCCCAAGCGCCCACCAATTATGACTTCTTTTT CATAGACTTAATTCGACGTCATGAAGCAGTCGTAACGGGTGTTC GCCATCCGACCGCTCTACATCCTCGATCAACGGATCGCCAAGCG ACCACCCAAACCGAGGATCAAGACA | 85 |
| CCNA_R0078 | ACCTGCGCCTGGGCCCCACGGCGGACGGGTCGCGGCCCGGCGCC ACCTTGCAAAGGTTTAATCCACCTGTCCGGCTTGTAACTTCCCT CAAGGGGAGCCGAGAGGCACCGTCGAACCCA | 86 |
| CCNA_00224 | GGAGCGGCGGTCTCAGAAAGGTGGCGAAAATAAAGCACTGATCA TAAGTAAATCGCGATCATCCAAGTAATGACGCCGGGCAATCGAT TGTAGAAAGATGAAAATCTCGTAATGCTATCGGATATGTAATCT ACATGTCAGGCTTGTAACTTGAGATGAATGTTCGGGGCGTTCAG ACCTGTCGCCACTGAGGGGAACCAG | 87 |

TABLE 7-continued

Exemplary UzcR regulated promoters

| Promoter | Promoter sequence | SEQ ID NO |
|---|---|---|
| CCNA_03098 | TCACGCGTCTTCATGGGGCTGCTCCTTGCGACATCGGCGACGAA ACACGCCGTAGACGCCCAGATGGGGGTCGCCCGGAGGCGCGACA ATGGTCGAACCGCATCACCGGGGCAGGCGCCGTGAAGATTACAG TCAATTAAATTGAACGCCGTTCTTCCTTTTCGGAAAGTGCCTTG GGAACTTCCGGACCGAGGGACGTGG | 88 |
| CCNA_00858 | CAGACACGCGGCGGTTTCCGCGACGGAAGAGTGTCGAGGCGGGC GCATACGCCTGTGGCGCGAATGCCACTTGGAGTCCCTCACCCGC AACATTGCCGAAAAGAAATTTGTCCCGGCGCGTCGGAGCGTCTT TACGGCTGGGGGTCGAGACCGCGCGGACGTCCGCAGCGTATCGC TCGACACTTGAAGTTGAGGTCTCCC | 89 |
| CCNA_03762 | ATGCAGGCCGCCTCAGGGGACAAAGTTTCTCACGAAACGGCCTT GTGCGATCACATTACACCGCTGTAACCTCGATTACGCGCGTCAA CGTTCCTTAAATCGGCGTCATGAAGCAAGAGTAACGTGTAATAA CCATGGGGCGGACCTATATCCCTCTCATCGGACGCCAACGGGGC GGCCGAAGAAAAAGGGATCAAGAC | 90 |
| CCNA_02172-02174 | TAACCAGACCGCAAGGCGCCTAAGTCATAAGCCTCTTACCGCCG AGGCCGCGCGCCGGCTGGCGAGCGACGAGGTCTGCCCTTCAGCG AGGCCGGCCCCGACTATTTCATGCCTGAAACGCGCCTTACCCCG ATTTAACTTGGCCACTCGTCGATCGGCGTTCATTGCTGCAACCG TCGATTGGGGGAGCACGAGTCCGCA | 91 |
| CCNA_01968 (P1968) | GCGGAGATGGATCGCGCGACGGGTCTGAAACAGAGTCAGTTGAG CCAGGCGTGCGGCGATGACTCCACGTTGTTGCCCCGCGGACTTT CCATTCCGCGCTGCCGTTAAATCCCCGTCATTACCGCAATTTAA GTGGTCTCTGGCCCTCCGTCGGTCCAAACCGTAACTCACACAGT CGCGTATGGACTGAACGGAGTAGTC | 92 |
| CCNA_03396 | ACCCTTATGGCATCGGCGGTGGATCCGCGCCTCTTGAAGGATGA CCAGCATGCGGATGCGCGGCTGGAAAAGCCGATCACCCCTGGAC GTCTTCTGCAGACGGTGCGCGCGCTGGAAAGCCGCCACGCAGCCG TGACAGAACTTTAAGCTGACCCCGACCACTTCGCGCCCCTAGGG TGTGACGCGTTTTTGGGGAGCTCAC | 93 |
| CCNA_02758 | GCTCGACCCGGCGTTCGCGGCGGGCTGGAGGCGGCGGCCAAGG CCGGGGTGGAGGTGCTGGTCTATGCGTGTGAAATGGGGACGCAG GCGGTGCGGATCGCGCGGCGCATTTTGTGGAGCCACGCCCACCT AACAGCGATTTAAGCTGCATTTCGCGCCCGCTGAGCTAACCCTT CTGCAGGCTCGCGAAATGGGGATCG | 94 |
| CCNA_01551 | GAAAGAGTGTTCAGGCGCAACCTGGGGGAAGGTCCCAAGGCCTA GACTGGCACCTAGGGCCGAGCGACGCTTGCGACAACCGTCGGAA TTCTAAGGGTGCTGTCAGATGTCGTGGAGCCCCCTTGCAAGACC ATCGGCCCTTCATGACCAAAAGTTCACTCGCCTGCTTTGCGAAA TGCTCGCATAACGCCGCTATGGGAT | 95 |
| CCNA_03997-CCNA_03786-03788 | GGTTCGCCGCGCGATCGCATGGCGTGACGACCATGACTAGAGGG GCCAAGCGCCAGAACCTGTCAGCTAAGCCGCCCAGCGACGCCGA ACGCCGTTACCGCGATGGGGCAAACCTGTAGAATTGTTCATGAA CCCGGACATTTTCGCGCCATAACCGCGTGGCCAAGCTCCAGGCT CGGACTACGACAGGGAGCTCACAAC | 96 |
| CCNA_00147-00149 | CCTCGATGATCGCGACCGACCCCTCCACGGCCTGAGTGTGCGCC GATAGCGCGGGCGACACGCCGCCGCCGATCATTGCCAAAGTTTA ATATCGTTTCTCGATAAACGACATTGGCGGAACCGCAAACCCGG CCTATCTGTTCAGTGTGGCGAAGGGGCGAATGTTTCGGCCCTGG CCATGTCTCTCAAACTGGAAAAAGC | 97 |
| CCNA_03324 | TCGTACGGCGATGGTCGATGTGCATGGCCAGTTGGATGAAACTC GCTTGCGCCTTGGCGTTAGGACCCGCATGGGCGGCTCGCTCAAG CCGATCGAGGAAACCACGCGTGGGTTGAAGGAAGTCGGCTGAGC AACGATCAACCGGACATTGCGATAGTTTAATAACCTTGGGCCTC TAATTTAGGTTAGAGGCCCAAGTCA | 98 |
| CCNA_01303 | CTCGCGACGCTCGCTCGCCGCTATCCCCGGCTGGGCGCGGCGCT GGGCCTCGGCTTCGGCCTGTGGGTCTGGCGATGATGGTGGACT AGCCTGACCCCAACATGACTTCGCGGTCATGACCTCGAATTAAG TCGAAACCTTGTCGGCCCCTCGGTAGCCTCTCCTCATCGAATTT CAACACGCGTCCTTGGGGAGACACT | 99 |

TABLE 7-continued

Exemplary UzcR regulated promoters

| Promoter | Promoter sequence | SEQ ID NO |
|---|---|---|
| CCNA_00913-00911 | GGTACGAACGCCGCGGCTACCGCCTGACCGGCGAAACCCAGCCCTTCCCCTATGGCGACGACCGCTTCGGCCTGCCGCAGCGGGATGATCTGGCGTTCGTGGTGATGGAGAAGGGGCTGTAGGGCCCCATTACCGAACCTTAAGTAGCTCCGTCCGGGCCGACGCGTTCAGATGCCGCGTCTTCGGCTCAGGGACTCTCCA | 100 |
| CCNA_03699 | CCTGACCGATCGGGTCTATGACTGGGTCGCCGCGAACCGCTATCGGATCTTCGGCAAGCATGACCAGTGCCGGATCCCGACGCCGGCGCAACGGGCGCGCTTTCTGATCGACTAGCCCCGCCCCTATATGAACTCTCGGTAAGGTTTCCCGGCGAACCGGCGGTGCTAGGGTCCCGCGCAAACATTCAGGAGACTCTCGCG | 101 |
| CCNA_02196 | GTCGTGGGCGCTGATCATCTCCGGCTCGGTCGTCTATGCCGGAATCTACCTGCTGGCGCTGGCGCCGGTGGGCAAGAGCCGCTGGGCGCGCCGCTGGCAGCTTCTGAAGTAGGGCGGTGAATTCGGCGTAATCCGCGTCGAATCCCCTTCACAGCGACGCCTTGCGGAGCCACCTCTAGGGTCTCTTCCTGGGGCAGCACA | 102 |
| CCNA_01521 | CTGCATGGCGCGCTGCTGAAAAACGAGCAGGACGTCCATCTGTTCGAACGTCTGGCGTTCCTCGCCCGCCGCGAAGGCTCGGGCACTCGTCCGGGCCAGTAAGGCGTCTGCGGCGAAACGGCCGTTACCGGGATTTCACTGGACGCGCGCCAGACGCGCGGCCACCTTCCCGCCCATCAGGGACGGCCGAGGAAACACCA | 103 |
| CCNA_01379-01380 | GTCGGCCGTCGCGCCGCGTTCGACGCTTCGCCGCCGCTGCTCGCCGGCTTCGAGGCTGAGACGGGCTTCAGCTTCTGACGATCTGGGCCCGATGGACCGTCGCAACGTTTGCGTGAAAAAAGCTTAACTGGCGACGACTGGCGGAGCGACTTACACGCGATCATATTGTGGCCGGCGCGAGCTTCGCGTGATTGGGGATAG | 104 |
| CCNA_01335-01334 | ACCAGGGACAGCAGGCGGCGCAGGATCATCTTCGGGCTCGACTTGGAACGACGGTTCCAGCGGTCATCCATGGCCCAGATTGCAGGCGTATGACGACCGGCGGTCTCCGAGGCATGACACCCTCTTAACTTGGCGTGGGCGGGCGCGCTCGCCATAGTCTTCGCGTCGAGTCGACTCAGGTCGGCGTCCGGAACCGCTCCA | 105 |
| CCNA_02866 | TGCAGCCGAACGCCAGGCGCGCGGGCAGGCGCGCCTCATGGAACTCGCTCATCAAGCGATCCTTCTGGAAAGTCGAGAAAAGGTTTGAGGAAAAGCAAGACGGCGCTTAGTCGACGCCATTAAGACGACGTCATGACCCGCTTTTCACTTCTTGCGCGGGACATCGGTCTCTAGGTTAGGGATCGAGATTGGAGACCACGA | 106 |
| CCNA_R0100 | GAAGAACAGCGGATTCTTAATTCGCATCCATGAAAGGGCCCCGCAGCGATTTCGCCATGGTCTCGCCACAGAGTGGCGGCGAGCTTGGCCGCG | 107 |
| CCNA_00851-00849 | GGTCTCGTCAGTTATGGAAGTCCTGTGCGGCATTACATTTCCGTTAGGTCAGCCAAACGCGCGGCGCCGGAGGTTGACTTGCGACACTCCAGCTCTTATGTCCAGCCCACATGAGAATGAACGTTCATTCTCAAATCGTTCATCATAGTGGCCGCGTCAAGGGTAAGAGCCCGCGCGACCCTCGCCTCCCGGGGTCAAACA | 108 |
| CCNA_03619 | AACCCGGGCAAATCCTTTCCCGGCCCGGATCCCCTGCAAGGCCGCCGCACGTTCCCCAACGTCGGCGGCCTTTTTGCGTCGCTTCTCGCGCCGAGGCCCGACCCGCCCTGTAAAAAATGGGTCACATGAACTTTTTTTAAGGGGGTAAAGTTTTCGCGCCGTTGCAGATTGCCGGCGGCTCACACCAACGGATGCGAATTC | 109 |
| CCNA_02933 | CCTGGCGATAACGCCGGTCTTCGCGCCAAAACCTGCCCAAGATTACAAAACGTTCAGACTCCCCCGTCTCGACAAGCTGTCACAGGCTCGACATGGTTCGCCGCCGTCGCGGACTTGGGGGTCTGCGGTGCGGGGATTGGGGCGGTCGCGCCTCCAACACCAAACATAATTTTGGCTACACGCCCGAGGAGCGTCTCAAGT | 110 |
| CCNA_02597 | CGGCCGCCTAGCAACAGCGACGCTCCGGGAGTTGGTCGTCGTTCCACCCTATGTGATCCGCTATTATGTGGCTGACGGTCTGGTCGATATCGTCCGCATCCGGCACGCCGCCCGGTTGTGACTTTTTCGTAATTCATCCTGGGTTCAGGCGGCGAGCGGTCCTCTCACGGTCAAGCTGACCAAAAAGAGGGGACACCAGCA | 111 |
| CCNA_01139 | AAGGACGCCGCCGAGCAGTCAGGGACCTATCTGGCGACCTGGAAGAAGGTCACGGGCCAGTGGGTGATCGAGAACGAGCTTTTCGTGACGCTGGCTTGAGCGACGGGCCTCTTCCCAGCGAGTATGACGCGGAATTAATTAAGCCCAAACAGGGGCGGGGCTTACGCCTTCGTCCTTCAATGCGCCTCTGGGGAGGAAAAC | 112 |

TABLE 7-continued

Exemplary UzcR regulated promoters

| Promoter | Promoter sequence | SEQ ID NO |
|---|---|---|
| CCNA_03816-03814 | CGCCTGGGGCAGACGCTGCACGAGGGCGCGGTGGACCGAGAGGC CGCCCACGCCAGAGTCAAAGACGCCGATCATGGGCCAAGCTGTA GCCGCCAAAGCGGGGCGCGTCCACGCACTGGGGAAGGTTACAGT CCTGTCATGTGACAGGTCGGCCGCCCATATCCTAGGGTCACGGC CAACACTTTCACCGGAGATCCTCCG | 113 |
| CCNA_02588 | GCGACCAGGCGGGCTTCGAGCGCGGCGTGAGACATGGGCACGGG ACAGCTACTCCGATCCTTCAACGACCTATGTGACCGGGATTCCT TAAAAACGGCCATACCCCGGGCCCACAGGTTACAACCCTAGTTA TAAAACCACTCATCGTTATGACCGAGAATTAATTGAATGTGGCG CCCGCTCCGGGCCATGTAGCGCCCA | 114 |
| CCNA_02218 | GGCGCCGTATCGGCCGCCAAGCGGAGCCATAGCCACTCGAAGCG CGTTCGGCTCCTTGGCGGTATTGGTGCGGGCTCTCGCCGCATTG CACTAAAGTCATGTGAACGATCATTCTCATTGTGCTAGAAGCGC GGAATGAGGTGATCCGGTCGCTTTGTCGTGCGTATCTCTCCTGT CCGTTGCTGGTTTCGAGGCGACCCA | 115 |
| CCNA_03097 | CGTCATCGCCATGCCACGTCCCTCGGTCCGGAAGTTCCCAAGGC ACTTTCCGAAAAGGAAGAACGGCGTTCAATTTAATTGACTGTAA TCTTCACGGCGCCTGCCCCGGTGATGCGGTTCGACCATTGTCGC GCCTCCGGGCGACCCCCATCTGGGCGTCTACGGCGTGTTTCGTC GCCGATGTCGCAAGGAGCAGCCCCA | 116 |
| CCNA_00419 | GTCGTCCTGCAGCGTCGGCGGGACGGCGGTGTCTGGGGTGGGGT CGGTCACGGTTGAGCCTGGAATAGTCTTGTTATCCAGATCGTCG CGCTGATCAGGCCGTGATGCAAATGAAGGTGGCGTCATGAAGGC GATGTCACGTTGGGCGCGTCCGCCGGACCTTACAAAAAAGTCAT CTCCTCGGATCGATCCGGCGCCGACGCCGGGCCGTAATCATCAT CAGACCGCGCGCCGTCGACCGCTTCAGATCCCCCAACCCGAAGA CTTGATGGAAGGTTTCAGACAATGATGCGTTCGATGC | 117 |
| CCNA_00417-00416 | GTCGTCCTGCAGCGTCGGCGGGACGGCGGTGTCTGGGGTGGGGT CGGTCACGGTTGAGCCTGGAATAGTCTTGTTATCCAGATCGTCG CGCTGATCAGGCCGTGATGCAAATGAAGGTGGCGTCATGAAGGC GATGTCACGTTGGGCGCGTCCGCCGGGACCTTACAAAAAAGTCAT CTCCTCGGATCGATCCGGCGCCGACGCCGGGCCGTAATCATCAT CAGACCGCGCGCCGTCGACCGCTTCAGATCCCCCAACCCGAAGA CTTGATGGAAGGTTTCAGACAATGATGCGTTCGATGC | 118 |
| CCNA_02914-02917 | AAGGACGAGGATTTCCAGCCGGCCTCGCGCCGAAATCTTGGCGA CGAAGCCTTTTCCCCGGGGGAAGGCACGTTTGCAGCCGGATCGG TAGCGAAATGCGTCACGCGTGCAAACACCGCGCGCTGAAACATT ACATCTGAGAAATATTTGACCTCAGACGCCAGTCTGCGTCAGAA CTTCGCTCGCGTGAGATTCCGGCCGATCCGGAACGGGCGAGACC GTGCCCCAATCGCGGGCACTGGGAGGAGAGACCTTGGATAGAC GACAGTTCCTCGCGGCCTGCGGCATCGGCGCCGGGGG | 119 |
| CCNA_00976 | CATGCGAAACGCCAAGCGCCGCTTTCGCGGCGCCGAGGGCTTTG ATTTTAGAGGATTTTCCCGCCTCTGGCTGGCGGGGAGGAAATGG TCGGAGTGGCAGGATTTGAACCTGCGACCCCTGCGTCCCGAACG CAGTGCTCTACCAGACTGAGCCACACTCCGACTTGGAGGCCGGC CTTATAGGTGGGTGTTCCGGGGGGCGCAAGCGCCTTTTTGCAGG TTGGTCGGGAGGCCTGAAAAAGTTCTGAAAAGGTCGTTGCATC CATCCGAGTCGTGAGCTATCTCCACCGCCTCGCCGGG | 120 |
| CCNA_03893-CCNA_01721 | CGCGCCGGTGCTGAACGTGCTGATCGGCGCGCTGGCGCCGGGTC TCGCCCCCGCTGCGGCGGCGCTGCCCCTGGTGGCGGCCACGCTG CTGGTCAGCAGTCCCTCGGTCCGGCGGCGACTGGGCTTGGCCGC CGTTTAGCGCCTTACGAAAGTTTCATGGCGAGCGGCGCCTCCAA ACGGGGGCGTGAGCGCCTCTTACCAGTGAAGGCGGCGCTGTGGC GTCGTTCACCGAACTGGAGGATTTGAGAATGGGTCCCGAAATCA TCGTCCCGGTCGCGCTCTTCGCGATGATCTGCGCCGT | 121 |
| CCNA_03456 | TTCTCGTGGCGCGCCTGCGCCGAGGAGTTCTTCCGCAACCTGCA GCCCTATCCGGAACCGGAAAAGACCCGCTTCTGGCGCCGGCTGC GGCGCCTGGCGCGCCTGCGCAAGAAGACGGCGGCGTAGTCGCTT CCTGTCCGCATTGTAATTGGCGCGGCGCGCAGACCTCGGATAAC GCTGGTCTCTCGATAGGGAGGGCGGCATGAAGCTCATCATGATC GTCATGGGACTGTGTCTGGCGGTCAGCGCCGCCCAGGCCCAAAC GAGCACGCCCGCGCCCGTCATCGAGACCTACAAGACA | 122 |

TABLE 7-continued

Exemplary UzcR regulated promoters

| Promoter | Promoter sequence | SEQ ID NO |
|---|---|---|
| CCNA_03519-03521 | CGCGCATCGCTAGCCCTTGCCAAGCGCCAGAGCCCACGCGCTGAGCATGGGAACAGCCCGTAACCCCCGCCCCGAGGGGGTTCAGTCGCGAATGCCTCTCAGAAACCCCCGAATTCGGCGTCCGGATCATTACGTATCATTCATGAGTAGGTACCTTGCACCACTCAGTACCGGGCGGTACAAGGGAGCATCAACGGAGGCAAGGACGCCGTGCCGGAAACAATTGAAATCCAACTGAAGAAAGGCGTGCTGGCGCTCTGTGTGCTGGCTCTGCTCTCGCACGCCGACAGCTACGCCTACG | 123 |
| CCNA_01712-01710 | CCAGCACCTCCTCGGCCGGCTTGGGGCTGTCGGCCCAGAGCACCTTCATGACTTCGCTCTCGGCGCCGCTGATACGTTGTGATGTCGTTTCCATGAGCGAACGATTACGCACGTAAACGTTTCCGTCAAGTGATCGATTACGCACGTAAACGAAATGTAATGCAGCGTTGGAGGCGTAAGCGAAGCGGCTTAACGCTCGAGAGCGGAGGAGTCGTACATGCCAGACACGCTTCAGCTTGGCCTGCCGGGCCTTGAGTCGCCCACGCCGACGGATCGGCTGATGTTCCTGCTGTATCCTGAC | 124 |
| CCNA_03195 | GCCCGGGACGATCTGGGTCGCCAGCCACAAGCCGAAGGCGGCGATCAGCAGGCGAAAAATGAGACGGACCATGACTTCTCTCCAACTTCAGCCGCAACGCGTCCAAACCATCGCCGCATTCGTACAATATCCGAGCCCGAAACTCGGACATTACAAATGCGTTACCGCTCTTCAAACTGCCGCAGCGTGAACTATCTACCCTCCTGTGTGGGGGATGATCGCGCGCGATTGGCGAGCGGATCCGCACGCAAGGGGATATGAGTAAGATGGCCGTGAATTCTCTATCGGTGATGTCGCCGGA | 125 |
| CCNA_03640 | CTCGTCCCCGATCAGGACAATCCGACCCTCGTGACCATACTGGCGCAGGAACGCGGCGACCGAGCCGCCCGCGTGACCCGCGCCGACGATGACGACGCATGCGTTCTGATTAACTTCAGCGCTCAATGACGCCCTCCCTTTCGTCAAAAATGACGCCGGCGTCACCTATTGGCAAGCGCCTTCGACAGAGGCGGATACGGAATGGGGCGGCTCGTTTCCGAAGCCGCCCCACATTTATCGCTCTGCAGCGTGCGTCAGACGACGCGCTCGACCATCATCTTCTTGATTTCGGCGATGGCCT | 126 |
| CCNA_02421-02419 | TGAATAGTCCGCCTGGAGCTCGATAGCTCTCCCCCCCAGCGGACCCGCTTCGCTGCGCTCGACCCGTTACGCCCCTCACGAGGACCAGCCTCCAGAAGGATCGTTTCGAAGCGCGTGCAACCGACGCCCTTTTGGGGCTCCGGTCTTACCGCAATGTTAGAATTGCGGCTGGGGTCCTTTGGCAACCCCTTTTCGTACCGTCAAGGGTCTCATTTGGGCACAATTCATCGTCACGCCCCCGCCCCCCTGGCGTTTGCCGCAGTGCACAAAACGGTTTTCCGGATTTCGGGCGGTTTTTC | 127 |
| CCNA_00974 | GTTTCGGGAGCGGAAAATAGCCTAGAAAAAACAGCCTCATGTTTGTGAGCGCGTGCTGTTTTCGATGCTTGCGTATCCATATTGAGCAATGATTTTCCGAAAAGCGTTCCTCCTGTGGCGATTTTGCGACAGGGGGGTCGGGATAATGATTACTTTTTTGCAATCAGAATTGACCCTCGCCCGATCCACCCCCTAACGTCGCTGCAACCGGAAGAGTTTGTTCCGGGACACATGTGATCGCGTGGTGGATTTACAGCGGATTTCGGCTCGAAAACGGACAGGTCGCTGAGGGGCTTCTTGT | 128 |
| CCNA_02370 | AGCCCGATTGGCAACCTGTCAATCCGTCAACTTGGGGGGATTTGCGCACCTAGCGCCCACCAGCATGGGCGATAAGTGGCGCAAAGAAGACACACATCGCCCGTTTCGAGCCGCCTCGCCGCACCGAACGGTCATCGTTTGCAGATTTTTGTGTTGATTACGGTCCGTTAATTTGCAGTAATTTGCAGCAACGGCCCGCCGCATGACCTCAACAGCGCAGAGCCGGACAGGGAGGGAACTCGTATGAACACCCAATTTTCGCGCCGTCGCGCCTGGCTGATGGCCGGCGGGGCCACGGGCC | 129 |
| CCNA_02287-02288 | GATGACAAGGAAATAGCCGGCGGCCATGCGGTCGAAGGCGGTTTCAAAGGCGTTCAGCGTGCGGTTCATGATGGAAGTCCCTCATTTTGGCTTGCCCCGACCCCCTGTGGGTCATCGCCCTCGAAAGTTACGAGGCGATCTGGACAGTGCTTAGATAGCACCAATCTGAACGCCGTCAAGATGGTCTTTACAGCGTTTAGATGAAATTTTAGAAAGCTATGGTTAGAGTGAGGCCGATGAGCACAGCGACCGCCGAATCCCGCCCCTATCACCATGGCGATCTGAGCCGCGCCCTGATCGA | 130 |

Example 12: Application of a Combinatorial Input Logic Towards U Detection

A combinatorial sensor approach using multiple regulators with broad specificity profiles can be adopted for the selective detection of compounds lacking specific regulators (e.g., butanol).

To apply the combinatorial input logic towards U detection, an AND gate circuit was developed by integrating two functionally independent, native U-responsive regulatory pathways into a single synthetic pathway in *Caulobacter crescentus*. Prior studies revealed that *C. crescentus* tolerates high U concentrations [125, 126] and exhibits a robust and specific gene expression response following U exposure. [125, 127, 128] Using the promoter of the highest U-induced gene, urcA,($P_{urcA}$) to drive expression of UV-excitable gfp, Hillson et al generated a whole-cell U sensor that was responsive to sub-micromolar U concentrations and successfully detected U in a groundwater sample.[128] Subsequent genetic and biochemical analyses revealed that the majority of U-dependent gene induction in this bacterium, including regulation of $P_{urcA}$, is mediated by the TCS UzcRS,[118] supporting a role for UzcRS as a U-responsive master regulator. However, characterization of the specificity of UzcRS revealed strong cross-reactivity with the common environmental metals Zn and Cu.[3]

To improve upon the selectivity of the UzcRS system, the selectivity of a second U-responsive regulatory system (UrpRS) in C. crescentus was identified and characterized. Leveraging the distinct selectivity profiles of the UzcRS and UrpRS TCS and the tripartite GFP genetic framework,[129] an AND gate circuit that integrates signaling input from both pathways was constructed and characterized.

Example 13: Identification of the U-responsive UrpRS TCS

Examination of U and Zn transcriptomic data [3, 125] in C. crescentus revealed a small subset of highly U-induced genes that are not regulated by UzcRS and only weakly induced by Zn (FIG. 1). Two operons (CCNA_01361-CCNA_01362-CCNA_01363 and CCNA_01353-CCNA_01352-CCNA_01351) were of particular interest based on several observations. First, both operons are highly induced by U in minimal and complex media, but lack induction by other known stress responses (e.g., DNA damage, heat shock, heavy metals; Table 8A to Table 8C).

TABLE 8A

Fold change in CCNA_01361 and CCNA_01362 expression under various stress conditions

| gene | Function | U - PYE | U - M2G[125] | Zn - PYE[125] | Cd - M2G[125] |
|---|---|---|---|---|---|
| CCNA_01361 | PepSY superfamily protein | 91.8 | 7.4 | 1.1 | no DE |
| CCNA_01362 | two-component response regulator | 103.3 | 9.7 | 2.3 | no DE |
| CCNA_01363 | two-component sensor histidine kinase | 74.4 | 7.7 | 3.4 | no DE |
| CCNA_01353 | myo-inositol-hexaphosphate 3-phosphohydrolase (phytase) | 115.1 | 5.5 | 2.4 | no DE |
| CCNA_01352 | two component sensor histidine kinase | 7.2 | 6.6 | 1.3 | no DE |
| CCNA_01351 | two-component response regulator protein | 4.4 | 9.5 | 1.6 | no DE |

TABLE 8B

Fold change in CCNA_01361 and CCNA_01362 expression under various stress conditions

| gene | Function | $CrO_4^{2-}$ - M2G[125] | $Cr_2O_7^{-2[125]}$ | $^2SeO_3^{2-[125]}$ | C starvation (Britos) [130] |
|---|---|---|---|---|---|
| CCNA_01361 | PepSY superfamily protein | no DE | no DE | no DE | 2.9 |
| CCNA_01362 | two-component response regulator | no DE | no DE | no DE | no DE |
| CCNA_01363 | two-component sensor histidine kinase | no DE | no DE | no DE | no DE |
| CCNA_01353 | myo-inositol-hexaphosphate 3-phosphohydrolase (phytase) | no DE | no DE | no DE | no DE |
| CCNA_01352 | two component sensor histidine kinase | no DE | no DE | no DE | no DE |
| CCNA_01351 | two-component response regulator protein | no DE | no DE | no DE | no DE |

TABLE 8C

Fold change in CCNA_01361 and CCNA_01362 expression under various stress conditions

| gene | Function | heat shock (DnaK/J depleted) [131] | DNA Damage [132] | Fe limitation [133] |
|---|---|---|---|---|
| CCNA_01361 | PepSY superfamily protein | 1.0 | 1.1 | no DE |
| CCNA_01362 | two-component response regulator | 0.8 | 1.1 | no DE |
| CCNA_01363 | two-component sensor histidine kinase | 0.6 | 1.0 | no DE |
| CCNA_01353 | myo-inositol-hexaphosphate 3-phosphohydrolase (phytase) | 2.1 | 1.1 | no DE |
| CCNA_01352 | two component sensor histidine kinase | 1.8 | 1.3 | no DE |
| CCNA_01351 | two-component response regulator protein | 0.8 | 1.3 | no DE |

The operons are furthermore likely regulated by the same transcription factor based on the presence of nearly identical DNA sites comprised of two tandem direct repeats (5'-GTCAG-3'; FIG. 7A-B) with 11-bp center-to-center (ctc) spacing within the CCNA_01353 ($P_{phyt}$) and CCNA_01361 promoters ($P_{1361}$). This direct repeat site is conserved within the promoters of closely related Alpha proteobacteria (FIG. 7C) and required for U-dependent induction of $P_{phyt}$ and $P_{1361}$; mutations away from consensus in both $P_{phyt}$- and $P_{1361}$-gfp fusions abrogate U-induction (FIG. 9A-B). The CCNA_01353-CCNA_01352-CCNA_01351operon encodes a phytase enzyme that confers U tolerance[127] and an uncharacterized response regulator and histidine kinase pair, while the CCNA_01361-CCNA_01362-CCNA_01363 operon encodes a PepSY superfamily protein and another uncharacterized response regulator and histidine kinase pair.

Figure 17:
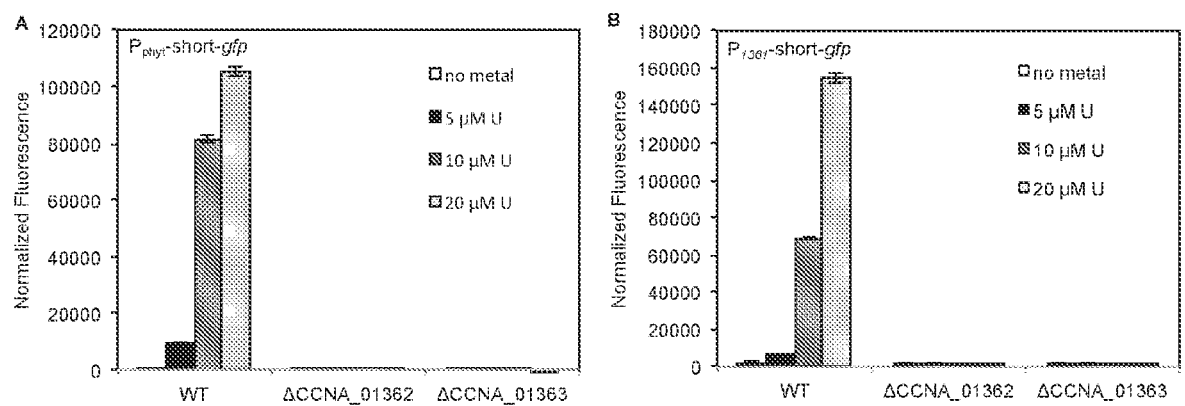
FIG. 17 shows graphs reporting quantification of exemplary fluorescence levels of a shortened $P_{phyt}$-gfp (FIG. 17 Panel A) and shortened $P_{1361}$-gfp (FIG. 17 Panel B) variants in response to U at 5 µM, 10 µM or 20 µM.
Figure 18:
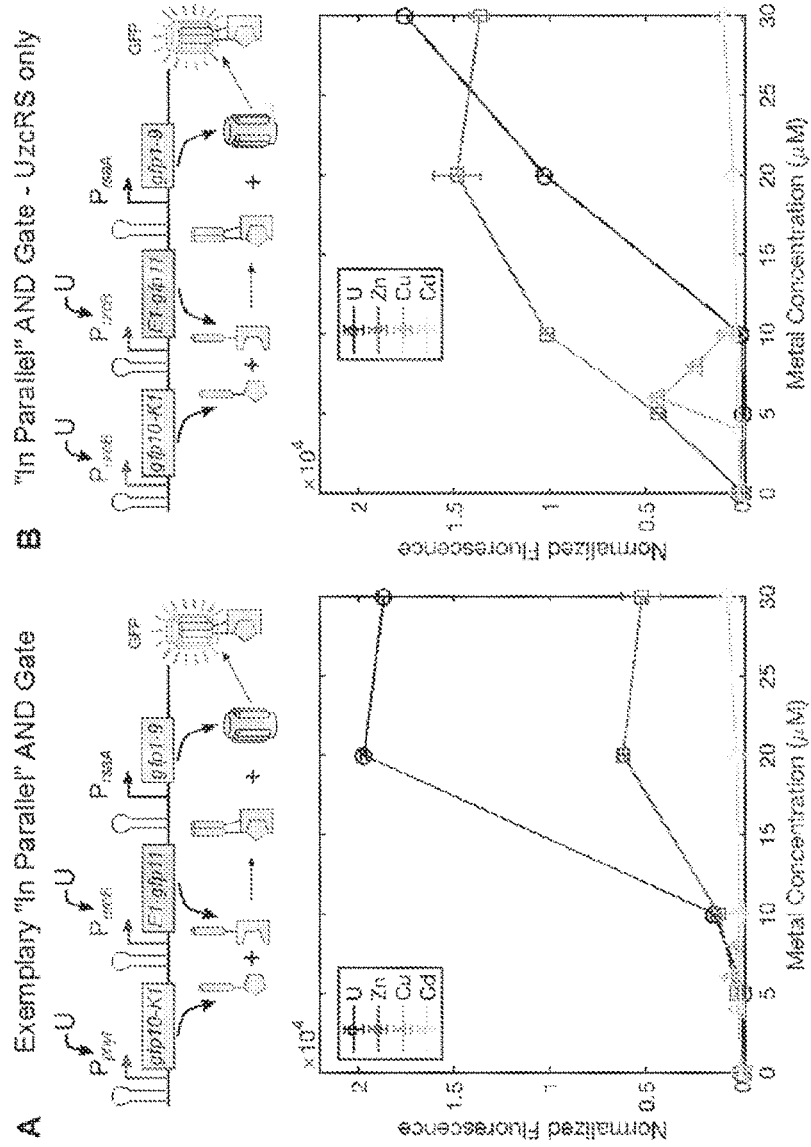
FIG. 18 shows schematics illustrating exemplary tripartite GFP U-sensitive genetic circuits together with graphs reporting quantification of exemplary GFP reporter fluorescence produced by the respective genetic circuits under the conditions indicated. In particular, FIG. 18 Panel A shows a schematic of the U-sensitive genetic circuit shown in FIG. 6 Panel B and FIG. 18 Panel B shows a schematic of a control circuit that incorporates input from only the UzcRS TCS, comprised in the host organism C. crescentus NA1000, upon exposure to U, Zn, Cu or Cd.
Figure 19:
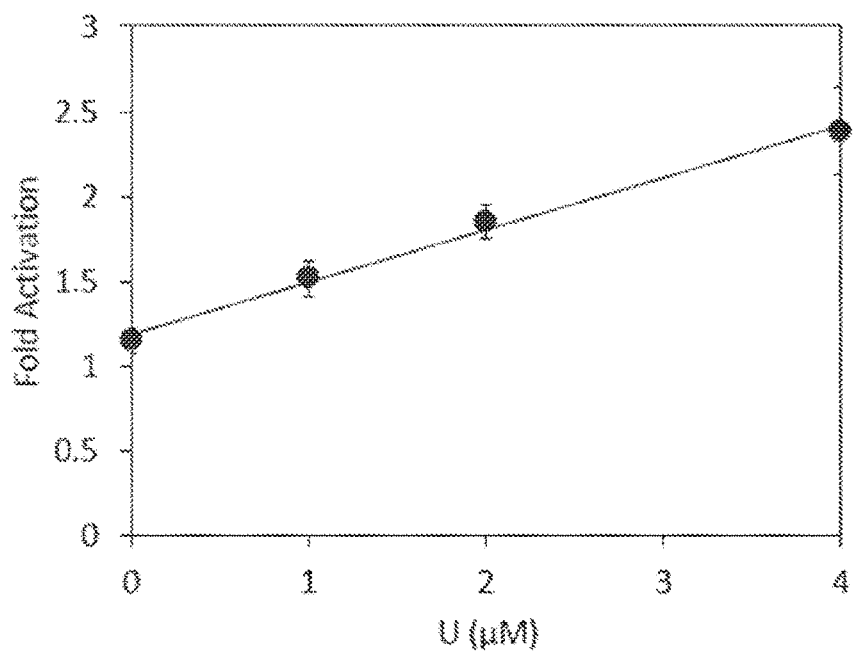
FIG. 19 shows a graph reporting exemplary data indicating the limit of U detection for the U biosensor described in FIG. 4 Panel B. Mid-exponential phase cells were washed twice in 10 mM Pipes pH 7 and then resuspended in 10 mM Pipes pH 7 containing uranyl nitrate. As shown in the graph, a linear response was observed for U concentrations in the low micromolar range.
Figure 20:
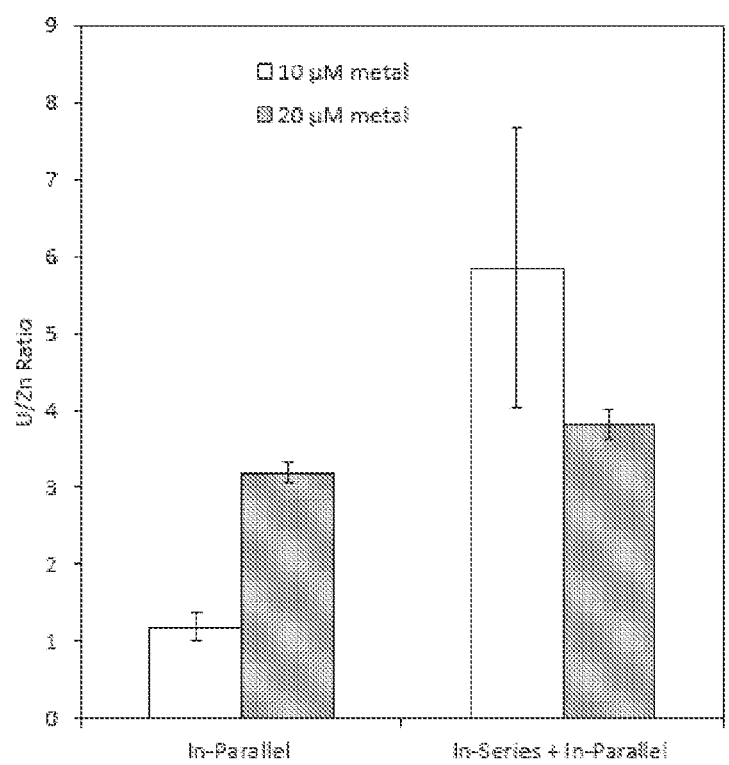
FIG. 20 shows a graph reporting exemplary data showing the ratio of the fluorescence output in response to 10 and 20 µM of U and Zn for the "In-parallel" AND-gate shown in FIG. 6 Panel C and the combined "In-series" plus "in-parallel" genetic circuit shown in FIG. 14. Cells were grown to mid-exponential phase in M5G-G2P media, washed once with fresh media, then resuspended in fresh media containing the indicated metal concentration. Fluorescence was quantified following a three-hour exposure of cells to each metal concentration and normalized to the $OD_{600}$. The U/Zn ratio was calculated by dividing the normalized fluorescence with U by that with Zn.

This direct repeat binding site bears striking resemblance to the binding sites of OmpR/PhoB family response regulators.[134, 135] As such, the OmpR/PhoB-family response regulators CCNA_01351 and CCNA_01362, whose expression is governed by $P_{phyt}$ and $P_{1361}$, respectively, are potential candidates for the U-responsive regulator. Deletion of CCNA_01351 or the histidine kinase CCNA_01352 had no effect on U-dependent induction of either promoter (data not shown), consistent with the results of transcriptomics performed with both mutants during U exposure.[125] In contrast, deletion of CCNA_01362 or the histidine kinase CCNA_01363 abolished U-dependent induction of both promoters (FIG. 17A-B).

Figure 28:
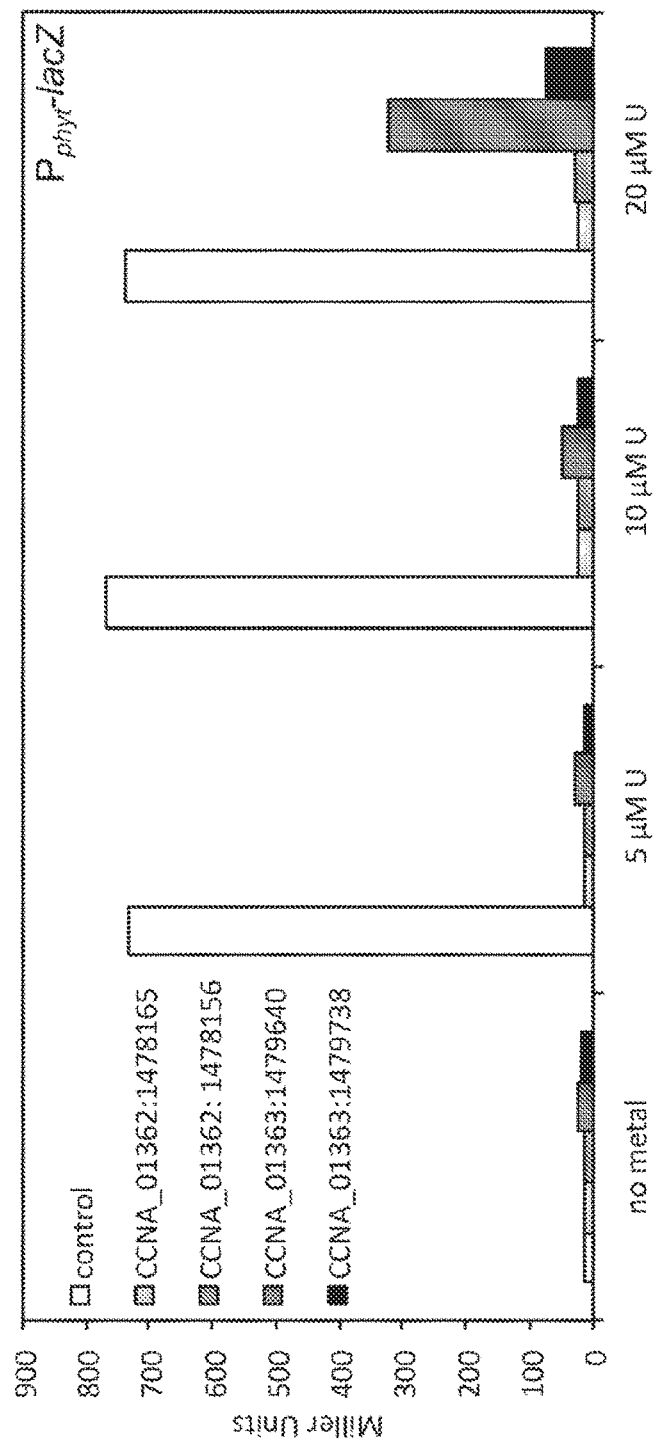
FIG. 28 shows diagrams illustrating the results of experiments showing that transposon insertions within CCNA_01362 and CCNA_01363 abrogate U-dependent induction of $P_{phyt}$. $P_{phyt}$-lacZ activity was assayed in strains containing transposons inserted within CCNA_01362 and CCNA_01363 using β-galactosidase assays. Error bars represent the standard deviation of triplicate measurements.

Furthermore, a forward genetic screen for mutants that failed to induce $P_{phyt}$-lacZ in response to U resulted in five transposons that mapped to unique locations within CCNA_01362 and CCNA_01363 (FIG. 28; Table 9), providing independent validation for a functional role of both proteins in U-dependent stimulation of $P_{phyt}$.

TABLE 9

Transposons in CCNA_01362 and CCNA_01363 that abolished U-dependent induction of $P_{phyt}$-lacZ

| Gene location | Chromosomal location | Number isolated |
|---|---|---|
| CCNA_01362 | 1478156 | 1 |
| CCNA_01362 | 1478165 | 4 |
| CCNA_01363 | 1479640 | 3 |
| CCNA_01363 | 1479645 | 3 |
| CCNA_01363 | 1479738 | 1 |

These proteins have been putatively named UrpR and UrpS (Uranium Responsive Phytase Regulator and Sensor, respectively), since this TCS strongly activates a gene encoding a phytase enzyme.

Figure 10:
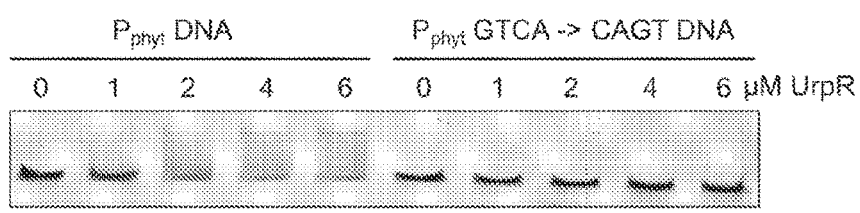
FIG. 10 illustrates the results of an electrophoretic mobility assay (EMSA) showing UrpR binding to wild type and mutant $P_{phyt}$ fragments. The mutant $P_{phyt}$ DNA ($P_{1361}$) contains a GTCA->CAGT mutation of DR2 (see FIG. 7B). The assays were performed with 50 nM 6-FAM-labeled DNA and UrpR, phosphorylated with carbamoyl phosphate. The concentrations indicate the total UrpR used in the assay. A representative example of three biological replicates is depicted.

To confirm that regulation by UrpR is direct, UrpR was purified, and its binding to $P_{phyt}$ was tested using an electrophoretic mobility shift assay. As expected, UrpR bound to $P_{phyt}$ in a concentration-dependent manner (FIG. 10). Binding was not observed to a $P_{phyt}$ fragment containing a 5'-GTCA-3' to 5'-CAGT-3' mutation at DR2 (FIG. 10), supporting the functional role of the direct repeat site in UrpR DNA binding. Collectively, these data suggest that the TCS comprised of UrpR and UrpS is the U-dependent activator of $P_{phyt}$ and $P_{1361}$, revealing a positive feedback loop within this regulatory system.

Example 14: UrpRS Exhibits Improved Metal Selectivity Compared to UzcRS

To test whether UrpRS functions independently of UzcRS with respect to U perception (a property that is important for its dual integration with UzcR in a synthetic U sensing pathway), the expression of $P_{phyt}$ and the UzcR-regulated promoter $P_{urcB}$ were tested in strains lacking the non-cognate TCS. The U-induction profile of a shortened $P_{phyt}$ reporter ($P_{phyt-short}$; diagrammed in FIG. 7A-B) was largely unaffected by deletion of uzcR or uzcS (FIG. 29A; FIG. 30), while the U-induction profile for $P_{urcB}$-gfp was unaffected by deletion of urpR or urpS (FIG. 29A; FIG. 30). Collectively, these data indicate that C. crescentus possesses at least two independent U-responsive TCS.

Figure 29:
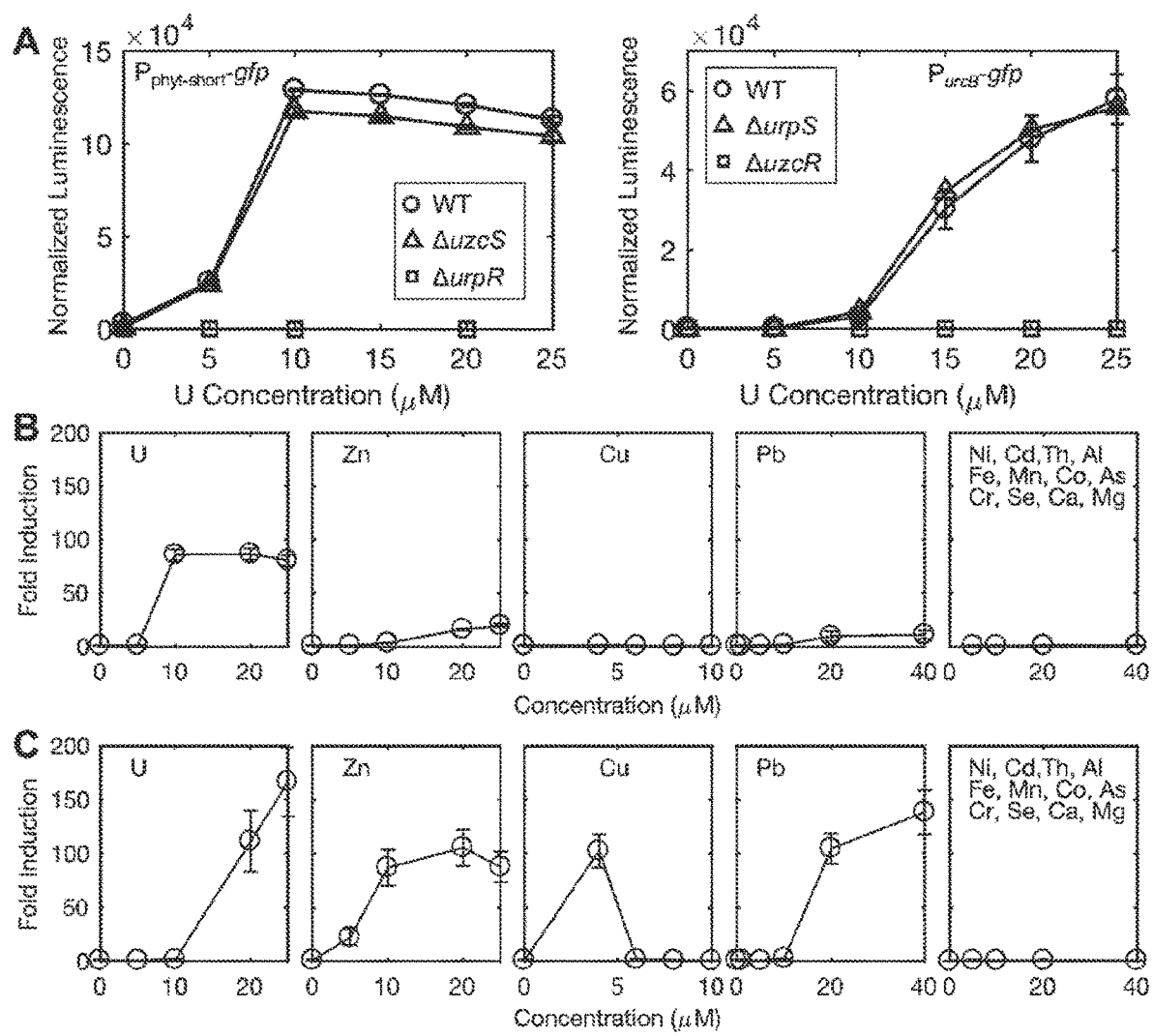
FIG. 29 shows diagrams illustrating the results of experiments showing metal selectivity of UrpRS and UzcRS in an exemplary embodiment. Panel A) Functional independence of UrpRS and UzcRS. U response curves of $P_{phyt-short}$-gfp and $P_{urcB}$-gfp reporters were determined by quantifying fluorescence following a two-hour exposure to a range of U concentrations in wild type C. crescentus and strains deleted for uzcS, urpS and the cognate response regulator. Error bars represent the average of biological triplicates. Metal selectivity profiles for $P_{phyt-short}$-gfp (panel B) and $P_{urcB}$-gfp (panel C). Reporter fluorescence was quantified following exposure to 16 metals. The furthest right plot depicts representative data for metals that failed to induce either promoter. Raw fluorescence values can be found in Table 10. Error bars represent the average of biological triplicates.
Figure 30:
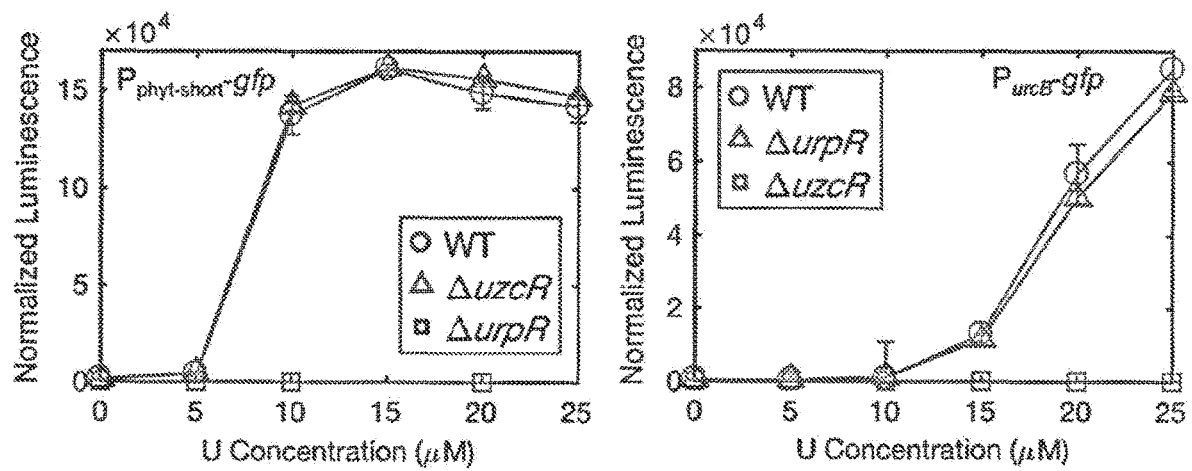
FIG. 30 shows diagrams illustrating the results of experiments showing in an exemplary embodiment functional independence of UrpRS and UzcRS. Fluorescence of a $P_{phyt-short}$-gfp and $P_{urcB}$-gfp were quantified following a two-hour exposure to a range of U concentrations in wild type C. crescentus and strains deleted for uzcR and urpR. Error bars represent the average of biological triplicates.

To determine the metal selectivity of UrpRS, $P_{phyt-short}$-gfp fluorescence was quantified following exposure to 16 metals of environmental relevance (FIG. 29B). To encourage metal solubility and thus bioavailability, minimal media containing glycerol-2-phosphate (G2P) was employed as the sole source of phosphate. As a control, the metal selectivity of the $P_{urcB}$-gfp reporter was also tested (FIG. 29C). For both promoters, the strongest induction was observed in response to U; however, $P_{phyt-short}$ exhibited greater U sensitivity, resembling a switch-like activation response (FIG. 29A) that can likely be attributed to the strong positive auto-regulation within the UrpRS system. Most metals, including Th, a radionuclide that is part of the U decay chain and likely co-occurs with U, failed to induce either reporter (Table 10).

TABLE 10

Metal selectivity of UrpRS and UzcRS

| Metal | $P_{phyt}$-gfp Fold Induction | $P_{phyt}$-gfp std dev | $P_{urcB}$-gfp Fold Induction | $P_{urcB}$-gfp std dev |
|---|---|---|---|---|
| 5 µM U | 1.3 | 0.2 | 0.8 | 0.1 |
| 10 µM U | 85.7 | 5.1 | 1.7 | 0.3 |
| 20 µM U | 86.4 | 5.3 | 111.5 | 28.3 |
| 25 µM U | 80.5 | 5.0 | 166.7 | 32.0 |
| 5 µM Zn | 1.2 | 0.1 | 22.2 | 7.4 |
| 10 µM Zn | 3.2 | 0.3 | 87.0 | 16.7 |
| 20 µM Zn | 16.1 | 1.0 | 105.5 | 17.0 |
| 25 µM Zn | 19.7 | 1.3 | 87.6 | 14.0 |
| 4 µM Cu | 1.3 | 0.1 | 102.5 | 15.5 |
| 6 µM Cu | 0.9 | 0.2 | 1.8 | 0.5 |
| 8 µM Cu | 0.8 | 0.1 | 0.9 | 0.2 |
| 10 µM Cu | 0.8 | 0.1 | 0.4 | 0.3 |
| 20 µM Ni | 1.1 | 0.1 | 0.9 | 0.1 |
| 40 µM Ni | 1.3 | 0.1 | 0.7 | 0.3 |
| 20 µM Cd | 1.0 | 0.1 | 1.6 | 0.6 |
| 40 µM Cd | 0.9 | 0.1 | 1.9 | 0.4 |
| 5 µM Th(IV) | 1.0 | 0.1 | 0.8 | 0.1 |
| 10 µM Th(IV) | 1.0 | 0.1 | 1.1 | 0.3 |
| 20 µM Th(IV) | 1.0 | 0.1 | 0.8 | 0.1 |
| 40 µM Th(IV) | 1.0 | 0.1 | 1.0 | 0.2 |
| 1 µM Pb | 1.0 | 0.1 | 1.0 | 0.2 |
| 5 µM Pb | 1.1 | 0.1 | 0.6 | 0.3 |
| 10 µM Pb | 1.8 | 0.5 | 2.7 | 0.4 |
| 20 µM Pb | 9.6 | 4.7 | 104.7 | 14.2 |
| 40 µM Pb | 11.1 | 4.1 | 138.5 | 20.1 |
| 20 µM Al | 2.4 | 0.3 | 1.0 | 0.3 |
| 40 µM Al | 2.5 | 0.4 | 1.0 | 0.1 |
| 20 µM Fe(III) | 1.0 | 0.1 | 1.1 | 0.1 |
| 40 µM Fe(III) | 1.1 | 0.1 | 1.1 | 0.1 |
| 20 µM Fe(II) | 1.0 | 0.1 | 0.9 | 0.4 |
| 40 µM Fe(II) | 1.1 | 0.1 | 0.7 | 0.1 |
| 20 µM Mn | 1.0 | 0.1 | 1.1 | 0.4 |
| 40 µM Mn | 1.0 | 0.1 | 1.0 | 0.1 |
| 20 µM Co | 0.7 | 0.1 | 0.4 | 0.1 |
| 40 µM Co | 0.7 | 0.1 | 0.2 | 0.1 |
| 20 µM As | 1.0 | 0.1 | 1.0 | 0.2 |
| 40 µM As | 1.1 | 0.1 | 0.9 | 0.2 |
| 100 µM As | 1.0 | 0.1 | 1.2 | 0.3 |
| 20 µM Cr(VI) | 1.5 | 0.1 | 3.2 | 0.7 |

TABLE 10-continued

Metal selectivity of UrpRS and UzcRS

| Metal | $P_{phyt}$-gfp Fold Induction | $P_{phyt}$-gfp std dev | $P_{urcB}$-gfp Fold Induction | $P_{urcB}$-gfp std dev |
|---|---|---|---|---|
| 40 µM Cr(VI) | 1.5 | 0.1 | 2.6 | 0.6 |
| 20 µM Se | 0.9 | 0.1 | 0.9 | 0.1 |
| 40 µM Se | 0.9 | 0.1 | 0.8 | 0.1 |

Importantly, $P_{phyt\text{-}short}$ was unresponsive to Cu and only minimally responsive to Zn or Pb (FIG. 29B). In contrast, strong $P_{urcB}$ induction was observed with Zn, Pb, and within a narrow Cu range. The Pb-dependent induction of $P_{urcB}$ was surprising and contrasts with prior reports.[118, 128] It is suspected that the Pb induction likely reflects the higher initial Pb bioavailability in the presence of G2P compared to orthophosphate, given the low solubility of lead phosphate. [136] These data suggest that while UrpRS is not exclusively selective for U, it exhibits an improved metal selectivity profile compared to UzcRS.

Example 15: Construction of a U-Responsive AND Gate Pathway in *C. crescentus*

Given the distinct metal selectivity profiles and functional independence of UzcRS and UrpRS, it is expected that a combinatorial approach that incorporates the U-responsive functionality of both UrpRS and UzcRS will yield a whole-cell U sensor with enhanced specificity. Accordingly, the recently developed Tripartite GFP system[129] was used as a template to construct a U sensing AND gate. In this system, GFP is split into three parts (gfp10, gfp11 and gfp1-9) that interact to reconstitute active GFP when co-expressed; the synthetic K1 and E1 coiled-coils[137] were fused to the C-terminus of gfp10 and the N-terminus of gfp11, respectively, to mediate dimerization.[129] An advantage of the tripartite system is the low basal level of GFP fluorescence, ensuring a robust OFF state.

Figure 31:
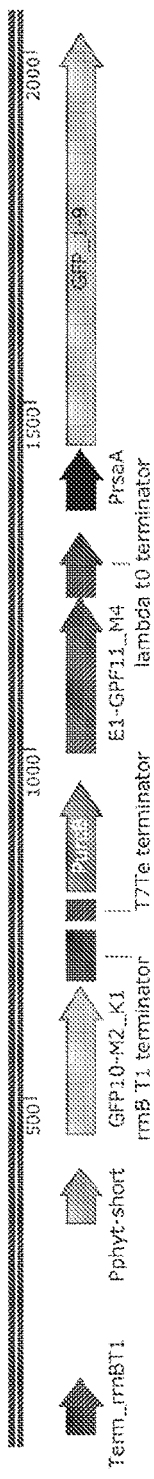
FIG. 31 illustrates a schematic of U-sensing AND gate configuration that was integrated at the chromosomal urcA locus. Details of AND gate construction and chromosomal integration are outlined in the methods sections.
Figure 32:
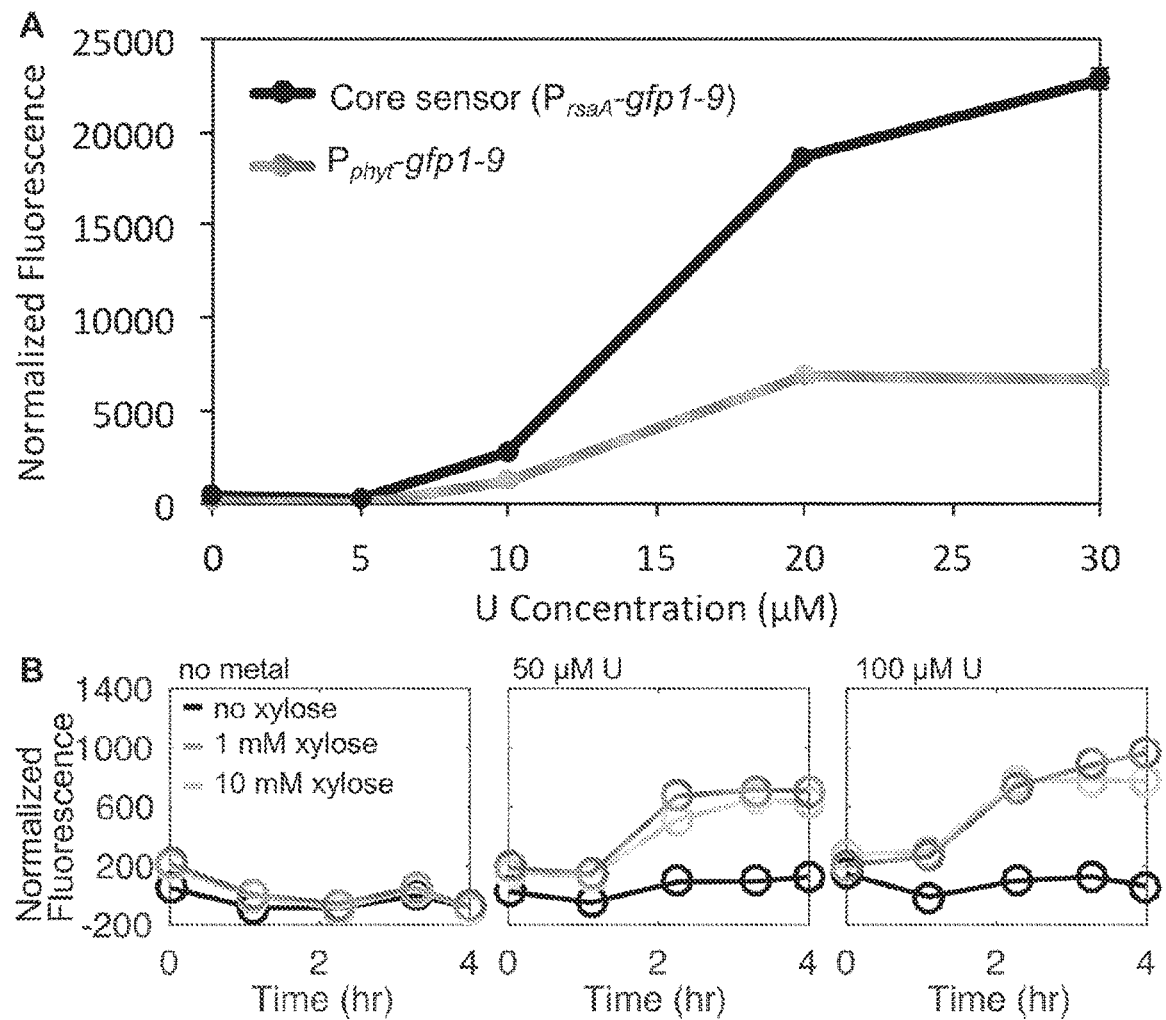
FIG. 32 shows diagrams illustrating the results of experiments showing in an exemplary embodiment U sensing AND gate variants with different mechanisms of gfp1-9 expression. Panel A shows the fluorescence output profile of the core sensor and a sensor variant with gfp1-9 expression driven by $P_{phyt}$ following a three-hour exposure to the indicated U concentration. Panel B shows the fluorescence output of a U-sensor variant with gfp1-9 expression driven by the xylose-inducible promoter $P_{xyl}$ as a function of time.

$P_{phyt\text{-}short}$ and $P_{urcB}$, which both exhibit low basal activity and a large U-dependent fold change, were used to drive expression of gfp10-K1 and E1-gfp11, respectively. The expression of gfp1-9 was driven by the strong, constitutive rsaA promoter ($P_{rsaA}$)[4] in order to produce high GFP1-9 levels at all stages of growth (FIG. 14A; diagrammed in FIG. 31). Hereafter, this sensor configuration in an otherwise wild type (WT) strain background is referred to as the core sensor. Sensor variants where gfp1-9 expression was driven by the xylose-inducible promoter ($P_{xyl}$)[6] or the UrpR-regulated $P_{phyt}$ were also tested, but exhibited a lower signal amplitude and were not pursued further (FIG. 32). Additionally, attempts to employ the hrp (hypersensitive response and pathogenicity) amplifier from *Pseudomonas syringae* as the AND gate template for U sensor construction by placing hrpR and hrpS under the control of $P_{phyt\text{-}short}$ and $P_{urcB}$, respectively, and using $P_{hrpL}$ to drive gfp expression, did not result in a functional sensor.

Figure 33:
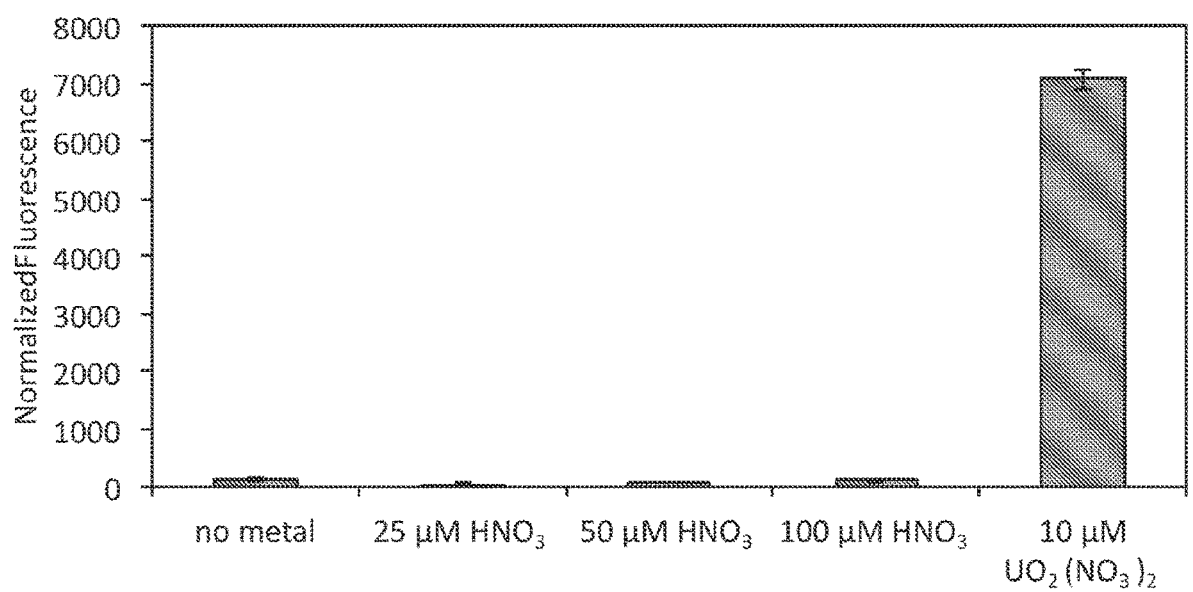
FIG. 33 shows a graph reporting that core sensor is not responsive to nitrate. Given the use of a uranyl nitrate stock in $HNO_3$ (100 mM $UO_2NO_3$ in 100 mM $HNO_3$) to characterize the U sensing performance of the core sensor, control experiments were conducted with $HNO_3$ nitrate alone. Relevant concentrations of $HNO_3$ failed to induce fluorescence, confirming that nitrate alone is not responsible for the core sensor output signal.

Initial characterization of the tripartite U sensor was performed in M5G G2P, given the robust U-dependent induction of both $P_{phyt}$ and $P_{urcB}$ under these conditions and the lack of induction in growth media containing orthophosphate, where U bioavailability is low as a result of uranyl phosphate mineralization.[126, 138] Notably, the basal fluorescence output of the sensor was indistinguishable from a control strain lacking GFP1-9 expression, supporting a very low OFF state (FIG. 14B). Addition of uranyl nitrate, but not nitrate alone (FIG. 33), yielded a nonlinear fluorescence response curve that deviated from background at concentrations as low as M and plateaued at ~15 µM (FIG. 14B). The hypersensitivity of the U response curve was quantified by fitting the data with a Hill function. It is noted that this approach is semiempirical, and it is not used as a basis to derive insight on the mechanisms of the reactions occurring in the system. The model revealed a hill coefficient hypersensitive nature of the U response curve suggests that the core sensor is well poised as a qualitative YES/NO digital sensor of environmental U.

Importantly, U-dependent fluorescence was not observed with control sensor variants that lacked either a functional UrpR binding site in $P_{phyt\text{-}short}$ or gfp1-9 expression (FIG. 14B). Additionally, deletion of uzcR severely impaired, but did not completely abolish, U-dependent fluorescence (FIG. 14B). Since the data in FIG. 29A indicate that $P_{urcB}$ activity is abolished by uzcR deletion, the minor induction of sensor fluorescence in the ΔuzcR strain may reflect low-level transcriptional read-through of the transcription terminator separating $P_{phyt\text{-}short}$-gfp10-K1 and $P_{urcB}$-E1-gfp11 modules (diagramed in FIG. 31). Collectively, these data highlight the requirement for expression from all three promoters for a U-dependent fluorescent output.

Figure 34:
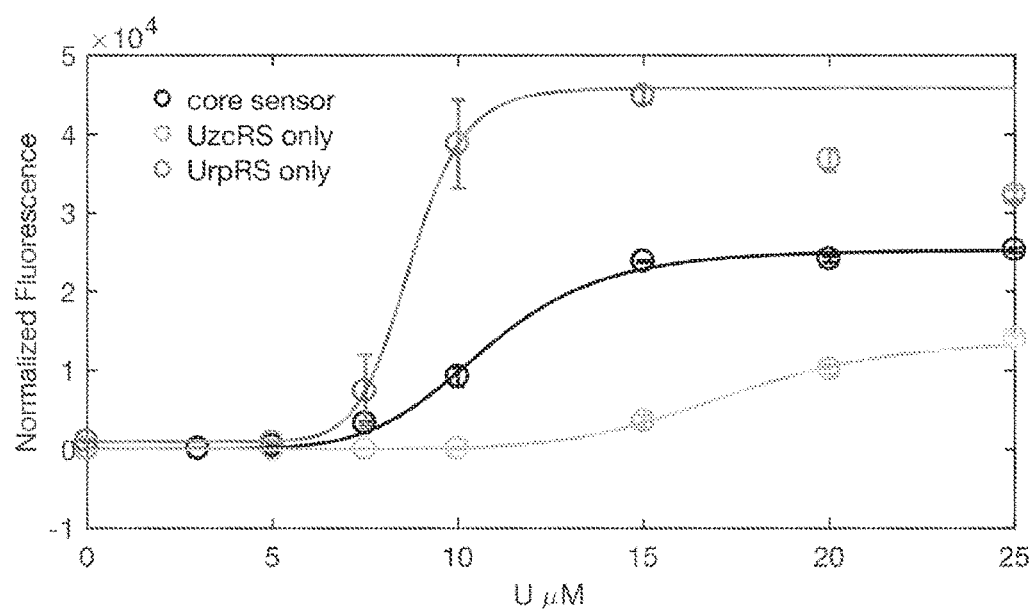
FIG. 34 shows in a graph the U response curves for the core sensor and control variants in which the expression of gfp10-K1 and E1-gfp11 components is driven by UzcRS or UrpRS alone. Fluorescence was quantified following a three-hour exposure to a range of U concentrations. The data were fit with a Hill equation to determine the U concentration that yields half-maximal fluorescence induction and the hill slope as an indicator of U sensitivity. Data points with diminished fluoresescence output were not included in the curve fitting.
Figure 40:
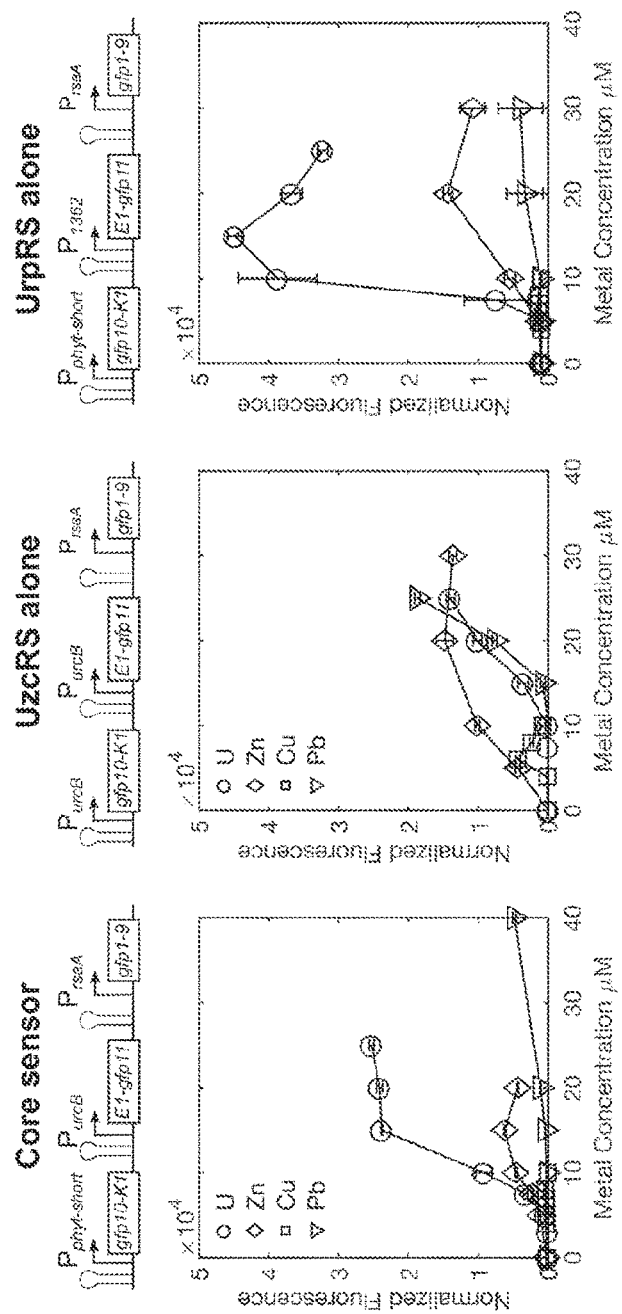
FIG. 40 shows a metal selectivity profile of core sensor and control variants. The top panel depicts simplified schematics of the core sensor and control variants in which the expression of gfp10-K1 and E1-gfp11 components is driven by UzcRS or UrpRS alone. The bottom panel depicts the U/Zn/Cu/Pb response curves for the core sensor and control variants. Fluorescence was quantified following a three-hour exposure to a range of metal concentrations. Error bars represent the average of biological triplicates.

Example 16: U-Sensing AND Gate Exhibits Improved Selectivity Relative to UzcRS Alone To characterize the selectivity of the core sensor, fluorescence was quantified in response to known inducers of either TCS and compared to results obtained with control sensor variants where either UzcRS or UrpRS governs the expression of both gfp10 and gfp11 (FIG. 40). Consistent with the U response curves for $P_{phyt\text{-}short}$- and $P_{urcB}$-gfp fusions (FIG. 29A), the control sensor driven by UrpRS alone yielded a U response curve with greater sensitivity compared to the sensor driven by UzcRS alone ($n^H$ of 12.5, K of 8.8 µM compared to $n^H$ of 7.9 and K of 17.4 µM; Table 11; FIG. 34).

TABLE 11

Hill function fitting

| Sensor Variant | Half maximal fluorescence (K) | Hill coefficient | $R^2$ |
|---|---|---|---|
| core sensor | 9.9 (0.1) | 7.6 (0.3) | 0.996 |
| constitutive UzcY | 6.3 (0.0) | 11.0 (0.6) | 1 |
| $P_{phyt}$-uzcY | 8.4 (0.1) | 9.5 (0.2) | 1 |
| UzcRS only | 17.4 (0.6) | 7.9 (0.3) | 0.995 |
| UrpRS only | 8.8 (0.7) | 12.5 (1.1) | 0.999 |

Figure 35:
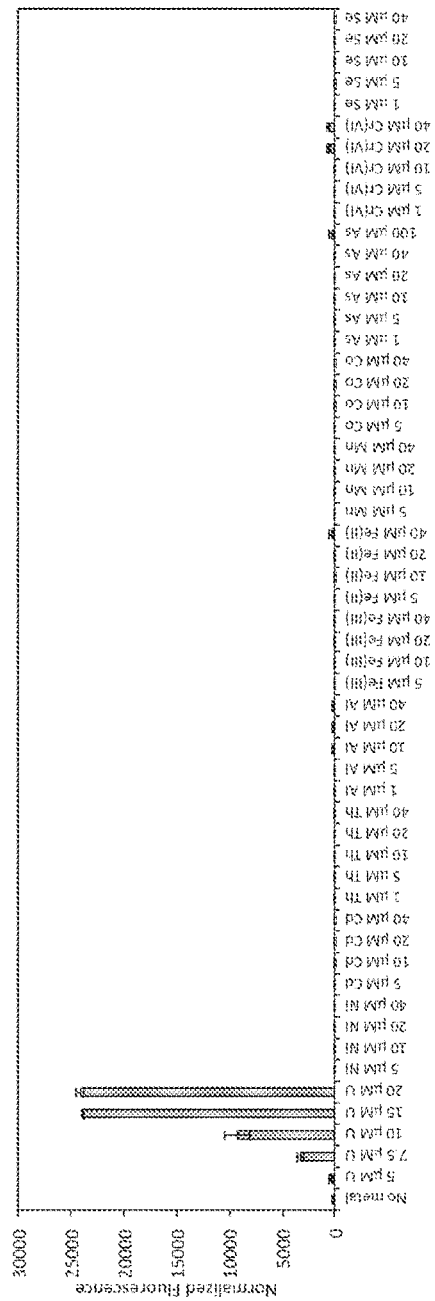
FIG. 35 shows diagrams illustrating the results of experiments showing metal selectivity profile of a core sensor. Fluorescence was quantified following a two-hour exposure to each metal. Error bars represent the average of biological triplicates.
Figure 37:
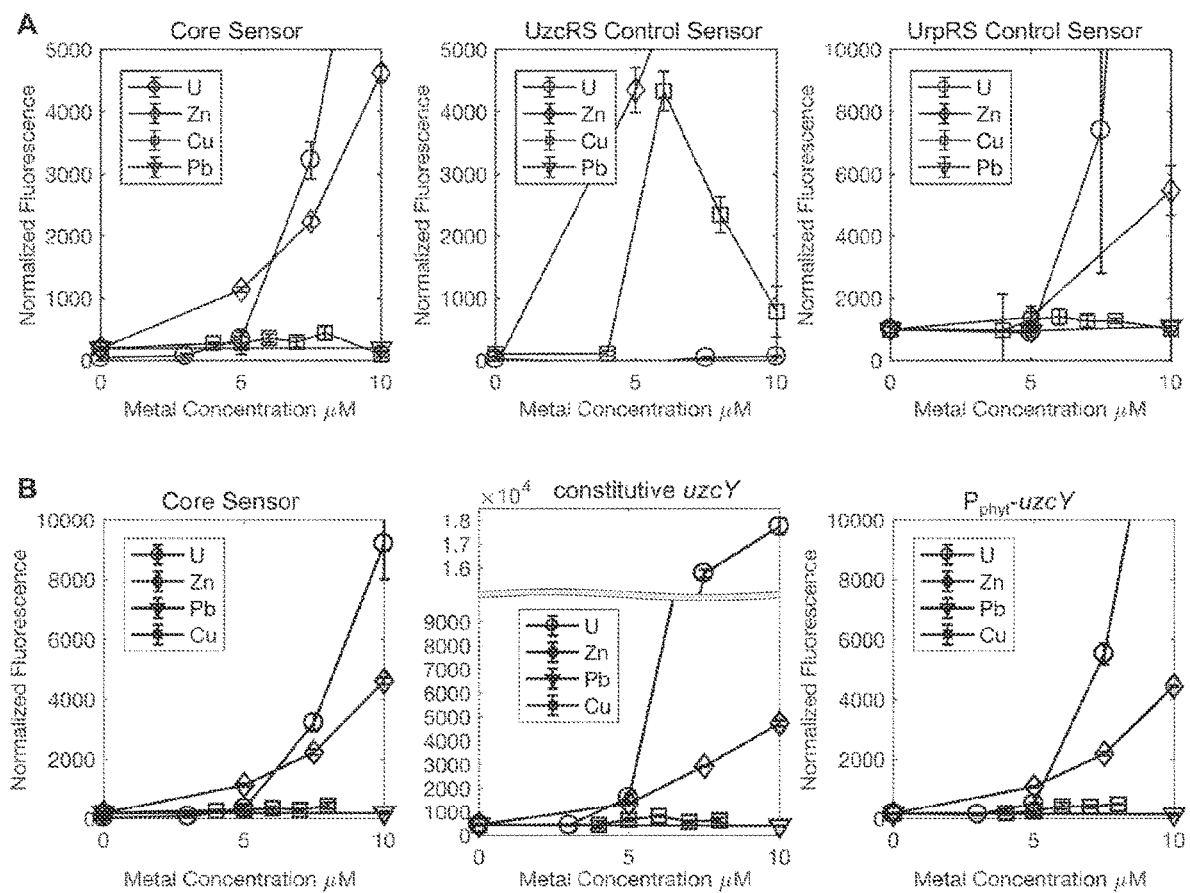
FIG. 37 shows a zoomed in version of the U/Zn/Cu/Pb response curves for the core sensor, control variants, and uzcY amplifier variants. Fluorescence was quantified following a three-hour exposure to a range of metal concentrations. The data represent a zoomed in version of data depicted in FIG. 40 and FIG. 36C. Error bars represent the average of biological triplicates.

As expected, the core sensor was unresponsive to Ni, Cd, Th, Al, Fe(III), Fe(II), Mn, Co, arsenate, Se, and chromate (FIG. 35). The core sensor and the sensor variant driven by UrpRS alone were also unresponsive to Cu, in contrast to the sensor driven exclusively by UzcRS (FIG. 40). Critically, the sensitivity of the core sensor to Zn and Pb was significantly diminished relative to the UzcRS control; high Pb concentrations (greater than 20 uM) were required for weak fluorescence induction while the Zn-induced fluorescence was reduced relative to U for every tested concentration. Despite the improved selectivity for U, low Zn concentrations (5 µM Zn) yielded a fluorescence response in the core sensor that exceeded the U response (FIG. 37). Nevertheless, the lack of Cu responsiveness and the weakened Zn/Pb responsiveness of the core sensor relative to a sensor constructed with UzcRS alone highlights the selectivity improvement of the AND gate approach.

Example 17: Integration of UzcY Signal Amplifier Improves U Sensitivity and Selectivity A notable limitation of this AND gate approach is that the improved selectivity comes at a cost to U sensitivity in the low micromolar range; incorporation of the less sensitive UzcRS TCS yielded a sensor with lower sensitivity compared to the control sensor driven by UrpRS alone (FIG. 34). Notably, swapping the UzcRS-regulated $P_{urcB}$ promoter with $P_{urcA}$, a promoter that is highly induced by UzcR and sensitive to low UzcR-P concentrations, failed to significantly improve sensor sensitivity (Data not shown). This suggests that simply swapping $P_{urcB}$ with an alternative UzcR-regulated promoter is unlikely to remedy the sensitivity limitation.

As an alternative approach to improve the coupling and matching of the UzcRS and UrpRS inputs, the use of a signal amplifier module was considered to boost the sensitivity of UzcRS. While the hrp (hypersensitive response and pathogenicity) amplifier from *Pseudomonas syringae* appeared to be a logical choice given its impressive ability to increase the sensitivity and output dynamic range of the ArsR-based arsenic sensor, it was unable to generate a functional U sensor using hrpR, hrpS, and $P_{hrpL}$ components in *C. crescentus*. Instead, the recently identified membrane protein UzcY that functions as a native signal amplifier for the UzcRS system was leveraged. Under normal growth conditions, uzcY expression is silenced by the MarR family regulator $MarR_1$ (CCNA_03498) and has no effect on UzcRS activity. However, when UzcY expression is induced by deleting $marR_1$, the sensitivity of UzcRS to its metal inducers is enhanced. The signal amplification mechanism was incorporated within the core sensor by either deleting $marR_1$, which yields a constitutive amplifier function, or by swapping the native uzcY promoter with the UrpRS-regulated $P_{phyt-short}$ (FIG. 36A), such that UzcY levels are modulated in a U-concentration dependent manner.

Figure 36:
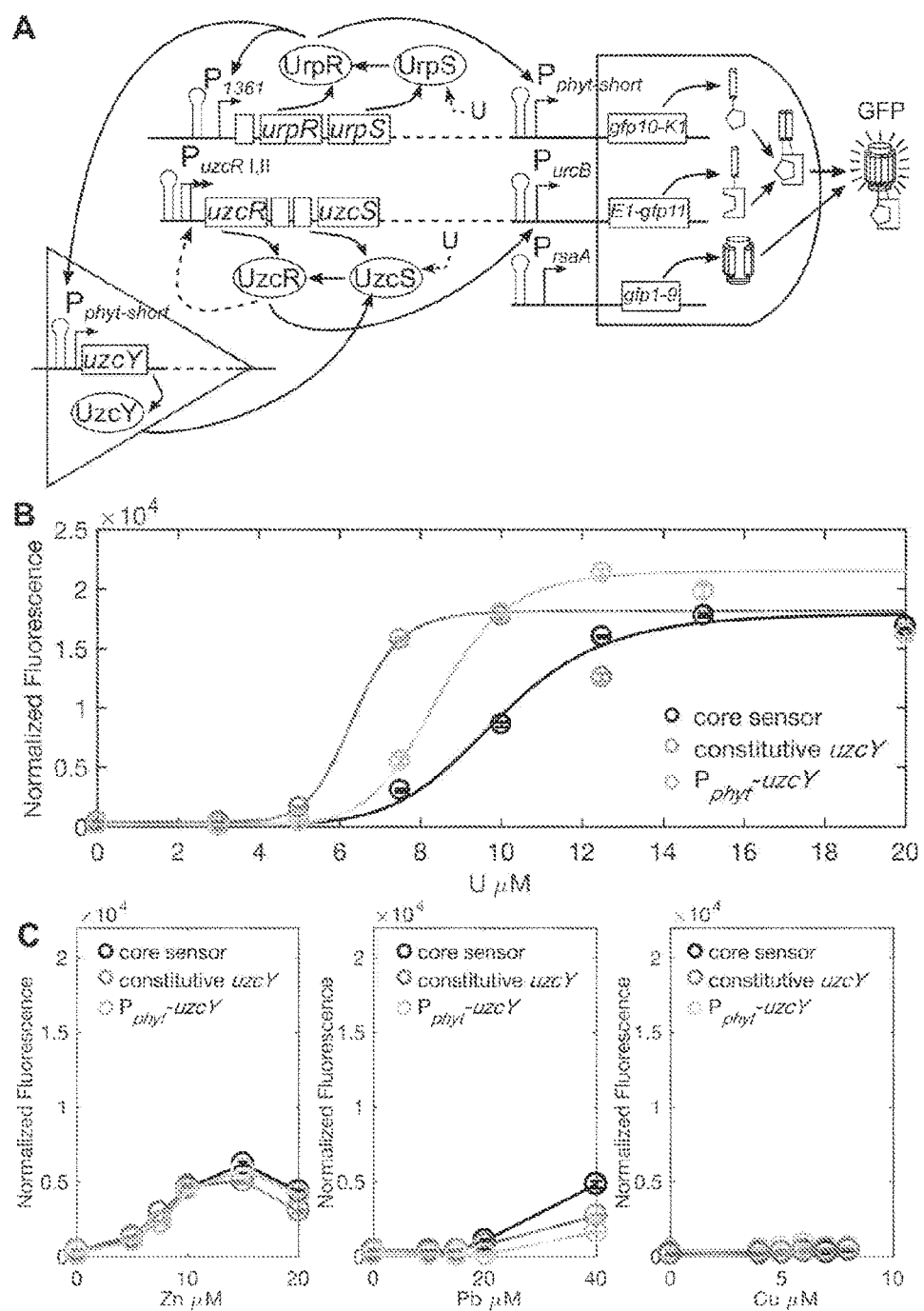
FIG. 36 shows graphs reporting incorporation of a signal amplifier module within the core sensor circuitry. Panel A: schematic for the integration of the UzcY signal amplifier within the U-sensing AND gate. In this variant, uzcY is placed under the control of the U-specific promoter $P_{phyt-short}$ such that the signal amplification is restricted to conditions of U exposure. Panel B: The fluorescence output of the core sensor and signal amplifier variants following a three-hour exposure to a range of U concentrations. The data were fit with a Hill equation to determine the U concentration that yields half-maximal fluorescence induction and the hill slope as an indicator of U sensitivity. Signal amplifier data points with diminished fluoresescence output were not included in the curve fitting. Panel C: The fluorescence output of the core sensor and signal amplifier variants following a three-hour exposure to a range of Zn, Pb, and Cu concentrations. Error bars represent the average of biological triplicates.

Constitutive UzcY expression significantly enhanced the U sensitivity of the core sensor in the low U concentration range (5-10 µM), yielding a U-dependent fluorescence profile with comparable sensitivity ($n^H$ of 11, K of 6.3 µM; FIG. 36B; Table 11) to the sensor driven exclusively by UrpRS alone ($n^H$ of 12.5; K of 8.8 µM). A diminished fluorescence output was observed at U concentrations above 10 µM, and may reflect reduced tolerance of the $\Delta marR_1$ strain to U toxicity compared to WT as was previously observed for Zn. Placing uzcY under the control of $P_{phyt-short}$, and, thus, conditionally restricting UzcY function to conditions of UrpRS stimulation, improved sensitivity ($n^H$ of 9.5, K of 8.4) in the 7.5-12.5 µM range, but not to the same degree as constitutive uzcY expression (FIG. 36B). Importantly, neither amplifier configuration altered the Zn—, Cu—, or Pb-dependent induction profile of the core sensor (FIG. 36C). By enhancing U sensitivity without affecting Zn sensitivity, the expression of UzcY significantly improved the U to Zn output ratio in the low concentration range (5-10 µM; FIG. 37).

Collectively, these data suggest that in M5G G2P, integration of the UzcRS-specific signal amplifier UzcY overcame the sensitivity limitations of the UzcRS TCS, and enhanced the selectivity for U compared to the core sensor. While the sensitivity and selectivity of this amplified sensor are comparable to the sensor driven by UzcRS alone, the use of a combinatorial sensing approach is expected to be beneficial for minimizing core sensor cross-reactivity with yet unidentified inducers of UrpRS. This is based on the expectation that UrpRS is directed to detect a stress that is likely to be encountered in the oligotrophic freshwater environment of this bacterium.

Example 18: Whole-Cell U Sensor Detects as Low as 1.0 PM in Groundwater

To test the efficacy of the sensor to detect U in ground water, samples from three distinct locations were obtained from LLNL site-300, a high-explosives test facility in the Altamont Hills of California where ground water concentrations of U exceed the EPA MCL. Quantification of the heavy metal content of each sample using ICP-MS or ICP-OES revealed U concentrations that range from 1.0 to 1.24 µM (238-295 ppb; Table 12), representing a challenging test for the whole-cell sensor given the ~5 µM detection limit observed in M5G G2P medium. The trace metals Zn, Pb, Cu, Cd, and Cr were either undetectable or in the low nanomolar range in all samples (Table 12), and thus not expected to affect sensor performance.

TABLE 12

Heavy metal concentrations in ground water samples

| Sample Site | U (µM) | Zn | Pb | Cu | Cd | Cr |
|---|---|---|---|---|---|---|
| Well W-815-2621 | 1.01 (0.02) | <150 nM | 6 nM | 13 nM | <9 nM | <19 nM |
| Well W-812-01 | 1.24 (0.02) | <150 nM | 5 nM | 11 nM | <9 nM | <19 nM |
| Well W-6C | 1.09 (0.00) | <150 nM | <5 nM | 8 nM | <9 nM | <19 nM |

Figure 38:
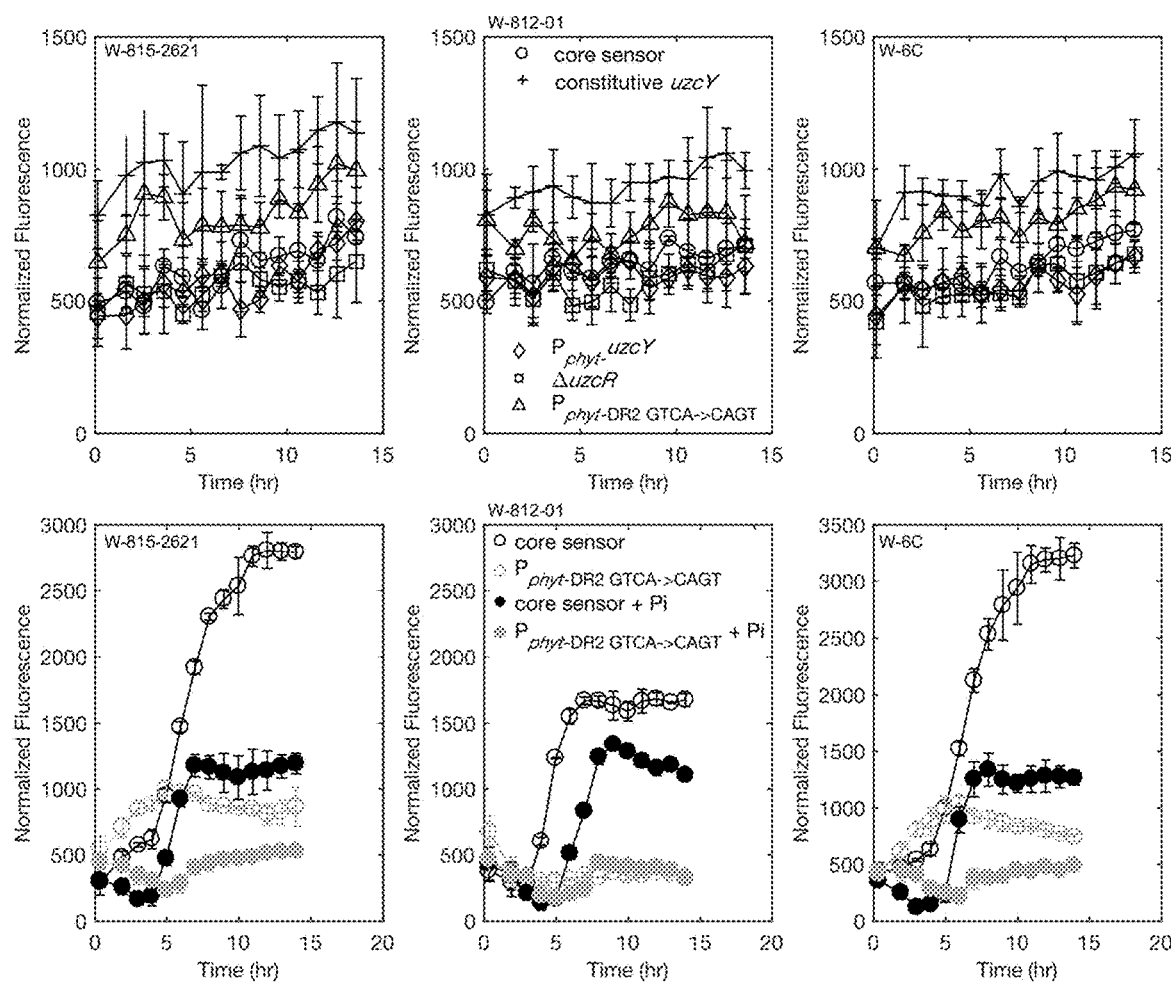
FIG. 38 shows graphs reporting fluorescence output of sensor variants in ground water samples without nutrient supplementation. (Panel A) Fluorescence output of the core sensor and control variants lacking critical regulatory components as a function of time in three distinct site 300 samples without nutrient supplementation. (Panel B) Fluorescence output of the core sensor and a control strain lacking a UrpR binding site as a function of time in three distinct site 300 samples supplemented with glucose (0.2%), orthophosphate (1 mM), and ammonium chloride (0.05%). The plot legend is depicted below the plots.
Figure 39:
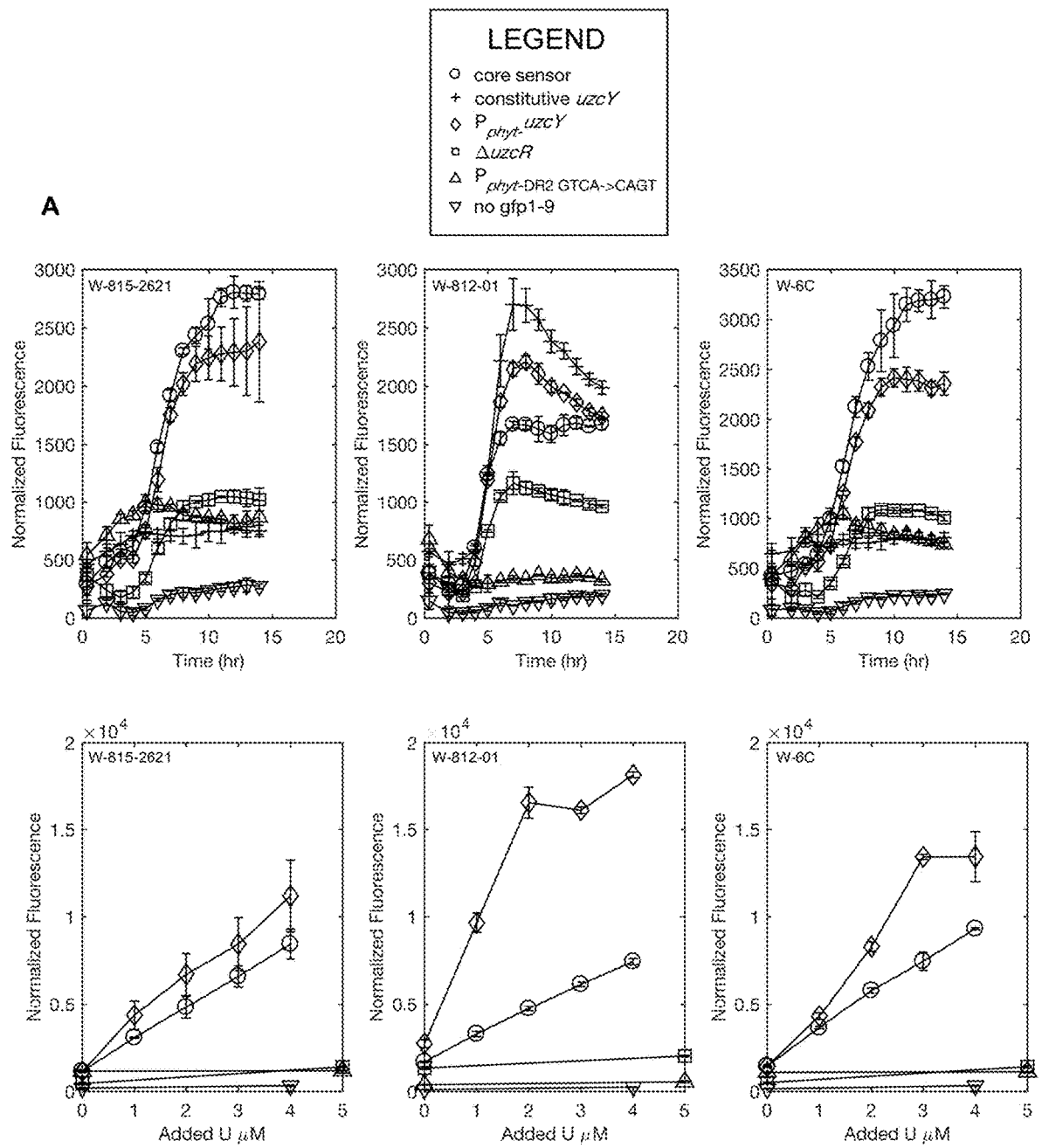
FIG. 39 shows detection of U in ground water samples in an exemplary embodiment. Panel A: Fluorescence output of the core sensor and control variants lacking critical regulatory components as a function of time in three distinct site 300 samples supplemented with glucose (0.2%), glycerol-2-phosphate (5 mM), and ammonium chloride (0.05%). Ground water samples from W-815-2621, W-812-01, and W-6C are referred to as 1,2, and 3, respectively, in the text. The plot legend is depicted below the plots. Panel B: The fluorescence of the core sensor and control variants was quantified six hours after exposure to site 300 samples supplemented with uranyl nitrate and the nutrients described in panel A. The x-axis concentrations represent the total U concentration in the ground water sample after addition of U in 1 µM increments.

The fluorescence output of the core sensor, UzcY amplifier variants, and negative controls lacking UzcRS, UrpRS, or gfp1-9 input were monitored as a function of time in the site-300 samples with and without growth nutrient supplementation. Exposure of the sensor strains to unmodified site-300 samples yielded no detectable increase in fluorescence and no cell growth (FIG. 38A; Data not shown). In contrast, supplementation with glucose, glycerol-2-phosphate (P source), and ammonium chloride (N source) together, but not glucose alone (data not shown), enabled cell growth and yielded a detectable increase in fluorescence for the core sensor within six hours of exposure to each sample (FIG. 39A). The fluorescence induction of the core sensor was significantly reduced in all samples when G2P was replaced with orthophosphate, which reduces U bioavailability (FIG. 38B). For samples 1 and 3 (~1 µM U), the $P_{phyt-short}$-uzCY amplifier variant yielded a fluorescence induction profile with slightly lower amplitude compared to the core sensor, while the constitutive amplifier failed to produce an output that differed from the negative controls (FIG. 39A). Future efforts will seek to optimize the constitutive level of UzcY to improve this sensor variants performance in environmental samples. In contrast, in sample 2 (~1.24 µM U), both signal amplifier variants yielded a fluorescence output signal that exceeded that of the core sensor (FIG. 39A), suggesting that UzcRS is limiting U sensor sensitivity in sample 2. Lastly, compared to the negative controls lacking a UrpR binding site or gfp1-9 expression, the ΔuzcR mutant yielded a fluorescence induction profile with similar kinetics, but lower signal amplitude compared to the core sensor. This result suggests that while $P_{urcB}$-E1-gfp11 is incompletely insulated from upstream UrpRS-mediated transcriptional activity, the function of both TCS is required to produce the fluorescence response of the core sensor in the ground water samples.

To further confirm U detectability in the ground water samples, uranyl nitrate was added in small, incremental amounts (1 uM increments), and fluorescence was quantified following a six-hour exposure (FIG. 39B). The rational is that if U is responsible for the fluorescence induction of the whole-cell sensors then small, incremental U additions should further boost sensor fluorescence. A nearly identical linear increase in fluorescence as a function of U concentration was observed for the core sensor in all three ground water samples. The $P_{phyt-short}$-uzCY amplifier variant yielded a comparable fluorescence output as the core sensor in sample 1, but enhanced the signal amplitude for all U concentrations in samples 2 and 3, supporting its ability to increase sensitivity in an environmental context. Collectively, these data confirm the functionality of the AND gate sensor to detect U in environmental samples and support a lower limit of detection for U of ~1 μM (~238 ppb). This result is in agreement with the ~0.5 μM detection limit reported for the UzcRS-regulated $P_{urcA}$-gfpUV sensor[128] and comparable with other field-portable U detection methodologies such as gamma spec and X-ray fluorescence. While additional work will be required to achieve a detection limit on par with the EPA MCL (30 ppb), the current sensitivity of the AND gate sensor is well suited as a screening mechanism (e.g., yes/no) for elevated U concentrations in regions with known or suspected anthropogenic activities.

The finding that cell growth and U solubility are required for robust U detection has important implications for further sensor development. The inability of the biosensor to detect insoluble forms of uranyl (e.g., uranyl phosphate minerals) may be exploited as a mechanism to distinguish natural from anthropogenic U since natural U commonly occurs in the form of insoluble minerals,[139] and aqueous phosphate concentrations are typically very low (<10 ppb).[140] To circumvent the U-Pi incompatibility, the organophosphate G2P was employed that serves the dual function of providing a phosphate source for cell growth while maintaining initial U solubility through complexation.[126, 138] Since the physicochemical form-or speciation of U—is dependent on the geochemical conditions and strongly influences bioavailability, and consequently the detectability by this biosensor, addition of G2P may be an effective means of conditioning the environmental samples for U detection. Evaluating this hypothesis, and ultimately, the utility of the sensor for environmental monitoring, will require systematic characterization of the solution matrix composition. Nevertheless, given the requirement for nutrient supplementation, it is expected that the path toward a fieldable sensor will entail encapsulation of the whole-cell sensor within an integrated detection device that maintains cells in an active state of growth and automates sampling and solution conditioning (e.g., addition of G2P) for detection. Recent efforts have yielded promising results for integrating cell sensors into field-applicable autonomous devices. [141-143]

By identifying and integrating two independent, U-responsive TCS within a synthetic AND gate circuit, a selective U-sensing functionality was developed in C. crescentus. The results highlight the value of a combinatorial approach for selective detection of compounds for which there are no known evolved regulators. This approach is expected to be generalizable and to drive the development of additional, bio-based modules for environmental toxin detection.

In summary described herein are U biosensors, and related U-sensing genetic molecular components, genetic circuits, compositions, methods and systems are described, which in several embodiments can be used to detect and/or neutralize uranium and in particular bioavailable U.

The examples set forth above are provided to give those of ordinary skill in the art a complete disclosure and description of how to make and use the embodiments of the U biosensors, and related U-sensitive genetic molecular components, genetic circuits, compositions, methods and systems of the disclosure, and are not intended to limit the scope of what the inventors regard as their disclosure. Those skilled in the art will recognize how to adapt the features of the exemplified U biosensors, and related U-sensitive genetic molecular components, genetic circuits, compositions, methods and systems herein disclosed to additional U biosensors, and related U-sensitive genetic molecular components, genetic circuits, compositions, methods and systems, and related genetic molecular components, sets of polynucleotides, polypeptides, proteins, and/or metabolites, in according to various embodiments and scope of the claims.

All patents and publications mentioned in the specification are indicative of the levels of skill of those skilled in the art to which the disclosure pertains.

The entire disclosure of each document cited (including patents, patent applications, journal articles, abstracts, laboratory manuals, books, or other disclosures) in the Background, Summary, Detailed Description, and Examples is hereby incorporated herein by reference. All references cited in this disclosure are incorporated by reference to the same extent as if each reference had been incorporated by reference in its entirety individually. However, if any inconsistency arises between a cited reference and the present disclosure, the present disclosure takes precedence.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure claimed. Thus, it should be understood that although the disclosure has been specifically disclosed by embodiments, exemplary embodiments and optional features, modification and variation of the concepts herein disclosed can be resorted to by those skilled in the art, and that such modifications and variations are considered to be within the scope of this disclosure as defined by the appended claims.

It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

When a Markush group or other grouping is used herein, all individual members of the group and all combinations and possible sub-combinations of the group are intended to be individually included in the disclosure. Every combination of components or materials described or exemplified herein can be used to practice the disclosure, unless otherwise stated. One of ordinary skill in the art will appreciate that methods, system elements, and materials other than those specifically exemplified may be employed in the practice of the disclosure without resort to undue experimentation. All art-known functional equivalents, of any such methods, device elements, and materials are intended to be included in this disclosure. Whenever a range is given in the specification, for example, a temperature range, a frequency range, a time range, or a composition range, all intermediate ranges and all subranges, as well as, all individual values included in the ranges given are intended to be included in the disclosure. Any one or more individual members of a range or group disclosed herein may be excluded from a claim of this disclosure. The disclosure illustratively described herein suitably may be practiced in the absence of any element or elements, limitation or limitations which is not specifically disclosed herein.

A number of embodiments of the disclosure have been described. The specific embodiments provided herein are examples of useful embodiments of the disclosure and it will be apparent to one skilled in the art that the disclosure can be carried out using a large number of variations of the genetic circuits, genetic molecular components, and methods steps set forth in the present description. As will be obvious to one of skill in the art, methods and systems useful for the present methods and systems may include a large number of optional composition and processing elements and steps.

In particular, it will be understood that various modifications may be made without departing from the spirit and scope of the present disclosure. Accordingly, other embodiments are within the scope of the following claims.

REFERENCES

1. Miller, J., *Experiments in molecular genetics. Cold Spring Laboratory Press.* 1972, Cold Spring Harbor, NY.
2. Ku, H., *Notes on the use of propagation of error formulas.* Journal of Research of the National Bureau of Standards, 1966. 70(4).
3. Park, D. M., et al., *Identification of a U/Zn/Cu responsive global regulatory two-component system in Caulobacter crescentus. Mol Microbiol,* 2017.
4. Fisher, J. A., J. Smit, and N. Agabian, *Transcriptional analysis of the major surface array gene of Caulobacter crescentus.* J Bacteriol, 1988. 170(10): p. 4706-13.
5. Cabantous, S., et al., *A new protein-protein interaction sensor based on tripartite split-GFP association.* Scientific reports, 2013. 3: p. 2854.
6. Meisenzahl, A. C., L. Shapiro, and U. Jenal, *Isolation and characterization of a xylose-dependent promoter from Caulobacter crescentus.* J Bacteriol, 1997. 179(3): p. 592-600.
7. Newsome, L., K. Morris, and J. R. Lloyd, *The biogeochemistry and bioremediation of uranium and other priority radionuclides.* Chemical Geology, 2014. 363: p. 164-184.
8. Langmuir, D., *Aqueous environmental geochemistry.* 1997.
9. Ewing, R. C., *Environmental impact of the nuclear fuel cycle.* Geological Society, London, Special Publications, 2004. 236(1): p. 7-23.
10. Bernier-Latmani, R., et al., *Non-uraninite products of microbial U (VI) reduction.* Environmental science & technology, 2010. 44(24): p. 9456-9462.
11. Brutinel, E. D. and J. A. Gralnick, *Shuttling happens: soluble flavin mediators of extracellular electron transfer in Shewanella.* Applied microbiology and biotechnology, 2012. 93(1): p. 41-48.
12. Lovley, D. R. and E. J. Phillips, *Microbial reduction of uranium. Nature,* 1991. 350(6317): p. 413.
13. Williams, K. H., et al., *Bioremediation of uranium-contaminated groundwater: a systems approach to subsurface biogeochemistry.* Current opinion in biotechnology, 2013. 24(3): p. 489-497.
14. Beazley, M. J., et al., *The effect of pH and natural microbial phosphatase activity on the speciation of uranium in subsurface soils.* Geochimica et Cosmochimica Acta, 2011. 75(19): p. 5648-5663.
15. Macaskie, L. E., et al., *Enzymically mediated biopreciptation of uranium by a Citrobacter sp.: a concerted role for exocellular lipopolysaccharide and associated phosphatase in biomineralformation.* Microbiology, 2000. 146(8): p. 1855-1867.
16. Macaskie, L. E., et al., *Uranium Bioaccumulation by a Citrobacter sp. as a Result of Enzymically Mediated Growth of Polycrystalline $HUO\_2 PO\_4$. Science,* 1992: p. 782-784.
17. Beveridge, T. and R. Murray, *Sites of metal deposition in the cell wall of Bacillus subtilis.* Journal of bacteriology, 1980. 141(2): p. 876-887.
18. Gadd, G. M., *Biosorption: critical review of scientific rationale, environmental importance and significance for pollution treatment.* Journal of Chemical Technology and Biotechnology, 2009. 84(1): p. 13-28.
19. Choudhary, S. and P. Sar, *Uranium biomineralization by a metal resistant Pseudomonas aeruginosa strain isolated from contaminated mine waste.* Journal of hazardous materials, 2011. 186(1): p. 336-343.
20. Ku, H. H., *Notes on the use of propagation of error formulas.* Journal of Research of the National Bureau of Standards C. Engineering and Instrumentation, 1966. 70C(4): p. 263-273.
21. Bailey, T. L. and C. Elkan, *Fitting a mixture model by expectation maximization to discover motifs in biopolymers.* Proc Int Conf Intell Syst Mol Biol, 1994. 2: p. 28-36.
22. Zhou, B., et al., *The global regulatory architecture of transcription during the Caulobacter cell cycle.* PLoS Genet, 2015. 11(1): p. e1004831.
23. McGrath, P. T., et al., *High-throughput identification of transcription start sites, conserved promoter motifs and predicted regulons.* Nat Biotechnol, 2007. 25(5): p. 584-92.
24. Markich, S. J., *Uranium speciation and bioavailability in aquatic systems: an overview.* The Scientific World Journal, 2002. 2: p. 707-729.
25. Focazio, M. J., et al., *The Chemical Quality of Self-Supplied Domestic Well Water in the United States.* Groundwater Monitoring & Remediation, 2006. 26(3): p. 92-104.
26. Hoover, J., et al., *Elevated Arsenic and Uranium Concentrations in Unregulated Water Sources on the Navajo Nation, USA.* Exposure and Health, 2016: p. 1-12.
27. Ferla, M. P., et al., *New rRNA gene-based phylogenies of the Alphaproteobacteria provide perspective on major groups, mitochondrial ancestry and phylogenetic instability.* PLoS One, 2013. 8(12): p. e83383.

28. Slonczewski J L, F. J., *Microbiology: An Evolving Science* W. W. Norton & Company, 2014: p. 742-3.
29. Dworkin M, F. S., Rosenberg E, Schleifer K H, Stackebrandt E, *The Prokaryotes: Proteobacteria: Alpha and Beta Subclasses*. 2006. 5: p. 15-18.
30. Stock, A. M., V. L. Robinson, and P. N. Goudreau, *Two-component signal transduction*. Annual review of biochemistry, 2000. 69(1): p. 183-215.
31. Mascher, T., J. D. Helmann, and G. Unden, *Stimulus perception in bacterial signal-transducing histidine kinases*. Microbiology and Molecular Biology Reviews, 2006. 70(4): p. 910-938.
32. Capra, E. J. and M. T. Laub, *Evolution of two-component signal transduction systems*. Annual review of microbiology, 2012. 66: p. 325-347.
33. Sanders, D., et al., *Phosphorylation site of NtrC, a protein phosphatase whose covalent intermediate activates transcription*. Journal of bacteriology, 1992. 174 (15): p. 5117-5122.
34. Sanders, D. A., et al., *Identification of the site of phosphorylation of the chemotaxis response regulator protein, CheY*. Journal of Biological Chemistry, 1989. 264(36): p. 21770-21778.
35. Datsenko, K. A. and B. L. Wanner, *One-step inactivation of chromosomal genes in Escherichia coli K-12 using PCR products*. Proc Natl Acad Sci USA, 2000. 97(12): p. 6640-5.
36. Sharma, C. M., et al., *The primary transcriptome of the major human pathogen Helicobacter pylori*. Nature, 2010. 464(7286): p. 250.
37. Carey, M. F., C. L. Peterson, and S. T. Smale, *The primer extension assay*. Cold Spring Harbor Protocols, 2013. 2013(2): p. pdb. prot071902.
38. Wade, J. T., *Where to begin? Mapping transcription start sites genome-wide in Escherichia coli*. Journal of bacteriology, 2015. 197(1): p. 4-6.
39. Poindexter, J. S., *The caulobacters: ubiquitous unusual bacteria*. Microbiological reviews, 1981. 45(1): p. 123.
40. Hu, P., et al., *Whole-genome transcriptional analysis of heavy metal stresses in Caulobacter crescentus*. Journal of bacteriology, 2005. 187(24): p. 8437-8449.
41. Park, D. M. and Y. Jiao, *Modulation of medium pH by Caulobacter crescentus facilitates recovery from uranium-induced growth arrest*. Applied and environmental microbiology, 2014. 80(18): p. 5680-5688.
42. Bollmann, A., et al., *Isolation and physiology of bacteria from contaminated subsurface sediments*. Applied and environmental microbiology, 2010. 76(22): p. 7413-7419.
43. Yung, M. C. and Y. Jiao, *Biomineralization of uranium by PhoY phosphatase activity aids cell survival in Caulobacter crescentus*. Applied and environmental microbiology, 2014. 80(16): p. 4795-4804.
44. Hillson, N.J., et al., *Caulobacter crescentus as a whole-cell uranium biosensor*. Applied and environmental microbiology, 2007. 73(23): p. 7615-7621.
45. Cormack, B. P., R. H. Valdivia, and S. Falkow, *FACS-optimized mutants of the green fluorescent protein (GFP)*. Gene, 1996. 173(1): p. 33-38.
46. Lovley, D. R. and E. Phillips, *Reduction of uranium by Desulfovibrio desulfuricans*. Applied and environmental microbiology, 1992. 58(3): p. 850-856.
47. Francis, A. J., et al., *XPS and XANES studies of uranium reduction by Clostridium sp*. Environmental science & technology, 1994. 28(4): p. 636-639.
48. Shelobolina, E. S., et al., *Isolation, characterization, and U (VI)-reducing potential of a facultatively anaerobic, acid-resistant Bacterium from Low-pH, nitrate-and U (VI)-contaminated subsurface sediment and description of Salmonella subterranea sp. nov*. Applied and Environmental Microbiology, 2004. 70(5): p. 2959-2965.
49. Wu, Q., R. A. Sanford, and F. E. Löffler, *Uranium (VI) reduction by Anaeromyxobacter dehalogenans strain 2CP-C*. Applied and environmental microbiology, 2006. 72(5): p. 3608-3614.
50. Begg, J. D., et al., *Bioreduction behavior of U (VI) sorbed to sediments*. Geomicrobiology Journal, 2011. 28(2): p. 160-171.
51. Istok, J., et al., *In situ bioreduction of technetium and uranium in a nitrate-contaminated aquifer*. Environmental Science & Technology, 2004. 38(2): p. 468-475.
52. Law, G. T., et al., *Uranium redox cycling in sediment and biomineral systems*. Geomicrobiology Journal, 2011. 28(5-6): p. 497-506.
53. Wilkins, M., et al., *The influence of microbial redox cycling on radionuclide mobility in the subsurface at a low-level radioactive waste storage site*. Geobiology, 2007. 5(3): p. 293-301.
54. Williams, K. H., et al., *Acetate availability and its influence on sustainable bioremediation of uranium-contaminated groundwater*. Geomicrobiology Journal, 2011. 28(5-6): p. 519-539.
55. Wu, W.-M., et al., *In situ bioreduction of uranium (VI) to submicromolar levels and reoxidation by dissolved oxygen*. Environmental Science & Technology, 2007. 41(16): p. 5716-5723.
56. Lovley, D. R., et al., *Geobacter metallireducens gen. nov. sp. nov., a microorganism capable of coupling the complete oxidation of organic compounds to the reduction of iron and other metals*. Archives of microbiology, 1993. 159(4): p. 336-344.
57. Richter, K., M. Schicklberger, and J. Gescher, *Dissimilatory reduction of extracellular electron acceptors in anaerobic respiration*. Applied and environmental microbiology, 2012. 78(4): p. 913-921.
58. Lovley, D. R., D. E. Holmes, and K. P. Nevin, *Dissimilatory fe (iii) and mn (iv) reduction*. Advances in microbial physiology, 2004. 49: p. 219-286.
59. Marsili, E., et al., *Shewanella secretes flavins that mediate extracellular electron transfer*. Proceedings of the National Academy of Sciences, 2008. 105(10): p. 3968-3973.
60. Suzuki, Y., et al., *Flavin mononucleotide mediated electron pathway for microbial U (VI) reduction*. Physical Chemistry Chemical Physics, 2010. 12(34): p. 10081-10087.
61. Von Canstein, H., et al., *Secretion of flavins by Shewanella species and their role in extracellular electron transfer*. Applied and environmental microbiology, 2008. 74(3): p. 615-623.
62. Anderson, R. T., et al., *Stimulating the in situ activity of Geobacter species to remove uranium from the groundwater of a uranium-contaminated aquifer*. Applied and environmental microbiology, 2003. 69(10): p. 5884-5891.
63. Senko, J. M., et al., *The effect of U (VI) bioreduction kinetics on subsequent reoxidation of biogenic U (IV)*. Geochimica et Cosmochimica Acta, 2007. 71(19): p. 4644-4654.
64. Martinez, R. J., et al., *Aerobic uranium (VI) bioprecipitation by metal-resistant bacteria isolated from radionuclide-and metal-contaminated subsurface soils*. Environmental microbiology, 2007. 9(12): p. 3122-3133.
65. Basnakova, G., et al., *The use of Escherichia coli bearing a phoN gene for the removal of uranium and

*nickel from aqueous flows.* Applied microbiology and biotechnology, 1998. 50(2): p. 266-272.
66. Powers, L. G., et al., *Introduction of a plasmid-encoded phoA gene for constitutive overproduction of alkaline phosphatase in three subsurface Pseudomonas isolates.* FEMS microbiology ecology, 2002. 41(2): p. 115-123.
67. Thomas, R. A. and L. Macaskie, *Biodegradation of tributyl phosphate by naturally occurring microbial isolates and coupling to the removal of uranium from aqueous solution.* Environmental science & technology, 1996. 30(7): p. 2371-2375.
68. Siuda, W. and R. Chróst, *Utilization of selected dissolved organic phosphorus compounds by bacteria in lake water under non-limiting orthophosphate conditions.* Polish Journal of Environmental Studies, 2001. 10(6): p. 475-484.
69. Lim, B. L., et al., *Distribution and diversity of phytate-mineralizing bacteria.* The ISME journal, 2007. 1(4): p. 321.
70. Ko, W.-h. and F. K. Hora, *Production of phospholipases by soil microorganisms.* Soil Science, 1970. 110(5): p. 355-358.
71. Kazy, S. K., S. F. D'Souza, and P. Sar, *Uranium and thorium sequestration by a Pseudomonas sp.: mechanism and chemical characterization.* J Hazard Mater, 2009. 163(1): p. 65-72.
72. Vanengelen, M. R., et al., *UO(2) 2+ speciation determines uranium toxicity and bioaccumulation in an environmental Pseudomonas sp. isolate.* Environ Toxicol Chem, 2010. 29(4): p. 763-9.
73. Choudhary, S. and P. Sar, *Uranium biomineralization by a metal resistant Pseudomonas aeruginosa strain isolated from contaminated mine waste.* J Hazard Mater, 2011. 186(1): p. 336-43.
74. Renninger, N., et al., *Uranyl precipitation by Pseudomonas aeruginosa via controlled polyphosphate metabolism.* Appl Environ Microbiol, 2004. 70(12): p. 7404-12.
75. Zhou, L., et al., *A protein engineered to bind uranyl selectively and with femtomolar affinity.* Nat Chem, 2014. 6(3): p. 236-41.
76. Pardoux, R., et al., *Modulating uranium binding affinity in engineered calmodulin EF-hand peptides: effect of phosphorylation.* PLoS One, 2012. 7(8): p. e41922.
77. Nomellini, J. F., et al., *S-layer-mediated display of the immunoglobulin G-binding domain of streptococcal protein G on the surface of Caulobacter crescentus: development of an immunoactive reagent.* Appl Environ Microbiol, 2007. 73(10): p. 3245-53.
78. Park, D. M., et al., *Bioadsorption of Rare Earth Elements through Cell Surface Display of Lanthanide Binding Tags.* Environ Sci Technol, 2016. 50(5): p. 2735-42.
79. Choppin, G., J. Liljenzin, and J. Rydberg, *Behavior of Radionuclides in the Environment. Radiochemistry and Nuclear Chemistry,* 1995.
80. Hsi, C.-k. D. and D. Langmuir, *Adsorption of uranyl onto ferric oxyhydroxides: application of the surface complexation site-binding model.* Geochimica et Cosmochimica Acta, 1985. 49(9): p. 1931-1941.
81. Koch-Steindl, H. and G. Pröhl, *Considerations on the behaviour of long-lived radionuclides in the soil.* Radiation and environmental biophysics, 2001. 40(2): p. 93-104.
82. Davis, J. A., et al., *Approaches to surface complexation modeling of uranium (VI) adsorption on aquifer sediments.* Geochimica et Cosmochimica Acta, 2004. 68(18): p. 3621-3641.
83. Pabalan, R. T., et al., *Uranium (VI) sorption onto selected mineral surfaces: Key geochemical parameters.* 1996, American Chemical Society, Washington, DC (United States).
84. Siegel, M. and C. Bryan, *Radioactive Contamination.* Environmental Geochemistry, 2005. 9: p. 205.
85. Bargar, J. R., et al., *Uranium redox transition pathways in acetate-amended sediments.* Proceedings of the National Academy of Sciences, 2013. 110(12): p. 4506-4511.
86. Utturkar, S. M., et al., *Draft genome sequence for Caulobacter sp. strain OR37, a bacterium tolerant to heavy metals.* Genome announcements, 2013. 1(3): p. e00322-13.
87. Brewster, R. C., et al., *The transcription factor titration effect dictates level of gene expression.* Cell, 2014. 156(6): p. 1312-23.
88. Shin, J. and V. Noireaux, *An E. coli cell-free expression toolbox: application to synthetic gene circuits and artificial cells.* ACS Synth Biol, 2012. 1(1): p. 29-41.
89. Procaccini, A., et al., *Dissecting the specificity of protein-protein interaction in bacterial two-component signaling: orphans and crosstalks.* PloS one, 2011. 6(5): p. e19729.
90. Buttner, D. and U. Bonas, *Who comes first? How plant pathogenic bacteria orchestrate type III secretion.* Current opinion in microbiology, 2006. 9(2): p. 193-200.
91. Hutcheson, S. W., et al., *Enhancer-Binding Proteins HrpR and HrpS Interact To Regulate hrp-Encoded Type III Protein Secretion in Pseudomonas syringae Strains.* Journal of Bacteriology, 2001. 183(19): p. 5589-5598.
92. Jin, Q., et al., *Type III protein secretion in Pseudomonas syringae.* Microbes and Infection, 2003. 5(4): p. 301-310.
93. Dove, S. L. and A. Hochschild, *Conversion of the co subunit of Escherichia coli RNA polymerase into a transcriptional activator or an activation target.* Genes & development, 1998. 12(5): p. 745-754.
94. Blondel, A. and H. Bedouelle, *Engineering the quaternary structure of an exported protein with a leucine zipper.* Protein Eng, 1991. 4(4): p. 457-61.
95. Cheng, P.-C., *The contrast formation in optical microscopy,* in *Handbook of Biological Confocal Microscopy.* 2006, Springer. p. 162-206.
96. Helms, V., *Principles of computational cell biology.* 2008: John Wiley & Sons.
97. Zheng, J., *Spectroscopy-based quantitative fluorescence resonance energy transfer analysis.* Ion channels: methods and protocols, 2006: p. 65-77.
98. Periasamy, A., *Fluorescence resonance energy transfer microscopy: a mini review.* Journal of biomedical optics, 2001. 6(3): p. 287-291.
99. Nguyen, A. W. and P. S. Daugherty, *Evolutionary optimization of fluorescent proteins for intracellular FRET.* Nature biotechnology, 2005. 23(3): p. 355.
100. Buchler, N. E., U. Gerland, and T. Hwa, *On schemes of combinatorial transcription logic.* Proceedings of the National Academy of Sciences, 2003. 100(9): p. 5136-5141.
101. Silva-Rocha, R. and V. de Lorenzo, *Mining logic gates in prokaryotic transcriptional regulation networks.* FEBS letters, 2008. 582(8): p. 1237-1244.
102. Wang, B., et al., *Engineering modular and orthogonal genetic logic gates for robust digital-like synthetic biology.* Nature communications, 2011. 2: p. 508.
103. Sambrook, J., E. Fritsch, and T. Maniatis, *Molecular cloning: a laboratory manual, 2nd edn. Cold Spring Laboratory Press.* New York, 1989.

104. Innis, M. A., D. H. Gelfand, and J. J. Sninsky, *PCR strategies*. 1995: Academic Press.
105. Myers, E. W. and W. Miller, *Optimal alignments in linear space*. Computer applications in the biosciences: CABIOS, 1988. 4(1): p. 11-17.
106. Smith, T. F. and M. S. Waterman, *Comparison of biosequences*. Advances in applied mathematics, 1981. 2 (4): p. 482-489.
107. Needleman, S. B. and C. D. Wunsch, *A general method applicable to the search for similarities in the amino acid sequence of two proteins*. Journal of molecular biology, 1970. 48(3): p. 443-453.
108. Pearson, W. R. and D. J. Lipman, *Improved tools for biological sequence comparison*. Proceedings of the National Academy of Sciences, 1988. 85(8): p. 2444-2448.
109. Karlin, S. and S. F. Altschul, *Methods for assessing the statistical significance of molecular sequence features by using general scoring schemes*. Proceedings of the National Academy of Sciences, 1990. 87(6): p. 2264-2268.
110. Karlin, S. and S. F. Altschul, *Applications and statistics for multiple high-scoring segments in molecular sequences*. Proceedings of the National Academy of Sciences, 1993. 90(12): p. 5873-5877.
111. Stephens, C., et al., *A cell cycle-regulated bacterial DNA methyltransferase is essential for viability*. Proceedings of the National Academy of Sciences, 1996. 93(3): p. 1210-1214.
112. Hierlemann, A. and H. Baltes, *CMOS-based chemical microsensors*. Analyst, 2003. 128(1): p. 15-28.
113. Hierlemann, A., et al., *Microfabrication techniques for chemical/biosensors*. Proceedings of the IEEE, 2003. 91(6): p. 839-863.
114. Evinger, M. and N. Agabian, *Envelope-associated nucleoid from Caulobacter crescentus stalked and swarmer cells*. J Bacteriol, 1977. 132(1): p. 294-301.
115. Arellano, B. H., et al., *Identification of a dehydrogenase required for lactose metabolism in Caulobacter crescentus*. Appl Environ Microbiol, 2010. 76(9): p. 3004-14.
116. Skerker, J. M., et al., *Two-component signal transduction pathways regulating growth and cell cycle progression in a bacterium: a system-level analysis*. PLoS Biol, 2005. 3(10): p. e334.
117. Christen, B., et al., *High-throughput identification of protein localization dependency networks*. Proc Natl Acad Sci USA, 2010. 107(10): p. 4681-6.
118. Park, D. M., et al., *Identification of a U/Zn/Cu responsive global regulatory two-component system in Caulobacter crescentus*. Mol Microbiol, 2016.
119. Stephens, C., et al., *A cell cycle-regulated bacterial DNA methyltransferase is essential for viability*. Proc Natl Acad Sci USA, 1996. 93(3): p. 1210-4.
120. Fiebig, A., et al., *Interaction specificity, toxicity and regulation of a paralogous set of ParE/RelE-family toxin-antitoxin systems*. Mol Microbiol, 2010. 77(1): p. 236-51.
121. Goodrich, R., Lorega, G., *LLNL Livermore Site and Site 300 Environmental Restoration Project Standard Operating Procedures (SOPs)*. Lawrence Livermore National Laboratory Livermore, Calif, 2016. (UCRL-MA-109115 Rev. 15).
122. Arellano, B. H., et al., *Identification of a dehydrogenase required for lactose metabolism in Caulobacter crescentus*. Applied and environmental microbiology, 2010. 76(9): p. 3004-3014.
123. Fiebig, A., et al., *Interaction specificity, toxicity and regulation of a paralogous set of ParE/RelE-family toxin-antitoxin systems*. Molecular microbiology, 2010. 77(1): p. 236-251.
124. Andersen, J. B., et al., *New unstable variants of green fluorescent protein for studies of transient gene expression in bacteria*. Appl Environ Microbiol, 1998. 64(6): p. 2240-6.
125. Hu, P., et al., *Whole-genome transcriptional analysis of heavy metal stresses in Caulobacter crescentus*. J Bacteriol, 2005. 187(24): p. 8437-49.
126. Park, D. M. and Y. Jiao, *Modulation of medium pH by Caulobacter crescentus facilitates recovery from uranium-induced growth arrest*. Appl Environ Microbiol, 2014. 80(18): p. 5680-8.
127. Yung, M. C., et al., *Shotgun proteomic analysis unveils survival and detoxification strategies by Caulobacter crescentus during exposure to uranium, chromium, and cadmium*. J Proteome Res, 2014. 13(4): p. 1833-47.
128. Hillson, N.J., et al., *Caulobacter crescentus as a whole-cell uranium biosensor*. Appl Environ Microbiol, 2007. 73(23): p. 7615-21.
129. Cabantous, S., et al., *A new protein-protein interaction sensor based on tripartite split-GFP association*. Sci Rep, 2013. 3: p. 2854.
130. Britos, L., et al., *Regulatory response to carbon starvation in Caulobacter crescentus*. PLoS One, 2011. 6(4): p. e18179.
131. Jonas, K., et al., *Proteotoxic stress induces a cell-cycle arrest by stimulating Lon to degrade the replication initiator DnaA*. Cell, 2013. 154(3): p. 623-36.
132. Modell, J. W., A. C. Hopkins, and M. T. Laub, *A DNA damage checkpoint in Caulobacter crescentus inhibits cell division through a direct interaction with FtsW*. Genes Dev, 2011. 25(12): p. 1328-43.
133. da Silva Neto, J. F., R. F. Lourenco, and M. V. Marques, *Global transcriptional response of Caulobacter crescentus to iron availability*. BMC Genomics, 2013. 14: p. 549.
134. Blanco, A. G., et al., *Tandem DNA Recognition by PhoB, a Two-Component Signal Transduction Transcriptional Activator*. Structure, 2002. 10(5): p. 701-713.
135. Park, D. M. and P. J. Kiley, *The influence of repressor DNA binding site architecture on transcriptional control*. MBio, 2014. 5(5): p. e01684-14.
136. Nriagu, J. O., *Lead orthophosphates. L Solubility and hydrolysis of secondary lead orthophosphate*. Inorganic Chemistry, 1972. 11(10): p. 2499-2503.
137. Tripet, B., et al., *Engineering a de novo designed coiled-coil heterodimerization domain for the rapid detection, purification and characterization of recombinantly expressed peptides and proteins*. Protein Eng, 1997. 10(3): p. 299.
138. Yung, M. C. and Y. Jiao, *Biomineralization of uranium by PhoYphosphatase activity aids cell survival in Caulobacter crescentus*. Appl Environ Microbiol, 2014. 80(16): p. 4795-804.
139. Nolan, J. and K. A. Weber, *Natural Uranium Contamination in Major U.S. Aquifers Linked to Nitrate*. Environmental Science & Technology Letters, 2015. 2 (8): p. 215-220.
140. Markich, S. J., *Uranium speciation and bioavailability in aquatic systems: an overview*. ScientificWorldJournal, 2002. 2: p. 707-29.
141. Roggo, C. and J. R. van der Meer, *Miniaturized and integrated whole cell living bacterial sensors infield applicable autonomous devices*. Curr Opin Biotechnol, 2017. 45: p. 24-33.

142. Buffi, N., et al., *An automated microreactor for semi-continuous biosensor measurements*. Lab Chip, 2016. 16(8): p. 1383-92.

143. Truffer, F., et al., *Compact portable biosensor for arsenic detection in aqueous samples with Escherichia coli bioreporter cells*. Rev Sci Instrum, 2014. 85(1): p. 015120.

45

The invention claimed is:
1. A gene cassette comprising a U-sensing genetic molecular component comprising:
a reporter gene and/or U-neutralizing gene under direct or indirect control of one or more U-sensitive promoters, each of the one or more U-sensitive promoters comprising a U-sensitive 1362 binding site having a DNA sequence

(SEQ ID NO: 1)
$N_1N_2N_3N_4N_5N_6N_7N_8N_9N_{10}N_{11}N_{12}N_{13}N_{14}N_{15}N_{16}N_{17}N_{18}$, wherein
$N_1$ is C or T;
$N_2$ is G or A;
$N_3$ is T or C;
$N_4$ is C;
$N_5$ is A or G;
$N_6$ is G or C;
$N_7$ is C or G;
$N_8$ is any nucleotide;
$N_9$ is any nucleotide;
$N_{10}$ is any nucleotide;
$N_{11}$ is any nucleotide;
$N_{12}$ is T or C;
$N_{13}$ is G;
$N_{14}$ is T or C;
$N_{15}$ is C;
$N_{16}$ is A or C;
$N_{17}$ is G; and
$N_{18}$ is C or G,
wherein $N_1$ to $N_{17}$ are selected independently,
the one or more U-sensitive promoters in a configuration wherein the one or more U-sensitive promoters directly or indirectly initiate expression of the reporter gene and/or the U-neutralizing gene in presence of bioavailable U.

2. The gene cassette of claim 1, wherein in the sequence SEQ ID NO: 1:
$N_1$ is C; and/or
$N_2$ is G; and/or
$N_3$ is T; and/or
$N_5$ is A; and/or
$N_6$ is G; and/or $N_{14}$ is T; and/or $N_{16}$ is A.

3. The gene cassette of claim 1, wherein the U-sensitive transcriptional 1362 binding site has a sequence selected from the group consisting of SEQ ID NO: 7, SEQ ID NO:8, SEQ ID NO:9, SEQ ID NO:10, SEQ ID NO:11, SEQ ID NO:12, SEQ ID NO: 13, SEQ ID NO:14, SEQ ID NO:15, SEQ ID NO:16, SEQ ID NO:17, SEQ ID NO:18, SEQ ID NO: 19, SEQ ID NO:20, SEQ ID NO:21, SEQ ID NO:22, SEQ ID NO:23, SEQ ID NO:24, SEQ ID NO: 25, SEQ ID NO:26 and SEQ ID NO:27.

4. The gene cassette of claim 1, wherein the U-sensitive promoter further comprises nucleotides $N_{19}N_{20}N_{21}$ downstream of SEQ ID NO: 1 wherein $N_{19}$ is any nucleotide; $N_{20}$ is any nucleotide; and $N_{21}$ is G (SEQ ID NO: 83).

5. The gene cassette of claim 4, wherein $N_{18}$ of the regulator direct repeat is located about-17 to about-40 upstream of a transcription start site.

6. The gene cassette of claim 1, wherein the U-sensitive promoter is $P_{1361}$ Or $P_{phyt}$.

7. A U-sensitive genetic circuit comprising a U-sensing genetic molecular component in combination with a reportable molecular component and/or a U-neutralizing molecular component, wherein the U-sensing genetic molecular component comprises:

one or more U-sensitive promoters each comprising a U-sensitive 1362 binding site having the DNA sequence of SEQ ID NO:1, (SEQ ID NO: 1)
$N_1N_2N_3N_4N_5N_6N_7N_8N_9N_{10}N_{11}N_{12}N_{13}N_{14}N_{15}N_{16}N_{17}N_{18}$, wherein $N_1$ is C or T;

$N_2$ is G or A;

$N_3$ is T or C;

$N_4$ is C;

$N_5$ is A or G;

$N_6$ is G or C;

$N_7$ is C or G;

$N_8$ is any nucleotide;

$N_9$ is any nucleotide;

$N_{10}$ is any nucleotide;

$N_{11}$ is any nucleotide;

$N_{12}$ is T or C;

$N_{13}$ is G;

$N_{14}$ is T or C;

$N_{15}$ is C;

$N_{16}$ is A or C;

$N_{17}$ is G; and $N_{18}$ is C or G, wherein $N_1$ to $N_{17}$ are selected independently, wherein the one or more U-sensitive promoters are in a configuration wherein the one or more U-sensitive promoters directly or indirectly initiate expression of (a) the reportable molecular component, and/or (b) the U-neutralizing molecular component, in presence of bioavailable U, and wherein the reportable molecular component and/or the U-neutralizing molecular component are expressed when the genetic circuit operates according to the circuit design in the presence of bioavailable U.

8. A U-sensing system comprising a combination of a plurality of bacterial cells and one or more vectors comprising the gene cassette of claim 1, wherein the one or more vectors are configured to introduce the gene cassette into the plurality of bacterial cells and wherein the plurality of bacterial cells natively and/or heterologously express histidine kinase 1363 and response regulator 1362 and histidine kinase UzcS and response regulator UzcR.

9. The U-sensing gene cassette of claim 1 wherein the gene cassette further comprises (a) a UzcR binding site having a DNA sequence: CATTACN$_7$N$_8$N$_9$N$_{10}$N$_{11}$N$_{12}$TTAA (SEQ ID NO: 2) wherein $N_7$-$N_{12}$ is independently any nucleotide, (b) a gene encoding histidine kinase UzcS, and (c) a gene encoding a U-sensitive transcriptional response regulator UzcR wherein the one or more U-sensitive promoters, the reporter gene, the U-neutralizing gene, the UzcR binding site, the gene encoding histidine kinase UzcS and the gene encoding a U-sensitive transcriptional response regulator UzcR are in a configuration in which (i) the one or more U-sensitive promoters directly initiate expression of genes encoding the histidine kinase UzcS, and the U-sensitive transcriptional response regulator UzcR in presence of bioavailable U, and (ii) when the U-sensitive transcriptional response regulator UzcR binds to the UzcR binding site, this binding directly initiates the expression of the reporter gene and/or the U-neutralizing gene; and wherein the one or more U-sensitive promoters indirectly initiate expression of the reporter gene and/or the U-neutralizing gene in presence of bioavailable U.

10. The gene cassette of claim 9, further comprising a UzcY gene and/or UzcZ gene under control of one or more U-sensitive promoters having SEQ ID NO: 1.

11. The gene cassette of claim 1, wherein the reporter gene encodes a reportable molecular component capable of being detected using fluorescence, luminescence, chemiluminescence, colorimetric analysis, radioactivity, or electrical.

12. The gene cassette of claim 1, wherein the U-neutralizing gene encodes a U-neutralizing component configured to decrease or eliminate toxicity of U by bioreduction, biomineralization, bioaccumulation, and/or biosorption.

13. A U biosensor comprising the gene cassette of claim 1 configured to report and/or neutralize U, within a genetically engineered bacterial cell capable of heterologously and/or natively expressing histidine kinase 1363, and U-sensitive transcriptional regulator 1362.

14. A U biosensor, comprising the gene cassette of claim 9 configured to report and/or neutralize U, within a genetically engineered bacterial cell capable of heterologously and/or natively expressing histidine kinase 1363, and U-sensitive transcriptional regulator 1362 wherein the genetically engineered bacterial cell is capable of natively expressing endogenous MarR family repressors and at least one gene of the endogenous MarR family is knocked out.

15. A U biosensor, comprising the gene cassette of claim 9 configured to report and/or neutralize U, within a genetically engineered bacterial cell capable of heterologously and/or natively expressing histidine kinase 1363, and U-sensitive transcriptional regulator 1362 wherein the genetically engineered bacterial cell is capable of natively expressing endogenous urtAP genes and at least one gene of the endogenous urtAP is knocked out.

16. The U biosensor of claim 13, wherein the bacterial cell is a proteobacterial cell.

17. The U biosensor of claim 16, wherein the proteobacterial cell is an alphaproteobacteria, a betaproteobacteria, or a gammaproteobacteria.

18. The U biosensor of claim 16, wherein the proteobacterial cell is a *Caulobacteridae* cell.

19. The U biosensor of claim 16, wherein the proteobacterial cell is a *Caulobacter crescentus* cell.

20. The U biosensor of claim 19, wherein the *Caulobacter crescentus* cell is a member of a strain selected from the group consisting of NA1000, CB15, and OR37.

21. The U biosensor of claim 13, wherein in the target environment the bioavailable U has a concentration greater than 100 nM, between 100 nM and 1 µM, or greater than 1 µM.

22. A vector comprising:
the gene cassette of claim 1,
wherein the vector is configured to introduce the gene cassette of claim 1 into a bacterial cell capable of heterologously and/or natively expressing histidine kinase 1363 and U-sensitive transcriptional regulator 1362.

23. A U-sensing system comprising:
a plurality of bacterial cells capable of heterologously and/or natively expressing histidine kinase 1363 and U-sensitive transcriptional regulator 1362; and
one or more vectors configured to introduce the gene cassette of claim 1 into the plurality of bacterial cells.

24. A composition comprising:
one or more U biosensors comprising the gene cassette of claim 1 within a cell capable of heterologously and/or natively expressing histidine kinase 1363 and U-sensitive transcriptional regulator 1362, and/or one or more vectors comprising the gene cassette of claim 1 together with a suitable vehicle.

* * * * *

```
                              SEQUENCE LISTING

Sequence total quantity: 200
SEQ ID NO: 1            moltype = DNA   length = 18
FEATURE                 Location/Qualifiers
misc_difference         1..17
                        note = N1 to N17 selected independently
misc_difference         5
                        note = N5 is A or G, preferably A
misc_difference         6
                        note = N6 is G or C, preferably G
misc_difference         7
                        note = N7 is G or C
misc_difference         8
                        note = N8 is any nucleotide
misc_difference         9
                        note = note = N9 is any nucleotide
misc_difference         10
                        note = N10 is any nucleotide
misc_difference         11
                        note = N11 is any nucleotide
misc_difference         12
                        note = N12 is T or C
misc_difference         14
                        note = N14 is T or C, preferably T
misc_difference         18
                        note = N18 is C or G
source                  1..18
                        mol_type = other DNA
                        organism = synthetic construct
misc_difference         1
                        note = N1 is C or T, preferably C
misc_difference         2
                        note = N2 is G or A, preferably G
misc_difference         3
                        note = N3 is T or C, preferably T
misc_difference         16
                        note = N16 is A or C, preferably A
SEQUENCE: 1
yrycrssnnn nygycmgs                                                 18

SEQ ID NO: 2            moltype = DNA   length = 16
FEATURE                 Location/Qualifiers
misc_difference         7..12
                        note = N7-N12 is independently any nucleotide
source                  1..16
                        mol_type = other DNA
                        organism = synthetic construct
SEQUENCE: 2
cattacnnnn nnttaa                                                   16

SEQ ID NO: 3            moltype = AA    length = 452
FEATURE                 Location/Qualifiers
source                  1..452
                        mol_type = protein
                        note = Strain NA1000
                        organism = Caulobacter crescentus
SEQUENCE: 3
MSGGSLRWRL IVGGMLAILA ALAVAWLAMT WLFERHIVRR ETADLTRAGQ VLVAGLRLEP   60
NGAPVIDATL SDPRLSKAAG GFYWQVSTTS GSERSVSLWD QALKPPQTAP AEGWSSRIAA  120
GPFDDRVLLV ERSVRPDRDG PAVLIQVASD EKVLRAARRE FGRELAIFLG GLWAILSGAA  180
ALQVVLGLSP LTRVRADLAR LRKSPSARMS LDHPREIAPL AEAINALAEA READLARARR  240
RAGDLAHSLK TPLAALSAQS RRAREDGAVA AADGLDAAIA SVAAALEAEL ARARAAAARE  300
AVFAAETAPL AVAERLVAVL ERTADGERLI FDIDVPADLK APASEDVVTE MLGALIENAA  360
RHARRQVRIS GAVVGQGAVL IVEDDGPGLD KGRAEAALAR GARLDEAGPG HGLGLAIVRD  420
LAEASGAVLS MDRGDLGGLR AMVSWTAPGA GP                                452

SEQ ID NO: 4            moltype = AA    length = 222
FEATURE                 Location/Qualifiers
source                  1..222
                        mol_type = protein
```

```
                        note = Strain NA1000
                        organism = Caulobacter crescentus
SEQUENCE: 4
MMRALVVEDD  PVVGPDLAKA  LSASGFVVDI  ARDGEDASFK  GEVEDYALVV  LDLGLPRLDG    60
LSVLRRWRAN  DRAFPVLILS  ARGDWTEKVE  GIEAGADDYL  AKPFEMGELL  ARARGLVRRA   120
AGRTSPVIGA  GRLALDTRRM  SATLDGAPIR  LSPLEFRLLD  CLAHNPGRAV  SAGELAEQLY   180
GVADTADTNA  IEALVARLRR  KIGADVIETR  RGFGYLLAGG  TA                       222

SEQ ID NO: 5            moltype = AA  length = 468
FEATURE                 Location/Qualifiers
source                  1..468
                        mol_type = protein
                        note = Strain NA1000
                        organism = Caulobacter crescentus
SEQUENCE: 5
MRLPRLLRTT  PFRLTLLFLA  LFAAAASAFL  GYIYVATAGE  VNRRAQAEIS  REFESLEAAY    60
RQGGVDALNQ  TIVERATSER  PFLYFLADKD  GKRISGSIEE  SPVSGFTGDG  PEWASFKVTE   120
TDLDGAEVKA  AARGVQQRLD  NGEILFVGAD  VDASEAYVRK  IVRALWGAGA  LVILLGMAGG   180
VLISRNVSRS  MQGLVDVVNA  VRGGDLHARA  RVRGTRDEYD  ELAEGLNDML  DRIERLMGGL   240
RHAGDAIAHD  LRSPLTRLRA  RMEVALIDAE  NGKGDPVAAL  ETALQDADGV  LKTFNAVLAI   300
ARLQAAGSAP  DQRQFDASEL  AGDMAELYEL  SCEDKGLDFK  AEIVPALTIK  GNREFLAQAL   360
ANILDNAIKY  TPEGGAIMLR  ARRTSSGELE  FSVTDTGPGV  PEADRARVVQ  RFVRLENSRS   420
EPGAGLGLSL  VSAVATSHGG  RLELAEGPGE  YNGMGPGLRV  ALVLPRVE                 468

SEQ ID NO: 6            moltype = AA  length = 223
FEATURE                 Location/Qualifiers
source                  1..223
                        mol_type = protein
                        note = Strain NA1000
                        organism = Caulobacter crescentus
SEQUENCE: 6
MRILIIEDDL  EAAGAMAHGL  KEAGYDVAHA  PDGEAGLAEA  QKGGWDVLVV  DRMMPKMDGV    60
TVVETLRREG  DQTPVLFLSA  LGEVNDRVVG  LKAGADDYLV  KPYAFPELMA  RVEALSRRRE   120
TGAVATTLKV  GELEMNLINR  TVHRQGKEID  LQPREFQLLE  FMMRHAGQSV  TRTMLLEKVW   180
EYHFDPQTNV  IDVHISRLRS  KIDKGFDRAM  LQTVRGAGYR  LDP                     223

SEQ ID NO: 7            moltype = DNA  length = 18
FEATURE                 Location/Qualifiers
misc_feature            1..18
                        note = Synthetic polynucleotide
misc_difference         8..11
                        note = n is a, c, g, or t
source                  1..18
                        mol_type = other DNA
                        organism = synthetic construct
SEQUENCE: 7
cgtcagcnnn ntgtcagc                                                       18

SEQ ID NO: 8            moltype = DNA  length = 18
FEATURE                 Location/Qualifiers
misc_feature            1..18
                        note = Synthetic polynucleotide
misc_difference         8..11
                        note = n is a, c, g, or t
source                  1..18
                        mol_type = other DNA
                        organism = synthetic construct
SEQUENCE: 8
cgtcaggnnn ntgtcagg                                                       18

SEQ ID NO: 9            moltype = DNA  length = 18
FEATURE                 Location/Qualifiers
misc_feature            1..18
                        note = Synthetic polynucleotide
misc_difference         8..11
                        note = n is a, c, g, or t
source                  1..18
                        mol_type = other DNA
                        organism = synthetic construct
SEQUENCE: 9
cgtcagcnnn ntgtcagg                                                       18

SEQ ID NO: 10           moltype = DNA  length = 18
FEATURE                 Location/Qualifiers
misc_feature            1..18
                        note = Synthetic polynucleotide
misc_difference         8..11
                        note = n is a, c, g, or t
source                  1..18
```

```
                        mol_type = other DNA
                        organism = synthetic construct
SEQUENCE: 10
cgtcagcnnn ncgtcagg                                                         18

SEQ ID NO: 11           moltype = DNA   length = 18
FEATURE                 Location/Qualifiers
misc_feature            1..18
                        note = Synthetic polynucleotide
misc_difference         8..11
                        note = n is a, c, g, or t
source                  1..18
                        mol_type = other DNA
                        organism = synthetic construct
SEQUENCE: 11
tgtcagcnnn ntgtcagc                                                         18

SEQ ID NO: 12           moltype = DNA   length = 18
FEATURE                 Location/Qualifiers
misc_feature            1..18
                        note = Synthetic polynucleotide
misc_difference         8..11
                        note = n is a, c, g, or t
source                  1..18
                        mol_type = other DNA
                        organism = synthetic construct
SEQUENCE: 12
cgcctgcnnn ncgtcagc                                                         18

SEQ ID NO: 13           moltype = DNA   length = 18
FEATURE                 Location/Qualifiers
misc_feature            1..18
                        note = Synthetic polynucleotide
misc_difference         8..11
                        note = n is a, c, g, or t
source                  1..18
                        mol_type = other DNA
                        organism = synthetic construct
SEQUENCE: 13
cgtcaggnnn ncgtcagc                                                         18

SEQ ID NO: 14           moltype = DNA   length = 18
FEATURE                 Location/Qualifiers
misc_feature            1..18
                        note = Synthetic polynucleotide
misc_difference         8..11
                        note = n is a, c, g, or t
source                  1..18
                        mol_type = other DNA
                        organism = synthetic construct
SEQUENCE: 14
cgtcagcnnn ntgtcagc                                                         18

SEQ ID NO: 15           moltype = DNA   length = 18
FEATURE                 Location/Qualifiers
misc_feature            1..18
                        note = Synthetic polynucleotide
misc_difference         8..11
                        note = n is a, c, g, or t
source                  1..18
                        mol_type = other DNA
                        organism = synthetic construct
SEQUENCE: 15
tgtcaggnnn ntgtcagc                                                         18

SEQ ID NO: 16           moltype = DNA   length = 18
FEATURE                 Location/Qualifiers
misc_feature            1..18
                        note = Synthetic polynucleotide
misc_difference         8..11
                        note = n is a, c, g, or t
source                  1..18
                        mol_type = other DNA
                        organism = synthetic construct
SEQUENCE: 16
cgtcagcnnn ncgtcagt                                                         18

SEQ ID NO: 17           moltype = DNA   length = 18
FEATURE                 Location/Qualifiers
```

```
misc_feature              1..18
                          note = Synthetic polynucleotide
misc_difference           8..11
                          note = n is a, c, g, or t
source                    1..18
                          mol_type = other DNA
                          organism = synthetic construct SEQUENCE: 17
ccgcgggnnn ntgtcagg                                                         18

SEQ ID NO: 18             moltype = DNA   length = 18
FEATURE                   Location/Qualifiers
misc_feature              1..18
                          note = Synthetic polynucleotide
misc_difference           8..11
                          note = n is a, c, g, or t
source                    1..18
                          mol_type = other DNA
                          organism = synthetic construct SEQUENCE: 18
cgtcgggnnn nagaccgg                                                         18

SEQ ID NO: 19             moltype = DNA   length = 18
FEATURE                   Location/Qualifiers
misc_feature              1..18
                          note = Synthetic polynucleotide
misc_difference           8..11
                          note = n is a, c, g, or t
source                    1..18
                          mol_type = other DNA
                          organism = synthetic construct SEQUENCE: 19
cgtccggnnn ncgtcaga                                                         18

SEQ ID NO: 20             moltype = DNA   length = 18
FEATURE                   Location/Qualifiers
misc_feature              1..18
                          note = Synthetic polynucleotide
misc_difference           8..11
                          note = n is a, c, g, or t
source                    1..18
                          mol_type = other DNA
                          organism = synthetic construct SEQUENCE: 20
caacgccnnn ncgtcagc                                                         18

SEQ ID NO: 21             moltype = DNA   length = 18
FEATURE                   Location/Qualifiers
misc_feature              1..18
                          note = Synthetic polynucleotide
misc_difference           8..11
                          note = n is a, c, g, or t
source                    1..18
                          mol_type = other DNA
                          organism = synthetic construct SEQUENCE: 21
catcaggnnn ncgtcagc                                                         18

SEQ ID NO: 22             moltype = DNA   length = 18
FEATURE                   Location/Qualifiers
misc_feature              1..18
                          note = Synthetic polynucleotide
misc_difference           8..11
                          note = n is a, c, g, or t
source                    1..18
                          mol_type = other DNA
                          organism = synthetic construct SEQUENCE: 22
cgcagggnnn ntgcaagc                                                         18

SEQ ID NO: 23             moltype = DNA   length = 18
FEATURE                   Location/Qualifiers
misc_feature              1..18
                          note = Synthetic polynucleotide
misc_difference           8..11
                          note = n is a, c, g, or t
source                    1..18
                          mol_type = other DNA
                          organism = synthetic construct
```

```
SEQUENCE: 23
catcagcnnn ncgtcagc                                                  18

SEQ ID NO: 24          moltype = DNA   length = 18
FEATURE                Location/Qualifiers
misc_feature           1..18
                       note = Synthetic polynucleotide
misc_difference        8..11
                       note = n is a, c, g, or t
source                 1..18
                       mol_type = other DNA
                       organism = synthetic construct
SEQUENCE: 24
cgtcatcnnn ntgtcacg                                                  18

SEQ ID NO: 25          moltype = DNA   length = 18
FEATURE                Location/Qualifiers
misc_feature           1..18
                       note = Synthetic polynucleotide
misc_difference        8..11
                       note = n is a, c, g, or t
source                 1..18
                       mol_type = other DNA
                       organism = synthetic construct
SEQUENCE: 25
cgtcagcnnn ncatcagc                                                  18

SEQ ID NO: 26          moltype = DNA   length = 18
FEATURE                Location/Qualifiers
misc_feature           1..18
                       note = Synthetic polynucleotide
misc_difference        8..11
                       note = n is a, c, g, or t
source                 1..18
                       mol_type = other DNA
                       organism = synthetic construct
SEQUENCE: 26
cttcgcgnnn ncgtccgg                                                  18

SEQ ID NO: 27          moltype = DNA   length = 18
FEATURE                Location/Qualifiers
misc_feature           1..18
                       note = Synthetic polynucleotide
misc_difference        8..11
                       note = n is a, c, g, or t
source                 1..18
                       mol_type = other DNA
                       organism = synthetic construct
SEQUENCE: 27
cgtcaggnnn nggtcagg                                                  18

SEQ ID NO: 28          moltype = DNA   length = 18
FEATURE                Location/Qualifiers
misc_feature           1..18
                       note = Synthetic polynucleotide
misc_difference        8..11
                       note = n is a, c, g, or t
source                 1..18
                       mol_type = other DNA
                       organism = synthetic construct
SEQUENCE: 28
tgtcagcnnn natcctgc                                                  18

SEQ ID NO: 29          moltype =       length =
SEQUENCE: 29
000

SEQ ID NO: 30          moltype =       length =
SEQUENCE: 30
000

SEQ ID NO: 31          moltype =       length =
SEQUENCE: 31
000

SEQ ID NO: 32          moltype =       length =
SEQUENCE: 32
000
```

| | | |
|---|---|---|
| SEQ ID NO: 33 | moltype = AA   length = 150 | |
| FEATURE | Location/Qualifiers | |
| source | 1..150<br>mol_type = protein<br>note = Strain N100<br>organism = Caulobacter Crescentus | |
| SEQUENCE: 33 | | |

```
MTRDQDTLRM LAEVEAANAD LARRAKAPLW YHPALGLLVG ALIAVQGQPT SILLVFYAAY   60
IAGLALLVRA YKRHTGLWVS GYRAGRTRWV ALGLATLTMI GGVIAVWLLR ERGLTAAPLI  120
FGAIVAVIVT VGGFVWEAAF RADLRDGRPL                                  150
```

| | | |
|---|---|---|
| SEQ ID NO: 34 | moltype = AA   length = 412 | |
| FEATURE | Location/Qualifiers | |
| source | 1..412<br>mol_type = protein<br>note = Strain N100<br>organism = Caulobacter Crescentus | |
| SEQUENCE: 34 | | |

```
MRRGSQPMHA PISATERSTI AQIGGRNAPI GALRAFVTLL VIAHHTVLAY TPNPPPIGDF   60
SQAPYLWQAF PVRDPQKFEL FGLLTLINDL FFMSLMFFIS GLFVADGLRA KGNGGLLSGR  120
AARLGVPFVL AAGLLAPLAY FPAWLQAGGD VSIAGFASAW LDLPSWPSGP AWFLWVLLAF  180
GAIVTLLNLI APGVIDALGR LVRGADRKPG LFFLGLVIAS AVAYIPMSAT FTFMHWTQLG  240
PFTVQTSRVV HYFVYPLAGV AVGAAGVGQG LTDSEGKLAK RWWAWQAAPI LPVVGVIAVI  300
IMAFSPKPPP RVALDIGGGV MFALACATLS FAALATFLRF VKKTGPVAAS LQANAYGMYL  360
THYVFTTWLA WLLLPQAWGG LAKGAAVFVG ATLLSWILTM ALRRLPLLGR IL          412
```

| | | |
|---|---|---|
| SEQ ID NO: 35 | moltype = AA   length = 98 | |
| FEATURE | Location/Qualifiers | |
| source | 1..98<br>mol_type = protein<br>note = Strain NA1000<br>organism = Caulobacter crescentus | |
| SEQUENCE: 35 | | |

```
MSAALDPVIH APNRLQMCCM LAAVDTIDFA TVREALDVSE SVLSKHVKTL EEAGYVKVKK   60
AASDGRQRTW LSLSKPGREA LKGHLAALKA MMAGVPEA                          98
```

| | | |
|---|---|---|
| SEQ ID NO: 36 | moltype = AA   length = 103 | |
| FEATURE | Location/Qualifiers | |
| source | 1..103<br>mol_type = protein<br>note = Strain NA1000<br>organism = Caulobacter crescentus | |
| SEQUENCE: 36 | | |

```
MAPRFDISGL DDVIHGRVRL GIVAYLASAE VADFTELKDV LEVTQGNLSI HLRKLEEAGY   60
VSIDKSFVGR KPLTRVRLTD TGRAAFSSYL RAMGQLVEQA GGG                   103
```

| | | |
|---|---|---|
| SEQ ID NO: 37 | moltype = DNA   length = 34 | |
| FEATURE | Location/Qualifiers | |
| misc_feature | 1..34<br>note = Synthetic polynucleotide | |
| source | 1..34<br>mol_type = other DNA<br>organism = synthetic construct | |
| SEQUENCE: 37 | | |

```
taacccttg caaaccggac ggtgaccggc aaac                               34
```

| | | |
|---|---|---|
| SEQ ID NO: 38 | moltype = DNA   length = 34 | |
| FEATURE | Location/Qualifiers | |
| misc_feature | 1..34<br>note = Synthetic polynucleotide | |
| source | 1..34<br>mol_type = other DNA<br>organism = synthetic construct | |
| SEQUENCE: 38 | | |

```
gatgaacttg cgcatggcgg agccctcgt tttc                               34
```

| | | |
|---|---|---|
| SEQ ID NO: 39 | moltype = DNA   length = 34 | |
| FEATURE | Location/Qualifiers | |
| misc_feature | 1..34<br>note = Synthetic polynucleotide | |
| source | 1..34<br>mol_type = other DNA<br>organism = synthetic construct | |
| SEQUENCE: 39 | | |

```
taacccttg caaacgaacg atagcgccgc ctgc                               34
```

| | | |
|---|---|---|
| SEQ ID NO: 40 | moltype = DNA   length = 56 | |
| FEATURE | Location/Qualifiers | |
| misc_feature | 1..56 | |

```
                        note        = Synthetic polynucleotide
source                  1..56
                        mol_type    = other DNA
                        organism    = synthetic construct
SEQUENCE: 40
tccctctggc tgggcggaaa gatcgggact gggtgatggc gcttaggatt ccacag        56

SEQ ID NO: 41           moltype = DNA  length = 22
FEATURE                 Location/Qualifiers
misc_feature            1..22
                        note        = Synthetic polynucleotide
source                  1..22
                        mol_type    = other DNA
                        organism    = synthetic construct
SEQUENCE: 41
atgcgcaagt tcatcatgag cc                                             22

SEQ ID NO: 42           moltype = DNA  length = 24
FEATURE                 Location/Qualifiers
misc_feature            1..24
                        note        = Synthetic polynucleotide
source                  1..24
                        mol_type    = other DNA
                        organism    = synthetic construct
SEQUENCE: 42
gtttgcaaag ggttaatcga cgcc                                           24

SEQ ID NO: 43           moltype = DNA  length = 32
FEATURE                 Location/Qualifiers
misc_feature            1..32
                        note        = Synthetic polynucleotide
source                  1..32
                        mol_type    = other DNA
                        organism    = synthetic construct
SEQUENCE: 43
ggaacgatag cgccggacgg tgaccggcaa ac                                  32

SEQ ID NO: 44           moltype = DNA  length = 23
FEATURE                 Location/Qualifiers
misc_feature            1..23
                        note        = Synthetic polynucleotide
source                  1..23
                        mol_type    = other DNA
                        organism    = synthetic construct
SEQUENCE: 44
cgcacaaaat cctcatcctg agc                                            23

SEQ ID NO: 45           moltype = DNA  length = 34
FEATURE                 Location/Qualifiers
misc_feature            1..34
                        note        = Synthetic polynucleotide
source                  1..34
                        mol_type    = other DNA
                        organism    = synthetic construct
SEQUENCE: 45
caattgaagc cggctcagaa ggtcgacgcc ctgg                                34

SEQ ID NO: 46           moltype = DNA  length = 23
FEATURE                 Location/Qualifiers
misc_feature            1..23
                        note        = Synthetic polynucleotide
source                  1..23
                        mol_type    = other DNA
                        organism    = synthetic construct
SEQUENCE: 46
cgcacaaaat cctcatcctg agc                                            23

SEQ ID NO: 47           moltype = DNA  length = 32
FEATURE                 Location/Qualifiers
misc_feature            1..32
                        note        = Synthetic polynucleotide
source                  1..32
                        mol_type    = other DNA
                        organism    = synthetic construct
SEQUENCE: 47
ggaacgatag cgccggacgg tgaccggcaa ac                                  32

SEQ ID NO: 48           moltype = DNA  length = 29
FEATURE                 Location/Qualifiers
```

```
                            -continued misc_feature               1..29
                           note = Synthetic polynucleotide
source                     1..29
                           mol_type = other DNA
                           organism = synthetic construct
SEQUENCE: 48
aatcagaatg cgcatggcgg agcccctcg                                        29

SEQ ID NO: 49              moltype = DNA  length = 25
FEATURE                    Location/Qualifiers
misc_feature               1..25
                           note = Synthetic polynucleotide
source                     1..25
                           mol_type = other DNA
                           organism = synthetic construct
SEQUENCE: 49
atgcgcattc tgattatcga ggacg                                            25

SEQ ID NO: 50              moltype = DNA  length = 20
FEATURE                    Location/Qualifiers
misc_feature               1..20
                           note = Synthetic polynucleotide
source                     1..20
                           mol_type = other DNA
                           organism = synthetic construct
SEQUENCE: 50
cggcgctatc gttccctagg                                                  20

SEQ ID NO: 51              moltype = DNA  length = 35
FEATURE                    Location/Qualifiers
misc_feature               1..35
                           note = Synthetic polynucleotide
source                     1..35
                           mol_type = other DNA
                           organism = synthetic construct
SEQUENCE: 51
gtgaaaaaag cttaactcga ggggctccgc catgc                                 35

SEQ ID NO: 52              moltype = DNA  length = 39
FEATURE                    Location/Qualifiers
misc_feature               1..39
                           note = Synthetic polynucleotide
source                     1..39
                           mol_type = other DNA
                           organism = synthetic construct
SEQUENCE: 52
ttaagctttt ttcacgcagt ctcgcagcta gcttagccg                             39

SEQ ID NO: 53              moltype = DNA  length = 44
FEATURE                    Location/Qualifiers
misc_feature               1..44
                           note = Synthetic polynucleotide
source                     1..44
                           mol_type = other DNA
                           organism = synthetic construct
SEQUENCE: 53
gtgaaaaaag cttaactccg agctccctaa ctaactaatc atct                       44

SEQ ID NO: 54              moltype = DNA  length = 42
FEATURE                    Location/Qualifiers
misc_feature               1..42
                           note = Synthetic polynucleotide
source                     1..42
                           mol_type = other DNA
                           organism = synthetic construct
SEQUENCE: 54
ttaagctttt ttcacgcagt gatggcgctt aggattccac ag                         42

SEQ ID NO: 55              moltype = DNA  length = 36
FEATURE                    Location/Qualifiers
misc_feature               1..36
                           note = Synthetic polynucleotide
source                     1..36
                           mol_type = other DNA
                           organism = synthetic construct
SEQUENCE: 55
tggggagacg accatatgcg taagggcgaa gagctg                                36

SEQ ID NO: 56              moltype = DNA  length = 37
```

```
FEATURE                    Location/Qualifiers
misc_feature               1..37
                           note = Synthetic polynucleotide
source                     1..37
                           mol_type = other DNA
                           organism = synthetic construct
SEQUENCE: 56
cacggctggc tgcaggccga atttcagggg tacagca                              37

SEQ ID NO: 57              moltype = DNA  length = 28
FEATURE                    Location/Qualifiers
misc_feature               1..28
                           note = Synthetic polynucleotide
source                     1..28
                           mol_type = other DNA
                           organism = synthetic construct
SEQUENCE: 57
gatcccgggg atttctcttc gcgccacc                                        28

SEQ ID NO: 58              moltype = DNA  length = 28
FEATURE                    Location/Qualifiers
misc_feature               1..28
                           note = Synthetic polynucleotide
source                     1..28
                           mol_type = other DNA
                           organism = synthetic construct
SEQUENCE: 58
gaaatccccg ggatccctgt gctctaga                                        28

SEQ ID NO: 59              moltype = DNA  length = 27
FEATURE                    Location/Qualifiers
misc_feature               1..27
                           note = Synthetic polynucleotide
source                     1..27
                           mol_type = other DNA
                           organism = synthetic construct
SEQUENCE: 59
gactctagac gaagactggg cgggcag                                         27

SEQ ID NO: 60              moltype = DNA  length = 29
FEATURE                    Location/Qualifiers
misc_feature               1..29
                           note = Synthetic polynucleotide
source                     1..29
                           mol_type = other DNA
                           organism = synthetic construct
SEQUENCE: 60
gacagatctc ggtttgggtg gtcgcttgg                                       29

SEQ ID NO: 61              moltype = DNA  length = 29
FEATURE                    Location/Qualifiers
misc_feature               1..29
                           note = Synthetic polynucleotide
source                     1..29
                           mol_type = other DNA
                           organism = synthetic construct
SEQUENCE: 61
ttgtcgacgt atgacgtttg ctctatagc                                       29

SEQ ID NO: 62              moltype = DNA  length = 22
FEATURE                    Location/Qualifiers
misc_feature               1..22
                           note = Synthetic polynucleotide
source                     1..22
                           mol_type = other DNA
                           organism = synthetic construct
SEQUENCE: 62
cgttcacatc gccatccagc tc                                              22

SEQ ID NO: 63              moltype = DNA  length = 23
FEATURE                    Location/Qualifiers
misc_feature               1..23
                           note = Synthetic polynucleotide
source                     1..23
                           mol_type = other DNA
                           organism = synthetic construct
SEQUENCE: 63
atggcgatgt gaacggccat aag                                             23
```

```
SEQ ID NO: 64           moltype = DNA   length = 37
FEATURE                 Location/Qualifiers
misc_feature            1..37
                        note = Synthetic polynucleotide
source                  1..37
                        mol_type = other DNA
                        organism = synthetic construct
SEQUENCE: 64
gtcatacgtc gacaagccga atttcagggg tacagca                              37

SEQ ID NO: 65           moltype = DNA   length = 42
FEATURE                 Location/Qualifiers
misc_feature            1..42
                        note = Synthetic polynucleotide
source                  1..42
                        mol_type = other DNA
                        organism = synthetic construct
SEQUENCE: 65
atgtttttcc tccttataaa gtagatcttt agttagttag gg                        42

SEQ ID NO: 66           moltype = DNA   length = 36
FEATURE                 Location/Qualifiers
misc_feature            1..36
                        note = Synthetic polynucleotide
source                  1..36
                        mol_type = other DNA
                        organism = synthetic construct
SEQUENCE: 66
aaggaggaaa acatatgcg taagggcgaa gagctg                                36

SEQ ID NO: 67           moltype = DNA   length = 37
FEATURE                 Location/Qualifiers
misc_feature            1..37
                        note = Synthetic polynucleotide
source                  1..37
                        mol_type = other DNA
                        organism = synthetic construct
SEQUENCE: 67
gaaatccccg ggatcgccga atttcagggg tacagca                              37

SEQ ID NO: 68           moltype = DNA   length = 24
FEATURE                 Location/Qualifiers
misc_feature            1..24
                        note = Synthetic polynucleotide
source                  1..24
                        mol_type = other DNA
                        organism = synthetic construct
SEQUENCE: 68
ggtcgctacc attaccagtt ggtc                                            24

SEQ ID NO: 69           moltype = DNA   length = 25
FEATURE                 Location/Qualifiers
misc_feature            1..25
                        note = Synthetic polynucleotide
source                  1..25
                        mol_type = other DNA
                        organism = synthetic construct
SEQUENCE: 69
tgcttgggtc gtttgagtat atggt                                           25

SEQ ID NO: 70           moltype = DNA   length = 35
FEATURE                 Location/Qualifiers
misc_feature            1..35
                        note = Synthetic polynucleotide
source                  1..35
                        mol_type = other DNA
                        organism = synthetic construct
SEQUENCE: 70
caaacgaccc aagcaggtgt cgcccttcgc tgaac                                35

SEQ ID NO: 71           moltype = DNA   length = 41
FEATURE                 Location/Qualifiers
misc_feature            1..41
                        note = Synthetic polynucleotide
source                  1..41
                        mol_type = other DNA
                        organism = synthetic construct
SEQUENCE: 71
gtaatggtag cgaccccaag ctcagctaat taagcctcga g                         41
```

```
SEQ ID NO: 72          moltype = DNA   length = 37
FEATURE                Location/Qualifiers
misc_feature           1..37
                       note = Synthetic polynucleotide
source                 1..37
                       mol_type = other DNA
                       organism = synthetic construct
SEQUENCE: 72
gaaatccccg ggatcgccga atttcagggg tacagca                                37

SEQ ID NO: 73          moltype = DNA   length = 39
FEATURE                Location/Qualifiers
misc_feature           1..39
                       note = Synthetic polynucleotide
source                 1..39
                       mol_type = other DNA
                       organism = synthetic construct
SEQUENCE: 73
ggctggcgcc aagcttggcc ggccgcacgc aagggcaga                              39

SEQ ID NO: 74          moltype = DNA   length = 25
FEATURE                Location/Qualifiers
misc_feature           1..25
                       note = Synthetic polynucleotide
source                 1..25
                       mol_type = other DNA
                       organism = synthetic construct
SEQUENCE: 74
ttattttga caccagacca actgg                                              25

SEQ ID NO: 75          moltype = DNA   length = 31
FEATURE                Location/Qualifiers
misc_feature           1..31
                       note = Synthetic polynucleotide
source                 1..31
                       mol_type = other DNA
                       organism = synthetic construct
SEQUENCE: 75
tggtgtcaaa aataatcgca caggcgaccg c                                      31

SEQ ID NO: 76          moltype = DNA   length = 34
FEATURE                Location/Qualifiers
misc_feature           1..34
                       note = Synthetic polynucleotide
source                 1..34
                       mol_type = other DNA
                       organism = synthetic construct
SEQUENCE: 76
gcgaattcgt ggatccaggc gtcgaggtga agta                                   34

SEQ ID NO: 77          moltype = DNA   length = 190
FEATURE                Location/Qualifiers
misc_feature           1..190
                       note = Synthetic polynucleotide
source                 1..190
                       mol_type = other DNA
                       organism = synthetic construct
SEQUENCE: 77
gaacgatagc gccgcctgcg agcgcgacct caggcctcgg acgaagcgcg tccggggcct       60
tttcttgtcg atgttcagcg cctggttacc ggcgatggcg cggtgtcagc gttcgggcgt      120
tgcgatgcgt caggagcgtg tcaggatgcc tgtggaatcc taagcgccat cacccagtcc      180
cgatctttcc                                                             190

SEQ ID NO: 78          moltype = DNA   length = 246
FEATURE                Location/Qualifiers
misc_feature           1..246
                       note = Synthetic polynucleotide
source                 1..246
                       mol_type = other DNA
                       organism = synthetic construct
SEQUENCE: 78
ccggacggtg accggcaaac caccgctgtc atgaatgcgt tttgaagctt cgccataacg       60
cgcctttggt atccggttcg gaacgcggcg ctttcgttga cctctggcca cggagaattc      120
tccatcccaa agagggtgtg gcccaaagag ggtgtggatt tctcttcgcg ccacccgttt      180
cgtcagccgg acgtcaggtc cagacggcta agctagctgc gagacatgaa aacgagggg      240
tccgcc                                                                 246

SEQ ID NO: 79          moltype = DNA   length = 555
```

| FEATURE | Location/Qualifiers |
|---|---|
| misc_feature | 1..555 |
| | note = Synthetic polynucleotide |
| source | 1..555 |
| | mol_type = other DNA |
| | organism = synthetic construct |

SEQUENCE: 79

```
tgaggatttt gtgcgccagg catcaaataa acgaaaggc tcagtcgaaa gactgggcct    60
ttcgttttat ctgttgtttg tcggtgaacg ctctctacta gagtcacact ggctcacctt   120
cgggtgggcc tttctgcgtt tatacctagg aacgatagc gccgcctgcg agcgcgacct   180
caggcctcgg acgaagcgcg tccggggcct tttcttgtcg atgttcagcg cctggttacc   240
ggcgatggcg cggtgtcagc gttcgggcgt tgcgatgcgt caggagcgtg tcaggatgcc   300
tgtggaatcc taagcgccat cacccagtcc cgatctttcc gagctccta actaactaat    360
catctacttt ataaggagga aaaacatatg cgcattctga ttatcgagga cgacctggaa   420
gccgccggcg ccatggcgca cgggctcaag gaagccggct acgacgtcgc ccacgcgccg   480
gacggcgagg cgggcctggc cgaggcccag aagggcggct gggacgtgct ggtcgtcgcc   540
cggatgatgc ccaag                                                    555
```

| SEQ ID NO: 80 | moltype = DNA length = 226 |
|---|---|
| FEATURE | Location/Qualifiers |
| misc_feature | 1..226 |
| | note = Synthetic polynucleotide |
| source | 1..226 |
| | mol_type = other DNA |
| | organism = synthetic construct |

SEQUENCE: 80

```
gacggatccg ccggattatg tccgctgagt gggtcacggt cccggatcag ttcccttgcg    60
aagctgaccg atgttttgt gccaaaagct gttgtggcaa aaacggtttt gcgcaaagtt    120
ttgtattaca aagaatttca cattttaaaa tatctttata aatcaatcag ttatttctat   180
ttttaagctg gcatggttat cgctataggg cttgtacaga tctgtc                  226
```

| SEQ ID NO: 81 | moltype = DNA length = 1622 |
|---|---|
| FEATURE | Location/Qualifiers |
| misc_feature | 1..1622 |
| | note = Synthetic polynucleotide |
| source | 1..1622 |
| | mol_type = other DNA |
| | organism = synthetic construct |

SEQUENCE: 81

```
cagagatcta ctttataagg aggaaaaaca tatggatctg cccgacgatc attacctgtc    60
cacccagacc atcctgtcga aggatctgaa tggcaccgac gtgggctccg gtggcgggag   120
tggtggtggc gggagcaagg tctccgccct caaggagaac gttagcgccc tgaaagagaa   180
agtctcggcc ctgaccgaaa aggtctccgc ccttaaggaa aaggtgagcg ctctcaaaga   240
gtaaccaggc atcaaataaa acgaaaggct cagtcgaaag actgggcctt cgttttatc    300
tgttgtttgt cggtgaacgc tctctactag agtcacactg gctcaccttc gggtgggcct   360
ttctgcgttt ataggtaccc gaagactggg cgggcagcag cccactccca agcgcccacc   420
aattatgact tcttttcat agacttaatt cgacgtcatg aacagtcgt aacgggtgtt    480
cgccatccga ccgctctaca tcctcgatca acggatcgcc aagcgaccac ccaaaccgcc   540
taggtaacta aagattaact ttataaggag gaaaaacata tgaaggtctc gcccttgaa    600
aatgaggtct cggctctcga aaaggaggtg tcggtcctgg agaaagaagt cagcgcgctt   660
gagaaggagg tccgtgccct ggagaagagt ggcggtgggg ggtctggggg cggttctggg   720
ggcggctcca cctcggagaa gcgtgaccac atggtgctgc tcgaatatgt caccgccgc    780
gggatcaccg atgcctccta agactcctgt tgatagatcc agtaatgacc tcagaactcc   840
atctggattt gttcagaacg ctcggttgcc gccgggcgtt ttttattggt gagaatgaaa   900
aatgctgtac ccctgaaatt cggctattgt cgacgtgatg cgtttgctct atagccatcg   960
ctgctcccat gcgcgccact cggtcgcagg gggtgtggga ttttttttgg gagacaatcc   1020
tcatgcgtaa gggcgaagag ctgttcacgg cgtcgtccc catcctcatc gagctggatg   1080
gcgatgtgaa cggccataag ttcttcgtcc gtggggaagg cgaggggat gccaccatcg   1140
gcaagctgag cctcaagttc atctgcacca ccggcaagct cccgtccc tggccgacgc    1200
tcgtcacgac cctcacctac ggggtgcagt gcttttccg ttacccgac cacatgaagc    1260
ggcacgactt ctttaagtcg gccatgcccg aaggctacgt gcaggagcgc accatctatt   1320
ttaaggacga tggcacgtat aagacccgcg cggaggtcaa gttcgaaggg gatccctgg   1380
tcaaccgtat cgagctgaag ggcatcgact ttaaggaaga tggcaacatc ctcgggcaca   1440
agctcgaata taattttaac tcccataagg tctacatcac cgccgacaaa caaaacaacg   1500
gcatcaaggc gaactttacg atccgtcaca atgtggagga cggcagcgtc cagctcgcgg   1560
atcattatca acagaatacc cccatcggcg atggtccgt cctcctccg tagctcgaga   1620
tt                                                                  1622
```

| SEQ ID NO: 82 | moltype = DNA length = 555 |
|---|---|
| FEATURE | Location/Qualifiers |
| misc_feature | 1..555 |
| | note = Synthetic polynucleotide |
| source | 1..555 |
| | mol_type = other DNA |
| | organism = synthetic construct |

SEQUENCE: 82

```
tgaggatttt gtgcgccagg catcaaataa acgaaaggc tcagtcgaaa gactgggcct    60
ttcgtttat ctgttgtttg tcggtgaacg ctctctacta gagtcacact ggctcacctt    120
cgggtgggcc tttctgcgtt tatacctagg aacgatagc gccgcctgcg agcgcgacct   180
```

```
caggcctcgg acgaagcgcg tccggggcct tttcttgtcg atgttcagcg cctggttacc    240
ggcgatggcg cggtgtcagc gttcgggcgt tgcgatgcgt caggagcgtg tcaggatgcc    300
tgtggaatcc taagcgccat cacccagtcc cgatctttcc gagctccta  actaactaat    360
catctacttt ataaggagga aaaacatatg cgcattctga ttatcgagga cgacctggaa    420
gccgccggcc ccatgcgcga cgggctcaag gaagccggct acgacgtcgc ccacgcgccg    480
gacggcgagg cgggcctggc cgaggcccag aagggcggct gggacgtgct ggtcgtcgac    540
cggatgatgc ccaag                                                     555

SEQ ID NO: 83          moltype =    length =
SEQUENCE: 83
000

SEQ ID NO: 84          moltype = DNA   length = 201
FEATURE                Location/Qualifiers
misc_feature           1..201
                       note = Synthetic polynucleotide
source                 1..201
                       mol_type = other DNA
                       organism = synthetic construct
SEQUENCE: 84
cccttTgcaa accatatact caaacgaccc aagcaatatg gtcacaaaaa cttcaaacat    60
tacagactgt ttagaatatt aaagcccccgt aattctctta attacgcgtc atgactgagg   120
tgtaacgaga cttcgcgaga acccgaatgt atccaatatt catcggcgca gcgaacagcg    180
cccagccaga gggatacttc a                                              201

SEQ ID NO: 85          moltype = DNA   length = 201
FEATURE                Location/Qualifiers
misc_feature           1..201
                       note = Synthetic polynucleotide
source                 1..201
                       mol_type = other DNA
                       organism = synthetic construct
SEQUENCE: 85
gaagacccaa gttttgcggt taatcattta cgaagactgg gcgggcagca gcccactccc    60
aagcgcccac caattatgac ttctttttca tagacttaat tcgacgtcat gaagcagtcg    120
taacgggtgt tcgccatccg accgctctac atcctcgatc aacggatcgc caagcgacca    180
cccaaaccga ggatcaagac a                                              201

SEQ ID NO: 86          moltype = DNA   length = 119
FEATURE                Location/Qualifiers
misc_feature           1..119
                       note = Synthetic polynucleotide
source                 1..119
                       mol_type = other DNA
                       organism = synthetic construct
SEQUENCE: 86
acctgcgcct gggcccacg  gcggacgggt cgcggcccgg cgccaccttg caaaggttta    60
atccacctgt ccggcttgta acttccctca aggggagccg agaggcaccg tcgaaccca     119

SEQ ID NO: 87          moltype = DNA   length = 201
FEATURE                Location/Qualifiers
misc_feature           1..201
                       note = Synthetic polynucleotide
source                 1..201
                       mol_type = other DNA
                       organism = synthetic construct
SEQUENCE: 87
ggagcggcgg tctcagaaag gtggcgaaaa taaagcactg atcataagta aatcgcgatc    60
atccaagtaa tgacgccggg caatcgattg tagaaagatg aaaatctcgt aatgctatcg   120
gatatgtaat ctacatgtca ggcttgtaac ttgagatgaa tgttcggggc gttcagacct   180
gtcgccactg aggggaacca g                                              201

SEQ ID NO: 88          moltype = DNA   length = 201
FEATURE                Location/Qualifiers
misc_feature           1..201
                       note = Synthetic polynucleotide
source                 1..201
                       mol_type = other DNA
                       organism = synthetic construct
SEQUENCE: 88
tcacgcgtct tcatgggct  gctccttgcg acatcggcga cgaaacacgc cgtagacgcc    60
cagatggggg tcgcccggag gcgcgacaat ggtcgaaccg catcaccggg gcaggcgccg   120
tgaagattac agtcaattaa attgaacgcc gttcttcctt ttcggaaagt gccttgggaa   180
cttccggacc gagggacgtg g                                              201

SEQ ID NO: 89          moltype = DNA   length = 201
FEATURE                Location/Qualifiers
misc_feature           1..201
                       note = Synthetic polynucleotide
```

```
                        source             1..201
                                           mol_type = other DNA
                                           organism = synthetic construct
SEQUENCE: 89
cagacacgcg gcggtttccg cgacggaaga gtgtcgaggc gggcgcatac gcctgtggcg    60
cgaatgccac ttggagtccc tcacccgcaa cattgccgaa aagaaatttg tcccggcgcg   120
tcggagcgtc tttacggctg ggggtcgaga ccgcgcggac gtccgcagcg tatcgctcga   180
cacttgaagt tgaggtctcc c                                             201

SEQ ID NO: 90           moltype = DNA  length = 201
FEATURE                 Location/Qualifiers
misc_feature            1..201
                        note = Synthetic polynucleotide
source                  1..201
                        mol_type = other DNA
                        organism = synthetic construct
SEQUENCE: 90
atgcaggccg cctcagggga caaagtttct cacgaaacgg ccttgtgcga tcacattaca    60
ccgctgtaac ctcgattacg cgcgtcaacg ttccttaaat cggcgtcatg aagcaagagt   120
aacgtgtaat aaccatgggg cggacctata tccctctcat cggacgccaa cggggcggcc   180
gaagaaaaaa gggatcaaga c                                             201

SEQ ID NO: 91           moltype = DNA  length = 201
FEATURE                 Location/Qualifiers
misc_feature            1..201
                        note = Synthetic polynucleotide
source                  1..201
                        mol_type = other DNA
                        organism = synthetic construct
SEQUENCE: 91
taaccagacc gcaaggcgcc taagtcataa gcctcttacc gccgaggccg cgcgccggct    60
ggcgagcgac gaggtctgcc cttcagcgag gccggccccg actatttcat gcctgaaacg   120
cgccttaccc cgatttaact tggccactcg tcgatcggcg ttcattgctg caaccgtcga   180
ttgggggagc acgagtccgc a                                             201

SEQ ID NO: 92           moltype = DNA  length = 201
FEATURE                 Location/Qualifiers
misc_feature            1..201
                        note = Synthetic polynucleotide
source                  1..201
                        mol_type = other DNA
                        organism = synthetic construct
SEQUENCE: 92
gcggagatgg atcgcgcgac gggtctgaaa cagagtcagt tgagccaggc gtgcggcgat    60
gactccacgt tgttgccccg cggactttcc attccgcgct gccgttaaat ccccgtcatt   120
accgcaattt aagtggtctc tggccctccg tcggtccaaa ccgtaactca cacagtcgcg   180
tatggactga acggagtagt c                                             201

SEQ ID NO: 93           moltype = DNA  length = 201
FEATURE                 Location/Qualifiers
misc_feature            1..201
                        note = Synthetic polynucleotide
source                  1..201
                        mol_type = other DNA
                        organism = synthetic construct
SEQUENCE: 93
acccttatgg catcggcggt ggatccgcgc ctcttgaagg atgaccagca tgcggatgcg    60
cggctggaaa agccgatcac ccctggacgt cttctgcaga cggtgcgcgc gctgaaagcc   120
cgccacgcag cgtgacagaa ctttaagctg accccgacca cttcgcgccc ctagggtgtg   180
acgcgttttt ggggagctca c                                             201

SEQ ID NO: 94           moltype = DNA  length = 201
FEATURE                 Location/Qualifiers
misc_feature            1..201
                        note = Synthetic polynucleotide
source                  1..201
                        mol_type = other DNA
                        organism = synthetic construct
SEQUENCE: 94
gctcgacccg gcgttcgcgg cggggctgga ggcggcggcc aaggccgggg tggaggtgct    60
ggtctatgcg tgtgaaatgg ggacgcaggc ggtgcggatc gcgcggcgca ttttgtggag   120
ccacgcccac ctaacagcga tttaagctgc atttcgcgcc cgctgagcta acccttctgc   180
aggctcgcga aatgggatc g                                              201

SEQ ID NO: 95           moltype = DNA  length = 201
FEATURE                 Location/Qualifiers
misc_feature            1..201
                        note = Synthetic polynucleotide
source                  1..201
```

```
                           mol_type = other DNA
                           organism = synthetic construct
SEQUENCE: 95
gaaagagtgt tcaggcgcaa cctgggggaa ggtcccaagg cctagactgg cacctagggc    60
cgagcgacgc ttgcgacaac cgtcggaatt ctaagggtgc tgtcagatgt cgtggagccc   120
ccttgcaaga ccatcggccc ttcatgacca aaagttcact cgcctgcttt gcgaaatgct   180
cgcataacgc cgctatggga t                                             201

SEQ ID NO: 96              moltype = DNA  length = 201
FEATURE                    Location/Qualifiers
misc_feature               1..201
                           note = Synthetic polynucleotide
source                     1..201
                           mol_type = other DNA
                           organism = synthetic construct
SEQUENCE: 96
ggttcgccgc gcgatcgcat ggcgtgacga ccatgactag aggggccaag cgccagaacc    60
tgtcagctaa gccgcccagc gacgccgaac gccgttaccg cgatgggca aacctgtaga   120
attgttcatg aacccggaca ttttcgcgcc ataaccgcgt ggccaagctc caggctcgga   180
ctacgacagg gagctcacaa c                                             201

SEQ ID NO: 97              moltype = DNA  length = 201
FEATURE                    Location/Qualifiers
misc_feature               1..201
                           note = Synthetic polynucleotide
source                     1..201
                           mol_type = other DNA
                           organism = synthetic construct
SEQUENCE: 97
cctcgatgat cgcgaccgac ccctccacgg cctgagtgtg cgccgatagc gcgggcgaca    60
cgccgccgcc gatcattgcc aaagtttaat atcgtttctc gataaacgac attggcggaa   120
ccgcaaaccc ggcctatctg ttcagtgtgg cgaaggggcg aatgtttcgg ccctggccat   180
gtctctcaaa ctggaaaaag c                                             201

SEQ ID NO: 98              moltype = DNA  length = 201
FEATURE                    Location/Qualifiers
misc_feature               1..201
                           note = Synthetic polynucleotide
source                     1..201
                           mol_type = other DNA
                           organism = synthetic construct
SEQUENCE: 98
tcgtacggcg atggtcgatg tgcatggcca gttggatgaa actcgcttgc gccttggcgt    60
taggacccgc atgggcggct cgctcaagcc gatcgaggaa accacgcgtg ggttgaagga   120
agtcggctga gcaacgatca accggacatt gcgatagttt aataaccttg ggcctctaat   180
ttaggttaga ggcccaagtc a                                             201

SEQ ID NO: 99              moltype = DNA  length = 201
FEATURE                    Location/Qualifiers
misc_feature               1..201
                           note = Synthetic polynucleotide
source                     1..201
                           mol_type = other DNA
                           organism = synthetic construct
SEQUENCE: 99
ctcgcgacgc tcgctcgccg ctatccccgg ctgggcgcgg cgctgggcct cggcttcggc    60
ctggtgggtc tggcgatgat ggtggactag cctgaccca acatgacttc gcggtcatga   120
cctcgaatta agtcgaaacc ttgtcggccc tcggtagcc tctcctcatc gaatttcaac   180
acgcgtcctt ggggagacac t                                             201

SEQ ID NO: 100             moltype = DNA  length = 201
FEATURE                    Location/Qualifiers
misc_feature               1..201
                           note = Synthetic polynucleotide
source                     1..201
                           mol_type = other DNA
                           organism = synthetic construct
SEQUENCE: 100
ggtacgaacg ccgcggctac cgcctgaccg gcgaaaccca gcccttcccc tatggcgacg    60
accgcttcgg cctgccgcag cgggatgatc tggcgttcgt ggtgatggag aaggggctgt   120
agggccccat taccgaacct taagtagctc cgtccgggcc gacgcgttca gatgccgcgt   180
cttcggctca gggactctcc a                                             201

SEQ ID NO: 101             moltype = DNA  length = 201
FEATURE                    Location/Qualifiers
misc_feature               1..201
                           note = Synthetic polynucleotide
source                     1..201
                           mol_type = other DNA
```

```
                        organism = synthetic construct
SEQUENCE: 101
cctgaccgat cgggtctatg actgggtcgc cgcgaaccgc tatccggatct tcggcaagca    60
tgaccagtgc cggatcccga cgccggcgca acgggcgcgc tttctgatcg actagccccg    120
cccctatatg aactctcggt aaggtttccc ggcgaaccgg cggtgctagg gtcccgcgca    180
aacattcagg agactctcgc g                                              201

SEQ ID NO: 102          moltype = DNA  length = 201
FEATURE                 Location/Qualifiers
misc_feature            1..201
                        note = Synthetic polynucleotide
source                  1..201
                        mol_type = other DNA
                        organism = synthetic construct
SEQUENCE: 102
gtcgtgggcg ctgatcatct ccggctcggt cgtctatgcc ggaatctacc tgctggcgct    60
ggcgccggtg ggcaagagcc gctgggcgcg ccgctggcag cttctgaagt agggcggtga    120
attcggcgta atccgcgtcg aatcccccttc acagcgacgc cttgcggagc cacctctagg   180
gtctcttcct ggggcagcac a                                              201

SEQ ID NO: 103          moltype = DNA  length = 201
FEATURE                 Location/Qualifiers
misc_feature            1..201
                        note = Synthetic polynucleotide
source                  1..201
                        mol_type = other DNA
                        organism = synthetic construct
SEQUENCE: 103
ctgcatggcg cgctgctgaa aaacgagcag gacgtccatc tgttcgaacg tctggcgttc    60
ctcgcccgcc gcgaaggctc gggcactcgt ccgggccagt aaggcgtctg cggcgaaacg    120
gccgttaccg ggatttcact ggacgcgcgc cagacgcgcg gccaccttcc cgcccatcag    180
gggacggccg aggaaacacc a                                              201

SEQ ID NO: 104          moltype = DNA  length = 201
FEATURE                 Location/Qualifiers
misc_feature            1..201
                        note = Synthetic polynucleotide
source                  1..201
                        mol_type = other DNA
                        organism = synthetic construct
SEQUENCE: 104
gtcggccgtc gcgccgcgtt cgacgcttcg ccgccgctgc tcgccggctt cgaggctgag    60
acgggcttca gcttctgacg atctgggccc gatggaccgt cgcaacgttt gcgtgaaaaa    120
agcttaactg gcgacgactg gcggagcgac ttacacgcga tcatattgtg gccggcgcga    180
gcttcgcgtg attggggata g                                              201

SEQ ID NO: 105          moltype = DNA  length = 201
FEATURE                 Location/Qualifiers
misc_feature            1..201
                        note = Synthetic polynucleotide
source                  1..201
                        mol_type = other DNA
                        organism = synthetic construct
SEQUENCE: 105
accagggaca gcaggcggcg caggatcatc ttcgggctcg acttggaacg acggttccag    60
cggtcatcca tggcccagat tgcaggcgta tgacgaccgg cggtctccga ggcatgacac    120
cctcttaact tggcgtgggc gggcgcgctc gccatagtct tcgcgtcgag tcgactcagg    180
tcggcgtccg gaaccgctcc a                                              201

SEQ ID NO: 106          moltype = DNA  length = 201
FEATURE                 Location/Qualifiers
misc_feature            1..201
                        note = Synthetic polynucleotide
source                  1..201
                        mol_type = other DNA
                        organism = synthetic construct
SEQUENCE: 106
tgcagccgaa cgccaggcgc gcgggcaggc gcgcctcatg gaactcgctc atcaagcgat    60
ccttctgaa agtcgagaaa aggtttgagg aaaagcaaga cggcgcttag tcgacgccat    120
taagacgacg tcatgacccg cttttcactt cttgcgcggg acatcggtct ctaggttagg    180
gatcgagatt ggagaccacg a                                              201

SEQ ID NO: 107          moltype = DNA  length = 93
FEATURE                 Location/Qualifiers
misc_feature            1..93
                        note = Synthetic polynucleotide
source                  1..93
                        mol_type = other DNA
                        organism = synthetic construct
```

```
SEQUENCE: 107
gaagaacagc ggattcttaa ttcgcatcca tgaaagggcc ccgcagcgat ttcgccatgg    60
tctcgccaca gagtggcggc gagcttggcc gcg                                 93

SEQ ID NO: 108            moltype = DNA  length = 201
FEATURE                   Location/Qualifiers
misc_feature              1..201
                          note = Synthetic polynucleotide
source                    1..201
                          mol_type = other DNA
                          organism = synthetic construct
SEQUENCE: 108
ggtctcgtca gttatggaag tcctgtgcgg cattacattt ccgttaggtc agccaaacgc    60
gcggcgccgg aggttgactt gcgacactcc agctcttatg tccagccgac atgagaatga   120
acgttcattc tcaaatcgtt catcatagtg gccgcgtcaa gggtaagagc ccgcgcgacc   180
ctcgcctccc ggggtcaaac a                                             201

SEQ ID NO: 109            moltype = DNA  length = 201
FEATURE                   Location/Qualifiers
misc_feature              1..201
                          note = Synthetic polynucleotide
source                    1..201
                          mol_type = other DNA
                          organism = synthetic construct
SEQUENCE: 109
aacccgggca aatcctttcc cggcccggat cccctgcaag gccgccgcac gttcccaac    60
gtcggcggcc ttttgcgtc gcttctcgcg ccgaggcccg accgccctg taaaaaatgg    120
gtcacatgaa cttttttaa gggggtaaag ttttcgcgcc gttgcagatt gccggcggct   180
cacaccaacg gatgcgaatt c                                             201

SEQ ID NO: 110            moltype = DNA  length = 201
FEATURE                   Location/Qualifiers
misc_feature              1..201
                          note = Synthetic polynucleotide
source                    1..201
                          mol_type = other DNA
                          organism = synthetic construct
SEQUENCE: 110
cctggcgata acgccggtct tcgcgccaaa acctgcccaa gattacaaaa cgttcagact    60
cccccgtctc gacaagctgt cacaggctcg acatggttcg ccgccgtcgc ggacttgggg   120
gtctgcggtg cggggattgg ggcggtcgcg cctccaacac caaacataat tttggctaca   180
cgcccgagga gcgtctcaag t                                             201

SEQ ID NO: 111            moltype = DNA  length = 201
FEATURE                   Location/Qualifiers
misc_feature              1..201
                          note = Synthetic polynucleotide
source                    1..201
                          mol_type = other DNA
                          organism = synthetic construct
SEQUENCE: 111
cggccgccta gcaacagcga cgctccggga gttggtcgtc gttccaccct atgtgatccg    60
ctattatgtg gctgacggtc tggtgcatat cgtccgcatc cggcacgccg cccgttgtg   120
acttttcgt aattcatcct gggttcaggc ggcgagcggt cctctcacgg tcaagctgac   180
caaaaagagg ggacaccagc a                                             201

SEQ ID NO: 112            moltype = DNA  length = 201
FEATURE                   Location/Qualifiers
misc_feature              1..201
                          note = Synthetic polynucleotide
source                    1..201
                          mol_type = other DNA
                          organism = synthetic construct
SEQUENCE: 112
aaggacgccg ccgagcagtc agggacctat ctggcgacct ggaagaaggt cacgggccag    60
tgggtgatcg agaacgagct tttcgtgacg ctggcttgag cgacgggcct cttcccagcg   120
agtatgacgc ggaattaatt aagcccaaac aggggcgggg cttacgcctt cgtccttcaa   180
tgcgcctctg gggaggaaaa c                                             201

SEQ ID NO: 113            moltype = DNA  length = 201
FEATURE                   Location/Qualifiers
misc_feature              1..201
                          note = Synthetic polynucleotide
source                    1..201
                          mol_type = other DNA
                          organism = synthetic construct
SEQUENCE: 113
cgcctggggc agacgctgca cgagggcgcg gtggaccgag aggccgccca cgccagagtc    60
aaagacgccg atcatgggcc aagctgtagc cgccaaagcg gggcgcgtcc acgcactggg   120
```

```
gaaggttaca gtcctgtcat gtgacaggtc ggccgcccat atcctagggt cacggccaac    180
actttcaccg gagatcctcc g                                              201

SEQ ID NO: 114         moltype = DNA   length = 201
FEATURE                Location/Qualifiers
misc_feature           1..201
                       note = Synthetic polynucleotide
source                 1..201
                       mol_type = other DNA
                       organism = synthetic construct
SEQUENCE: 114
gcgaccaggc gggcttcgag cgcggcgtga gacatgggca cgggacagct actccgatcc    60
ttcaacgacc tatgtgaccg ggattcctta aaaacggcca taccccgggc ccacaggtta    120
caaccctagt tataaaacca ctcatcgtta tgaccgagaa ttaattgaat gtggcgcccg    180
ctccgggcca tgtagcgccc a                                              201

SEQ ID NO: 115         moltype = DNA   length = 201
FEATURE                Location/Qualifiers
misc_feature           1..201
                       note = Synthetic polynucleotide
source                 1..201
                       mol_type = other DNA
                       organism = synthetic construct
SEQUENCE: 115
ggcgccgtat cggccgccaa gcggagccat agccactcga agcgcgttcg gctccttggc    60
ggtattggtg cgggctctcg ccgcattgca ctaaagtcat gtgaacgatc attctcattg    120
tgctagaagc gcggaatgag gtgatccggt cgctttgtcg tgcgtatctc tcctgtccgt    180
tgctggtttc gaggcgaccc a                                              201

SEQ ID NO: 116         moltype = DNA   length = 201
FEATURE                Location/Qualifiers
misc_feature           1..201
                       note = Synthetic polynucleotide
source                 1..201
                       mol_type = other DNA
                       organism = synthetic construct
SEQUENCE: 116
cgtcatcgcc atgccacgtc cctcggtccg gaagttccca aggcactttc cgaaaaggaa    60
gaacggcgtt caatttaatt gactgtaatc ttcacggcgc ctgccccggt gatgcggttc    120
gaccattgtc gcgcctccgg gcgacccccca tctgggcgtc tacggcgtgt ttcgtcgccg    180
atgtcgcaag gagcagcccc a                                              201

SEQ ID NO: 117         moltype = DNA   length = 301
FEATURE                Location/Qualifiers
misc_feature           1..301
                       note = Synthetic polynucleotide
source                 1..301
                       mol_type = other DNA
                       organism = synthetic construct
SEQUENCE: 117
gtcgtcctgc agcgtcggcg ggacggcggt gtctggggtg gggtcggtca cggttgagcc    60
tggaatagtc ttgttatcca gatcgtcgcg ctgatcaggc cgtgatgcaa atgaaggtgg    120
cgtcatgaag gcgatgtcac gttgggcgcg tccgccggac cttacaaaaa agtcatctcc    180
tcggatcgat ccggcgccga cgccgggccg taatcatcat cagaccgcgc gccgtcgacc    240
gcttcagatc ccccaacccg aagacttgat ggaaggtttc agacaatgat gcgttcgatg    300
c                                                                    301

SEQ ID NO: 118         moltype = DNA   length = 301
FEATURE                Location/Qualifiers
misc_feature           1..301
                       note = Synthetic polynucleotide
source                 1..301
                       mol_type = other DNA
                       organism = synthetic construct
SEQUENCE: 118
gtcgtcctgc agcgtcggcg ggacggcggt gtctggggtg gggtcggtca cggttgagcc    60
tggaatagtc ttgttatcca gatcgtcgcg ctgatcaggc cgtgatgcaa atgaaggtgg    120
cgtcatgaag gcgatgtcac gttgggcgcg tccgccggac cttacaaaaa agtcatctcc    180
tcggatcgat ccggcgccga cgccgggccg taatcatcat cagaccgcgc gccgtcgacc    240
gcttcagatc ccccaacccg aagacttgat ggaaggtttc agacaatgat gcgttcgatg    300
c                                                                    301

SEQ ID NO: 119         moltype = DNA   length = 301
FEATURE                Location/Qualifiers
misc_feature           1..301
                       note = Synthetic polynucleotide
source                 1..301
                       mol_type = other DNA
                       organism = synthetic construct
```

```
SEQUENCE: 119
aaggacgagg atttccagcc ggcctcgcgc cgaaatcttg gcgacgaagc ctttccccg    60
ggggaaggca cgtttgcagc cggatcggta gcgaaatgcg tcacgcgtgc aaacaccgcg  120
cgctgaaaca ttacatctga gaaatatttg acctcagacg ccagtctgcg tcagaacttc  180
gctcgcgtga gattccggcc gatccggaac gggcgagacc gtgccccaat cgcgggccac  240
tgggaggaga gaccttggat agacgacagt tcctcgcggc ctgcggcatc ggcgccgggg  300
g                                                                  301

SEQ ID NO: 120        moltype = DNA  length = 301
FEATURE               Location/Qualifiers
misc_feature          1..301
                      note = Synthetic polynucleotide
source                1..301
                      mol_type = other DNA
                      organism = synthetic construct
SEQUENCE: 120
catgcgaaac gccaagcgcc gctttcgcgg cgccgagggc tttgatttta gaggattttc   60
ccgcctctgg ctggcgggga ggaaatggtc ggagtggcag gatttgaacc tgcgacccct  120
gcgtcccgaa cgcagtgctc taccagactg agccacactc cgacttggag gccggcctta  180
taggtgggtg ttccgggggg cgcaagcgcc tttttgcagg ttggtcggga ggcctgaaaa  240
aagttctgaa aaggtcgttg catccatccg agtcgtgagc tatctccacc gcctcgccgg  300
g                                                                  301

SEQ ID NO: 121        moltype = DNA  length = 301
FEATURE               Location/Qualifiers
misc_feature          1..301
                      note = Synthetic polynucleotide
source                1..301
                      mol_type = other DNA
                      organism = synthetic construct
SEQUENCE: 121
cgcgccggtg ctgaacgtgc tgatcggcgc gctggcgccg ggtctcgccc ccgctgcggc   60
ggcgctggcc ctggtggcgg ccacgctgct ggtcagcagt ccctcggtcc ggcggcgact  120
gggcttggcc gccgtttagc gccttacgaa agtttcatgg cgagcggcgc ctccaaacgg  180
gggcgtgagc gcctcttacc agtgaaggcg gcgctgtggc gtcgttcacc gaactggagg  240
atttgagaat gggtcccgaa atcatcgtcc cggtcgcgct cttcgcgatg atctgcgccg  300
t                                                                  301

SEQ ID NO: 122        moltype = DNA  length = 301
FEATURE               Location/Qualifiers
misc_feature          1..301
                      note = Synthetic polynucleotide
source                1..301
                      mol_type = other DNA
                      organism = synthetic construct
SEQUENCE: 122
ttctcgtggc gcgcctgcgc cgaggagttc ttccgcaacc tgcagcccta tccggaaccg   60
gaaaagaccc gcttctggcg ccggctgcgg cgcctggcgc gcctgcgcaa gaagacggcg  120
gcgtagtcgc ttcctgtccg cattgtaatt ggcgcggcgc gcagacctcg gataacgctg  180
gtctctcgat agggagggcg gcatgaagct catcatgatc gtcatgggac tgtgtctggc  240
ggtcagcgcc gcccaggccc aaacgagcac gcccgcgccc gtcatcgaga cctacaagac  300
a                                                                  301

SEQ ID NO: 123        moltype = DNA  length = 301
FEATURE               Location/Qualifiers
misc_feature          1..301
                      note = Synthetic polynucleotide
source                1..301
                      mol_type = other DNA
                      organism = synthetic construct
SEQUENCE: 123
cgcgcatcgc tagcccttgc caagcgccag agcccacgcg ctgagcatgg gaacagcccg   60
taaccccgc cccgagggggg ttcagtcgcg aatgcctctc agaaaccccc gaattcggcg  120
tccggatcat tacgtatcat tcatgagtag gtaccttgca ccactcagta ccgggcggta  180
caagggagca tcaacggagg caaggacgcc gtgccggaaa caattgaaat ccaactgaag  240
aaaggcgtgc tggcgctctg tgtgctggct ctgctctcgc acgccgacag ctacgcctac  300
g                                                                  301

SEQ ID NO: 124        moltype = DNA  length = 301
FEATURE               Location/Qualifiers
misc_feature          1..301
                      note = Synthetic polynucleotide
source                1..301
                      mol_type = other DNA
                      organism = synthetic construct
SEQUENCE: 124
ccagcacctc ctcggccggc ttggggctgt cggcccagag caccttcatg acttcgctct   60
cggcgccgct gatacgttgt gatgtcgttt ccatgagcga acgattacgc acgtaaacgt  120
ttccgtcaag tgatcgatta cgcacgtaaa cgaaatgtaa tgcagcgttg gaggcgtaag  180
```

```
cgaagcggct taacgctcga gagcggagga gtcgtacatg ccagacacgc ttcagcttgg  240
cctgccgggc cttgagtcgc ccacgccgac ggatcggctg atgttcctgc tgtatcctga  300
c                                                                 301

SEQ ID NO: 125           moltype = DNA  length = 301
FEATURE                  Location/Qualifiers
misc_feature             1..301
                         note = Synthetic polynucleotide
source                   1..301
                         mol_type = other DNA
                         organism = synthetic construct
SEQUENCE: 125
gcccgggacg atctgggtcg ccagccacaa gccgaaggcg gcgatcagca ggcgaaaaat  60
gagacggacc atgacttctc tccaacttca gccgcaacgc gtccaaacca tcgccgcatt  120
cgtacaatat ccgagcccga aactcggaca ttacaaatgc gttaccgctc ttcaaactgc  180
cgcagcgtga actatctacc ctcctgtgtg ggggatgatc gcgcgcgatt ggcgagcgga  240
tccgcacgca agggatatg agtaagatgg ccgtgaattc tctatcggtg atgtcgccgg  300
a                                                                 301

SEQ ID NO: 126           moltype = DNA  length = 301
FEATURE                  Location/Qualifiers
misc_feature             1..301
                         note = Synthetic polynucleotide
source                   1..301
                         mol_type = other DNA
                         organism = synthetic construct
SEQUENCE: 126
ctcgtccccg atcaggacaa tccgaccctc gtgaccatac tggcgcagga acgcggcgac  60
cgagccgccc gcgtgacccg cgccgacgat gacgacgcat gcgttctgat taacttcagc  120
gctcaatgac gccctccctt tcgtcaaaaa tgacgccgga gtcacctatt ggcaagcgcc  180
ttcgacagag gcggatacgg aatggggcgg ctcgtttccg aagccgcccc acatttatcg  240
ctctgcagcg tgcgtcagac gacgcgctcg accatcatct tcttgatttc ggcgatggcc  300
t                                                                 301

SEQ ID NO: 127           moltype = DNA  length = 301
FEATURE                  Location/Qualifiers
misc_feature             1..301
                         note = Synthetic polynucleotide
source                   1..301
                         mol_type = other DNA
                         organism = synthetic construct
SEQUENCE: 127
tgaatagtcc gcctggagct cgatagctct cccccccagc ggaccccgctt cgctgcgctc  60
gacccgttac gcccctcacg aggaccagcc tccagaagga tcgtttcgaa gcgcgtgcaa  120
ccgacgcccc ttttggggctc cggtcttacc gcaatgttag aattgcggct ggggtccttt  180
ggcaaccccct tttcgtaccg tcaagggtct catttgggca caaattcatc gtcacgcccc  240
cgccccccctg gcgtttgccg cagtgcacaa aacggttttc cggatttcgg ggcggttttt  300
c                                                                 301

SEQ ID NO: 128           moltype = DNA  length = 301
FEATURE                  Location/Qualifiers
misc_feature             1..301
                         note = Synthetic polynucleotide
source                   1..301
                         mol_type = other DNA
                         organism = synthetic construct
SEQUENCE: 128
gtttcgggag cggaaaatag cctagaaaaa acagcctcat gtttgtgagc gcgtgctgtt  60
ttcgatgctt gcgtatccat attgagcaat gattttccga aaagcgttcc tcctgtggcg  120
attttgcgac aggggggtcg ggataatgat tacttttttg caatcagaat tgaccctcgc  180
ccgatccacc ccctaacgtc gctgcaaccg aagagtttg ttccgggaca catgtgatcg  240
cgtggtggat ttacagcgga tttcggctcg aaaacggaca ggtcgctgag gggcttcttg  300
t                                                                 301

SEQ ID NO: 129           moltype = DNA  length = 301
FEATURE                  Location/Qualifiers
misc_feature             1..301
                         note = Synthetic polynucleotide
source                   1..301
                         mol_type = other DNA
                         organism = synthetic construct
SEQUENCE: 129
agcccgattg gcaacctgtc aatccgtcaa cttgggggga tttgcgcacc tagcgcccac  60
cagcatgggc gataagtggc gcaaagaaga cacacatgcc ccgtttcgag ccgcctcgcc  120
gcaccgaacg gtcatcgttt gcagattttt gtgttgatta cggtccgtta atttgcagta  180
atttgcagca acggcccgcc gcatgacctc aacagcgcag agccggacag ggagggaact  240
cgtatgaaca cccaatttc gcgccgtcgc gcctggctga tggccggcgg ggccacgggc  300
c                                                                 301
```

```
SEQ ID NO: 130          moltype = DNA   length = 301
FEATURE                 Location/Qualifiers
misc_feature            1..301
                        note = Synthetic polynucleotide
source                  1..301
                        mol_type = other DNA
                        organism = synthetic construct
SEQUENCE: 130
gatgacaagg aaatagccgg cggccatgcg gtcgaaggcg gtttcaaagg cgttcagcgt    60
gcggttcatg atggaagtcc ctcatttggg cttgccccga cccctgtgg gtcatcgccc    120
tcgaaagtta cgaggcgatc tggacagtgc ttagatagca ccaatctgaa cgccgtcaag   180
atggtcttta cagcgtttag atgaaatttt agaaagctat ggttagagtg aggccgatga   240
gcacagcgac cgccgaatcc cgcccctatc accatggcga tctgagccgc gccctgatcg   300
a                                                                   301

SEQ ID NO: 131          moltype = DNA   length = 37
FEATURE                 Location/Qualifiers
misc_feature            1..37
                        note = Synthetic polynucleotide
source                  1..37
                        mol_type = other DNA
                        organism = synthetic construct
SEQUENCE: 131
attcttcctt tttcaatatt attgaagcat ttatcag                             37

SEQ ID NO: 132          moltype = DNA   length = 30
FEATURE                 Location/Qualifiers
misc_feature            1..30
                        note = Synthetic polynucleotide
source                  1..30
                        mol_type = other DNA
                        organism = synthetic construct
SEQUENCE: 132
aagcttaata agatgatctt cttgagatcg                                     30

SEQ ID NO: 133          moltype = DNA   length = 34
FEATURE                 Location/Qualifiers
misc_feature            1..34
                        note = Synthetic polynucleotide
source                  1..34
                        mol_type = other DNA
                        organism = synthetic construct
SEQUENCE: 133
catcttatta agcttttacg ccccgccctg ccac                                34

SEQ ID NO: 134          moltype = DNA   length = 49
FEATURE                 Location/Qualifiers
misc_feature            1..49
                        note = Synthetic polynucleotide
source                  1..49
                        mol_type = other DNA
                        organism = synthetic construct
SEQUENCE: 134
tgaaaaagga agaatatgga gaaaaaatc actggatata ccaccgttg                 49

SEQ ID NO: 135          moltype = DNA   length = 30
FEATURE                 Location/Qualifiers
misc_feature            1..30
                        note = Synthetic polynucleotide
source                  1..30
                        mol_type = other DNA
                        organism = synthetic construct
SEQUENCE: 135
gacgctagcc tgcgcaaccc aagtgctacc                                     30

SEQ ID NO: 136          moltype = DNA   length = 30
FEATURE                 Location/Qualifiers
misc_feature            1..30
                        note = Synthetic polynucleotide
source                  1..30
                        mol_type = other DNA
                        organism = synthetic construct
SEQUENCE: 136
cagaagcttg gatatgtgga cgatggccgc                                     30

SEQ ID NO: 137          moltype = DNA   length = 30
FEATURE                 Location/Qualifiers
misc_feature            1..30
                        note = Synthetic polynucleotide
```

```
source                  1..30
                        mol_type = other DNA
                        organism = synthetic construct
SEQUENCE: 137
gacggatccg agtcagttga gccaggcgtg                                       30

SEQ ID NO: 138          moltype = DNA   length = 32
FEATURE                 Location/Qualifiers
misc_feature            1..32
                        note = Synthetic polynucleotide
source                  1..32
                        mol_type = other DNA
                        organism = synthetic construct
SEQUENCE: 138
gacgaattcc gttcagtcca tacgcgactg tg                                    32

SEQ ID NO: 139          moltype = DNA   length = 27
FEATURE                 Location/Qualifiers
misc_feature            1..27
                        note = Synthetic polynucleotide
source                  1..27
                        mol_type = other DNA
                        organism = synthetic construct
SEQUENCE: 139
atagcgcaat ttaagtggtc tctggcc                                          27

SEQ ID NO: 140          moltype = DNA   length = 36
FEATURE                 Location/Qualifiers
misc_feature            1..36
                        note = Synthetic polynucleotide
source                  1..36
                        mol_type = other DNA
                        organism = synthetic construct
SEQUENCE: 140
cttaaattgc gctattgacg gggatttaac ggcagc                                36

SEQ ID NO: 141          moltype = DNA   length = 21
FEATURE                 Location/Qualifiers
misc_feature            1..21
                        note = Synthetic polynucleotide
source                  1..21
                        mol_type = other DNA
                        organism = synthetic construct
SEQUENCE: 141
aatgtggtct ctggccctcc g                                                21

SEQ ID NO: 142          moltype = DNA   length = 36
FEATURE                 Location/Qualifiers
misc_feature            1..36
                        note = Synthetic polynucleotide
source                  1..36
                        mol_type = other DNA
                        organism = synthetic construct
SEQUENCE: 142
gccagagacc acattaattg cggtaatgac ggggat                                36

SEQ ID NO: 143          moltype = AA    length = 294
FEATURE                 Location/Qualifiers
source                  1..294
                        mol_type = protein
                        note = Strain NA1000
                        organism = Caulobacter crescentus
SEQUENCE: 143
MLIIENLTHV YGNGTRALDE VSLTIPRGMY GLLGPNGAGK STLMRTIATL QAPTSGHIRF       60
GDIDVLKHPE ELRKTLGYLP QDFGVYPRVS AYDMLDHMAV LKGISGGKER KATVEHLLNQ      120
VNLWDVRKKA IAGFSGGMRQ RFGIAQALIG DPRLIIVDEP TAGLDPEERN RFLNLLAEIG      180
ENVVILSTH IVEDVSDLCP AMAIICNGAI VREGAPADLV AQLKGRIWKK IIDKAELEAA       240
KARYKVISTR LLAGRTVIHI ESETDPGDGF TAVEGGLEDV YFSTLSSTRS RQAA            294

SEQ ID NO: 144          moltype = AA    length = 1195
FEATURE                 Location/Qualifiers
source                  1..1195
                        mol_type = protein
                        note = Strain NA1000
                        organism = Caulobacter crescentus
SEQUENCE: 144
MFGKIAGFEL RYQLKSPVFW VVAVIFFLMT FGAATIDQIR IGGGGNIHKN APYAIAQTHL       60
ILAIFYMFVT TAFVANVVVR DDETGFGPIL RSTRIRKFDY LYGRFTGAFL AAAISFLVVP      120
LAIFVGSFMP WVDPERLGPN DLNAYLFSYF ALALPAILLT SAIFFALATV TRSMMWTYVG      180
```

```
VIAFLVLYII AGIALDRPEY EKGAALWEPL GTAAFGLATK YWTASERNSL TPPLAGALLF    240
NRVFVLVLAA GFLALAYSLF RFQSAELSGQ RKSAKKTKAA PTEAAPAASG PLPTPVFDRR    300
TAWAQLVVRT RLDMGQVFKS PAFFVLLFLG LANAMGALWF ATEAGRYGGV VYPVTRILLF    360
PLLGSFGLIP IIIAIYYSGE LVWREREKKT HEIIDATPVP DWAFVAPKTL AISLVLISTL    420
LISVVAAMLS QVFHGYFNFE LEKYLLWYVL PQALDFILLA VLAVFLQTIS PHKFIGWALM    480
VIYIVSTITF TNLGFEHKLY NYGATTETPF SDMNGLGKFW MGAWWLRAYW TAFALVLLVL    540
AYGLWRRGTE SRLLPRLRRL PLRLNGGAGA LMGVSLVAFA GLGGFIYVNT NVWNEYRTNI    600
DGEKWQAEYE KTLLPFENTP QPKIIAQTLD IDIQPHAPSL ETKGSYVLEN KTGAALKEIH    660
VRFDRDLEVK GLSIEGARPK KTFEKFNYRI FAFDTPMAPG EQRKMSFITL RAQRGFPNSG    720
AETRVVDNGT FVNNLEIAPI LGMSRDGLLT DRAKRRKYGL PPEQRMAKLG DVSSMQFNGL    780
RKDADFIQSD ITVTTVADQT PIAPGYKVSD SVRNGRRTAR FVTEAPIMPF VSIQSARYKV    840
AEETYKGVQL AVYYDPQHAW NIDRMKTSMK RSLDYMGTNF SPYQFRQLRY QEFPDYAQFA    900
QSFANTIPWS EGMFFISDYR DPTKIDMVTY VGAHEIGHQW WAHQVIGANQ QGGAMLSETF    960
AQYSALMVMK HTYGEDQIRK FLKFELDSYL RARGGDVIDE QPLYKVENQP YIYYRKGSLV   1020
MYRLQDQIGE EAVNRALRKL IADHAFKGAP YPTTLDFMAA LRAEAPADKQ ALITDLFEKI   1080
TLYDLKTKSA AVKKRADGKF DVTVVVEAQK KYADGKGKET VAALNETMEI GLFTAKPGDK   1140
GFVAKNVVLY QRRPIRSGEN TFTFIVDKAP TFAGIDPYNT VIDRNGDDNT VKVGG        1195

SEQ ID NO: 145          moltype = DNA   length = 34
FEATURE                 Location/Qualifiers
misc_feature            1..34
                        note = Synthetic polynucleotide
source                  1..34
                        mol_type = other DNA
                        organism = synthetic construct
SEQUENCE: 145
taacccttg caaaccggac ggtgaccggc aaac                                 34

SEQ ID NO: 146          moltype = DNA   length = 34
FEATURE                 Location/Qualifiers
misc_feature            1..34
                        note = Synthetic polynucleotide
source                  1..34
                        mol_type = other DNA
                        organism = synthetic construct
SEQUENCE: 146
gatgaacttg cgcatggcgg agcccctcgt tttc                                34

SEQ ID NO: 147          moltype = DNA   length = 22
FEATURE                 Location/Qualifiers
misc_feature            1..22
                        note = Synthetic polynucleotide
source                  1..22
                        mol_type = other DNA
                        organism = synthetic construct
SEQUENCE: 147
atgcgcaagt tcatcatgag cc                                             22

SEQ ID NO: 148          moltype = DNA   length = 24
FEATURE                 Location/Qualifiers
misc_feature            1..24
                        note = Synthetic polynucleotide
source                  1..24
                        mol_type = other DNA
                        organism = synthetic construct
SEQUENCE: 148
gtttgcaaag ggttaatcga cgcc                                           24

SEQ ID NO: 149          moltype = DNA   length = 32
FEATURE                 Location/Qualifiers
misc_feature            1..32
                        note = Synthetic polynucleotide
source                  1..32
                        mol_type = other DNA
                        organism = synthetic construct
SEQUENCE: 149
ggaacgatag cgccggacgg tgaccggcaa ac                                  32

SEQ ID NO: 150          moltype = DNA   length = 23
FEATURE                 Location/Qualifiers
misc_feature            1..23
                        note = Synthetic polynucleotide
source                  1..23
                        mol_type = other DNA
                        organism = synthetic construct
SEQUENCE: 150
cgcacaaaat cctcatcctg agc                                            23

SEQ ID NO: 151          moltype = DNA   length = 28
```

```
FEATURE                 Location/Qualifiers
misc_feature            1..28
                        note = Synthetic polynucleotide
source                  1..28
                        mol_type = other DNA
                        organism = synthetic construct
SEQUENCE: 151
gacggatccc ggacggtgac cggcaaac                                        28

SEQ ID NO: 152          moltype = DNA  length = 35
FEATURE                 Location/Qualifiers
misc_feature            1..35
                        note = Synthetic polynucleotide
source                  1..35
                        mol_type = other DNA
                        organism = synthetic construct
SEQUENCE: 152
gacgaattcc ctcgttttca tgtctcgcag ctagc                                35

SEQ ID NO: 153          moltype = DNA  length = 28
FEATURE                 Location/Qualifiers
misc_feature            1..28
                        note = Synthetic polynucleotide
source                  1..28
                        mol_type = other DNA
                        organism = synthetic construct
SEQUENCE: 153
gacggatccg aacgatagcg ccgcctgc                                        28

SEQ ID NO: 154          moltype = DNA  length = 50
FEATURE                 Location/Qualifiers
misc_feature            1..50
                        note = Synthetic polynucleotide
source                  1..50
                        mol_type = other DNA
                        organism = synthetic construct
SEQUENCE: 154
gacgaattcg gaaagatcgg gactgggtga tggcgcttag gattccacag                50

SEQ ID NO: 155          moltype = DNA  length = 23
FEATURE                 Location/Qualifiers
misc_feature            1..23
                        note = Synthetic polynucleotide
source                  1..23
                        mol_type = other DNA
                        organism = synthetic construct
SEQUENCE: 155
cgttttcatg tctcgcagct agc                                             23

SEQ ID NO: 156          moltype = DNA  length = 33
FEATURE                 Location/Qualifiers
misc_feature            1..33
                        note = Synthetic polynucleotide
source                  1..33
                        mol_type = other DNA
                        organism = synthetic construct
SEQUENCE: 156
ctctttcagg gacccttgat gcgcgcgctc gtc                                  33

SEQ ID NO: 157          moltype = DNA  length = 33
FEATURE                 Location/Qualifiers
misc_feature            1..33
                        note = Synthetic polynucleotide
source                  1..33
                        mol_type = other DNA
                        organism = synthetic construct
SEQUENCE: 157
caccagagcg agctctcacg ccgtcccgcc ggc                                  33

SEQ ID NO: 158          moltype = DNA  length = 19
FEATURE                 Location/Qualifiers
misc_feature            1..19
                        note = Synthetic polynucleotide
source                  1..19
                        mol_type = other DNA
                        organism = synthetic construct
SEQUENCE: 158
gagctcgctc tggtgccac                                                  19
```

```
SEQ ID NO: 159         moltype = DNA   length = 24
FEATURE                Location/Qualifiers
misc_feature           1..24
                       note = Synthetic polynucleotide
source                 1..24
                       mol_type = other DNA
                       organism = synthetic construct
SEQUENCE: 159
gggtccctga aagaggactt caag                                            24

SEQ ID NO: 160         moltype = DNA   length = 34
FEATURE                Location/Qualifiers
misc_feature           1..34
                       note = Synthetic polynucleotide
source                 1..34
                       mol_type = other DNA
                       organism = synthetic construct
SEQUENCE: 160
caattgaagc cggctcagaa ggtcgacgcc ctgg                                 34

SEQ ID NO: 161         moltype = DNA   length = 23
FEATURE                Location/Qualifiers
misc_feature           1..23
                       note = Synthetic polynucleotide
source                 1..23
                       mol_type = other DNA
                       organism = synthetic construct
SEQUENCE: 161
cgcacaaaat cctcatcctg agc                                             23

SEQ ID NO: 162         moltype = DNA   length = 32
FEATURE                Location/Qualifiers
misc_feature           1..32
                       note = Synthetic polynucleotide
source                 1..32
                       mol_type = other DNA
                       organism = synthetic construct
SEQUENCE: 162
ggaacgatag cgccggacgg tgaccggcaa ac                                   32

SEQ ID NO: 163         moltype = DNA   length = 29
FEATURE                Location/Qualifiers
misc_feature           1..29
                       note = Synthetic polynucleotide
source                 1..29
                       mol_type = other DNA
                       organism = synthetic construct
SEQUENCE: 163
aatcagaatg cgcatggcgg agcccctcg                                       29

SEQ ID NO: 164         moltype = DNA   length = 25
FEATURE                Location/Qualifiers
misc_feature           1..25
                       note = Synthetic polynucleotide
source                 1..25
                       mol_type = other DNA
                       organism = synthetic construct
SEQUENCE: 164
atgcgcattc tgattatcga ggacg                                           25

SEQ ID NO: 165         moltype = DNA   length = 20
FEATURE                Location/Qualifiers
misc_feature           1..20
                       note = Synthetic polynucleotide
source                 1..20
                       mol_type = other DNA
                       organism = synthetic construct
SEQUENCE: 165
cggcgctatc gttccctagg                                                 20

SEQ ID NO: 166         moltype = DNA   length = 35
FEATURE                Location/Qualifiers
misc_feature           1..35
                       note = Synthetic polynucleotide
source                 1..35
                       mol_type = other DNA
                       organism = synthetic construct
SEQUENCE: 166
gtgaaaaaag cttaactcga ggggctccgc catgc                                35
```

```
SEQ ID NO: 167           moltype = DNA  length = 39
FEATURE                  Location/Qualifiers
misc_feature             1..39
                         note = Synthetic polynucleotide
source                   1..39
                         mol_type = other DNA
                         organism = synthetic construct
SEQUENCE: 167
ttaagctttt ttcacgcagt ctcgcagcta gcttagccg                              39

SEQ ID NO: 168           moltype = DNA  length = 44
FEATURE                  Location/Qualifiers
misc_feature             1..44
                         note = Synthetic polynucleotide
source                   1..44
                         mol_type = other DNA
                         organism = synthetic construct
SEQUENCE: 168
gtgaaaaaag cttaactccg agctccctaa ctaactaatc atct                        44

SEQ ID NO: 169           moltype = DNA  length = 42
FEATURE                  Location/Qualifiers
misc_feature             1..42
                         note = Synthetic polynucleotide
source                   1..42
                         mol_type = other DNA
                         organism = synthetic construct
SEQUENCE: 169
ttaagctttt ttcacgcagt gatggcgctt aggattccac ag                          42

SEQ ID NO: 170           moltype = DNA  length = 36
FEATURE                  Location/Qualifiers
misc_feature             1..36
                         note = Synthetic polynucleotide
source                   1..36
                         mol_type = other DNA
                         organism = synthetic construct
SEQUENCE: 170
tggggagacg accatatgcg taagggcgaa gagctg                                 36

SEQ ID NO: 171           moltype = DNA  length = 37
FEATURE                  Location/Qualifiers
misc_feature             1..37
                         note = Synthetic polynucleotide
source                   1..37
                         mol_type = other DNA
                         organism = synthetic construct
SEQUENCE: 171
cacggctggc tgcaggccga atttcagggg tacagca                                37

SEQ ID NO: 172           moltype = DNA  length = 28
FEATURE                  Location/Qualifiers
misc_feature             1..28
                         note = Synthetic polynucleotide
source                   1..28
                         mol_type = other DNA
                         organism = synthetic construct
SEQUENCE: 172
gatcccgggg atttctcttc gcgccacc                                          28

SEQ ID NO: 173           moltype = DNA  length = 28
FEATURE                  Location/Qualifiers
misc_feature             1..28
                         note = Synthetic polynucleotide
source                   1..28
                         mol_type = other DNA
                         organism = synthetic construct
SEQUENCE: 173
gaaatccccg ggatccctgt gctctaga                                          28

SEQ ID NO: 174           moltype = DNA  length = 27
FEATURE                  Location/Qualifiers
misc_feature             1..27
                         note = Synthetic polynucleotide
source                   1..27
                         mol_type = other DNA
                         organism = synthetic construct
SEQUENCE: 174
```

```
gactctagac gaagactggg cgggcag                                         27

SEQ ID NO: 175         moltype = DNA  length = 29
FEATURE                Location/Qualifiers
misc_feature           1..29
                       note = Synthetic polynucleotide
source                 1..29
                       mol_type = other DNA
                       organism = synthetic construct
SEQUENCE: 175
gacagatctc ggtttgggtg gtcgcttgg                                       29

SEQ ID NO: 176         moltype = DNA  length = 29
FEATURE                Location/Qualifiers
misc_feature           1..29
                       note = Synthetic polynucleotide
source                 1..29
                       mol_type = other DNA
                       organism = synthetic construct
SEQUENCE: 176
ttgtcgacgt atgacgtttg ctctatagc                                       29

SEQ ID NO: 177         moltype = DNA  length = 22
FEATURE                Location/Qualifiers
misc_feature           1..22
                       note = Synthetic polynucleotide
source                 1..22
                       mol_type = other DNA
                       organism = synthetic construct
SEQUENCE: 177
cgttcacatc gccatccagc tc                                              22

SEQ ID NO: 178         moltype = DNA  length = 23
FEATURE                Location/Qualifiers
misc_feature           1..23
                       note = Synthetic polynucleotide
source                 1..23
                       mol_type = other DNA
                       organism = synthetic construct
SEQUENCE: 178
atggcgatgt gaacggccat aag                                             23

SEQ ID NO: 179         moltype = DNA  length = 37
FEATURE                Location/Qualifiers
misc_feature           1..37
                       note = Synthetic polynucleotide
source                 1..37
                       mol_type = other DNA
                       organism = synthetic construct
SEQUENCE: 179
gtcatacgtc gacaagccga atttcagggg tacagca                              37

SEQ ID NO: 180         moltype = DNA  length = 42
FEATURE                Location/Qualifiers
misc_feature           1..42
                       note = Synthetic polynucleotide
source                 1..42
                       mol_type = other DNA
                       organism = synthetic construct
SEQUENCE: 180
atgttttttcc tccttataaa gtagatcttt agttagttag gg                       42

SEQ ID NO: 181         moltype = DNA  length = 36
FEATURE                Location/Qualifiers
misc_feature           1..36
                       note = Synthetic polynucleotide
source                 1..36
                       mol_type = other DNA
                       organism = synthetic construct
SEQUENCE: 181
aaggaggaaa aacatatgcg taagggcgaa gagctg                               36

SEQ ID NO: 182         moltype = DNA  length = 24
FEATURE                Location/Qualifiers
misc_feature           1..24
                       note = Synthetic polynucleotide
source                 1..24
                       mol_type = other DNA
                       organism = synthetic construct
```

```
SEQUENCE: 182
ggtcgctacc attaccagtt ggtc                                               24

SEQ ID NO: 183           moltype = DNA  length = 25
FEATURE                  Location/Qualifiers
misc_feature             1..25
                         note = Synthetic polynucleotide
source                   1..25
                         mol_type = other DNA
                         organism = synthetic construct
SEQUENCE: 183
tgcttgggtc gtttgagtat atggt                                              25

SEQ ID NO: 184           moltype = DNA  length = 35
FEATURE                  Location/Qualifiers
misc_feature             1..35
                         note = Synthetic polynucleotide
source                   1..35
                         mol_type = other DNA
                         organism = synthetic construct
SEQUENCE: 184
caaacgaccc aagcaggtgt cgcccttcgc tgaac                                   35

SEQ ID NO: 185           moltype = DNA  length = 41
FEATURE                  Location/Qualifiers
misc_feature             1..41
                         note = Synthetic polynucleotide
source                   1..41
                         mol_type = other DNA
                         organism = synthetic construct
SEQUENCE: 185
gtaatggtag cgaccccaag ctcagctaat taagcctcga g                            41

SEQ ID NO: 186           moltype = DNA  length = 39
FEATURE                  Location/Qualifiers
misc_feature             1..39
                         note = Synthetic polynucleotide
source                   1..39
                         mol_type = other DNA
                         organism = synthetic construct
SEQUENCE: 186
ggctggcgcc aagcttggcc ggccgcacgc aagggcaga                               39

SEQ ID NO: 187           moltype = DNA  length = 25
FEATURE                  Location/Qualifiers
misc_feature             1..25
                         note = Synthetic polynucleotide
source                   1..25
                         mol_type = other DNA
                         organism = synthetic construct
SEQUENCE: 187
ttattttga caccagacca actgg                                               25

SEQ ID NO: 188           moltype = DNA  length = 31
FEATURE                  Location/Qualifiers
misc_feature             1..31
                         note = Synthetic polynucleotide
source                   1..31
                         mol_type = other DNA
                         organism = synthetic construct
SEQUENCE: 188
tggtgtcaaa aataatcgca caggcgaccg c                                       31

SEQ ID NO: 189           moltype = DNA  length = 34
FEATURE                  Location/Qualifiers
misc_feature             1..34
                         note = Synthetic polynucleotide
source                   1..34
                         mol_type = other DNA
                         organism = synthetic construct
SEQUENCE: 189
gcgaattcgt ggatccaggc gtcgaggtga agta                                    34

SEQ ID NO: 190           moltype = DNA  length = 37
FEATURE                  Location/Qualifiers
misc_feature             1..37
                         note = Synthetic polynucleotide
source                   1..37
                         mol_type = other DNA
```

```
                        organism = synthetic construct
SEQUENCE: 190
attcttcctt tttcaatatt attgaagcat ttatcag                              37

SEQ ID NO: 191          moltype = DNA  length = 30
FEATURE                 Location/Qualifiers
misc_feature            1..30
                        note = Synthetic polynucleotide
source                  1..30
                        mol_type = other DNA
                        organism = synthetic construct
SEQUENCE: 191
aagcttaata agatgatctt cttgagatcg                                      30

SEQ ID NO: 192          moltype = DNA  length = 28
FEATURE                 Location/Qualifiers
misc_feature            1..28
                        note = Synthetic polynucleotide
source                  1..28
                        mol_type = other DNA
                        organism = synthetic construct
SEQUENCE: 192
gacggtaccg aacgatagcg ccgcctgc                                        28

SEQ ID NO: 193          moltype = DNA  length = 50
FEATURE                 Location/Qualifiers
misc_feature            1..50
                        note = Synthetic polynucleotide
source                  1..50
                        mol_type = other DNA
                        organism = synthetic construct
SEQUENCE: 193
gaccctaggg gaaagatcgg gactgggtga tggcgcttag gattccacag                50

SEQ ID NO: 194          moltype = DNA  length = 51
FEATURE                 Location/Qualifiers
misc_feature            1..51
                        note = Synthetic polynucleotide
source                  1..51
                        mol_type = other DNA
                        organism = synthetic construct
SEQUENCE: 194
ggaagatcta ctttataagg aggaaaaaca tatgacccga gaccaagaca c              51

SEQ ID NO: 195          moltype = DNA  length = 24
FEATURE                 Location/Qualifiers
misc_feature            1..24
                        note = Synthetic polynucleotide
source                  1..24
                        mol_type = other DNA
                        organism = synthetic construct
SEQUENCE: 195
gacctcgagt cataggggc gtcc                                             24

SEQ ID NO: 196          moltype = DNA  length = 19
FEATURE                 Location/Qualifiers
misc_feature            1..19
                        note = Synthetic polynucleotide
source                  1..19
                        mol_type = other DNA
                        organism = synthetic construct
SEQUENCE: 196
tcataggggg cgtccgtcg                                                  19

SEQ ID NO: 197          moltype = DNA  length = 21
FEATURE                 Location/Qualifiers
misc_feature            1..21
                        note = Synthetic polynucleotide
source                  1..21
                        mol_type = other DNA
                        organism = synthetic construct
SEQUENCE: 197
gggatttctc ttcgcgccac c                                               21

SEQ ID NO: 198          moltype = DNA  length = 18
FEATURE                 Location/Qualifiers
misc_feature            1..18
                        note = Synthetic polynucleotide
source                  1..18
```

```
                    mol_type = other DNA
                    organism = synthetic construct
SEQUENCE: 198
ggacgccccc tatgagcg                                                    18

SEQ ID NO: 199      moltype = DNA   length = 34
FEATURE             Location/Qualifiers
misc_feature        1..34
                    note = Synthetic polynucleotide
source              1..34
                    mol_type = other DNA
                    organism = synthetic construct
SEQUENCE: 199
gcgaagagaa atcccatcat cgccagccct agcg                                  34

SEQ ID NO: 200      moltype = DNA   length = 1622
FEATURE             Location/Qualifiers
misc_feature        1..1622
                    note = Synthetic polynucleotide
source              1..1622
                    mol_type = other DNA
                    organism = synthetic construct
SEQUENCE: 200
cagagatcta ctttataagg aggaaaaaca tatggatctg cccgacgatc attacctgtc      60
cacccagacc atcctgtcga aggatctgaa tggcaccgac gtgggctccg gtggcgggag     120
tggtggtggc gggagcaagg tctccgccct caaggagaa gttagcgccc tgaaagagaa     180
agtctcggcc ctgaccgaaa aggtctccgc ccttaaggaa aaggtgagcg ctctcaaaga     240
gtaaccaggc atcaaataaa acgaaaggct cagtcgaaag actgggcctt tcgttttatc     300
tgttgtttgt cggtgaacgc tctctactag agtcacactg gctcaccttc gggtgggcct     360
ttctgcgttt ataggtaccc gaagactggg cgggcagcag cccactccca agcgcccacc     420
aattatgact tcttttttcat agacttaatt cgacgtcatg aagcagtcgt aacgggtgtt     480
cgccatccga ccgctctaca tcctcgatca acggatcgcc aagcgaccac ccaaaccgcc     540
taggtaacta aagattaact ttataaggag gaaaaacata tgaaggtctc cgcccttgaa     600
aatgaggtct cggctctcga aaaggaggtg tcggtcctgg agaaagaagt cagcgcgctt     660
gagaaggagg tccgtgccct ggagaagagt ggcggtgggg ggtctggggg cggttctggg     720
ggcggctcca cctcggagaa gcgtgaccac atggtgctgc tcgaatatgt caccgccgcc     780
gggatcaccg atgcctccta agactcctgt tgatagatcc agtaatgacc tcagaactcc     840
atctggattt gttcagaacg ctcggttgcc gccgggcgtt ttttattggt gagaatgaaa     900
aatgctgtac ccctgaaatt cggctattgt cgacgtatga cgtttgctct atagccatcg     960
ctgctcccat gcgcgccact cggtcgcagg gggtgtggga ttttttttgg gagacaatcc    1020
tcatgcgtaa gggcgaagag ctgttcacgg cgtcgtccc catcctcatc gagctggatg    1080
gcgatgtgaa cggccataag ttcttcgtcc gtggggaagg cgaggggat gccaccatcg    1140
gcaagctgag cctcaagttc atctgcacca ccggcaagct cccggtcccc tggccgaccc    1200
tcgtcacgac cctcacctac ggggtgcagt gcttttcccg ttaccccgac cacatgaagc    1260
ggcacgactt ctttaagtcg gccatgcccg aaggctacgt gcaggagcgc accatctatt    1320
ttaaggacga tggcacgtat aagacccgcg cggaggtcaa gttcgaaggg gatacctgg    1380
tcaaccgtat cgagctgaag ggcatcgact ttaaggaaga tggcaactc ctcgggcaca    1440
agctcgaata taattttaac tcccataagg tctacatcac cgccgacaag caaaacaacg    1500
gcatcaaggc gaacttacg atccgtcaca atgtggagga cggcagcgtc cagctcgcgg    1560
atcattatca acagaatacc cccatcggcg atggtcccgt cctcctcccg tagctcgaga    1620
tt                                                                  1622
```